(12) United States Patent
Ding

(10) Patent No.: US 12,091,672 B2
(45) Date of Patent: Sep. 17, 2024

(54) PLANT FIBER QUALITY

(71) Applicant: Board of Trustees of Michigan State University, East Lansing, MI (US)

(72) Inventor: Shi-You Ding, Okemos, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 0 days.

(21) Appl. No.: 16/967,931

(22) PCT Filed: Feb. 7, 2019

(86) PCT No.: PCT/US2019/017038
§ 371 (c)(1),
(2) Date: Aug. 6, 2020

(87) PCT Pub. No.: WO2019/157173
PCT Pub. Date: Aug. 15, 2019

(65) Prior Publication Data
US 2020/0370064 A1    Nov. 26, 2020

Related U.S. Application Data

(60) Provisional application No. 62/628,383, filed on Feb. 9, 2018.

(51) Int. Cl.
*C12N 15/82* (2006.01)
(52) U.S. Cl.
CPC .............................. *C12N 15/8262* (2013.01)
(58) Field of Classification Search
CPC ................................................... C12N 15/82
See application file for complete search history.

(56) References Cited

U.S. PATENT DOCUMENTS

| 8,173,866 | B1 * | 5/2012 | Bao ..................... | C12N 9/1077 |
| | | | | 800/278 |
| 2010/0115659 | A1 * | 5/2010 | Engelen ............. | C12N 15/8234 |
| | | | | 800/278 |
| 2014/0173782 | A1 | 6/2014 | Dhugga et al. | |
| 2017/0260540 | A1 * | 9/2017 | Tresch ................ | C12N 15/8274 |

FOREIGN PATENT DOCUMENTS

WO    WO    2/2019
      PCT/US2019/017038
WO    WO-2019157173 A1    8/2019

OTHER PUBLICATIONS

"International Application Serial No. PCT/US2019/017038, International Search Report mailed Jun. 7, 2019", 5 pgs.
"International Application Serial No. PCT/US2019/017038, Invitation to Pay Additional Fees mailed Apr. 1, 2019", 3 pgs.
"International Application Serial No. PCT/US2019/017038, Written Opinion mailed Jun. 7, 2019", 8 pgs.
Gu, et al., "Identification of a cellulose synthase-associated protein required for cellulose biosynthesis", Proc Natl Acad Sci USA. vol. 107(29), (2010), 12866-71.
Hu, et al., "Three AtCesA6-like members enhance biomass production by distinctively promoting cell growth in *Arabidopsis*", Plant Biotechnol J. 2018, vol. 16(5), (Oct. 23. 2017), 976-988.
"International Application Serial No. PCT/US2019/017038, International Preliminary Report on Patentability mailed Aug. 20, 2020", 10 pgs.
Chen, Yani, et al., "IRE1: ER stress sensor and cell fate executor", Trends in Cell Biology, 23(11), (Nov. 2013), 547-555.
Kim, Sang-Jin, et al., "In the grass species *Brachypodium distachyon*, the production of mixed-linkage (1,3;1,4)-ß-glucan (MLG) occurs in the Golgi apparatus", The Plant Journal, 93(6), (2018).
Kim, Sang-Jin, et al., "Modulating hemicellulose to improve bioenergy crop", Abstract, Great Lakes Bioenergy Research Center (GLBRC) Annual Science Meeting, May 7-9, 2018, (2018), 2 pgs.
Kim, Sang-Jin, et al., "The cytoplasmic localization of the catalytic site of CSLF6 supports a channeling model for the biosynthesis of mixed-linkage glucan", The Plant Journal, 81(4), (2015), 537-547.
U.S. Appl. No. 62/628,383, filed Feb. 9, 2018, Improved Plant Fiber Quality.

* cited by examiner

*Primary Examiner* — Brent T Page
(74) *Attorney, Agent, or Firm* — McKee, Voorhees & Sease, PLC

(57) ABSTRACT

Described herein are plants, plant seeds, and plants cells that are modified to express particular types of cellulose synthase enzymes (but not CesA3, CesA9, or CesA7 enzymes). Such plants, plant seeds and plant cells can be cotton, flax, hemp, jute, sisal, poplar, or eucalyptus plants, plant seeds or plant cells. The modified plants tend to grow taller, have increased cellulose synthesis, have more crystalline cellulose, have wider secondary cell walls, increased biomass, and increased mechanical strength than in a control plant without the expression cassette (e.g., a wild type or parental plant without the expression cassette).

13 Claims, 30 Drawing Sheets
Specification includes a Sequence Listing.

SEQUENCE LISTING

```
<160> NUMBER OF SEQ ID NOS: 48

<210> SEQ ID NO 1
<211> LENGTH: 1084
<212> TYPE: PRT
<213> ORGANISM: Arabidopsis thaliana

<400> SEQUENCE: 1

Met Asn Thr Gly Gly Arg Leu Ile Ala Gly Ser His Asn Arg Asn Glu
1               5                   10                  15
```

-continued

```
Phe Val Leu Ile Asn Ala Asp Glu Ser Ala Arg Ile Arg Ser Val Gln
            20                  25                  30

Glu Leu Ser Gly Gln Thr Cys Gln Ile Cys Gly Asp Glu Ile Glu Leu
        35                  40                  45

Thr Val Ser Ser Glu Leu Phe Val Ala Cys Asn Glu Cys Ala Phe Pro
    50                  55                  60

Val Cys Arg Pro Cys Tyr Glu Tyr Glu Arg Arg Glu Gly Asn Gln Ala
65                  70                  75                  80

Cys Pro Gln Cys Lys Thr Arg Tyr Lys Arg Ile Lys Gly Ser Pro Arg
                85                  90                  95

Val Asp Gly Asp Asp Glu Glu Glu Asp Ile Asp Asp Leu Glu Tyr
                100                 105                 110

Glu Phe Asp His Gly Met Asp Pro Glu His Ala Ala Glu Ala Ala Leu
        115                 120                 125

Ser Ser Arg Leu Asn Thr Gly Arg Gly Gly Leu Asp Ser Ala Pro Pro
    130                 135                 140

Gly Ser Gln Ile Pro Leu Leu Thr Tyr Cys Asp Glu Asp Ala Asp Met
145                 150                 155                 160

Tyr Ser Asp Arg His Ala Leu Ile Val Pro Pro Ser Thr Gly Tyr Gly
                165                 170                 175

Asn Arg Val Tyr Pro Ala Pro Phe Thr Asp Ser Ser Ala Pro Pro Gln
                180                 185                 190

Ala Arg Ser Met Val Pro Gln Lys Asp Ile Ala Glu Tyr Gly Tyr Gly
            195                 200                 205

Ser Val Ala Trp Lys Asp Arg Met Glu Val Trp Lys Arg Gln Gly
    210                 215                 220

Glu Lys Leu Gln Val Ile Lys His Glu Gly Gly Asn Asn Gly Arg Gly
225                 230                 235                 240

Ser Asn Asp Asp Asp Glu Leu Asp Asp Pro Asp Met Pro Met Met Asp
                245                 250                 255

Glu Gly Arg Gln Pro Leu Ser Arg Lys Leu Pro Ile Arg Ser Ser Arg
                260                 265                 270

Ile Asn Pro Tyr Arg Met Leu Ile Leu Cys Arg Leu Ala Ile Leu Gly
            275                 280                 285

Leu Phe Phe His Tyr Arg Ile Leu His Pro Val Asn Asp Ala Tyr Gly
        290                 295                 300

Leu Trp Leu Thr Ser Val Ile Cys Glu Ile Trp Phe Ala Val Ser Trp
305                 310                 315                 320

Ile Leu Asp Gln Phe Pro Lys Trp Tyr Pro Ile Glu Arg Glu Thr Tyr
                325                 330                 335

Leu Asp Arg Leu Ser Leu Arg Tyr Glu Lys Glu Gly Lys Pro Ser Gly
                340                 345                 350

Leu Ala Pro Val Asp Val Phe Val Ser Thr Val Asp Pro Leu Lys Glu
            355                 360                 365

Pro Pro Leu Ile Thr Ala Asn Thr Val Leu Ser Ile Leu Ala Val Asp
    370                 375                 380

Tyr Pro Val Asp Lys Val Ala Cys Tyr Val Ser Asp Asp Gly Ala Ala
385                 390                 395                 400

Met Leu Thr Phe Glu Ala Leu Ser Asp Thr Ala Glu Phe Ala Arg Lys
                405                 410                 415

Trp Val Pro Phe Cys Lys Lys Phe Asn Ile Glu Pro Arg Ala Pro Glu
                420                 425                 430
```

```
Trp Tyr Phe Ser Gln Lys Met Asp Tyr Leu Lys Asn Lys Val His Pro
            435                 440                 445

Ala Phe Val Arg Glu Arg Ala Met Lys Arg Asp Tyr Glu Glu Phe
450                 455                 460

Lys Val Lys Ile Asn Ala Leu Val Ala Thr Ala Gln Lys Val Pro Glu
465                 470                 475                 480

Glu Gly Trp Thr Met Gln Asp Gly Thr Pro Trp Pro Gly Asn Asn Val
                485                 490                 495

Arg Asp His Pro Gly Met Ile Gln Val Phe Leu Gly His Ser Gly Val
            500                 505                 510

Arg Asp Thr Asp Gly Asn Glu Leu Pro Arg Leu Val Tyr Val Ser Arg
            515                 520                 525

Glu Lys Arg Pro Gly Phe Asp His His Lys Lys Ala Gly Ala Met Asn
530                 535                 540

Ser Leu Ile Arg Val Ser Ala Val Leu Ser Asn Ala Pro Tyr Leu Leu
545                 550                 555                 560

Asn Val Asp Cys Asp His Tyr Ile Asn Asn Ser Lys Ala Ile Arg Glu
                565                 570                 575

Ser Met Cys Phe Met Met Asp Pro Gln Ser Gly Lys Lys Val Cys Tyr
            580                 585                 590

Val Gln Phe Pro Gln Arg Phe Asp Gly Ile Asp Arg His Asp Arg Tyr
            595                 600                 605

Ser Asn Arg Asn Val Val Phe Phe Asp Ile Asn Met Lys Gly Leu Asp
            610                 615                 620

Gly Ile Gln Gly Pro Ile Tyr Val Gly Thr Gly Cys Val Phe Arg Arg
625                 630                 635                 640

Gln Ala Leu Tyr Gly Phe Asp Ala Pro Lys Lys Lys Pro Pro Gly
                645                 650                 655

Lys Thr Cys Asn Cys Trp Pro Lys Trp Cys Cys Leu Cys Cys Gly Leu
                660                 665                 670

Arg Lys Lys Ser Lys Thr Lys Ala Lys Asp Lys Lys Thr Asn Thr Lys
                675                 680                 685

Glu Thr Ser Lys Gln Ile His Ala Leu Glu Asn Val Asp Glu Gly Val
690                 695                 700

Ile Val Pro Val Ser Asn Val Glu Lys Arg Ser Glu Ala Thr Gln Leu
705                 710                 715                 720

Lys Leu Glu Lys Lys Phe Gly Gln Ser Pro Val Phe Val Ala Ser Ala
                725                 730                 735

Val Leu Gln Asn Gly Gly Val Pro Arg Asn Ala Ser Pro Ala Cys Leu
                740                 745                 750

Leu Arg Glu Ala Ile Gln Val Ile Ser Cys Gly Tyr Glu Asp Lys Thr
            755                 760                 765

Glu Trp Gly Lys Glu Ile Gly Trp Ile Tyr Gly Ser Val Thr Glu Asp
770                 775                 780

Ile Leu Thr Gly Phe Lys Met His Cys His Gly Trp Arg Ser Val Tyr
785                 790                 795                 800

Cys Met Pro Lys Arg Ala Ala Phe Lys Gly Ser Ala Pro Ile Asn Leu
                805                 810                 815

Ser Asp Arg Leu His Gln Val Leu Arg Trp Ala Leu Gly Ser Val Glu
            820                 825                 830

Ile Phe Leu Ser Arg His Cys Pro Ile Trp Tyr Gly Tyr Gly Gly Gly
            835                 840                 845

Leu Lys Trp Leu Glu Arg Phe Ser Tyr Ile Asn Ser Val Val Tyr Pro
```

```
                  850             855             860
Trp Thr Ser Leu Pro Leu Ile Val Tyr Cys Ser Leu Pro Ala Val Cys
865                 870             875             880

Leu Leu Thr Gly Lys Phe Ile Val Pro Glu Ile Ser Asn Tyr Ala Gly
                  885             890             895

Ile Leu Phe Met Leu Met Phe Ile Ser Ile Ala Val Thr Gly Ile Leu
                900             905             910

Glu Met Gln Trp Gly Gly Val Gly Ile Asp Asp Trp Trp Arg Asn Glu
              915             920             925

Gln Phe Trp Val Ile Gly Gly Ala Ser Ser His Leu Phe Ala Leu Phe
930             935             940

Gln Gly Leu Leu Lys Val Leu Ala Gly Val Asn Thr Asn Phe Thr Val
945             950             955             960

Thr Ser Lys Ala Ala Asp Asp Gly Ala Phe Ser Glu Leu Tyr Ile Phe
                965             970             975

Lys Trp Thr Thr Leu Leu Ile Pro Pro Thr Thr Leu Leu Ile Ile Asn
              980             985             990

Ile Ile Gly Val Ile Val Gly Val Ser Asp Ala Ile Ser Asn Gly Tyr
            995             1000            1005

Asp Ser Trp Gly Pro Leu Phe Gly Arg Leu Phe Phe Ala Leu Trp Val
    1010            1015            1020

Ile Val His Leu Tyr Pro Phe Leu Lys Gly Met Leu Gly Lys Gln Asp
1025            1030            1035            1040

Lys Met Pro Thr Ile Ile Val Val Trp Ser Ile Leu Leu Ala Ser Ile
              1045            1050            1055

Leu Thr Leu Leu Trp Val Arg Val Asn Pro Phe Val Ala Lys Gly Gly
          1060            1065            1070

Pro Val Leu Glu Ile Cys Gly Leu Asn Cys Gly Asn
        1075            1080

<210> SEQ ID NO 2
<211> LENGTH: 3255
<212> TYPE: DNA
<213> ORGANISM: Arabidopsis thaliana

<400> SEQUENCE: 2
atgaatactg gtggtcggct cattgctggc tctcacaaca gaaacgaatt cgttctcatt      60
aacgccgatg agagtgccag aatacgatca gtacaagaac tgagtgggca acatgtcaa     120 atctgtggag atgaaatcga attaacggtt agcagtgagc tctttgttgc ttgcaacgaa     180
tgcgcattcc cggtttgtag accatgctat gagtatgaac gtagagaagg aaatcaagct     240
tgtcctcagt gcaaaactcg atacaaaagg attaaaggta gtccacgggt tgatggagat     300
gatgaagaag aagaagacat tgatgatctt gagtatgagt ttgatcatgg atggacccct     360
gaacatgccg ctgaagccgc actctcttca cgccttaaca ccggtcgtgg tggattggat     420
tcagctccac ctggctctca gattcctctt ttgacttatt gtgatgaaga tgctgatatg     480
tattctgatc gtcatgctct tatcgtgcct ccttcaacgg gatatgggaa tcgcgtctat     540
cctgcaccgt ttacagattc ttctgcacct ccacaggcga atcaatggtt ccctcagaaa     600
gatattgcgg aatatggtta tggaagtgtt gcttggaagg accgtatgga agtttggaag     660
agacgacaag gcgaaaagct tcaagtcatt aagcatgaag aggaaacaa tggtcgaggt     720 tccaatgatg acgacgaact agatgatcct gacatgccta tgatggatga aggaagacaa     780
cctctctcaa gaaagctacc tattcgttca agcagaataa atccttacag gatgttaatt     840
```

```
ctgtgtcgcc tcgcgattct tggtcttttc tttcattata gaattctcca tccagtcaat    900
gatgcatatg gattatggtt aacgtcagtt atatgcgaga tatggtttgc agtgtcttgg    960
attcttgatc aattccccaa atggtatcct atagaacgtg aaacatacct cgatagactc   1020
tctctcaggt acgagaagga aggaaaaccg tcaggattag cacctgttga tgtttttgtt   1080
agtacagtgg atccgttgaa agagccaccc ttgattacag caaacacagt tctttccatt   1140
ctagcagttg attatcctgt ggataaggtt gcgtgttatg tatcagacga tggtgcagct   1200
atgcttacat ttgaagctct ctctgataca gctgagtttg ctagaaaatg gttccttttt   1260
tgtaagaagt ttaatatcga gccacgagct cctgagtggt attttctca gaagatggat    1320
tacctgaaga acaaagttca tcctgctttt gtcagggaac gtcgtgctat aagagagat    1380
tatgaggagt ttaaagtgaa gataaatgca ctggttgcta ctgcacagaa agtgcctgag   1440
gaaggttgga ctatgcaaga tggaactcct tggcctggaa acaacgtccg tgaccatcct   1500
ggaatgattc aggtgttctt gggtcatagt ggagttcgtg atacgatgg taatgagtta    1560
ccacgtctag tgtatgtttc tcgtgagaag cggcctggat ttgatcacca caagaaagct   1620
ggagctatga attccttgat ccgagtctct gctgttctat caaacgctcc ttaccttctt   1680
aatgtcgatt gtgatcacta catcaacaac agcaaagcaa ttagagaatc tatgtgtttc   1740
atgatggacc cgcaatcggg aaagaaagtt tgttatgttc agtttccgca gagatttgat   1800
gggattgata gacatgatag atactcaaac cgtaacgttg tgttctttga tattaacatg   1860
aaaggtcttg atgggataca aggaccgata tatgtcggga caggttgtgt gtttagaaga   1920
caggctcttt atggttttga tgcaccaaag aagaagaaac caccaggcaa aacctgtaac   1980
tgttggccta aatggtgttg tttgtgttgt gggttgagaa agaagagtaa aacgaaagcc   2040
aaagataaga aaactaacac taagagact tcaaagcaga ttcatgcgct agagaatgtc    2100
gacgaaggtg ttatcgtccc agtgtcaaat gttgagaaga gatctgaagc aacacaattg   2160
aaattggaga agaagtttgg acaatctccg gttttcgttg cctctgctgt tctacagaac   2220
ggtggagttc cccgtaacgc aagccccgca tgtttgttaa gagaagccat tcaagttatt   2280
agctgcgggt acgaagataa aaccgaatgg ggaaaagaga tcgggtggat ttatggatcg   2340
gtgactgaag atatcctgac gggttttcaag atgcattgcc atggatggag atctgtgtac   2400
tgtatgccta agcgtgcagc ttttaaagga tctgctccta ttaacttgtc agatcgtctt   2460
catcaagttc tacgttgggc tcttggctct gtagagattt tcttgagcag acattgtccg   2520
atatggtatg ttatggtgg tggtttaaaa tggttggaga gattctctta catcaactct   2580
gtcgtctatc cttggactc acttccattg atcgtctatt gttctctccc cgcggtttgt    2640
ttactcacag gaaaattcat cgtccctgag ataagcaact acgcaggtat actcttcatg   2700
ctcatgttca tatccatagc agtaactgga atcctcgaaa tgcaatgggg aggtgtcgga   2760
atcgatgatt ggtggagaaa cgagcagttt tgggtaatcg gaggggcctc ctcgcatcta   2820
tttgctctgt ttcaaggttt gctcaaagtt ctagccggag ttaacacgaa tttcacagtc   2880
acttcaaaag cagcagacga tggagctttc tctgagcttt acatcttcaa gtggacaact   2940
ttgttgattc ctccgacaac acttctgatc attaacatca ttggagttat tgtcggcgtt   3000
tctgatgcca ttagcaatgg ctatgactca tggggacctc tctttgggag acttttcttc   3060
gctcttgggg tcattgttca tttataccca ttccctcaagg gaatgcttgg gaagcaagac   3120
aaaatgccta cgattattgt ggtctggtct attcttctag cttcgatctt gacactcttg   3180
```

-continued

```
tgggtcagag ttaacccgtt tgtggctaaa gggggaccag tgttggagat ctgtggtctg    3240
aattgtggaa actaa                                                     3255
```

<210> SEQ ID NO 3
<211> LENGTH: 1069
<212> TYPE: PRT
<213> ORGANISM: Arabidopsis thaliana

<400> SEQUENCE: 3

```
Met Asn Thr Gly Gly Arg Leu Ile Ala Gly Ser His Asn Arg Asn Glu
1               5                   10                  15

Phe Val Leu Ile Asn Ala Asp Glu Ser Ala Arg Ile Arg Ser Val Glu
            20                  25                  30

Glu Leu Ser Gly Gln Thr Cys Gln Ile Cys Gly Asp Glu Ile Glu Leu
        35                  40                  45

Ser Val Asp Gly Glu Ser Phe Val Ala Cys Asn Glu Cys Ala Phe Pro
    50                  55                  60

Val Cys Arg Pro Cys Tyr Glu Tyr Glu Arg Arg Glu Gly Asn Gln Ser
65                  70                  75                  80

Cys Pro Gln Cys Lys Thr Arg Tyr Lys Arg Ile Lys Gly Ser Pro Arg
                85                  90                  95

Val Glu Gly Asp Glu Glu Asp Gly Ile Asp Asp Leu Asp Phe Glu
            100                 105                 110

Phe Asp Tyr Ser Arg Ser Gly Leu Glu Ser Glu Thr Phe Ser Arg Arg
        115                 120                 125

Asn Ser Glu Phe Asp Leu Ala Ser Ala Pro Gly Ser Gln Ile Pro
    130                 135                 140

Leu Leu Thr Tyr Gly Glu Glu Asp Val Glu Ile Ser Ser Asp Ser His
145                 150                 155                 160

Ala Leu Ile Val Ser Pro Ser Pro Gly His Ile His Arg Val His Gln
                165                 170                 175

Pro His Phe Pro Asp Pro Ala Ala His Pro Arg Pro Met Val Pro Gln
            180                 185                 190

Lys Asp Leu Ala Val Tyr Gly Tyr Gly Ser Val Ala Trp Lys Asp Arg
        195                 200                 205

Met Glu Glu Trp Lys Arg Lys Gln Asn Glu Lys Tyr Gln Val Val Lys
    210                 215                 220

His Asp Gly Asp Ser Ser Leu Gly Asp Gly Asp Ala Asp Ile Pro
225                 230                 235                 240

Met Met Asp Glu Gly Arg Gln Pro Leu Ser Arg Lys Val Pro Ile Lys
                245                 250                 255

Ser Ser Lys Ile Asn Pro Tyr Arg Met Leu Ile Val Leu Arg Leu Val
            260                 265                 270

Ile Leu Gly Leu Phe Phe His Tyr Arg Ile Leu His Pro Val Asn Asp
        275                 280                 285

Ala Tyr Ala Leu Trp Leu Ile Ser Val Ile Cys Glu Ile Trp Phe Ala
    290                 295                 300

Val Ser Trp Val Leu Asp Gln Phe Pro Lys Trp Tyr Pro Ile Glu Arg
305                 310                 315                 320

Glu Thr Tyr Leu Asp Arg Leu Ser Leu Arg Tyr Glu Lys Glu Gly Lys
                325                 330                 335

Pro Ser Glu Leu Ala Gly Val Asp Val Phe Val Ser Thr Val Asp Pro
            340                 345                 350

Met Lys Glu Pro Pro Leu Ile Thr Ala Asn Thr Val Leu Ser Ile Leu
```

```
                355                 360                 365
Ala Val Asp Tyr Pro Val Asp Arg Val Ala Cys Tyr Val Ser Asp Asp
    370                 375                 380

Gly Ala Ala Met Leu Thr Phe Glu Ala Leu Ser Glu Thr Ala Glu Phe
385                 390                 395                 400

Ala Arg Lys Trp Val Pro Phe Cys Lys Lys Tyr Thr Ile Glu Pro Arg
                405                 410                 415

Ala Pro Glu Trp Tyr Phe Cys His Lys Met Asp Tyr Leu Lys Asn Lys
                420                 425                 430

Val His Pro Ala Phe Val Arg Glu Arg Ala Met Lys Arg Asp Tyr
    435                 440                 445

Glu Glu Phe Lys Val Lys Ile Asn Ala Leu Val Ala Thr Ala Gln Lys
    450                 455                 460

Val Pro Glu Glu Gly Trp Thr Met Gln Asp Gly Thr Pro Trp Pro Gly
465                 470                 475                 480

Asn Asn Val Arg Asp His Pro Gly Met Ile Gln Val Phe Leu Gly Asn
                485                 490                 495

Asn Gly Val Arg Asp Val Glu Asn Asn Glu Leu Pro Arg Leu Val Tyr
                500                 505                 510

Val Ser Arg Glu Lys Arg Pro Gly Phe Asp His His Lys Lys Ala Gly
    515                 520                 525

Ala Met Asn Ser Leu Ile Arg Val Ser Gly Val Leu Ser Asn Ala Pro
    530                 535                 540

Tyr Leu Leu Asn Val Asp Cys Asp His Tyr Ile Asn Asn Ser Lys Ala
545                 550                 555                 560

Leu Arg Glu Ala Met Cys Phe Met Met Asp Pro Gln Ser Gly Lys Lys
                565                 570                 575

Ile Cys Tyr Val Gln Phe Pro Gln Arg Phe Asp Gly Ile Asp Lys Ser
                580                 585                 590

Asp Arg Tyr Ser Asn Arg Asn Val Val Phe Phe Asp Ile Asn Met Lys
                595                 600                 605

Gly Leu Asp Gly Leu Gln Gly Pro Ile Tyr Val Gly Thr Gly Cys Val
    610                 615                 620

Phe Arg Arg Gln Ala Leu Tyr Gly Phe Asp Ala Pro Lys Lys Lys Lys
625                 630                 635                 640

Thr Lys Arg Met Thr Cys Asn Cys Trp Pro Lys Trp Cys Leu Phe Cys
                645                 650                 655

Cys Gly Leu Arg Lys Asn Arg Lys Ser Lys Thr Thr Asp Lys Lys Lys
                660                 665                 670

Lys Asn Arg Glu Ala Ser Lys Gln Ile His Ala Leu Glu Asn Ile Glu
    675                 680                 685

Glu Gly Thr Lys Gly Thr Asn Asp Ala Ala Lys Ser Pro Glu Ala Ala
    690                 695                 700

Gln Leu Lys Leu Glu Lys Lys Phe Gly Gln Ser Pro Val Phe Val Ala
705                 710                 715                 720

Ser Ala Gly Met Glu Asn Gly Gly Leu Ala Arg Asn Ala Ser Pro Ala
                725                 730                 735

Ser Leu Leu Arg Glu Ala Ile Gln Val Ile Ser Cys Gly Tyr Glu Asp
                740                 745                 750

Lys Thr Glu Trp Gly Lys Glu Ile Gly Trp Ile Tyr Gly Ser Val Thr
    755                 760                 765

Glu Asp Ile Leu Thr Gly Phe Lys Met His Ser His Gly Trp Arg Ser
    770                 775                 780
```

-continued

```
Val Tyr Cys Thr Pro Lys Ile Pro Ala Phe Lys Gly Ser Ala Pro Ile
785                 790                 795                 800

Asn Leu Ser Asp Arg Leu His Gln Val Leu Arg Trp Ala Leu Gly Ser
            805                 810                 815

Val Glu Ile Phe Leu Ser Arg His Cys Pro Ile Trp Tyr Gly Tyr Gly
        820                 825                 830

Gly Gly Leu Lys Trp Leu Glu Arg Leu Ser Tyr Ile Asn Ser Val Val
            835                 840                 845

Tyr Pro Trp Thr Ser Ile Pro Leu Leu Val Tyr Cys Ser Leu Pro Ala
850                 855                 860

Ile Cys Leu Leu Thr Gly Lys Phe Ile Val Pro Glu Ile Ser Asn Tyr
865                 870                 875                 880

Ala Ser Ile Leu Phe Met Ala Leu Phe Gly Ser Ile Ala Val Thr Gly
            885                 890                 895

Ile Leu Glu Met Gln Trp Gly Lys Val Gly Ile Asp Asp Trp Trp Arg
        900                 905                 910

Asn Glu Gln Phe Trp Val Ile Gly Gly Val Ser Ala His Leu Phe Ala
            915                 920                 925

Leu Phe Gln Gly Leu Leu Lys Val Leu Ala Gly Val Glu Thr Asn Phe
    930                 935                 940

Thr Val Thr Ser Lys Ala Ala Asp Asp Gly Glu Phe Ser Glu Leu Tyr
945                 950                 955                 960

Ile Phe Lys Trp Thr Ser Leu Leu Ile Pro Pro Thr Thr Leu Leu Ile
            965                 970                 975

Ile Asn Val Ile Gly Val Ile Val Gly Ile Ser Asp Ala Ile Ser Asn
        980                 985                 990

Gly Tyr Asp Ser Trp Gly Pro Leu Phe Gly Arg Leu Phe Phe Ala Phe
            995                 1000                1005

Trp Val Ile Leu His Leu Tyr Pro Phe Leu Lys Gly Leu Gly Lys
    1010                1015                1020

Gln Asp Arg Met Pro Thr Ile Ile Leu Val Trp Ser Ile Leu Leu Ala
1025                1030                1035                1040

Ser Ile Leu Thr Leu Leu Trp Val Arg Val Asn Pro Phe Val Ala Lys
            1045                1050                1055

Gly Gly Pro Ile Leu Glu Ile Cys Gly Leu Asp Cys Leu
            1060                1065
```

<210> SEQ ID NO 4
<211> LENGTH: 3210
<212> TYPE: DNA
<213> ORGANISM: Arabidopsis thaliana

<400> SEQUENCE: 4

```
atgaatactg gtggtcggct catcgctggt tctcacaata ggaatgagtt cgtgttgatt    60
aatgcagacg agagtgccag aattagatca gtggaagaac taagtggaca acatgtcaa   120
atctgtggag atgagattga gctaagtgtt gatggagagt cttttgtggc atgtaatgaa   180
tgtgctttcc ctgtctgtag accttgctat gagtatgaga acgagaaagg aaaccaatct   240
tgtcctcagt gcaaaactcg ttacaagcgc atcaaaggaa gtccaagggt tgaaggagat   300
gaggaggatg atggaattga tgatcttgat tttgagtttg attatagtag gagtggcctt   360
gaatctgaaa ctttctctcg ccgcaactcg gagtttgatt tggcctctgc tccacctggc   420
tcacagattc ctttgttaac ttatggagag gaggacgttg aaatttcttc tgatagtcat   480
```

```
gctctcattg tttctccatc acctggccat atccataggg ttcatcaacc tcattttcct    540
gaccccgctg cacatccaag accaatggta cctcagaaag accttgcggt ctatggatat    600
ggaagtgttg cgtggaagga tcgtatggag gagtggaaga gaaagcagaa cgaaaaatat    660
caggtggtta acatgatgg agattctagt cttggagacg gagatgatgc tgatattcct    720
atgatggatg agggaaggca gcctttgtct aggaaagtac cgataaagtc gagcaaaata    780
aatccgtaca ggatgctaat tgttctgcgt cttgtgattc tcggtctctt tttccattac    840
cgtattcttc accccgtcaa tgatgcttac gccttgtggc taatatctgt gatatgcgaa    900
atatggtttg cggtttcatg ggttcttgat cagttcccta aatggtatcc tatagaaaga    960
gagacatact tggacaggct ctcattgagg tacgaaaaag aagggaaacc atctgaacta   1020
gctggtgttg atgtttttgt gagtacagtg gatccgatga agagcctcc gcttattaca   1080
gcaaacactg ttctgtctat tcttgcggtt gattatccgg tagacagagt tgcctgttat   1140
gtttctgatg atggtgctgc tatgcttact tttgaagccc tttcagaaac agcagagttt   1200
gctaggaaat gggttccttt ctgtaagaaa tacactatcg agccacgagc tcccgaatgg   1260
tattttttgcc acaagatgga ttatttaaag aataaagttc accctgcatt tgttagggaa   1320
cgccgagcca tgaagagaga ttatgaagaa ttcaaggtta agatcaatgc tttagttgcg   1380
actgcacaga aagtgcctga agaaggttgg actatgcaag acggtactcc ttggcccggt   1440
aataacgtgc gagatcaccc tggcatgatc caggtattcc ttggaaataa cggtgtccgc   1500
gatgtagaaa caacgagtt gcctcggctg gtttatgttt ctcgtgagaa gagacccgga   1560
tttgaccatc acaagaaggc tggagccatg aactccctga tacgagtctc tggagttcta   1620
tcaaatgctc cttatcttct aaatgtcgat tgtgatcact acatcaataa tagcaaagct   1680
cttagagaag caatgtgttt catgatggat cctcagtcgg gaaagaaaat ttgttatgtt   1740
caattccctc aaagattcga tgggattgat aaaagtgaca gatactctaa tcgtaatgtt   1800
gtattcttcg atattaatat gaaaggtttg gatggattac aagggcctat atacgtggga   1860
accgggtgtg tttttaggag acaagcactt tatggatttg atgcgccaaa aaagaagaag   1920
actaagcgta tgacttgcaa ttgctggcct aagtggtgtt tgttttgttg tggtctaaga   1980
aagaatcgta agtcaaagac aacggataag aaaaagaaga acagggaagc ctcaaagcag   2040
atacacgcgc tagaaaatat cgaagagggc accaaaggca ctaatgatgc ggcgaaatca   2100
ccagaggcgg cacaattgaa gttggagaag aagtttggac agtctcctgt ttttgttgcg   2160
tctgctggta tggagaatgg tgggcttgct aggaatgcga gtccagcttc tctgcttaga   2220
gaagccatcc aagtcattag ttgtggatac gaagataaaa ccgaatgggg aaaagagatt   2280
gggtggatct acggttctgt caccgaggat atccttacgg gtttcaagat gcattctcat   2340
ggctggagat cggtttactg tacacctaag ataccggcct ttaaaggatc agcacctatc   2400
aatctttctg accgtcttca tcaagttctt cggtgggcgc tcgggtctgt tgagattttc   2460
ttgagcagac attgtcctat ttggtatggt tatgagggtg gtttgaaatg gcttgagaga   2520
ttgtcttaca tcaactctgt ggtttatcca tggacctcta ttccactcct tgtttactgt   2580
tctctcccag ctatctgtct ctcaccgga aaattcatcg tccctgagat tagcaactat   2640
gcaagtatcc tcttcatggc acttttcggg tcgattgctg taacgggcat tctcgagatg   2700
caatggggta aagtagggat cgatgattgg tggagaaacg aacagttttg ggtgattgga   2760
ggtgtttcag ctcatctctt tgctctcttc caaggtctcc taaaggtttt agccggtgtt   2820
gagacaaaact tcacagttac atctaaagca gcagatgatg gtgaattctc tgagctttac   2880
```

```
atcttcaaat ggacatcact cttgatccct ccaaccacac tactcatcat aaacgtaatc    2940
ggagtcattg tgggaatatc tgatgcgatc agtaacggat atgactcgtg gggtcctctt    3000
ttcggaagat tgttctttgc cttttgggtc atcctccatc tatatccttt ccttaaaggt    3060
ctgcttggga acaagacag aatgcctaca atcattcttg tctggtcgat ccttctcgcc    3120
tctatcctta cgcttctttg ggtacgagtc aatccgtttg tggcgaaagg cggtcctatc    3180
ctcgagatat gtggcttgga ctgcctttga                                    3210
```

<210> SEQ ID NO 5
<211> LENGTH: 1084
<212> TYPE: PRT
<213> ORGANISM: Arabidopsis thaliana

<400> SEQUENCE: 5

```
Met Asn Thr Gly Gly Arg Leu Ile Ala Gly Ser His Asn Arg Asn Glu
1               5                   10                  15

Phe Val Leu Ile Asn Ala Asp Glu Asn Ala Arg Ile Arg Ser Val Gln
            20                  25                  30

Glu Leu Ser Gly Gln Thr Cys Gln Ile Cys Arg Asp Glu Ile Glu Leu
        35                  40                  45

Thr Val Asp Gly Glu Pro Phe Val Ala Cys Asn Glu Cys Ala Phe Pro
    50                  55                  60

Val Cys Arg Pro Cys Tyr Glu Tyr Glu Arg Arg Glu Gly Asn Gln Ala
65                  70                  75                  80

Cys Pro Gln Cys Lys Thr Arg Phe Lys Arg Leu Lys Gly Ser Pro Arg
                85                  90                  95

Val Glu Gly Asp Glu Glu Asp Asp Ile Asp Asp Leu Asp Asn Glu
            100                 105                 110

Phe Glu Tyr Gly Asn Asn Gly Ile Gly Phe Asp Gln Val Ser Glu Gly
        115                 120                 125

Met Ser Ile Ser Arg Arg Asn Ser Gly Phe Pro Gln Ser Asp Leu Asp
    130                 135                 140

Ser Ala Pro Pro Gly Ser Gln Ile Pro Leu Leu Thr Tyr Gly Asp Glu
145                 150                 155                 160

Asp Val Glu Ile Ser Ser Asp Arg His Ala Leu Ile Val Pro Pro Ser
                165                 170                 175

Leu Gly Gly His Gly Asn Arg Val His Pro Val Ser Leu Ser Asp Pro
            180                 185                 190

Thr Val Ala Ala His Pro Arg Pro Met Val Pro Gln Lys Asp Leu Ala
        195                 200                 205

Val Tyr Gly Tyr Gly Ser Val Ala Trp Lys Asp Arg Met Glu Glu Trp
    210                 215                 220

Lys Arg Lys Gln Asn Glu Lys Leu Gln Val Val Arg His Glu Gly Asp
225                 230                 235                 240

Pro Asp Phe Glu Asp Gly Asp Ala Asp Phe Pro Met Met Asp Glu
                245                 250                 255

Gly Arg Gln Pro Leu Ser Arg Lys Ile Pro Ile Lys Ser Ser Lys Ile
            260                 265                 270

Asn Pro Tyr Arg Met Leu Ile Val Leu Arg Leu Val Ile Leu Gly Leu
        275                 280                 285

Phe Phe His Tyr Arg Ile Leu His Pro Val Lys Asp Ala Tyr Ala Leu
    290                 295                 300

Trp Leu Ile Ser Val Ile Cys Glu Ile Trp Phe Ala Val Ser Trp Val
```

```
                305                 310                 315                 320
Leu Asp Gln Phe Pro Lys Trp Tyr Pro Ile Glu Arg Glu Thr Tyr Leu
                325                 330                 335

Asp Arg Leu Ser Leu Arg Tyr Glu Lys Glu Gly Lys Pro Ser Gly Leu
                340                 345                 350

Ser Pro Val Asp Val Phe Val Ser Thr Val Asp Pro Leu Lys Glu Pro
                355                 360                 365

Pro Leu Ile Thr Ala Asn Thr Val Leu Ser Ile Leu Ala Val Asp Tyr
    370                 375                 380

Pro Val Asp Lys Val Ala Cys Tyr Val Ser Asp Asp Gly Ala Ala Met
385                 390                 395                 400

Leu Thr Phe Glu Ala Leu Ser Glu Thr Ala Glu Phe Ala Arg Lys Trp
                405                 410                 415

Val Pro Phe Cys Lys Lys Tyr Cys Ile Glu Pro Arg Ala Pro Glu Trp
                420                 425                 430

Tyr Phe Cys His Lys Met Asp Tyr Leu Lys Asn Lys Val His Pro Ala
                435                 440                 445

Phe Val Arg Glu Arg Arg Ala Met Lys Arg Asp Tyr Glu Glu Phe Lys
                450                 455                 460

Val Lys Ile Asn Ala Leu Val Ala Thr Ala Gln Lys Val Pro Glu Asp
465                 470                 475                 480

Gly Trp Thr Met Gln Asp Gly Thr Pro Trp Pro Gly Asn Ser Val Arg
                485                 490                 495

Asp His Pro Gly Met Ile Gln Val Phe Leu Gly Ser Asp Gly Val Arg
                500                 505                 510

Asp Val Glu Asn Asn Glu Leu Pro Arg Leu Val Tyr Val Ser Arg Glu
                515                 520                 525

Lys Arg Pro Gly Phe Asp His His Lys Lys Ala Gly Ala Met Asn Ser
                530                 535                 540

Leu Ile Arg Val Ser Gly Val Leu Ser Asn Ala Pro Tyr Leu Leu Asn
545                 550                 555                 560

Val Asp Cys Asp His Tyr Ile Asn Asn Ser Lys Ala Leu Arg Glu Ala
                565                 570                 575

Met Cys Phe Met Met Asp Pro Gln Ser Gly Lys Lys Ile Cys Tyr Val
                580                 585                 590

Gln Phe Pro Gln Arg Phe Asp Gly Ile Asp Arg His Asp Arg Tyr Ser
                595                 600                 605

Asn Arg Asn Val Val Phe Phe Asp Ile Asn Met Lys Gly Leu Asp Gly
                610                 615                 620

Leu Gln Gly Pro Ile Tyr Val Gly Thr Gly Cys Val Phe Arg Arg Gln
625                 630                 635                 640

Ala Leu Tyr Gly Phe Asp Ala Pro Lys Lys Lys Gly Pro Arg Lys
                645                 650                 655

Thr Cys Asn Cys Trp Pro Lys Trp Cys Leu Leu Cys Phe Gly Ser Arg
                660                 665                 670

Lys Asn Arg Lys Ala Lys Thr Val Ala Ala Asp Lys Lys Lys Lys Asn
                675                 680                 685

Arg Glu Ala Ser Lys Gln Ile His Ala Leu Glu Asn Ile Glu Glu Gly
                690                 695                 700

Arg Val Thr Lys Gly Ser Asn Val Glu Gln Ser Thr Glu Ala Met Gln
705                 710                 715                 720

Met Lys Leu Glu Lys Lys Phe Gly Gln Ser Pro Val Phe Val Ala Ser
                725                 730                 735
```

Ala Arg Met Glu Asn Gly Gly Met Ala Arg Asn Ala Ser Pro Ala Cys
            740                 745                 750

Leu Leu Lys Glu Ala Ile Gln Val Ile Ser Cys Gly Tyr Glu Asp Lys
            755                 760                 765

Thr Glu Trp Gly Lys Glu Ile Gly Trp Ile Tyr Gly Ser Val Thr Glu
            770                 775                 780

Asp Ile Leu Thr Gly Phe Lys Met His Ser His Gly Trp Arg Ser Val
785                 790                 795                 800

Tyr Cys Thr Pro Lys Leu Ala Ala Phe Lys Gly Ser Ala Pro Ile Asn
                805                 810                 815

Leu Ser Asp Arg Leu His Gln Val Leu Arg Trp Ala Leu Gly Ser Val
            820                 825                 830

Glu Ile Phe Leu Ser Arg His Cys Pro Ile Trp Tyr Gly Tyr Gly Gly
            835                 840                 845

Gly Leu Lys Trp Leu Glu Arg Leu Ser Tyr Ile Asn Ser Val Val Tyr
    850                 855                 860

Pro Trp Thr Ser Leu Pro Leu Ile Val Tyr Cys Ser Leu Pro Ala Ile
865                 870                 875                 880

Cys Leu Leu Thr Gly Lys Phe Ile Val Pro Glu Ile Ser Asn Tyr Ala
                885                 890                 895

Ser Ile Leu Phe Met Ala Leu Phe Ser Ser Ile Ala Ile Thr Gly Ile
            900                 905                 910

Leu Glu Met Gln Trp Gly Lys Val Gly Ile Asp Asp Trp Trp Arg Asn
            915                 920                 925

Glu Gln Phe Trp Val Ile Gly Gly Val Ser Ala His Leu Phe Ala Leu
            930                 935                 940

Phe Gln Gly Leu Leu Lys Val Leu Ala Gly Val Asp Thr Asn Phe Thr
945                 950                 955                 960

Val Thr Ser Lys Ala Ala Asp Asp Gly Glu Phe Ser Asp Leu Tyr Leu
                965                 970                 975

Phe Lys Trp Thr Ser Leu Leu Ile Pro Pro Met Thr Leu Leu Ile Ile
            980                 985                 990

Asn Val Ile Gly Val Ile Gly Val Ser Asp Ala Ile Ser Asn Gly
            995                 1000                1005

Tyr Asp Ser Trp Gly Pro Leu Phe Gly Arg Leu Phe Phe Ala Leu Trp
    1010                1015                1020

Val Ile Ile His Leu Tyr Pro Phe Leu Lys Gly Leu Leu Gly Lys Gln
1025                1030                1035                1040

Asp Arg Met Pro Thr Ile Ile Val Val Trp Ser Ile Leu Leu Ala Ser
                1045                1050                1055

Ile Leu Thr Leu Leu Trp Val Arg Val Asn Pro Phe Val Ala Lys Gly
            1060                1065                1070

Gly Pro Ile Leu Glu Ile Cys Gly Leu Asp Cys Leu
        1075                1080

<210> SEQ ID NO 6
<211> LENGTH: 3255
<212> TYPE: DNA
<213> ORGANISM: Arabidopsis thaliana

<400> SEQUENCE: 6
atgaacaccg gtggtcggtt aatcgccggt tctcacaaca ggaatgagtt tgtcctcatt      60
aatgccgatg agaatgcccg aataagatca gtccaagagc tgagtggaca gacatgtcaa     120

```
atctgcagag atgagatcga attgactgtt gatggagaac cgtttgtggc atgtaacgaa    180
tgtgcattcc ctgtgtgtag accttgctat gagtacgaaa gacgagaagg caatcaagct    240
tgtccacagt gcaaaacccg tttcaaacgt cttaaaggaa gtccaagagt tgaaggtgat    300
gaagaggaag atgacattga tgatttagac aatgagtttg agtatggaaa taatgggatt    360
ggatttgatc aggtttctga aggtatgtca atctctcgtc gcaactccgg tttcccacaa    420
tctgatttgg attcagctcc acctggctct cagattccat tgctgactta cggcgacgag    480
gacgttgaga tttcttctga tagacatgct cttattgttc ctccttcact tggtggtcat    540
ggcaatagag ttcatcctgt ttctctttct gacccgaccg tggctgcaca tccaaggcct    600
atggtacctc agaaagatct tgcggtttat ggttatggaa gtgtcgcttg gaaagatcgg    660
atggaggaat ggaagagaaa gcagaatgag aaacttcagg ttgttaggca tgaaggagat    720
cctgattttg aagatggtga tgatgctgat tttccaatga tggatgaggg aaggcagcca    780
ttgtctagga agataccaat caaatcgagc aagataaatc cttaccggat gttaattgtg    840
ctacgtcttg tgattcttgg tctcttcttt cactaccgta ttcttcaccc cgtcaaagat    900
gcatatgctt tgtggcttat ttctgttata tgtgagatat ggtttgctgt ttcatgggtt    960
cttgatcagt tccctaaatg gtaccctatc gagcgagaaa cgtacttgga ccgactctca   1020
ttaagatatg agaaagaagg gaaaccgtcg ggactatccc ctgtggatgt atttgttagt   1080
acagtggatc cattgaaaga gcctccgctt attactgcaa atactgtctt gtctattctt   1140
gctgttgatt atcctgtcga taaggttgct tgttacgtat ctgatgatgg tgctgctatg   1200
cttactttcg aagctctttc tgagaccgct gaattcgcaa ggaaatgggt tcctttctgc   1260
aagaaatatt gtattgagcc tcgtgctccc gaatggtatt tctgccataa aatggactac   1320
ttgaagaata aagttcatcc cgcatttgtt agggagcggc gagccatgaa gagagattat   1380
gaagaattca agtaaagat caatgcttta gtagcaacag cacagaaagt gcctgaggat   1440
ggttggacta tgcaagacgg tacaccttgg cccggtaata gtgtgcgaga tcatcctggc   1500
atgattcagg tcttccttgg aagtgacggt gttcgtgatg tcgaaaacaa cgagttgcct   1560
cgattagttt acgtttctcg tgagaagaga cccggatttg atcaccataa gaaggctgga   1620
gctatgaatt ccctgatacg agtctctggg gttctatcaa atgctcctta ccttctgaat   1680
gtcgattgtg atcactacat caacaatagc aaagctctta gagaagcaat gtgtttcatg   1740
atggatcctc agtcaggaaa gaaaatctgt tatgttcagt ccctcaaag gttcgatggg   1800
attgataggc acgatcgata ctcaaatcgc aatgttgtgt tctttgatat caatatgaaa   1860
ggtttggatg ggctacaagg gcctatatac gtcggtacag gttgtgtttt caggaggcaa   1920
gcgctttacg gatttgatgc accgaagaag aagaagggcc cacgtaagac atgcaattgc   1980
tggccaaaat ggtgtctcct atgttttggt tcaagaaaga atcgtaaagc aaagacagtg   2040
gctgcggata agaagaagaa gaatagggaa gcgtcaaagc agatccacgc attagaaaat   2100
atcgaagagg gccgcgtcac taaaggttct aacgtagaac agtcaaccga ggcaatgcaa   2160
atgaagttgg agaagaaatt tgggcagtct cctgtatttg ttgcatctgc gcgtatggag   2220
aatggtggga tggctagaaa cgcaagcccg gcttgtctgc ttaaagaagc catccaagtc   2280
attagttgcg gatatgaaga taaaactgaa tggggaaaag agattgggtg gatctatggt   2340
tctgttaccg aagatattct tacgggtttt aagatgcatt ctcatggttg gagatctgtt   2400
tattgtacac caaagttagc ggcttttcaa ggatcagctc caatcaatct ttcggatcgt   2460
ctccatcaag ttcttcgatg ggcgcttggg tcggttgaga ttttcttgag taggcattgt   2520
```

```
cctatttggt atggttatgg aggtgggttg aaatggcttg agcggttgtc ctacattaac    2580
tctgtggttt acccgtggac ctctctaccg ctcatcgttt actgttctct ccctgccatc    2640
tgtcttctca ctggaaaatt catcgttccc gagattagca actatgcgag tatcctcttc    2700
atggcgctct ctcgtcgat tgcaataacg ggtattctcg agatgcaatg gggcaaagtt    2760
gggatcgatg attggtggag aaacgaacag ttttgggtca ttggaggtgt ttctgcgcat    2820
ctgtttgctc tcttccaagg tctcctcaag gttcttgctg gtgtcgacac taacttcaca    2880
gtcacatcaa aagcagctga tgatggagag ttctctgacc tttacctctt caaatggact    2940
tcacttctca tccctccaat gactctactc atcataaacg tcattggagt catagtcgga    3000
gtctctgatg ccatcagcaa tggatacgac tcgtgggac cgcttttcgg aagactgttc    3060
tttgcacttt gggtcatcat tcatctttac ccgttcctta aaggtttgct tgggaaacaa    3120
gatagaatgc caaccattat tgtcgtctgg tccatcctcc tggcctcgat tcttacactt    3180
ctttgggtcc gggttaatcc gtttgtggcg aaaggcggtc ctattctcga gatctgtggt    3240
ttagactgct tgtga                                                    3255
```

<210> SEQ ID NO 7
<211> LENGTH: 1096
<212> TYPE: PRT
<213> ORGANISM: Gossypium hirsutum

<400> SEQUENCE: 7

```
Met Asp Thr Gly Gly Arg Leu Ile Ala Gly Ser His Asn Arg Asn Glu
1               5                   10                  15

Phe Val Leu Ile Asn Ala Asp Glu Asn Ala Arg Ile Lys Ser Val Gln
            20                  25                  30

Glu Leu Ser Gly Gln Thr Cys Gln Ile Cys Gly Asp Glu Ile Glu Ile
        35                  40                  45

Thr Val Asp Gly Glu Pro Phe Val Ala Cys Asn Glu Cys Ala Phe Pro
    50                  55                  60

Val Cys Arg Pro Cys Tyr Glu Tyr Glu Arg Arg Glu Gly Asn Gln Ala
65                  70                  75                  80

Cys Pro Gln Cys Lys Thr Arg Tyr Lys Arg Ile Lys Gly Ser Pro Arg
                85                  90                  95

Val Glu Gly Asp Glu Glu Asp Gly Ile Asp Asp Leu Asp Asn Glu
            100                 105                 110

Phe Asp Tyr Asp Ala Ser Asp Pro Gln Gln Val Ala Glu Ala Met Leu
        115                 120                 125

Asn Ala Arg Leu Asn Thr Gly Arg Gly Thr His Gln Asn Ala Ser Gly
    130                 135                 140

Met Pro Ala Ser Ser Glu Leu Asp Ser Ser Leu Pro Ser Ser Gln Ile
145                 150                 155                 160

Pro Leu Leu Thr Tyr Gly Glu Glu Asp Leu Glu Ile Ser Ala Asp His
                165                 170                 175

His Ala Leu Ile Val Pro Gln Phe Met Gly Asn Gly Asn Arg Val His
            180                 185                 190

Pro Met Pro Cys Ser Asp Pro Ser Val Pro Leu Gln Pro Arg Pro Met
        195                 200                 205

Val Pro Lys Lys Asp Ile Ala Val Tyr Gly Tyr Gly Ser Val Ala Trp
    210                 215                 220

Lys Asp Arg Met Glu Glu Trp Lys Lys Arg Gln Asn Asp Lys Leu Gln
225                 230                 235                 240
```

```
Val Val Lys His Glu Gly Gly Asn Asp Gly Gly Asn Phe Asp Gly Lys
                245                 250                 255

Glu Leu Asp Asp Ala Asp Leu Pro Met Met Asp Glu Gly Arg Gln Pro
            260                 265                 270

Leu Ser Arg Lys Leu Pro Ile Pro Ser Ser Lys Ile Asn Pro Tyr Arg
        275                 280                 285

Met Ile Ile Ile Leu Arg Leu Ala Ile Leu Gly Leu Phe Phe His Tyr
    290                 295                 300

Arg Leu Leu His Pro Val Arg Asp Ala Tyr Gly Leu Trp Leu Thr Ser
305                 310                 315                 320

Val Ile Cys Glu Ile Trp Phe Ala Val Ser Trp Ile Leu Asp Gln Phe
                325                 330                 335

Pro Lys Trp Cys Pro Ile Glu Arg Glu Thr Tyr Leu Asp Arg Leu Ser
                340                 345                 350

Leu Arg Tyr Glu Lys Glu Gly Lys Pro Ser Glu Leu Ala Ser Val Asp
            355                 360                 365

Ile Phe Val Ser Thr Val Asp Pro Met Lys Glu Pro Pro Leu Ile Thr
        370                 375                 380

Ala Asn Thr Val Leu Ser Ile Leu Ala Val Asp Tyr Pro Val Asp Lys
385                 390                 395                 400

Val Ala Cys Tyr Val Ser Asp Asp Gly Ala Ala Met Leu Thr Phe Glu
                405                 410                 415

Ala Leu Ser Glu Thr Ala Glu Phe Ala Arg Lys Trp Val Pro Phe Cys
                420                 425                 430

Lys Lys Phe Asn Ile Glu Pro Arg Ala Pro Glu Trp Tyr Phe Ser Gln
            435                 440                 445

Lys Ile Asp Tyr Leu Arg Asn Lys Val His Pro Ala Phe Val Arg Glu
450                 455                 460

Arg Arg Ala Met Lys Arg Glu Tyr Glu Glu Phe Lys Val Gln Ile Asn
465                 470                 475                 480

Gly Leu Val Ala Thr Ala Gln Lys Val Pro Glu Asp Gly Trp Thr Met
                485                 490                 495

Gln Asp Gly Thr Pro Trp Pro Gly Asn Asn Val Arg Asp His Pro Gly
            500                 505                 510

Met Ile Gln Val Phe Leu Gly Asp Asn Gly Val Arg Asp Val Glu Gly
        515                 520                 525

Asn Glu Leu Pro Ser Leu Val Tyr Val Ser Arg Glu Lys Arg Pro Gly
    530                 535                 540

Phe Glu His His Lys Lys Ala Gly Ala Met Asn Ala Leu Ile Arg Val
545                 550                 555                 560

Ser Ala Val Leu Ser Asn Ala Pro Tyr Leu Leu Asn Val Asp Cys Asp
                565                 570                 575

His Tyr Ile Asn Asn Ser Lys Ala Leu Arg Glu Ala Met Cys Phe Met
                580                 585                 590

Met Asp Pro Thr Ser Gly Lys Lys Val Cys Tyr Val Gln Phe Pro Gln
            595                 600                 605

Arg Phe Asp Gly Ile Asp Arg His Asp Arg Tyr Ser Asn Arg Asn Val
        610                 615                 620

Val Phe Phe Asp Ile Asn Met Lys Gly Leu Asp Gly Leu Gln Gly Pro
625                 630                 635                 640

Ile Tyr Val Gly Thr Gly Cys Val Phe Arg Arg Gln Ala Leu Tyr Gly
                645                 650                 655
```

```
Phe Asp Ala Pro Val Thr Lys Lys Pro Pro Gly Lys Thr Cys Asn Cys
            660                 665                 670

Leu Pro Lys Trp Cys Cys Phe Leu Cys Cys Ser Arg Lys Asn Lys
        675                 680                 685

Lys Gln Lys Gln Lys Lys Glu Lys Thr Lys Lys Ser Lys Gln Arg Glu
    690                 695                 700

Ala Ser Lys Gln Ile His Ala Leu Glu Asn Ile Glu Gly Ala Ile Ser
705                 710                 715                 720

Glu Ser Asn Ser Gln Ser Ser Val Thr Ser Gln Met Lys Leu Glu Lys
                725                 730                 735

Lys Phe Gly Gln Ser Pro Val Phe Val Ala Ser Thr Leu Pro Glu Asp
        740                 745                 750

Gly Gly Val Pro Gln Asn Ala Ser Pro Ala Ser Leu Leu Arg Glu Ala
            755                 760                 765

Ile Gln Val Ile Ser Cys Gly Tyr Glu Asp Lys Thr Glu Trp Gly Lys
770                 775                 780

Glu Val Gly Trp Ile Tyr Gly Ser Val Thr Glu Asp Ile Leu Thr Gly
785                 790                 795                 800

Phe Lys Met His Cys His Gly Trp Arg Ser Val Tyr Cys Ile Pro Lys
                805                 810                 815

Arg Pro Ala Phe Lys Gly Ser Ala Pro Ile Asn Leu Ser Asp Arg Leu
            820                 825                 830

His Gln Val Leu Arg Trp Ala Leu Gly Ser Val Glu Ile Phe Leu Ser
                835                 840                 845

Arg His Cys Pro Ile Trp Tyr Gly Tyr Gly Gly Leu Lys Trp Leu
850                 855                 860

Glu Arg Phe Ser Tyr Ile Asn Ser Val Val Tyr Pro Trp Thr Ser Ile
865                 870                 875                 880

Pro Leu Leu Val Tyr Cys Thr Leu Pro Ala Ile Cys Leu Leu Thr Gly
                885                 890                 895

Lys Phe Ile Val Pro Glu Ile Ser Asn Tyr Ala Ser Leu Val Phe Met
                900                 905                 910

Gly Leu Phe Ile Ser Ile Ala Ala Thr Gly Ile Leu Glu Met Gln Trp
        915                 920                 925

Gly Gly Val Gly Ile Asp Asp Trp Trp Arg Asn Glu Gln Phe Trp Val
    930                 935                 940

Ile Gly Gly Val Ser Ser His Leu Phe Ala Leu Phe Gln Gly Leu Leu
945                 950                 955                 960

Lys Val Leu Ala Gly Val Ser Thr Ser Phe Thr Val Thr Ser Lys Ala
                965                 970                 975

Ala Asp Asp Gly Glu Phe Ser Glu Leu Tyr Leu Phe Lys Trp Thr Ser
            980                 985                 990

Leu Leu Ile Pro Pro Thr Thr Leu Leu Ile Ile Asn Ile Val Gly Val
        995                 1000                1005

Val Val Gly Ile Ser Asp Ala Ile Asn Asn Gly Tyr Asp Ser Trp Gly
    1010                1015                1020

Pro Leu Phe Gly Arg Leu Phe Phe Ala Phe Trp Val Ile Ile His Leu
1025                1030                1035                1040

Tyr Pro Phe Leu Lys Gly Leu Leu Gly Lys Gln Asp Arg Met Pro Thr
            1045                1050                1055

Ile Ile Leu Val Trp Ser Ile Leu Leu Ala Ser Ile Leu Thr Leu Met
        1060                1065                1070

Trp Val Arg Ile Asn Pro Phe Val Ser Lys Asp Gly Pro Val Leu Glu
```

-continued

```
                1075                1080                1085

Ile Cys Gly Leu Asn Cys Asp Asp
    1090                1095

<210> SEQ ID NO 8
<211> LENGTH: 1096
<212> TYPE: PRT
<213> ORGANISM: Gossypium hirsutum

<400> SEQUENCE: 8

Met Asp Thr Gly Gly Arg Leu Ile Ala Gly Ser His Asn Arg Asn Glu
1               5                   10                  15

Phe Val Leu Ile Asn Ala Asp Glu Asn Ala Arg Ile Lys Ser Val Gln
            20                  25                  30

Glu Leu Ser Gly Gln Thr Cys Gln Ile Cys Gly Asp Glu Ile Glu Ile
        35                  40                  45

Thr Val Asp Gly Glu Pro Phe Val Ala Cys Asn Glu Cys Ala Phe Pro
    50                  55                  60

Val Cys Arg Pro Cys Tyr Glu Tyr Glu Arg Arg Glu Gly Asn Gln Val
65                  70                  75                  80

Cys Pro Gln Cys Lys Thr Arg Tyr Lys Arg Ile Lys Gly Ser Pro Arg
                85                  90                  95

Val Glu Gly Asp Glu Glu Glu Asp Ile Asp Asp Leu Asp Asn Glu
            100                 105                 110

Phe Asp Tyr Asp Ala Leu Asp Pro Gln Gln Val Ala Glu Ala Met Leu
        115                 120                 125

Asn Ala Arg Ile Asn Thr Gly Arg Gly Thr His Gln Asn Ala Tyr Gly
    130                 135                 140

Met Pro Ala Ser Ser Glu Leu Asp Ser Ser Leu Pro Ser Ser Gln Ile
145                 150                 155                 160

Pro Leu Leu Thr Tyr Gly Glu Glu Asp Ser Glu Ile Ser Ala Asp His
                165                 170                 175

His Ala Leu Ile Val Pro Gln Phe Met Gly Asn Gly Asn Arg Val His
            180                 185                 190

Pro Met Pro Cys Ser Asp Pro Ser Val Pro Leu Gln Pro Arg Pro Met
        195                 200                 205

Val Pro Lys Lys Asp Ile Ala Val Tyr Gly Tyr Gly Ser Val Ala Trp
    210                 215                 220

Lys Asp Arg Met Glu Glu Trp Lys Lys Arg Gln Asn Asp Lys Leu Gln
225                 230                 235                 240

Val Val Lys His Glu Gly Gly Asn Asp Gly Asn Phe Asp Gly Lys
                245                 250                 255

Glu Leu Asp Asp Ala Asp Leu Pro Met Met Asp Glu Gly Arg Gln Pro
            260                 265                 270

Leu Ser Arg Lys Leu Pro Ile Pro Ser Ser Lys Ile Asn Pro Tyr Arg
        275                 280                 285

Met Ile Ile Ile Leu Arg Leu Ala Ile Leu Gly Leu Phe Phe His Tyr
    290                 295                 300

Arg Leu Leu His Pro Val Arg Asp Ala Tyr Gly Leu Trp Leu Thr Ser
305                 310                 315                 320

Val Ile Cys Glu Ile Trp Phe Ala Val Ser Trp Ile Leu Asp Gln Phe
                325                 330                 335

Pro Lys Trp Cys His Ile Glu Arg Glu Thr Tyr Leu Asp Arg Leu Ser
            340                 345                 350
```

```
Leu Arg Tyr Glu Lys Glu Gly Lys Pro Ser Glu Leu Ala Ser Val Asp
        355                 360                 365

Ile Phe Val Ser Thr Val Asp Pro Met Lys Glu Pro Pro Leu Ile Thr
370                 375                 380

Ala Asn Thr Val Leu Ser Ile Leu Ala Val Asp Tyr Pro Val Asp Lys
385                 390                 395                 400

Val Ala Cys Tyr Val Ser Asp Asp Gly Ala Ala Met Leu Thr Phe Glu
                405                 410                 415

Ala Leu Ser Glu Thr Ala Glu Phe Ala Arg Lys Trp Val Pro Phe Cys
            420                 425                 430

Lys Lys Phe Asn Ile Glu Pro Arg Ala Pro Glu Trp Tyr Phe Ser Gln
        435                 440                 445

Lys Ile Asp Tyr Leu Arg Asn Lys Val His Pro Ala Phe Val Arg Glu
    450                 455                 460

Arg Arg Ala Met Lys Arg Glu Tyr Glu Glu Phe Lys Val Gln Ile Asn
465                 470                 475                 480

Gly Leu Val Ala Thr Ala Gln Lys Val Pro Glu Asp Gly Trp Thr Met
                485                 490                 495

Gln Asp Gly Thr Pro Trp Pro Gly Asn Asn Val Arg Asp His Pro Gly
            500                 505                 510

Met Ile Gln Val Phe Leu Gly Asp Asn Gly Val Arg Asp Val Glu Gly
        515                 520                 525

Asn Glu Leu Pro Ser Leu Val Tyr Val Ser Arg Glu Lys Arg Pro Gly
    530                 535                 540

Phe Glu His His Lys Lys Ala Gly Ala Met Asn Ala Leu Ile Arg Val
545                 550                 555                 560

Ser Ala Val Leu Ser Asn Ala Pro Tyr Leu Leu Asn Val Asp Cys Asp
                565                 570                 575

His Tyr Ile Asn Asn Ser Lys Ala Leu Arg Glu Ala Met Cys Phe Met
            580                 585                 590

Met Asp Pro Thr Ser Gly Lys Lys Val Cys Tyr Val Gln Phe Pro Gln
        595                 600                 605

Arg Phe Asp Gly Ile Asp Arg His Asp Arg Tyr Ser Asn Arg Asn Val
    610                 615                 620

Val Phe Phe Asp Ile Asn Met Lys Gly Leu Asp Gly Ile Gln Gly Pro
625                 630                 635                 640

Ile Tyr Val Gly Thr Gly Cys Val Phe Arg Arg Gln Ala Leu Tyr Gly
                645                 650                 655

Phe Asp Ala Pro Val Thr Lys Lys Pro Pro Gly Lys Thr Cys Asn Cys
            660                 665                 670

Leu Pro Lys Trp Cys Cys Phe Leu Cys Cys Cys Ser Arg Lys Asn Lys
        675                 680                 685

Lys Gln Lys Gln Lys Lys Glu Lys Thr Lys Lys Ser Lys Gln Arg Glu
    690                 695                 700

Ala Ser Lys Gln Ile His Ala Leu Glu Asn Ile Glu Gly Ala Ile Ser
705                 710                 715                 720

Glu Ser Asn Ser Gln Ser Ser Val Thr Ser Glu Met Lys Leu Glu Lys
                725                 730                 735

Lys Phe Gly Gln Ser Pro Val Phe Val Ala Ser Thr Leu Leu Glu Asp
            740                 745                 750

Gly Gly Val Pro Gln Asn Ala Ser Pro Ala Ser Leu Leu Arg Glu Ala
        755                 760                 765

Ile Gln Val Ile Ser Cys Gly Tyr Glu Asp Lys Thr Glu Trp Gly Lys
```

```
    770                 775                 780

Glu Val Gly Trp Met Tyr Gly Ala Val Thr Glu Asp Ile Leu Thr Gly
785                 790                 795                 800

Phe Lys Met His Cys His Gly Trp Arg Ser Val Tyr Cys Ile Pro Lys
                805                 810                 815

Arg Pro Ala Phe Lys Gly Ser Ala Pro Ile Asn Leu Ser Asp Arg Leu
            820                 825                 830

His Gln Val Leu Arg Trp Ala Leu Gly Ser Val Glu Ile Phe Leu Ser
        835                 840                 845

Arg His Cys Pro Ile Trp Tyr Gly Tyr Gly Gly Gly Leu Lys Trp Leu
    850                 855                 860

Glu Arg Phe Ser Tyr Ile Asn Ser Val Val Tyr Pro Trp Thr Ser Ile
865                 870                 875                 880

Pro Leu Leu Val Tyr Cys Thr Leu Pro Ala Ile Cys Leu Leu Thr Gly
                885                 890                 895

Lys Phe Ile Val Pro Glu Ile Ser Asn Tyr Ala Ser Leu Val Phe Met
            900                 905                 910

Gly Leu Phe Ile Ser Ile Ala Ala Thr Gly Ile Leu Glu Met Gln Trp
        915                 920                 925

Gly Gly Val Gly Ile Asp Asp Trp Trp Arg Asn Glu Gln Phe Trp Val
    930                 935                 940

Ile Gly Gly Val Ser Ser His Leu Phe Ala Leu Phe Gln Gly Leu Leu
945                 950                 955                 960

Lys Val Leu Ala Gly Val Ser Thr Ser Phe Thr Val Thr Ser Lys Ala
                965                 970                 975

Ala Asp Asp Gly Glu Phe Ser Glu Leu Tyr Leu Phe Lys Trp Thr Ser
            980                 985                 990

Leu Leu Ile Pro Pro Thr Thr Leu Leu Ile Ile Asn Ile Val Gly Val
        995                 1000                1005

Val Val Gly Ile Ser Asp Ala Ile Asn Asn Gly Tyr Asp Ser Trp Gly
    1010                1015                1020

Pro Leu Phe Gly Arg Leu Phe Phe Ala Phe Trp Val Ile Ile His Leu
1025                1030                1035                1040

Tyr Pro Phe Leu Lys Gly Leu Leu Gly Lys Gln Asp Arg Met Pro Thr
                1045                1050                1055

Ile Ile Leu Val Trp Ser Ile Leu Leu Ala Ser Ile Leu Thr Leu Met
            1060                1065                1070

Trp Val Arg Ile Asn Pro Phe Val Ser Lys Asp Gly Pro Leu Leu Glu
        1075                1080                1085

Ile Cys Gly Leu Asn Cys Asp Asp
    1090                1095
```

<210> SEQ ID NO 9
<211> LENGTH: 1090
<212> TYPE: PRT
<213> ORGANISM: Gossypium hirsutum

<400> SEQUENCE: 9

```
Met Asp Thr Lys Gly Arg Leu Val Ala Gly Ser His Asn Arg Asn Glu
1               5                   10                  15

Phe Val Leu Ile Asn Ala Asp Glu Val Ala Arg Val Thr Ser Val Lys
            20                  25                  30

Glu Leu Ser Gly Gln Ile Cys Gln Ile Cys Gly Asp Glu Ile Glu Ile
        35                  40                  45
```

```
Ser Val Asp Gly Glu Pro Phe Val Ala Cys Asn Glu Cys Ala Phe Pro
    50                  55                  60
Val Cys Arg Ala Cys Tyr Glu Tyr Glu Arg Arg Glu Gly Asn Gln Ala
65                  70                  75                  80
Cys Pro Gln Cys Lys Thr Arg Tyr Lys Arg Ile Lys Gly Cys Pro Arg
                85                  90                  95
Val Glu Gly Asp Glu Glu Asp Gly Ala Asp Leu Glu Asn Glu
                100                 105                 110
Phe Asp Ile Ala Ser His Asp Arg Asp Pro His His Ile Ala Ala
            115                 120                 125
Ala Met Leu Ser Gly Arg Tyr Asn Ile Asn His Gly Ser Gln Pro His
    130                 135                 140
Val Ser Gly Ile Ser Thr Pro Ala Glu Leu Asp Ala Ala Ser Val Ala
145                 150                 155                 160
Ala Gly Ile Pro Leu Leu Thr Tyr Gly Gln Glu Asp Val Gly Ile Ser
                165                 170                 175
Pro Asp Lys His Ala Leu Ile Val Pro Pro Phe Met Ser Arg Gly Lys
            180                 185                 190
Arg Val His Pro Met Pro Met Pro Asp Pro Ser Met Thr Leu Pro Pro
        195                 200                 205
Arg Pro Met Asp Pro Lys Lys Asp Leu Ala Val Tyr Gly Tyr Gly Thr
    210                 215                 220
Val Ala Trp Lys Glu Arg Met Glu Asp Trp Lys Lys Gln Asn Glu
225                 230                 235                 240
Lys Leu Gln Val Val Lys His Glu Gly Asn Asn Gly Asp Glu Phe Glu
                245                 250                 255
Asp Ser Asp Leu Pro Met Met Asp Glu Gly Arg Gln Pro Leu Ser Arg
            260                 265                 270
Lys Leu Pro Ile Pro Ser Ser Lys Ile Asn Pro Tyr Arg Leu Ile Ile
        275                 280                 285
Leu Leu Arg Leu Ala Val Leu Gly Leu Phe Phe His Tyr Arg Ile Leu
    290                 295                 300
His Pro Val Asn Asp Ala Tyr Val Leu Trp Leu Ile Ser Val Ile Cys
305                 310                 315                 320
Glu Ile Trp Phe Ala Val Ser Trp Ile Leu Asp Gln Phe Pro Lys Trp
                325                 330                 335
Tyr Pro Ile Glu Arg Glu Thr Tyr Leu Asp Arg Leu Ser Leu Arg Tyr
            340                 345                 350
Glu Lys Glu Gly Lys Pro Ser Glu Leu Ala Ser Val Asp Val Phe Val
        355                 360                 365
Ser Thr Val Asp Pro Met Lys Glu Pro Pro Leu Ile Thr Ala Asn Thr
    370                 375                 380
Val Leu Ser Ile Leu Ser Val Asp Tyr Pro Val Asp Lys Val Ala Cys
385                 390                 395                 400
Tyr Val Ser Asp Asp Gly Ala Ala Met Leu Thr Phe Glu Ala Leu Ser
                405                 410                 415
Glu Thr Ser Glu Phe Ala Arg Lys Trp Val Pro Phe Cys Lys Lys Phe
            420                 425                 430
Ser Ile Glu Pro Arg Ala Pro Glu Trp Tyr Phe Ala Gln Lys Val Asp
        435                 440                 445
Tyr Leu Arg Asp Lys Val Asp Pro Thr Phe Val Arg Glu Arg Arg Ala
    450                 455                 460
Met Lys Arg Glu Tyr Glu Glu Phe Lys Val Arg Ile Asn Ser Leu Val
```

-continued

```
            465                 470                 475                 480
       Ala Met Ala Gln Lys Val Pro Glu Glu Gly Trp Thr Met Gln Asp Gly
                       485                 490                 495

Thr Pro Trp Pro Gly Asn Asn Val Arg Asp His Pro Gly Met Ile Gln
                       500                 505                 510

Val Phe Leu Gly His Asp Gly Val Arg Asp Ile Glu Gly Asn Glu Leu
                       515                 520                 525

Pro Arg Leu Ile Tyr Val Ser Arg Glu Lys Arg Pro Gly Phe Asp His
                       530                 535                 540

His Lys Lys Ala Gly Ala Met Asn Ser Leu Val Arg Val Ser Ala Val
       545                 550                 555                 560

Ile Ser Asn Ala Pro Phe Leu Leu Asn Val Asp Cys Asp His Tyr Ile
                           565                 570                 575

Asn Asn Ser Lys Ala Leu Arg Glu Ala Met Cys Phe Met Met Asp Pro
                       580                 585                 590

Ile Ser Gly Lys Lys Ile Cys Tyr Val Gln Phe Pro Gln Arg Phe Asp
                       595                 600                 605

Gly Ile Asp Arg His Asp Arg Tyr Ser Asn Arg Asn Val Val Phe Phe
                       610                 615                 620

Asp Ile Asn Met Lys Gly Leu Asp Gly Ile Gln Gly Pro Ile Tyr Val
       625                 630                 635                 640

Gly Thr Gly Cys Val Phe Arg Arg Gln Ala Leu Tyr Gly Tyr Asp Ala
                           645                 650                 655

Pro Val Lys Lys Lys Pro Pro Arg Arg Thr Cys Asn Cys Leu Pro Lys
                       660                 665                 670

Trp Cys Cys Cys Cys Cys Cys Arg Ser Lys Arg Lys Asn Lys Lys
                       675                 680                 685

Ser Lys Ser Ile Asp Lys Lys Lys Glu Val Pro Lys His Lys His
                       690                 695                 700

Ala Leu Glu Asn Ile Glu Glu Gly Ile Glu Gly Ile Asp Asn Glu Lys
       705                 710                 715                 720

Ser Ala Leu Met Pro Gln Ile Lys Phe Glu Lys Lys Phe Gly Gln Ser
                       725                 730                 735

Pro Val Phe Ile Ala Ser Thr Leu Met Glu Asp Gly Gly Ile Pro Lys
                       740                 745                 750

Gly Ala Thr Thr Ala Ser Leu Leu Lys Glu Ala Ile His Val Ile Ser
                       755                 760                 765

Cys Gly Tyr Glu Asp Lys Thr Asp Trp Gly Lys Glu Val Gly Trp Ile
                       770                 775                 780

Tyr Gly Ser Val Thr Glu Asp Ile Leu Thr Gly Phe Lys Met His Cys
       785                 790                 795                 800

His Gly Trp Arg Ser Val Tyr Cys Ile Pro Lys Arg Pro Ala Phe Lys
                       805                 810                 815

Gly Ser Ala Pro Ile Asn Leu Ser Asp Arg Leu His Gln Val Leu Arg
                       820                 825                 830

Trp Ala Leu Gly Ser Val Glu Ile Phe Leu Ser Arg His Cys Pro Ile
                       835                 840                 845

Trp Tyr Gly Tyr Gly Cys Gly Leu Lys Ser Leu Glu Arg Phe Ser Tyr
                       850                 855                 860

Ile Ala Ser Val Val Tyr Pro Leu Thr Ser Val Pro Leu Leu Val Tyr
       865                 870                 875                 880

Cys Thr Leu Pro Ala Ile Cys Leu Leu Thr Gly Lys Phe Ile Val Pro
                       885                 890                 895
```

```
Glu Ile Ser Asn Tyr Ala Ser Leu Leu Phe Met Ser Leu Phe Ile Val
            900                 905                 910

Ile Ala Val Thr Ser Ile Leu Glu Met Gln Trp Gly Gly Val Gly Ile
            915                 920                 925

His Asp Trp Trp Arg Asn Glu Gln Phe Trp Val Ile Gly Gly Val Ser
        930                 935                 940

Ser His Leu Phe Ala Leu Phe Gln Gly Leu Leu Lys Val Leu Ala Gly
945                 950                 955                 960

Val Asn Thr Asn Phe Thr Val Thr Ser Lys Gly Gly Asp Asp Gly Glu
                965                 970                 975

Phe Ser Glu Leu Tyr Leu Phe Lys Trp Thr Ser Leu Leu Ile Pro Pro
            980                 985                 990

Met Thr Leu Leu Ile Ile Asn Ile Ile Gly Val Ile Val Gly Ile Ser
            995                 1000                1005

Asp Ala Ile Ser Asn Gly Tyr Asp Ser Trp Gly Pro Leu Phe Gly Arg
            1010                1015                1020

Leu Phe Phe Ala Phe Trp Val Ile Val His Leu Tyr Pro Phe Leu Lys
1025                1030                1035                1040

Gly Leu Met Gly Lys Gln Asp Arg Leu Pro Thr Ile Ile Val Val Trp
                1045                1050                1055

Ser Ile Leu Leu Ala Ser Ile Phe Ser Leu Leu Trp Ala Arg Val Asn
                1060                1065                1070

Pro Phe Ile Ser Lys Gly Gly Ile Val Leu Glu Val Cys Gly Leu Asn
            1075                1080                1085

Cys Asp
    1090

<210> SEQ ID NO 10
<211> LENGTH: 1095
<212> TYPE: PRT
<213> ORGANISM: Gossypium hirsutum

<400> SEQUENCE: 10

Met Asp Thr Gly Gly Arg Leu Ile Ala Gly Ser His Asn Arg Asn Glu
1               5                   10                  15

Phe Val Leu Ile Asn Ala Asp Glu Asn Ala Arg Ile Lys Ser Val Lys
                20                  25                  30

Glu Leu Ser Gly Gln Thr Cys Gln Ile Cys Gly Asp Glu Ile Glu Ile
            35                  40                  45

Thr Val Asp Gly Glu Pro Phe Val Ala Cys Asn Glu Cys Ala Phe Pro
        50                  55                  60

Val Cys Arg Pro Cys Tyr Glu Tyr Glu Arg Arg Glu Gly Asn Gln Ala
65                  70                  75                  80

Cys Pro Gln Cys Lys Thr Arg Tyr Lys Arg Ile Lys Gly Ser Pro Arg
                85                  90                  95

Val Glu Gly Asp Glu Glu Glu Asp Ile Asp Leu Asp Asn Glu
            100                 105                 110

Phe Asp Tyr Asp Ala Leu Asp Pro Gln Gln Val Ala Glu Ala Met Leu
            115                 120                 125

Gly Gly His Leu Asn Thr Gly Arg Gly Phe His Pro Asn Gly Ser Gly
        130                 135                 140

Leu Pro Ala His Ser Glu Ile Asp Ser Phe Pro Pro Ser Ser Gln Ile
145                 150                 155                 160

Pro Leu Leu Thr Tyr Gly Glu Glu His Ser Glu Ile Ser Ala Asp His
```

```
            165                 170                 175
His Ala Leu Ile Val Pro Pro Phe Met Gly His Gly Asn Arg Val His
            180                 185                 190
Pro Met Pro Tyr Thr Asp Pro Ala Val Pro Leu Gln Pro Arg Pro Met
            195                 200                 205
Val Pro Lys Lys Asp Ile Ala Val Tyr Gly Tyr Gly Ser Val Ala Trp
            210                 215                 220
Lys Asp Arg Met Glu Glu Trp Lys Lys Trp Gln Asn Glu Lys Leu Gln
225                 230                 235                 240
Val Val Lys His Lys Gly Gly Asn Asp Gly Asn Gly Glu Leu
                    245                 250                 255
Asp Asp Ala Asp Leu Pro Met Met Asp Glu Gly Arg Gln Pro Leu Ser
            260                 265                 270
Arg Lys Leu Pro Ile Pro Ser Ser Lys Ile Asn Pro Tyr Arg Met Ile
            275                 280                 285
Ile Ile Ile Arg Leu Ala Ile Leu Gly Leu Phe Phe His Tyr Arg Leu
            290                 295                 300
Leu His Pro Val Arg Asp Ala Tyr Gly Leu Trp Leu Thr Ser Val Ile
305                 310                 315                 320
Cys Glu Ile Trp Phe Ala Val Ser Trp Ile Leu Asp Gln Phe Pro Lys
                    325                 330                 335
Trp Tyr Pro Ile Glu Arg Glu Thr Tyr Leu Asp Arg Leu Ser Leu Arg
            340                 345                 350
Tyr Glu Lys Glu Gly Lys Leu Ser Glu Leu Ala Ser Ile Asp Val Phe
            355                 360                 365
Val Ser Thr Val Asp Pro Met Lys Glu Pro Pro Leu Ile Thr Ala Asn
            370                 375                 380
Thr Val Leu Ser Ile Leu Ala Val Asp Tyr Pro Val Asp Lys Val Ala
385                 390                 395                 400
Cys Tyr Val Ser Asp Asp Gly Ala Ala Met Leu Thr Phe Glu Ala Leu
            405                 410                 415
Ser Glu Thr Ser Glu Phe Ala Arg Lys Trp Val Pro Phe Cys Lys Lys
            420                 425                 430
Phe Asn Ile Glu Pro Arg Ala Pro Glu Trp Tyr Phe Ser Gln Lys Ile
            435                 440                 445
Asp Tyr Leu Lys Asn Lys Val His Pro Ala Phe Val Arg Glu Arg Arg
            450                 455                 460
Ala Met Lys Arg Glu Tyr Glu Glu Phe Lys Val Arg Ile Asn Gly Leu
465                 470                 475                 480
Val Ser Ala Ala Gln Lys Val Pro Glu Asp Gly Trp Thr Met Gln Asp
                    485                 490                 495
Gly Thr Pro Trp Pro Gly Asn Cys Val Arg Asp His Pro Gly Met Ile
            500                 505                 510
Gln Val Phe Leu Gly His Ser Gly Val Arg Asp Val Glu Gly Asn Glu
            515                 520                 525
Leu Pro His Leu Val Tyr Val Ser Arg Glu Lys Arg Pro Gly Phe Glu
            530                 535                 540
His His Lys Lys Ala Gly Ala Met Asn Ala Leu Ile Arg Val Ser Ser
545                 550                 555                 560
Val Leu Ser Asn Ala Pro Tyr Leu Leu Asn Val Asp Cys Asp His Tyr
                    565                 570                 575
Ile Asn Asn Ser Lys Ala Leu Arg Glu Ala Met Cys Phe Met Met Asp
            580                 585                 590
```

```
Pro Thr Ser Gly Lys Lys Val Cys Tyr Val Gln Phe Pro Gln Arg Phe
    595                 600                 605

Asp Gly Ile Asp Arg His Asp Arg Tyr Ser Asn Arg Asn Val Val Phe
    610                 615                 620

Phe Asp Ile Asn Met Lys Gly Leu Asp Gly Ile Gln Gly Pro Ile Tyr
625                 630                 635                 640

Val Gly Thr Gly Cys Val Phe Arg Arg Gln Ala Leu Tyr Gly Phe Asp
                645                 650                 655

Ala Pro Ile Thr Lys Lys Pro Pro Gly Lys Thr Cys Asn Cys Leu Pro
                660                 665                 670

Lys Trp Cys Cys Cys Leu Cys Cys Cys Ser Arg Lys Asn Lys Lys Thr
                675                 680                 685

Lys Gln Lys Lys Asp Lys Thr Lys Lys Ser Lys Gln Arg Glu Ala Ser
    690                 695                 700

Lys Gln Ile His Ala Leu Glu Asn Ile Glu Glu Gly Ile Ser Glu Ser
705                 710                 715                 720

Asn Thr Leu Lys Ser Ser Glu Ala Ser Gln Ile Lys Leu Glu Lys Lys
                725                 730                 735

Phe Gly Gln Ser Pro Val Phe Val Ala Ser Thr Leu Leu Glu Asp Gly
                740                 745                 750

Gly Ile Pro Gln Asn Ala Ser Pro Ala Ser Leu Leu Ser Glu Ala Ile
                755                 760                 765

Gln Val Ile Ser Cys Gly Tyr Glu Asp Lys Thr Glu Trp Gly Lys Glu
    770                 775                 780

Val Gly Trp Ile Tyr Gly Ser Val Thr Glu Asp Ile Leu Thr Gly Phe
785                 790                 795                 800

Lys Met His Cys His Gly Trp Arg Ser Val Tyr Cys Ile Pro Lys Arg
                805                 810                 815

Pro Ala Phe Lys Gly Ser Ala Pro Ile Asn Leu Ser Asp Arg Leu His
                820                 825                 830

Gln Val Leu Arg Trp Ala Leu Gly Ser Val Glu Ile Phe Leu Ser Arg
    835                 840                 845

His Cys Pro Ile Trp Tyr Gly Tyr Gly Gly Gly Leu Lys Trp Leu Glu
    850                 855                 860

Arg Phe Ser Tyr Ile Asn Ser Val Val Tyr Pro Trp Thr Ser Ile Pro
865                 870                 875                 880

Leu Leu Val Tyr Cys Thr Leu Pro Ala Ile Cys Leu Leu Thr Gly Lys
                885                 890                 895

Phe Ile Val Pro Glu Ile Ser Asn Tyr Ala Ser Leu Ile Phe Met Ala
                900                 905                 910

Leu Phe Ile Ser Ile Ala Ala Thr Gly Ile Leu Glu Met Gln Trp Gly
    915                 920                 925

Gly Val Gly Ile Asp Asp Trp Trp Arg Asn Glu Gln Phe Trp Val Ile
    930                 935                 940

Gly Gly Val Ser Ser His Leu Phe Ala Leu Phe Gln Gly Leu Leu Lys
945                 950                 955                 960

Val Leu Ala Gly Val Ser Thr Ser Phe Thr Val Thr Ser Lys Ala Ala
                965                 970                 975

Asp Asp Gly Glu Phe Ser Glu Leu Tyr Leu Phe Lys Trp Thr Ser Leu
                980                 985                 990

Leu Ile Pro Pro Thr Thr Leu Leu Val Ile Asn Ile Ile Gly Val Val
    995                 1000                1005
```

Val Gly Ile Ser Asp Ala Ile Asn Asn Gly Tyr Asp Ser Trp Gly Pro
    1010                1015                1020

Leu Phe Gly Arg Leu Phe Phe Ala Phe Trp Val Ile Ile His Leu Tyr
1025                1030                1035                1040

Pro Phe Leu Lys Gly Leu Leu Gly Lys Gln Asp Arg Met Pro Thr Ile
                1045                1050                1055

Ile Leu Val Trp Ser Ile Leu Leu Ala Ser Ile Leu Thr Leu Met Trp
                1060                1065                1070

Val Arg Ile Asn Pro Phe Val Ser Lys Asp Gly Pro Val Leu Glu Val
                1075                1080                1085

Cys Gly Leu Asn Cys Asp Asp
    1090                1095

<210> SEQ ID NO 11
<211> LENGTH: 1096
<212> TYPE: PRT
<213> ORGANISM: Populus tomentosa

<400> SEQUENCE: 11

Met Asn Thr Gly Gly Arg Leu Ile Ala Gly Ser His Asn Arg Asn Glu
1               5                   10                  15

Phe Val Leu Ile Asn Ala Asp Glu Asn Ala Arg Ile Lys Ser Val Gln
                20                  25                  30

Glu Leu Ser Gly Gln Val Cys His Ile Cys Gly Asp Glu Ile Glu Ile
            35                  40                  45

Thr Val Asp Gly Glu Leu Phe Val Ala Cys Asn Glu Cys Ala Phe Pro
        50                  55                  60

Val Cys Arg Pro Cys Tyr Glu Tyr Glu Arg Arg Glu Gly Asn Gln Ala
65                  70                  75                  80

Cys Pro Gln Cys Lys Thr Arg Tyr Lys Arg Leu Lys Gly Ser Pro Arg
                85                  90                  95

Val Glu Gly Asp Glu Glu Asp Asp Ile Asp Asp Leu Glu His Glu
            100                 105                 110

Phe Asp Tyr Gly Asn Phe Asp Gly Leu Ser Pro Glu Gln Val Ala Glu
            115                 120                 125

Ala Met Leu Ala Ser Arg Met Asn Thr Gly Arg Ala Ser His Ser Asn
    130                 135                 140

Ile Ser Gly Ile Pro Thr His Gly Glu Leu Asp Ser Ser Pro Leu Asn
145                 150                 155                 160

Ser Lys Ile Pro Leu Leu Thr Tyr Gly Glu Glu Asp Thr Glu Ile Ser
                165                 170                 175

Ser Asp Arg His Ala Leu Ile Val Pro Pro Ser His Gly Asn Arg Phe
            180                 185                 190

His Pro Ile Ser Phe Pro Asp Pro Ser Ile Pro Leu Ala Gln Pro Arg
        195                 200                 205

Pro Met Val Pro Lys Lys Asp Ile Ala Val Tyr Gly Tyr Gly Ser Val
    210                 215                 220

Ala Trp Lys Asp Arg Met Glu Asp Trp Lys Lys Arg Gln Asn Asp Lys
225                 230                 235                 240

Leu Gln Val Val Lys His Glu Gly Gly Asn Asp Asn Gly Asn Phe Glu
                245                 250                 255

Gly Asp Glu Leu Asp Asp Pro Asp Leu Pro Met Met Asp Glu Gly Arg
            260                 265                 270

Gln Pro Leu Ser Arg Lys Leu Pro Ile Pro Ser Ser Lys Ile Asn Pro
        275                 280                 285

```
Tyr Arg Met Ile Ile Ile Leu Arg Leu Val Val Gly Leu Phe Phe
        290             295             300

His Tyr Arg Ile Leu His Pro Val Asn Asp Ala Tyr Gly Leu Trp Leu
305             310             315             320

Thr Ser Val Ile Cys Glu Ile Trp Phe Ala Val Ser Trp Ile Leu Asp
                325             330             335

Gln Phe Pro Lys Trp Tyr Pro Ile Glu Arg Glu Thr Tyr Leu Asp Arg
            340             345             350

Leu Ser Leu Arg Tyr Glu Lys Glu Gly Lys Pro Ser Glu Leu Ala Ser
            355             360             365

Val Asp Val Phe Val Ser Thr Val Asp Pro Met Lys Glu Pro Pro Leu
            370             375             380

Ile Thr Ala Asn Thr Val Leu Ser Ile Leu Ala Val Asp Tyr Pro Val
385             390             395             400

Asp Lys Val Ala Cys Tyr Val Ser Asp Gly Ala Ala Met Leu Thr
                405             410             415

Phe Glu Ala Leu Ser Glu Thr Ser Glu Phe Ala Arg Lys Trp Val Pro
            420             425             430

Phe Cys Lys Lys Phe Asn Ile Glu Pro Arg Ala Pro Glu Trp Tyr Phe
            435             440             445

Ser Gln Lys Met Asp Tyr Leu Lys Asn Lys Val His Pro Ala Phe Val
    450             455             460

Arg Glu Arg Arg Ala Met Lys Arg Glu Tyr Glu Glu Phe Lys Val Lys
465             470             475             480

Ile Asn Gly Leu Val Ala Thr Ala Gln Lys Val Pro Glu Asp Gly Trp
                485             490             495

Thr Met Gln Asp Gly Thr Pro Trp Pro Gly Asn Asn Val Arg Asp His
            500             505             510

Pro Gly Met Ile Gln Val Phe Leu Gly Gln Ser Gly Val Arg Asp Val
            515             520             525

Glu Gly Asn Glu Leu Pro Arg Leu Val Tyr Val Ser Arg Glu Lys Arg
            530             535             540

Pro Gly Phe Glu His His Lys Lys Ala Gly Ala Met Asn Ala Leu Met
545             550             555             560

Arg Val Thr Ala Val Leu Ser Asn Ala Pro Tyr Leu Leu Asn Val Asp
                565             570             575

Cys Asp His Tyr Ile Asn Asn Ser Arg Ala Leu Arg Glu Ala Met Cys
            580             585             590

Phe Leu Met Asp Pro Thr Ser Gly Lys Lys Val Cys Tyr Val Gln Phe
        595             600             605

Pro Gln Arg Phe Asp Gly Ile Asp Arg His Asp Arg Tyr Ser Asn Arg
    610             615             620

Asn Val Val Phe Phe Asp Ile Asn Met Lys Gly Leu Asp Gly Leu Gln
625             630             635             640

Gly Pro Ile Tyr Val Gly Thr Gly Cys Val Phe Arg Arg Gln Ala Leu
                645             650             655

Tyr Gly Tyr Asp Ala Pro Val Lys Lys Arg Pro Pro Gly Lys Thr Cys
            660             665             670

Asn Cys Trp Pro Lys Trp Cys Cys Leu Cys Cys Gly Ser Arg Lys Asn
            675             680             685

Lys Lys Leu Lys Gln Lys Lys Glu Lys Lys Ser Lys Asn Arg Glu
    690             695             700
```

```
Ala Ser Lys Gln Ile His Ala Leu Glu Asn Ile Glu Glu Gly Ile Glu
705                 710                 715                 720

Glu Ser Thr Ser Glu Lys Ser Ser Glu Thr Ser Gln Met Lys Leu Glu
            725                 730                 735

Lys Lys Phe Gly Gln Ser Pro Val Phe Val Ala Ser Thr Leu Leu Glu
                740                 745                 750

Asn Gly Gly Val Pro Arg Asp Ala Ser Pro Ala Ser Leu Leu Arg Glu
            755                 760                 765

Ala Ile Gln Val Ile Ser Cys Gly Tyr Glu Asp Lys Thr Glu Trp Gly
770                 775                 780

Lys Glu Val Gly Trp Ile Tyr Gly Ser Val Thr Glu Asp Ile Leu Thr
785                 790                 795                 800

Gly Phe Lys Met His Cys His Gly Trp Arg Ser Val Tyr Cys Ile Pro
                805                 810                 815

Lys Arg Pro Ala Phe Lys Gly Ser Ala Pro Ile Asn Leu Ser Asp Arg
                820                 825                 830

Leu His Gln Val Leu Arg Trp Ala Leu Gly Ser Val Glu Ile Phe Phe
            835                 840                 845

Ser Arg His Cys Pro Ile Trp Tyr Gly Tyr Gly Gly Gly Leu Lys Trp
850                 855                 860

Leu Glu Arg Phe Ser Tyr Ile Asn Ser Val Val Tyr Pro Trp Thr Ser
865                 870                 875                 880

Ile Pro Leu Leu Val Tyr Cys Thr Leu Pro Ala Ile Cys Leu Leu Thr
                885                 890                 895

Gly Lys Phe Ile Val Pro Glu Ile Ser Asn Tyr Ala Ser Ile Val Phe
                900                 905                 910

Met Ala Leu Phe Ile Ser Ile Ala Ala Thr Gly Ile Leu Glu Met Gln
            915                 920                 925

Trp Gly Gly Val Gly Ile Asp Asp Trp Trp Arg Asn Glu Gln Phe Trp
930                 935                 940

Val Ile Gly Gly Ala Ser Ala His Leu Phe Ala Leu Phe Gln Gly Leu
945                 950                 955                 960

Leu Lys Val Leu Ala Gly Val Ser Thr Asn Phe Thr Val Thr Ser Lys
                965                 970                 975

Ala Ala Asp Asp Gly Glu Phe Ser Glu Leu Tyr Leu Phe Lys Trp Thr
                980                 985                 990

Ser Leu Leu Ile Pro Pro Thr Thr Leu Leu Ile Met Asn Ile Val Gly
            995                 1000                1005

Val Val Val Gly Val Ser Asp Ala Ile Asn Asn Gly Tyr Asp Ser Trp
    1010                1015                1020

Gly Pro Leu Phe Gly Arg Leu Phe Phe Ala Leu Trp Val Ile Ile His
1025                1030                1035                1040

Leu Tyr Pro Phe Leu Lys Gly Leu Leu Gly Lys Gln Asp Arg Met Pro
                1045                1050                1055

Thr Ile Ile Leu Val Trp Ser Ile Leu Leu Ala Ser Ile Leu Thr Leu
                1060                1065                1070

Leu Trp Val Arg Ile Asn Pro Phe Val Ser Lys Gly Pro Val Leu
                1075                1080                1085

Glu Leu Cys Gly Leu Asn Cys Asp
    1090                1095

<210> SEQ ID NO 12
<211> LENGTH: 1096
<212> TYPE: PRT
```

-continued

<213> ORGANISM: Populus trichocarpa

<400> SEQUENCE: 12

| Met | Asn | Thr | Gly | Gly | Arg | Leu | Ile | Ala | Gly | Ser | His | Asn | Arg | Asn | Glu |
| 1 | | | | 5 | | | | | 10 | | | | | 15 | |

Phe Val Leu Ile Asn Ala Asp Glu Asn Ala Arg Ile Lys Ser Val Gln
                20                  25                  30

Glu Leu Ser Gly Gln Val Cys His Ile Cys Gly Asp Glu Ile Glu Ile
            35                  40                  45

Thr Val Asp Gly Glu Pro Phe Val Ala Cys Asn Glu Cys Ala Phe Pro
        50                  55                  60

Val Cys Arg Pro Cys Tyr Glu Tyr Glu Arg Arg Glu Gly Asn Gln Ala
65                  70                  75                  80

Cys Pro Gln Cys Lys Thr Arg Tyr Lys Arg Leu Lys Gly Ser Pro Arg
                85                  90                  95

Val Glu Gly Asp Glu Glu Glu Asp Ile Asp Asp Leu Glu His Glu
                100                 105                 110

Phe Asp Tyr Gly Asn Phe Asp Gly Leu Ser Pro Glu Gln Val Ala Glu
            115                 120                 125

Ala Met Leu Ser Ser Arg Met Asn Thr Gly Arg Ala Ser His Ser Asn
    130                 135                 140

Ile Ser Gly Ile Pro Thr His Gly Glu Leu Asp Ser Ser Pro Leu Asn
145                 150                 155                 160

Ser Lys Ile Pro Leu Leu Thr Tyr Gly Glu Glu Asp Thr Glu Ile Ser
                165                 170                 175

Ser Asp Arg His Ala Leu Ile Val Pro Ser His Gly Asn Arg Phe
            180                 185                 190

His Pro Ile Ser Phe Pro Asp Pro Ser Ile Pro Leu Ala Gln Pro Arg
        195                 200                 205

Pro Met Val Pro Lys Lys Asp Ile Ala Val Tyr Gly Tyr Gly Ser Val
    210                 215                 220

Ala Trp Lys Asp Arg Met Glu Asp Trp Lys Lys Arg Gln Asn Asp Lys
225                 230                 235                 240

Leu Gln Val Val Lys His Glu Gly Gly His Asp Asn Gly Asn Phe Glu
                245                 250                 255

Gly Asp Glu Leu Asp Asp Pro Asp Leu Pro Met Met Asp Glu Gly Arg
            260                 265                 270

Gln Pro Leu Ser Arg Lys Leu Pro Ile Pro Ser Ser Lys Ile Asn Pro
        275                 280                 285

Tyr Arg Met Ile Ile Ile Leu Arg Leu Val Val Gly Leu Phe Phe
    290                 295                 300

His Tyr Arg Ile Leu His Pro Val Asn Asp Ala Tyr Gly Leu Trp Leu
305                 310                 315                 320

Thr Ser Val Ile Cys Glu Ile Trp Phe Ala Val Ser Trp Ile Leu Asp
                325                 330                 335

Gln Phe Pro Lys Trp Tyr Pro Ile Glu Arg Glu Thr Tyr Leu Asp Arg
            340                 345                 350

Leu Ser Leu Arg Tyr Glu Lys Glu Gly Lys Pro Ser Glu Leu Ala Ser
        355                 360                 365

Val Asp Val Phe Val Ser Thr Val Asp Pro Met Lys Glu Pro Pro Leu
    370                 375                 380

Ile Thr Ala Asn Thr Val Leu Ser Ile Leu Ala Val Asp Tyr Pro Val
385                 390                 395                 400

-continued

```
Asp Lys Val Ala Cys Tyr Val Ser Asp Asp Gly Ala Ala Met Leu Thr
                405                 410                 415
Phe Glu Ala Leu Ser Glu Thr Ser Glu Phe Ala Arg Lys Trp Val Pro
            420                 425                 430
Phe Cys Lys Lys Phe Asn Ile Glu Pro Arg Ala Pro Glu Trp Tyr Phe
        435                 440                 445
Ser Gln Lys Met Asp Tyr Leu Lys Asn Lys Val His Pro Ala Phe Val
    450                 455                 460
Arg Glu Arg Arg Ala Met Lys Arg Glu Tyr Glu Phe Lys Val Lys
465                 470                 475                 480
Ile Asn Gly Leu Val Ala Thr Ala Gln Lys Val Pro Glu Asp Gly Trp
                485                 490                 495
Thr Met Gln Asp Gly Thr Pro Trp Pro Gly Asn Asn Val Arg Asp His
            500                 505                 510
Pro Gly Met Ile Gln Val Phe Leu Gly Gln Ser Gly Val Arg Asp Val
        515                 520                 525
Glu Gly Asn Glu Leu Pro Arg Leu Val Tyr Val Ser Arg Glu Lys Arg
    530                 535                 540
Pro Gly Phe Glu His His Lys Lys Ala Gly Ala Met Asn Ala Leu Met
545                 550                 555                 560
Arg Val Thr Ala Val Leu Ser Asn Ala Pro Tyr Leu Leu Asn Val Asp
                565                 570                 575
Cys Asp His Tyr Ile Asn Asn Ser Arg Ala Leu Arg Glu Ala Met Cys
            580                 585                 590
Phe Leu Met Asp Pro Thr Ser Gly Lys Lys Val Cys Tyr Val Gln Phe
        595                 600                 605
Pro Gln Arg Phe Asp Gly Ile Asp Arg His Asp Arg Tyr Ser Asn Arg
    610                 615                 620
Asn Val Val Phe Phe Asp Ile Asn Met Lys Gly Leu Asp Gly Leu Gln
625                 630                 635                 640
Gly Pro Ile Tyr Val Gly Thr Gly Cys Val Phe Arg Arg Gln Ala Leu
                645                 650                 655
Tyr Gly Tyr Asp Ala Pro Val Lys Lys Arg Pro Pro Gly Lys Thr Cys
            660                 665                 670
Asn Cys Trp Pro Lys Trp Cys Cys Leu Phe Cys Gly Ser Arg Lys Asn
        675                 680                 685
Lys Lys Ser Lys Gln Lys Lys Glu Lys Lys Ser Lys Asn Arg Glu
    690                 695                 700
Ala Ser Lys Gln Ile His Ala Leu Glu Asn Ile Glu Glu Gly Ile Glu
705                 710                 715                 720
Glu Ser Thr Ser Glu Lys Ser Ser Glu Thr Ser Gln Met Lys Leu Glu
                725                 730                 735
Lys Lys Phe Gly Gln Ser Pro Val Phe Val Ala Ser Thr Leu Leu Glu
            740                 745                 750
Asn Gly Gly Val Pro Arg Asp Ala Ser Pro Ala Ser Leu Leu Arg Glu
        755                 760                 765
Ala Ile Gln Val Ile Ser Cys Gly Tyr Glu Asp Lys Thr Glu Trp Gly
    770                 775                 780
Lys Glu Val Gly Trp Ile Tyr Gly Ser Val Thr Glu Asp Ile Leu Thr
785                 790                 795                 800
Gly Phe Lys Met His Cys His Gly Trp Arg Ser Val Tyr Cys Ile Pro
                805                 810                 815
Lys Arg Pro Ala Phe Lys Gly Ser Ala Pro Ile Asn Leu Ser Asp Arg
```

```
                    820                 825                 830
Leu His Gln Val Leu Arg Trp Ala Leu Gly Ser Val Glu Ile Phe Phe
                835                 840                 845

Ser Arg His Cys Pro Ile Trp Tyr Gly Tyr Gly Gly Leu Lys Trp
        850                 855                 860

Leu Glu Arg Phe Ser Tyr Ile Asn Ser Val Val Tyr Pro Trp Thr Ser
865                 870                 875                 880

Ile Pro Leu Leu Val Tyr Cys Thr Leu Pro Ala Ile Cys Leu Leu Thr
                885                 890                 895

Gly Lys Phe Ile Val Pro Glu Ile Ser Asn Tyr Ala Ser Ile Val Phe
            900                 905                 910

Met Ala Leu Phe Ile Ser Ile Ala Ala Thr Gly Ile Leu Glu Met Gln
            915                 920                 925

Trp Gly Gly Val Gly Ile Asp Asp Trp Trp Arg Asn Glu Gln Phe Trp
            930                 935                 940

Val Ile Gly Gly Ala Ser Ala His Leu Phe Ala Leu Phe Gln Gly Leu
945                 950                 955                 960

Leu Lys Val Leu Ala Gly Val Ser Thr Asn Phe Thr Val Thr Ser Lys
                965                 970                 975

Ala Ala Asp Asp Gly Glu Phe Ser Glu Leu Tyr Leu Phe Lys Trp Thr
            980                 985                 990

Ser Leu Leu Ile Pro Pro Thr Thr Leu Leu Ile Met Asn Ile Val Gly
            995                 1000                1005

Val Val Val Gly Val Ser Asp Ala Ile Asn Asn Gly Tyr Asp Ser Trp
    1010                1015                1020

Gly Pro Leu Phe Gly Arg Leu Phe Phe Ala Leu Trp Val Ile Ile His
1025                1030                1035                1040

Leu Tyr Pro Phe Leu Lys Gly Leu Leu Gly Lys Gln Asp Arg Met Pro
                1045                1050                1055

Thr Ile Ile Leu Val Trp Ser Ile Leu Leu Ala Ser Ile Leu Thr Leu
            1060                1065                1070

Leu Trp Val Arg Ile Asn Pro Phe Val Ser Lys Gly Pro Val Leu
                1075                1080                1085

Glu Leu Cys Gly Leu Asn Cys Asp
        1090                1095

<210> SEQ ID NO 13
<211> LENGTH: 1084
<212> TYPE: PRT
<213> ORGANISM: Populus trichocarpa

<400> SEQUENCE: 13

Met Glu Val Ser Ala Gly Leu Val Ala Gly Ser His Asn Arg Asn Glu
1               5                   10                  15

Leu Val Val Ile Arg Arg Asp Gly Glu Phe Ala Pro Arg Ser Leu Glu
                20                  25                  30

Arg Val Ser Arg Gln Ile Cys His Ile Cys Gly Asp Asp Val Gly Leu
            35                  40                  45

Thr Val Asp Gly Glu Leu Phe Val Ala Cys Asn Glu Cys Ala Phe Pro
    50                  55                  60

Ile Cys Arg Thr Cys Tyr Glu Tyr Glu Arg Lys Glu Gly Asn Gln Val
65                  70                  75                  80

Cys Pro Gln Cys Lys Thr Arg Phe Lys Arg Leu Lys Gly Cys Ala Arg
                85                  90                  95
```

-continued

Val His Gly Asp Asp Glu Glu Asp Gly Thr Asp Asp Leu Glu Asn Glu
                100                 105                 110

Phe Asn Phe Asp Gly Arg Asn Ser Asn Arg His Asp Met Gln His His
            115                 120                 125

Gly Gly Pro Glu Ser Met Leu His Tyr Asp Pro Asp Leu Pro His Asp
        130                 135                 140

Leu His His Pro Leu Pro Arg Val Pro Leu Leu Thr Asn Gly Gln Met
145                 150                 155                 160

Val Asp Asp Ile Pro Pro Glu Gln His Ala Leu Val Pro Ser Tyr Met
                165                 170                 175

Ala Pro Val Gly Gly Asp Gly Lys Arg Ile His Pro Leu Pro Phe Ser
            180                 185                 190

Asp Ser Ser Leu Pro Ala Gln Pro Arg Ser Leu Asp Pro Ser Lys Asp
        195                 200                 205

Leu Ala Ala Tyr Gly Tyr Gly Ser Ile Ala Trp Lys Glu Arg Met Glu
    210                 215                 220

Ser Trp Lys Gln Lys Gln Asp Lys Leu Gln Ile Met Lys Arg Glu Asn
225                 230                 235                 240

Gly Asp Tyr Asp Asp Asp Pro Asp Leu Pro Leu Met Asp Glu Ala
                245                 250                 255

Arg Gln Pro Leu Ser Arg Lys Met Pro Ile Pro Ser Ser Gln Ile Asn
            260                 265                 270

Pro Tyr Arg Met Ile Ile Ile Arg Leu Val Val Leu Gly Phe Phe
        275                 280                 285

Phe His Tyr Arg Val Thr His Pro Val Asn Asp Ala Phe Ala Leu Trp
    290                 295                 300

Leu Ile Ser Val Ile Cys Glu Ile Trp Phe Ala Val Ser Trp Ile Leu
305                 310                 315                 320

Asp Gln Phe Pro Lys Trp Leu Pro Ile Asp Arg Glu Thr Tyr Leu Asp
                325                 330                 335

Arg Leu Ser Leu Arg Tyr Glu Lys Glu Gly Gln Pro Ser Gln Leu Ser
            340                 345                 350

Pro Val Asp Ile Tyr Val Ser Thr Val Asp Pro Leu Lys Glu Pro Pro
        355                 360                 365

Leu Val Thr Ala Asn Thr Val Leu Ser Ile Leu Ala Val Asp Tyr Pro
    370                 375                 380

Val Asp Lys Ile Ser Cys Tyr Val Ser Asp Asp Gly Ala Ala Met Leu
385                 390                 395                 400

Thr Phe Glu Ala Leu Ser Glu Thr Ser Glu Phe Ala Lys Lys Trp Val
                405                 410                 415

Pro Phe Cys Lys Lys Phe Ser Ile Glu Pro Arg Ala Pro Glu Phe Tyr
            420                 425                 430

Phe Ala Gln Lys Ile Asp Tyr Leu Lys Asp Lys Val Asp Ala Ser Phe
        435                 440                 445

Val Lys Glu Arg Arg Ala Met Lys Arg Glu Tyr Glu Glu Phe Lys Val
    450                 455                 460

Arg Val Asn Ala Leu Val Ala Lys Ala His Lys Val Pro Glu Asp Gly
465                 470                 475                 480

Trp Thr Met Gln Asp Gly Thr Pro Trp Pro Gly Asn Asn Val Arg Asp
                485                 490                 495

His Pro Gly Met Ile Gln Val Phe Leu Gly Gln Ser Gly Gly His Asp
            500                 505                 510

Thr Asp Gly Asn Glu Leu Pro Arg Leu Val Tyr Val Ser Arg Glu Lys

```
              515                 520                 525
Arg Pro Gly Phe Asn His His Lys Ala Gly Ala Met Asn Ala Leu
    530                 535                 540

Val Arg Val Ser Ala Val Leu Ser Asn Ala Arg Tyr Leu Leu Asn Leu
545                 550                 555                 560

Asp Cys Asp His Tyr Ile Asn Asn Ser Lys Ala Leu Arg Glu Ser Met
                    565                 570                 575

Cys Phe Met Met Asp Pro Leu Leu Gly Lys Arg Val Cys Tyr Val Gln
                580                 585                 590

Phe Pro Gln Arg Phe Asp Gly Ile Asp Arg Asn Asp Arg Tyr Ala Asn
            595                 600                 605

Arg Asn Thr Val Phe Phe Asp Ile Asn Met Lys Gly Leu Asp Gly Ile
        610                 615                 620

Gln Gly Pro Ile Tyr Val Gly Thr Gly Cys Val Phe Arg Arg His Ala
625                 630                 635                 640

Leu Tyr Gly Tyr Asp Ala Pro Lys Thr Lys Lys Pro Pro Thr Arg Thr
                645                 650                 655

Cys Asn Cys Leu Pro Lys Trp Cys Cys Gly Cys Phe Cys Ser Gly Arg
                660                 665                 670

Lys Lys Lys Lys Lys Thr Asn Lys Pro Lys Ser Glu Leu Lys Lys Arg
            675                 680                 685

Asn Ser Arg Thr Phe Ala Pro Val Gly Thr Leu Glu Gly Ile Glu Glu
        690                 695                 700

Gly Ile Glu Gly Ile Glu Thr Glu Asn Val Ala Val Thr Ser Glu Lys
705                 710                 715                 720

Lys Leu Glu Asn Lys Phe Gly Gln Ser Ser Val Phe Val Ala Ser Thr
                725                 730                 735

Leu Leu Glu Asp Gly Gly Thr Leu Lys Ser Ala Ser Pro Ala Ser Leu
                740                 745                 750

Leu Lys Glu Ala Ile His Val Ile Ser Cys Gly Tyr Glu Asp Lys Thr
            755                 760                 765

Glu Trp Gly Lys Glu Val Gly Trp Ile Tyr Gly Ser Val Thr Glu Asp
        770                 775                 780

Ile Leu Thr Gly Phe Lys Met His Cys His Gly Trp Arg Ser Ile Tyr
785                 790                 795                 800

Cys Ile Pro Ala Arg Pro Ala Phe Lys Gly Ser Ala Pro Ile Asn Leu
                805                 810                 815

Ser Asp Arg Leu His Gln Val Leu Arg Trp Ala Leu Gly Ser Val Glu
                820                 825                 830

Ile Phe Leu Ser Arg His Cys Pro Leu Trp Tyr Gly Tyr Gly Gly Gly
            835                 840                 845

Leu Lys Trp Leu Glu Arg Leu Ser Tyr Ile Asn Ala Thr Val Tyr Pro
        850                 855                 860

Leu Thr Ser Ile Pro Leu Leu Ala Tyr Cys Thr Leu Pro Ala Val Cys
865                 870                 875                 880

Leu Leu Thr Gly Lys Phe Ile Thr Pro Glu Leu Ser Asn Ala Ala Ser
                885                 890                 895

Leu Trp Phe Leu Ser Leu Phe Ile Cys Ile Phe Ala Thr Ser Ile Leu
                900                 905                 910

Glu Met Arg Trp Ser Gly Val Gly Ile Asp Glu Trp Trp Arg Asn Glu
            915                 920                 925

Gln Phe Trp Val Ile Gly Gly Val Ser Ala His Leu Phe Ala Val Phe
        930                 935                 940
```

```
Gln Gly Leu Leu Lys Val Leu Ala Gly Val Asp Thr Asn Phe Thr Val
945                 950                 955                 960

Thr Ser Lys Gly Gly Asp Asp Glu Phe Ser Glu Leu Tyr Ala Phe
            965                 970                 975

Lys Trp Thr Thr Leu Leu Ile Pro Pro Thr Thr Leu Leu Ile Ile Asn
            980                 985                 990

Leu Val Gly Val Val Ala Gly Val Ser Asn Ala Ile Asn Asn Gly Tyr
            995                 1000                1005

Glu Ser Trp Gly Pro Leu Phe Gly Lys Leu Phe Phe Ala Phe Trp Val
        1010                1015                1020

Ile Val His Leu Tyr Pro Phe Leu Lys Gly Leu Leu Gly Arg Gln Asn
1025                1030                1035                1040

Arg Thr Pro Thr Ile Ile Ile Val Trp Ser Ile Leu Leu Ala Ser Ile
                1045                1050                1055

Phe Ser Leu Leu Trp Val Arg Ile Asp Pro Phe Leu Ala Lys Ser Asn
            1060                1065                1070

Gly Pro Leu Leu Glu Glu Cys Gly Leu Asp Cys Asn
            1075                1080

<210> SEQ ID NO 14
<211> LENGTH: 1092
<212> TYPE: PRT
<213> ORGANISM: Eucalyptus grandis

<400> SEQUENCE: 14

Met Asn Thr Gly Gly Arg Leu Ile Ala Gly Ser His Asn Arg Asn Glu
1               5                   10                  15

Phe Val Leu Ile Asn Ala Asp Glu Ser Ser Arg Ile Lys Ser Val Lys
                20                  25                  30

Glu Leu Ser Gly Gln Ile Cys Gln Ile Cys Gly Asp Glu Val Glu Ile
            35                  40                  45

Ala Asp Gly Glu Leu Phe Val Ala Cys Asn Glu Cys Ala Phe Pro Val
        50                  55                  60

Cys Arg Pro Cys Tyr Glu Tyr Glu Arg Arg Glu Gly Asn Gln Ala Cys
65                  70                  75                  80

Pro Gln Cys Lys Thr Arg Tyr Lys Arg Leu Lys Gly Ser Pro Arg Val
                85                  90                  95

Glu Gly Asp Glu Glu Asp Asp Ile Asp Asp Leu Asp Asn Glu Phe
            100                 105                 110

Asp Tyr Asp Pro Ser Asp Pro Gln His Val Ala Glu Lys Thr Phe Ser
            115                 120                 125

Ser Arg Leu Asn Tyr Gly Arg Gly Ala His Arg Asn Ala Ser Gly Met
        130                 135                 140

Pro Thr Asp Val Glu Ser Ser Pro Leu Ser Ser Gln Ile Pro Leu Leu
145                 150                 155                 160

Thr Tyr Gly Gln Glu Asp Ala Glu Ile Ser Pro Asp Gln His Ala Leu
                165                 170                 175

Ile Val Pro Pro Ala Thr Gly His Ala Tyr Arg Val His Pro Met Pro
            180                 185                 190

Tyr Pro Asp Ser Ser Asn Pro Leu His Pro Arg Pro Met Ala Pro Glu
        195                 200                 205

Lys Asp Ile Thr Leu Tyr Gly Tyr Gly Ser Val Ala Trp Lys Asp Lys
210                 215                 220

Met Glu Lys Trp Arg Lys Lys Gln Asn Glu Lys Leu Gln Val Val Lys
```

-continued

```
           225                 230                 235                 240
His Glu Gly Ala Gly Asp Gly Asp Phe Gly Ser Asp Glu Leu Asp
                    245                 250                 255

Asp Pro Asp Leu Pro Met Met Asp Glu Gly Arg Gln Pro Leu Ser Arg
                    260                 265                 270

Lys Leu Pro Ile Pro Ser Ser Lys Ile Asn Pro Tyr Arg Leu Leu Ile
                    275                 280                 285

Ile Leu Arg Leu Val Ile Leu Gly Leu Phe Leu His Tyr Arg Ile Leu
            290                 295                 300

His Pro Val Asn Asp Ala Tyr Gly Leu Trp Leu Thr Ser Val Ile Cys
305                 310                 315                 320

Glu Ile Trp Phe Ala Val Ser Trp Ile Leu Asp Gln Phe Pro Lys Trp
                    325                 330                 335

Tyr Pro Ile Glu Arg Glu Thr Tyr Leu Asp Arg Leu Ser Leu Arg Tyr
                    340                 345                 350

Glu Arg Glu Gly Lys Pro Ser Glu Leu Ala Pro Val Asp Val Phe Val
                    355                 360                 365

Ser Thr Val Asp Pro Met Lys Glu Pro Pro Leu Ile Thr Ala Asn Thr
            370                 375                 380

Val Leu Ser Ile Leu Ala Val Asp Tyr Pro Val Asp Lys Val Ala Cys
385                 390                 395                 400

Tyr Val Ser Asp Asp Gly Ala Ala Met Leu Thr Phe Glu Ala Leu Ser
                    405                 410                 415

Glu Thr Ser Glu Phe Ala Lys Lys Trp Val Pro Phe Cys Lys Arg Phe
                    420                 425                 430

Asn Ile Glu Pro Arg Ala Pro Glu Trp Tyr Phe Ser Gln Lys Met Asp
            435                 440                 445

Tyr Leu Lys Asn Lys Val His Pro Glu Phe Val Arg Glu Arg Arg Ala
            450                 455                 460

Ile Lys Arg Glu Tyr Glu Glu Phe Lys Val Arg Ile Asn Ala Leu Val
465                 470                 475                 480

Ala Met Ala Gln Lys Val Pro Glu Glu Gly Trp Thr Met Gln Asp Gly
                    485                 490                 495

Thr Pro Trp Pro Gly Asn Asn Val Arg Asp His Pro Gly Met Ile Gln
                    500                 505                 510

Val Phe Leu Gly His Ser Gly Val Cys Asp Asp Gly Asn Glu Leu
            515                 520                 525

Pro Arg Leu Val Tyr Val Ser Arg Glu Lys Arg Pro Gly Phe Glu His
            530                 535                 540

His Lys Lys Ala Gly Ala Met Asn Ala Leu Ile Arg Val Ser Ala Val
545                 550                 555                 560

Ile Ser Asn Ala Pro Tyr Leu Leu Asn Val Asp Cys Asp His Tyr Ile
                    565                 570                 575

Asn Asn Ser Lys Ala Leu Arg Glu Ala Met Cys Phe Met Met Asp Pro
            580                 585                 590

Thr Ser Gly Lys Lys Val Cys Tyr Val Gln Phe Pro Gln Arg Phe Asp
            595                 600                 605

Gly Ile Asp Arg His Asp Arg Tyr Ser Asn Arg Asn Val Val Phe Phe
            610                 615                 620

Asp Ile Asn Met Lys Gly Leu Asp Gly Leu Gln Gly Pro Ile Tyr Val
625                 630                 635                 640

Gly Thr Gly Cys Val Phe Arg Arg Gln Ala Leu Tyr Gly His Asp Ala
                    645                 650                 655
```

-continued

```
Pro Ser Lys Lys Lys Pro Ser Lys Thr Cys Asn Cys Trp Pro Lys
        660             665             670
Trp Cys Cys Leu Cys Cys Gly Gly Arg Lys Asn Lys Lys Gly Lys Thr
        675             680             685
Lys Lys Glu Arg Ser Lys Lys Thr Lys Asn Arg Glu Thr Ser Lys Gln
        690             695             700
Ile His Ala Leu Glu Asn Ile Glu Glu Gly Val Ser Glu Val Ser Asn
705             710             715             720
Glu Lys Ser Ser Glu Met Thr Gln Ile Lys Leu Glu Lys Lys Phe Gly
                725             730             735
Gln Ser Pro Val Phe Val Ala Ser Thr Thr Leu Glu Asp Gly Gly Val
            740             745             750
Pro Pro Asp Ala Ser Pro Ala Ser Leu Leu Lys Glu Ala Ile Gln Val
        755             760             765
Ile Ser Cys Gly Tyr Glu Asp Lys Thr Glu Trp Gly Lys Glu Val Gly
        770             775             780
Trp Ile Tyr Gly Ser Val Thr Glu Asp Ile Leu Thr Gly Phe Lys Met
785             790             795             800
His Cys His Gly Trp Arg Ser Val Tyr Cys Ile Pro Lys Arg Pro Ala
                805             810             815
Phe Lys Gly Ser Ala Pro Ile Asn Leu Ser Asp Arg Leu His Gln Val
            820             825             830
Leu Arg Trp Ala Leu Gly Ser Val Glu Ile Phe Leu Ser Arg His Cys
        835             840             845
Pro Ile Trp Tyr Gly Tyr Gly Gly Gly Leu Lys Trp Leu Glu Arg Phe
        850             855             860
Ser Tyr Ile Asn Ser Val Val Tyr Pro Trp Thr Ser Ile Pro Leu Ile
865             870             875             880
Val Tyr Cys Ser Leu Pro Ala Ile Cys Leu Leu Thr Gly Gln Phe Ile
                885             890             895
Val Pro Glu Ile Ser Asn Tyr Ala Ser Leu Val Phe Met Ala Leu Phe
            900             905             910
Ile Ser Ile Ala Ala Thr Gly Ile Leu Glu Met Gln Trp Gly Gly Val
        915             920             925
Gly Ile Asp Asp Trp Trp Arg Asn Glu Gln Phe Trp Val Ile Gly Gly
        930             935             940
Val Ser Ser His Leu Phe Ala Leu Val Gln Gly Leu Leu Lys Val Leu
945             950             955             960
Gly Gly Val Asn Thr Asn Phe Thr Val Thr Ser Lys Ala Ala Asp Asp
                965             970             975
Gly Ala Phe Ser Glu Leu Tyr Ile Phe Lys Trp Thr Ser Leu Leu Ile
            980             985             990
Pro Pro Met Thr Leu Leu Ile Met Asn Ile Val Gly Val Val Val Gly
        995             1000            1005
Ile Ser Asp Ala Ile Asn Asn Gly Tyr Asp Ser Trp Gly Pro Leu Phe
        1010            1015            1020
Gly Arg Leu Phe Phe Ala Phe Trp Val Ile Val His Leu Tyr Pro Phe
1025            1030            1035            1040
Leu Lys Gly Leu Leu Gly Lys Gln Asp Arg Met Pro Thr Ile Val Val
                1045            1050            1055
Val Trp Ser Ile Leu Leu Ala Ser Ile Leu Thr Leu Leu Trp Val Arg
            1060            1065            1070
```

```
Ile Asn Pro Phe Val Ser Arg Asp Gly Pro Val Leu Glu Val Cys Gly
        1075                1080                1085

Leu Asn Cys Asp
    1090

<210> SEQ ID NO 15
<211> LENGTH: 1097
<212> TYPE: PRT
<213> ORGANISM: Eucalyptus grandis

<400> SEQUENCE: 15

Met Glu Val Ser Ser Gly Leu Val Ala Gly Ser His Asn Arg Asn Glu
1               5                   10                  15

Leu Val Val Ile Arg Arg Glu Asn Glu Leu Gly Gln Lys Pro Leu Gln
            20                  25                  30

Lys Leu Ser Gly Gln Ile Cys Gln Ile Cys Gly Asp Asp Val Gly Leu
        35                  40                  45

Thr Val Asp Gly Glu Leu Phe Val Ala Cys Asn Glu Cys Ala Phe Pro
    50                  55                  60

Ile Cys Arg Thr Cys Tyr Glu Tyr Glu Arg Arg Glu Gly Ser Gln Ile
65                  70                  75                  80

Cys Pro Gln Cys Lys Thr Arg Phe Lys Arg Leu Arg Gly Cys Ala Arg
                85                  90                  95

Val Asp Gly Asp Glu Glu Asp Gly Val Asp Asp Leu Glu Asn Glu
            100                 105                 110

Phe Asn Phe Asp Gly Arg His Arg Gln Glu Met Asp Arg Gln Gly Tyr
        115                 120                 125

Gly Ala Glu Ala Met Leu His Gly His Met Ser Tyr Gly Arg Gly Ser
    130                 135                 140

Asp Leu Asp Leu Pro His Val His Pro Leu Pro Gln Val Pro Leu Leu
145                 150                 155                 160

Ala Asn Gly Gln Met Val Asp Asp Val Pro Pro Glu His His Ala Leu
                165                 170                 175

Val Pro Ala Tyr Met Gly Ala Gly Gly Gly Gly Gly Gly Gly Gly Lys
            180                 185                 190

Arg Ile His Pro Leu Pro Phe Thr Asp Ser Gly Leu Pro Val Gln Pro
        195                 200                 205

Arg Ser Met Asp Pro Ser Lys Asp Leu Ala Ala Tyr Gly Tyr Gly Ser
    210                 215                 220

Val Ala Trp Lys Glu Arg Met Glu Ser Trp Lys Gln Lys Gln Glu Lys
225                 230                 235                 240

Leu Gln Thr Met Lys Asn Glu Lys Gly Gly Lys Glu Trp Asp Asp Asp
                245                 250                 255

Gly Asp Asn Pro Asp Leu Pro Leu Met Asp Glu Ala Arg Gln Pro Leu
            260                 265                 270

Ser Arg Arg Leu Pro Ile Ser Ser Gln Ile Asn Pro Tyr Arg Met
        275                 280                 285

Ile Ile Val Ile Arg Leu Val Val Leu Gly Phe Phe His Tyr Arg
    290                 295                 300

Val Val His Pro Val Asn Asp Ala Tyr Ala Leu Trp Leu Ile Ser Val
305                 310                 315                 320

Ile Cys Glu Ile Trp Phe Gly Leu Ser Trp Ile Leu Asp Gln Phe Pro
                325                 330                 335

Lys Trp Leu Pro Ile Asp Arg Glu Thr Tyr Leu Asp Arg Leu Ser Leu
            340                 345                 350
```

```
Arg Tyr Glu Lys Glu Gly Gln Pro Ser Gln Leu Ala Pro Val Asp Ile
        355                 360                 365
Phe Val Ser Thr Val Asp Pro Leu Lys Glu Pro Pro Leu Val Thr Ala
    370                 375                 380
Asn Thr Val Leu Ser Ile Leu Ala Val Asp Tyr Pro Val Asp Lys Val
385                 390                 395                 400
Ser Cys Tyr Val Ser Asp Asp Gly Ala Ala Met Leu Thr Phe Glu Ala
                405                 410                 415
Leu Ser Glu Thr Ser Glu Phe Ala Arg Lys Trp Ala Pro Phe Cys Lys
            420                 425                 430
Lys Phe Asn Ile Glu Pro Arg Ala Pro Glu Phe Tyr Phe Ala Gln Lys
        435                 440                 445
Ile Asp Tyr Leu Lys Asp Lys Val Glu Ala Ser Phe Val Lys Glu Arg
    450                 455                 460
Arg Ala Met Lys Arg Glu Tyr Glu Glu Phe Lys Val Arg Ile Asn Ala
465                 470                 475                 480
Leu Val Ala Lys Ala Gln Lys Val Pro Glu Glu Gly Trp Thr Met Gln
                485                 490                 495
Asp Gly Thr Pro Trp Pro Gly Asn Asn Val Arg Asp His Pro Gly Met
            500                 505                 510
Ile Gln Val Phe Leu Gly Gln Ser Gly Gly His Asp Ser Asp Gly Asn
        515                 520                 525
Glu Leu Pro Arg Leu Val Tyr Val Ser Arg Glu Lys Arg Pro Gly Tyr
    530                 535                 540
Asn His His Lys Lys Ala Gly Ala Met Asn Ala Leu Val Arg Val Ser
545                 550                 555                 560
Ala Val Leu Thr Asn Ala Pro Tyr Leu Leu Asn Leu Asp Cys Asp His
                565                 570                 575
Tyr Phe Asn Asn Ser Lys Ala Ile Arg Glu Ala Met Cys Phe Met Val
            580                 585                 590
Asp Pro Leu Ile Gly Lys Arg Val Cys Tyr Val Gln Phe Pro Gln Arg
        595                 600                 605
Phe Asp Gly Ile Asp Arg His Asp Arg Tyr Ala Asn Arg Asn Thr Val
    610                 615                 620
Phe Phe Asp Ile Asn Met Lys Gly Leu Asp Gly Ile Gln Gly Pro Ile
625                 630                 635                 640
Tyr Val Gly Thr Gly Cys Val Phe Arg Arg Leu Ala Leu Tyr Gly Tyr
                645                 650                 655
Asp Ala Pro Lys Ala Lys Lys Pro Pro Thr Arg Thr Cys Asn Cys Leu
            660                 665                 670
Pro Lys Trp Cys Cys Cys Gly Cys Cys Ser Gly Lys Lys Lys
        675                 680                 685
Lys Lys Thr Thr Lys Pro Lys Thr Glu Leu Lys Lys Arg Phe Phe Lys
        690                 695                 700
Lys Lys Asp Ala Gly Thr Pro Pro Leu Glu Gly Ile Glu Glu Gly
705                 710                 715                 720
Ile Glu Val Ile Glu Ser Glu Asn Pro Thr Pro Gln His Lys Leu Glu
                725                 730                 735
Lys Lys Phe Gly Gln Ser Ser Val Phe Val Ala Ser Thr Leu Leu Glu
            740                 745                 750
Asp Gly Gly Thr Leu Lys Gly Thr Ser Pro Ala Ser Leu Leu Lys Glu
        755                 760                 765
```

-continued

```
Ala Ile His Val Ile Ser Cys Gly Tyr Glu Asp Lys Thr Glu Trp Gly
770                 775                 780

Lys Glu Val Gly Trp Ile Tyr Gly Ser Val Thr Glu Asp Ile Leu Thr
785                 790                 795                 800

Gly Phe Lys Met His Cys His Gly Trp Arg Ser Ile Tyr Cys Ile Pro
                805                 810                 815

Ala Arg Pro Ala Phe Lys Gly Ser Ala Pro Ile Asn Leu Ser Asp Arg
            820                 825                 830

Leu His Gln Val Leu Arg Trp Ala Leu Gly Ser Ile Glu Ile Phe Leu
        835                 840                 845

Ser Arg His Cys Pro Leu Trp Tyr Gly Tyr Gly Gly Leu Lys Trp
    850                 855                 860

Leu Glu Arg Leu Ser Tyr Ile Asn Ala Thr Val Tyr Pro Trp Thr Ser
865                 870                 875                 880

Ile Pro Leu Leu Ala Tyr Cys Thr Leu Pro Ala Val Cys Leu Leu Thr
                885                 890                 895

Gly Lys Phe Ile Thr Pro Glu Leu Ser Asn Val Ala Ser Leu Trp Phe
                900                 905                 910

Leu Ser Leu Phe Ile Cys Ile Phe Ala Thr Ser Ile Leu Glu Met Arg
            915                 920                 925

Trp Ser Gly Val Gly Ile Glu Glu Trp Trp Arg Asn Glu Gln Phe Trp
        930                 935                 940

Val Ile Gly Gly Val Ser Ala His Leu Phe Ala Val Phe Gln Gly Leu
945                 950                 955                 960

Leu Lys Val Leu Ala Gly Val Asp Thr Asn Phe Thr Val Thr Ser Lys
                965                 970                 975

Gly Gly Asp Asp Lys Glu Phe Ser Glu Leu Tyr Ala Phe Lys Trp Thr
            980                 985                 990

Thr Leu Leu Ile Pro Pro Thr Thr Leu Leu Ile Ile Asn Leu Ile Gly
        995                 1000                1005

Val Val Ala Gly Val Ser Asn Ala Ile Asn Asn Gly His Glu Ser Trp
    1010                1015                1020

Gly Pro Leu Phe Gly Lys Leu Phe Phe Ala Phe Trp Val Ile Val His
1025                1030                1035                1040

Leu Tyr Pro Phe Leu Lys Gly Leu Leu Gly Arg Gln Asn Arg Thr Pro
                1045                1050                1055

Thr Ile Ile Ile Val Trp Ser Ile Leu Leu Ala Ser Ile Phe Ser Leu
            1060                1065                1070

Leu Trp Val Arg Ile Asp Pro Phe Leu Ala Lys Ser Asp Gly Pro Leu
        1075                1080                1085

Leu Glu Glu Cys Gly Leu Asp Cys Asn
    1090                1095

<210> SEQ ID NO 16
<211> LENGTH: 1092
<212> TYPE: PRT
<213> ORGANISM: Eucalyptus grandis

<400> SEQUENCE: 16

Met Asp Thr Gly Arg Leu Val Thr Gly Ser His Asn Arg Asn Glu Ile
1               5                   10                  15

Ile Leu Ile Asn Ala Asp Glu Val Gly Arg Val Thr Cys Val Lys His
                20                  25                  30

Leu Ser Gly Lys Ile Cys Gln Ile Cys Ala Asp Glu Ile Glu Ile Thr
            35                  40                  45
```

Gly Asp Gly Glu Pro Phe Val Ala Cys Asn Glu Cys Ala Phe Pro Val
    50                  55                  60

Cys Arg His Cys Tyr Glu Tyr Glu Arg Ser Glu Gly Thr Gln Ala Cys
65                  70                  75                  80

Pro His Cys Lys Thr Arg Tyr Lys Arg Ile Lys Gly Ser Pro Arg Val
                85                  90                  95

Glu Gly Asp Glu Glu Glu Asn Thr Asp Asp Leu Glu Arg Glu Phe
            100                 105                 110

Asp Ile Gly Glu Ser Gly Arg Gly Asn Leu His Cys Met Ala Glu Gly
            115                 120                 125

Met Pro Ser Thr His Leu Asn Phe Gly Pro Asn Leu Gln Thr His Ala
    130                 135                 140

Ser Gly Phe Thr Thr Pro Ser Glu Leu Asp Ala Ser Ser Val Val Pro
145                 150                 155                 160

Glu Ile Pro Leu Leu Thr Tyr Gly Gln Glu Asn Val Gly Ile Ser Phe
                165                 170                 175

Asn Lys His Ala Leu Ile Ile Pro Pro Leu Met Gly Gln Gly Arg Arg
            180                 185                 190

Ile His Pro Met Pro Asn Ser Asp Ser Ser Val Pro Leu Pro Pro Arg
    195                 200                 205

Thr Leu Asp Pro Asn Lys Asp Ser Ala Val Tyr Gly Tyr Gly Thr Val
    210                 215                 220

Ala Trp Lys Glu Arg Met Glu Glu Trp Lys Lys Gln Asn Glu Arg
225                 230                 235                 240

Ile Gln Val Val Lys His Asp Arg Gly Ser Asp Gly Gln Glu Pro Asp
                245                 250                 255

Asp Ala Asp Leu Pro Thr Met Asp Glu Gly Arg Gln Pro Leu Ser Arg
            260                 265                 270

Lys Leu Pro Ile Pro Ser Ser Lys Ile Ser Pro Tyr Arg Leu Ile Ile
    275                 280                 285

Ile Leu Arg Leu Val Ile Leu Gly Leu Phe Phe His Tyr Arg Ile Leu
    290                 295                 300

His Pro Val Asn Asp Ala Tyr Gly Leu Trp Leu Thr Ser Val Ile Cys
305                 310                 315                 320

Glu Ile Trp Phe Ala Met Ser Trp Ile Leu Asp Gln Phe Pro Lys Trp
                325                 330                 335

Tyr Pro Ile Lys Arg Glu Thr Tyr Leu Asp Arg Leu Ser Leu Arg Tyr
            340                 345                 350

Glu Lys Glu Glu Arg Pro Ser Lys Leu Ala Asp Ile Asp Ile Phe Val
    355                 360                 365

Ser Thr Val Asp Pro Met Lys Glu Pro Pro Leu Ile Thr Ala Asn Thr
    370                 375                 380

Val Leu Ser Ile Leu Ala Val Asp Tyr Pro Val Asp Lys Val Ala Cys
385                 390                 395                 400

Tyr Val Ser Asp Asp Gly Ala Ala Met Leu Thr Phe Glu Ala Leu Ser
                405                 410                 415

Glu Thr Ser Glu Phe Ala Met Lys Trp Val Pro Phe Cys Lys Arg Phe
            420                 425                 430

Asn Ile Glu Pro Arg Ala Pro Glu Trp Tyr Phe Ser Gln Lys Val Asp
    435                 440                 445

Tyr Leu Lys Asp Lys Val Asn Pro Glu Phe Val Arg Glu Arg Arg Asp
    450                 455                 460

```
Met Lys Arg Glu Tyr Glu Glu Phe Lys Val Arg Ile Asn Gly Leu Val
465                 470                 475                 480

Ala Met Ala Gln Lys Val Pro Glu Glu Gly Trp Thr Met Gln Asp Gly
                485                 490                 495

Thr Pro Trp Pro Gly Asn Asn Val Arg Asp His Pro Gly Met Ile Gln
            500                 505                 510

Val Phe Leu Gly Gln Asn Gly Asp Arg Asp Val Glu Gly Asn Glu Leu
        515                 520                 525

Pro Arg Leu Val Tyr Val Ser Arg Glu Lys Arg Pro Gly Phe Asp His
    530                 535                 540

His Lys Lys Ala Gly Ala Met Asn Ala Leu Val Arg Val Ser Ala Val
545                 550                 555                 560

Ile Thr Asn Ala Pro Tyr Leu Leu Asn Val Asp Cys Asp His Tyr Ile
                565                 570                 575

Asn Asn Ser Lys Ala Leu Arg Glu Ala Met Cys Phe Met Met Asp Pro
            580                 585                 590

Ile Ser Gly Lys Lys Ile Cys Tyr Val Gln Phe Pro Gln Arg Phe Asp
        595                 600                 605

Gly Ile Asp Arg His Asp Arg Tyr Ser Asn Arg Asn Val Val Phe Phe
    610                 615                 620

Asp Ile Asn Met Lys Gly Leu Asp Gly Ile Gln Gly Pro Ile Tyr Val
625                 630                 635                 640

Gly Thr Gly Cys Val Phe Arg Arg Gln Ala Leu Tyr Gly Tyr Asp Ala
                645                 650                 655

Pro Ile Lys Lys Lys Pro Pro Gly Lys Thr Cys Asn Cys Trp Pro Lys
            660                 665                 670

Trp Cys Cys Leu Cys Cys Gly Ser Arg Lys Gly Arg Lys Met Lys
        675                 680                 685

Ser Asn Glu Gln Lys Lys Thr Leu Arg Asn Arg Glu Ala Ser Lys Gln
    690                 695                 700

Ile His Ala Leu Glu Asn Ile Glu Glu Gly Ile Glu Gly Ile Asp Asn
705                 710                 715                 720

Glu Lys Ser Ser Leu Met Ser Arg Val Lys Phe Glu Lys Lys Phe Gly
                725                 730                 735

Gln Ser Pro Val Phe Ile Ala Thr Thr Leu Met Glu Glu Gly Gly Val
            740                 745                 750

Pro Lys Gly Ala Thr Thr Ala Ser Leu Leu Lys Glu Ala Ile His Val
        755                 760                 765

Ile Ser Cys Gly Tyr Glu Asp Lys Thr Glu Trp Gly Lys Glu Val Gly
    770                 775                 780

Trp Ile Tyr Gly Ser Val Thr Glu Asp Ile Leu Thr Gly Phe Lys Met
785                 790                 795                 800

His Cys His Gly Trp Arg Ser Val Tyr Cys Ile Pro Lys Arg Pro Ala
                805                 810                 815

Phe Lys Gly Ser Ala Pro Ile Asn Leu Ser Asp Arg Leu His Gln Val
            820                 825                 830

Leu Arg Trp Ala Leu Gly Ser Val Glu Ile Leu Leu Ser Arg His Cys
        835                 840                 845

Pro Ile Trp Tyr Gly Tyr Gly Cys Gly Leu Lys Trp Leu Glu Arg Phe
    850                 855                 860

Ser Tyr Ile Asn Ser Val Val Tyr Pro Leu Thr Ser Ile Pro Leu Ile
865                 870                 875                 880

Ala Tyr Cys Thr Leu Pro Ala Val Cys Leu Leu Thr Gly Lys Phe Ile
```

```
                885                 890                 895
Val Pro Glu Ile Ser Asn Tyr Ala Ser Leu Ile Phe Met Ala Leu Phe
            900                 905                 910

Ile Ser Ile Ala Ala Thr Gly Ile Leu Glu Met Gln Trp Gly Gly Val
            915                 920                 925

Gly Ile His Asp Trp Trp Arg Asn Glu Gln Phe Trp Val Ile Gly Gly
            930                 935                 940

Val Ser Cys His Leu Phe Ala Leu Phe Gln Gly Leu Leu Lys Val Leu
945                 950                 955                 960

Ala Gly Val Asn Thr Asn Phe Thr Val Thr Ser Lys Ala Gly Asp Asp
            965                 970                 975

Gly Glu Phe Ser Glu Leu Tyr Leu Phe Lys Trp Thr Ser Leu Leu Ile
            980                 985                 990

Pro Pro Leu Thr Leu Leu Ile Leu Asn Ile Ile Gly Val Ile Val Gly
            995                1000                1005

Val Ser Asp Ala Ile Asn Asn Gly Tyr Glu Thr Trp Gly Pro Leu Phe
           1010                1015                1020

Gly Lys Leu Leu Phe Ala Leu Trp Val Ile Val His Leu Tyr Pro Phe
1025                1030                1035                1040

Leu Lys Gly Phe Met Gly Lys Gln Asp Arg Leu Pro Thr Ile Ile Ile
           1045                1050                1055

Val Trp Ala Ile Leu Leu Ala Ser Ile Leu Thr Leu Leu Trp Val Arg
           1060                1065                1070

Ile Asn Pro Phe Ile Ser Lys Asp Gly Ile Val Leu Glu Val Cys Gly
           1075                1080                1085

Leu Asp Cys Asn
    1090

<210> SEQ ID NO 17
<211> LENGTH: 29
<212> TYPE: DNA
<213> ORGANISM: Artificial Sequence
<220> FEATURE:
<223> OTHER INFORMATION: A synthetic oligonucleotide

<400> SEQUENCE: 17
gctctagaat ggaatccgaa ggagaaacc                                        29

<210> SEQ ID NO 18
<211> LENGTH: 31
<212> TYPE: DNA
<213> ORGANISM: Artificial Sequence
<220> FEATURE:
<223> OTHER INFORMATION: A synthetic oligonucleotide

<400> SEQUENCE: 18
aactgcagca ccaagacaga agaacgaaca g                                     31

<210> SEQ ID NO 19
<211> LENGTH: 27
<212> TYPE: DNA
<213> ORGANISM: Artificial Sequence
<220> FEATURE:
<223> OTHER INFORMATION: A synthetic oligonucleotide

<400> SEQUENCE: 19
aaagagctca tgaacaccgg tggtcgg                                          27

<210> SEQ ID NO 20
```

```
<211> LENGTH: 31
<212> TYPE: DNA
<213> ORGANISM: Artificial Sequence
<220> FEATURE:
<223> OTHER INFORMATION: A synthetic oligonucleotide

<400> SEQUENCE: 20
aaatctagat cacaagcagt ctaaaccaca g                              31

<210> SEQ ID NO 21
<211> LENGTH: 31
<212> TYPE: DNA
<213> ORGANISM: Artificial Sequence
<220> FEATURE:
<223> OTHER INFORMATION: A synthetic oligonucleotide

<400> SEQUENCE: 21
gctctagaat gaatactggt ggtcggctca t                              31

<210> SEQ ID NO 22
<211> LENGTH: 34
<212> TYPE: DNA
<213> ORGANISM: Artificial Sequence
<220> FEATURE:
<223> OTHER INFORMATION: A synthetic oligonucleotide

<400> SEQUENCE: 22
aactgcagtt agtttccaca attcagacca caga                           34

<210> SEQ ID NO 23
<211> LENGTH: 32
<212> TYPE: DNA
<213> ORGANISM: Artificial Sequence
<220> FEATURE:
<223> OTHER INFORMATION: A synthetic oligonucleotide

<400> SEQUENCE: 23
gctctagaat gaatactggt ggtcggctca tc                             32

<210> SEQ ID NO 24
<211> LENGTH: 32
<212> TYPE: DNA
<213> ORGANISM: Artificial Sequence
<220> FEATURE:
<223> OTHER INFORMATION: A synthetic oligonucleotide

<400> SEQUENCE: 24
aactgcagtc aaaggcagtc caagccacat at                             32

<210> SEQ ID NO 25
<211> LENGTH: 29
<212> TYPE: DNA
<213> ORGANISM: Artificial Sequence
<220> FEATURE:
<223> OTHER INFORMATION: A synthetic oligonucleotide

<400> SEQUENCE: 25
gctctagaat gaacactgga gggagactc                                 29

<210> SEQ ID NO 26
<211> LENGTH: 32
<212> TYPE: DNA
<213> ORGANISM: Artificial Sequence
<220> FEATURE:
<223> OTHER INFORMATION: A synthetic oligonucleotide

<400> SEQUENCE: 26
```
aactgcagct cactttaaac agtcaagacc ac                                    32

<210> SEQ ID NO 27
<211> LENGTH: 27
<212> TYPE: DNA
<213> ORGANISM: Artificial Sequence
<220> FEATURE:
<223> OTHER INFORMATION: A synthetic oligonucleotide

<400> SEQUENCE: 27
ggggtaccat ggaagctagc gccggtc                                          27

<210> SEQ ID NO 28
<211> LENGTH: 32
<212> TYPE: DNA
<213> ORGANISM: Artificial Sequence
<220> FEATURE:
<223> OTHER INFORMATION: A synthetic oligonucleotide

<400> SEQUENCE: 28
acgcgtcgac tcagcagttg atgccacact tg                                    32

<210> SEQ ID NO 29
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 29
aagtgctgct atgtccagtt ccc                                              23

<210> SEQ ID NO 30
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 30
tgttgatgcc tctcctctttt tcg                                             23

<210> SEQ ID NO 31
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 31
ccctatcacc tccattcctc ttct                                             24

<210> SEQ ID NO 32
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 32
cgtctatgcc tacgccactc c                                                21

<210> SEQ ID NO 33
<211> LENGTH: 21
<212> TYPE: DNA

```
<213> ORGANISM: Artificial Sequence
<220> FEATURE:
<223> OTHER INFORMATION: A synthetic oligonucleotide

<400> SEQUENCE: 33
acagcacaga aagtgcctga g                                              21

<210> SEQ ID NO 34
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 34
ggagcatttg atagaacccc a                                              21

<210> SEQ ID NO 35
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 35
tcgtccctga gataagcaac tac                                            23

<210> SEQ ID NO 36
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 36
cccctccgat tacccaaaa                                                 19

<210> SEQ ID NO 37
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 37
gatgcaatgg ggtaaagtag gg                                             22

<210> SEQ ID NO 38
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 38
tgatgagtag tgtggttgga ggg                                            23

<210> SEQ ID NO 39
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 39
ggagggagac tcattgctgg                                                20
```

```
<210> SEQ ID NO 40
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 40
tgtatcgggt tccgcactg                                                   19

<210> SEQ ID NO 41
<211> LENGTH: 18
<212> TYPE: DNA
<213> ORGANISM: Artificial Sequence
<220> FEATURE:
<223> OTHER INFORMATION: A synthetic oligonucleotide

<400> SEQUENCE: 41
attctgggtg attggcgg                                                    18

<210> SEQ ID NO 42
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 42
aataatgaga gttgtcggag gg                                               22

<210> SEQ ID NO 43
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 43
ttcttgccta ctgtatcctt cc                                               22

<210> SEQ ID NO 44
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 44
gctaactccg ctccatctca                                                  20

<210> SEQ ID NO 45
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 45
catcccaacg ctatcaaacc ta                                               22

<210> SEQ ID NO 46
<211> LENGTH: 22
<212> TYPE: DNA
<213> ORGANISM: Artificial Sequence
<220> FEATURE:
```

-continued

```
<223> OTHER INFORMATION: A synthetic oligonucleotide

<400> SEQUENCE: 46
ctgagacacc tccaataacc ca                                              22

<210> SEQ ID NO 47
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 47
gcaacatacg acgaaatcaa gaa                                             23

<210> SEQ ID NO 48
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 48
cgacacgaga actgtaaccc c                                               21
```

PLANT FIBER QUALITY

This application is a U.S. national stage filing under 35 U.S.C. 371 from International Application No. PCT/US2019/017038, filed on 7 Feb. 2019, and published as WO 2019/157173 A1 on 15 Aug. 2019, which claims benefit of priority to the filing date of U.S. Provisional Application Ser. No. 62/628,383, filed Feb. 9, 2018, the contents of which are specifically incorporated herein by reference in their entity.

BACKGROUND OF THE INVENTION

Plant cell walls provide the raw material for a range of important industries, including feed, food, fuel and materials (Carroll and Somerville, 2009; Somerville, 2006). The cell wall is also essential for plant growth and development as it determines plant cell size and shape and provides structural qowth support and protection against various environmental stresses (Landrein and Hamant, 2013; Le Gall et al., 2015; Malinovsky et al., 2014; Szymanski and Cosgrove, 2009). Plant cell walls are comprised largely of polysaccharides (cellulose, hemicellulose, pectin) and the polypheraolic structure, lignin (Somerville et al., 2004). In general, two major types of plant cell walls exist: first, a thin, pectin-rich primary cell wall that surrounds all dividing and expanding cells; and, second, a thickened lignin-rich secondary cell wall that provides structural support to specialized cells, such as xylem cells (Harholt et al., 2010; Scheller and Ulvskov, 2010; Somerville et al., 2004; Wang et al., 2016a). Primary wall synthesis is closely associated with cell division and expansion that determine the size of an organ/tissue, whereas secondary wall deposition is initiated during the process of cellular differentiation to contribute plant strength and overall biomass production (Keegstra, 2010; Schuetz et al., 2013). As the most prominent and load-bearing component of many plant cell walls, cellulose plays a central role in plant mechanical strength and morphogenesis (Cosgrove, 2005; Liu et al., 2016).

SUMMARY

Described herein are plants, plant seeds, and plant cells that are modified to express certain types of cellulose synthases, such as one or more of the CesA2, CesA5 and CesA6 enzymes. Such plants, plant seeds and plant cells can be cotton, flax, hemp, jute, sisal, poplar, or eucalyptus plants, plant seeds and plant cells. As illustrated herein modified plants that overexpress certain cellulose synthases (but not a CesA3, CesA7 or CesA9 gene) tend to grow taller, have increased cellulose synthesis, have more crystalline cellulose, have wider secondary cell walls, have increased biomass, and have increased mechanical strength than in a control plant without the expression cassette (e.g., a wild type or parental plant without the expression cassette).

Methods of making ad using such plants, plant seeds, and plant cells are also described herein.

DESCRIPTION OF THE FIGURES

FIG. 1A-1G illustrate enhanced seedling growth in three *Arabidopsis* plants that overexpress CesA2, CesA5 and CesA6. FIG. 1A-1 shows an image of a Western blot of CesA2 (A2) proteins expressed by nine day old (D9) seedlings Shown in FIG. 1B. FIG. 1A-2 shows an image of a Western blot of CesA5 (A5) proteins expressed by D9 seedlings Shown in FIG. 1B, FIG. 1A-3 shows an image of a Western blot of CesA6 (A6) proteins expressed by D9 seedlings shown in FIG. 1B. Numerical data provided below the blots for FIGS. 1A-1, 1A-2, and 1A3 are band density values indicated with ±SD; three WT lanes were derived from the same reference gel, and all blot analyses used the same amounts of protein samples. FIG. 1B shows images of D9 seedlings where the seedlings were generated from homozygous *Arabidopsis* seeds that were germinated and grown on ½ MS media for 9 days under dark (D9; 24 hours dark) or light (L9; 16-hours light: 8-hours dark) conditions. WT refers to wild type (Col-0); EV refers to transgenic plants transformed with empty vector; the A2, A5, A6 refer to the transgenic plants that overexpressed CesA2, CesA5 and CesA6 genes, respectively; Scale bars, 5 mm. FIG. 1C shows hypocotyl and root lengths of seedlings shown in FIG. 1B. Bars indicated means±SD (n=3 biological replicates), and at least 50 seedlings were measured in each replicate; Student's t-tests were performed between WT and transgenic plants as **P<0.01. FIG. 1D-1 graphically illustrates growth over time (days 2-7; D2-7) of hypocotyls from plant lines expressing CesA2 (A2, upper graph) compared to wild type (lower graph). FIG. 1D-2 graphically illustrates growth over time (days 2-7; D2-7) of hypocotyls from plant lines expressing CesA5 (A5, upper graph). FIG. 1D-3 graphically illustrates growth over time (days 2-7; D2-7) of hypocotyls from plant lines expressing CesA6 (A6, upper graph) compared to wild type (lower graph). Data for FIGS. 1D-1 to 1D-3 show means indicated as ±SD (n=3 biological replicates), and at least 30 seedlings were measured in each replicate. As illustrated hypocotyl lengths are longer in plant lines expressing CesA2, CesA5, and CesA6. FIG. 1E graphically illustrates hypocotyl and root lengths of *Arabidopsis* wild type (WT; Col-0) seedlings grown in dark (D) or light (L) from 3 days (D3) to 12 days (D12) after sowing. Bars indicated means±SD (n=3 biological replicates), and at least 30 plants were measured for each replicate; LSD (Least Significant Difference) test is used for multiple comparisons. Different letters above bars indicate that the means differ according to analysis of variance and LSD test (P<0.01). FIG. 1F graphically illustrates Q-PCR analyses of CesA1, CesA3, CesA6, CesA2, and CesA5 endogenous gene expression levels using total RNA extracted from hypocotyl samples illustrated in FIG. 1E. FIG. 1G graphically illustrates Q-PCR analyses of CesA1, CesA3, CesA6 CesA2, and CesA5 endogenous gene expression levels using total RNA extracted from L9 hypocotyl and root samples illustrated in FIG. 1E. GAPDH was used as the internal control and the expression value of GAPDH was defined as 100. Bars indicated means±SD (n=3 biological replicates); **P<0.01 by Student's t-test.

FIG. 2A graphically illustrates the relative expression level of Ces A2 (lighter, left bars), CesA5 (middle bars) or CesA6 (darker right bars) genes in D9 hypocotyls of plant lines that overexpress CesA2 (A2), CesA5 (A5) and CesA6 (A6) proteins. FIG. 2B graphically illustrates the relative expression level of CesA1 (lighter bars) or CesA3 (darker bars) genes in D9 hypocotyls of plant lines that overexpress CesA2 (A2), CesA5 (A5) and CesA6 (A6) proteins. FIG. 2C graphically illustrates the relative expression level of CesA8 in D9 hypocotyls of plant lines that overexpress CesA2 (A2), CesA5 (A5) and CesA6 (A6) proteins. FIG. 2D graphically illustrates the relative expression level of CesA2 (lighter, left bars), CesA5 (middle bars) or CesA6 (darker right bars) genes in L9 roots of plant lines that overexpress CesA2 (A2), CesA5 (A5) and CesA6 (A6)

proteins where the plants were grown for 9 days under light (L9; 16-hours light: 8-hours dark) conditions. FIG. 2E graphically illustrates the relative expression levels of CesA1 (lighter bars) or CesA3 (darker bars) genes in L9 roots of plant lines that overexpress CesA2 (A2), CesA5 (A5) and CesA6 (A6) proteins, FIG. 2F graphically illustrates the relative expression level of CesA8 in 19 roots of plant lines that overexpress CesA2 (A2), CesA5 (A5) and CesA6 (A6) proteins. GAPDH was used as the internal control, and the expression value of GAPDH was defined as 100; bars indicate means±SD (n=3 biological replicates); Student's t-tests were performed between WT and transgenic plants as **P<0.01 for increase or ##P<0.01 for decrease.

FIG. 3A shows images of GFP-CesA3 dynamic movements in epidermal cells of D3 hypocotyls that overexpress CesA2 (A2), CesA5 (A5) and CesA6 (A6) proteins. Scale bar, 5 µm, FIG. 3B graphically illustrates GFP-CesA3 particle density (spot/µm$^2$) in plant lines that overexpress CesA2 (A2), CesA5 (A5) and CesA6 (A6) proteins. FIG. 3C graphically illustrates GFP-CesA3 mean velocity (nm/min) in plant lines that overexpress Ces A2 (A2), CesA5 (A5) and CesA6 (A6) proteins. FIG. 3D graphically illustrates the velocity distribution of GFP-CesA3 particles in wild type plants (light first bar) compared to plant lines that overexpress CesA2 (A2; light second bar), CesA5 (A5; darker, third bar) and CesA6 (A6; darkest, fourth bar) proteins. Data indicated are the means±SD; 578-1257 CesA3 particles were detected with n≥4 cells from four different seedlings for each genotype; **P<0.01 by Student's t-test.

FIG. 4A graphically illustrates absolute crystalline cellulose contents of D9 seedlings of plant lines that overexpress CesA2 (A2), CesA5 (A5) and CesA6 (A6) proteins. FIG. 4B graphically illustrates absolute crystalline cellulose contents of L9 seedlings of plant lines that overexpress CesA2 (A2), Ces A5 (A5) and CesA6 (A6) proteins. For FIGS. 4A and 4B, the bars indicate means±SD for n=3 biological replicates, where 100 seedlings were measured for each replicate; *P<0.05 and **P<0.01 by Student's t-test; the differences in increased rates (%) were calculated by subtraction of values between overexpression transgenic lines and wild type (WT), divided by WT, FIG. 4C illustrates reassembly of macrofibrils from purified cellulose using atomic force microscopy (AFM). The relative average particle size (width D9 length) was calculated from randomly selecting ten particles in each image from three biological replicates. FIG. 4D graphically illustrates crystalline cellulose levels (percent dry matter) in D9 seedlings from plant lines that overexpress CesA2 (A2), CesA5 (A5) and CesA6 (A6) proteins. FIG. 4E graphically illustrates pectin levels (percent dry matter) in D9 seedlings from plant lines that overexpress CesA2 (A2), CesA5 (A5) and CesA6 (A6) proteins. FIG. 4F graphically illustrates hemicellulose levels (percent dry matter) in D9 seedlings from plant lines that overexpress CesA2 (A2), CesA5 (A5) and CesA6 (A6) proteins. FIG. 4G graphically illustrates the monosaccharide composition in the total wall polysaccharides of D9 seedlings from plant lines that overexpress CesA2 (A2), CesA5 (A5) and CesA6 (A6) proteins as detected by gas chromatography-mass spectrometer (GC-MS); Rha, rhamnose; Fuc, fucose; Ara, arabinose; Xyl, xylose; Man, mannose; Glu, glucose; Gal, galactose; Bars indicated means±SD (n=3 biological replicates); *P<0.05 and **P<0.01 by Student's t-test.

FIG. 5A graphically illustrates ral cell lengths of basal longest epidermal cells of D9 hypocotyls of plant lines that overexpress CesA2 (A2), CesA5 (A5) and CesA6 (A6) proteins. FIG. 5B graphically illustrates cell number of L9 root apical meristems of plant lines that overexpress CesA2 (A2), CesA5 (A5) and CesA6 (A6) proteins. For FIGS. 5A-5B, bars indicate means±SD for n=3 biological replicates, where at least 30 seedlings were measured for each replicate; **P<0.01 by Student's t-tests. FIG. 5C shows confocal laser scanning microscopy images of basal longest epidermal cells of D4 hypocotyls of plant lines that overexpress CesA2 (A2), CesA5 (A5) and Ces A6 (A6) proteins as visualized using propidium iodide (PI) staining (red-fluorescent). Arrowheads indicate a single cell to illustrate cell lengths; scale bars, 100 µm. FIG. 5D illustrates typical expression of the G2/M-specific marker proAtCYCB1; 1:AtCYCB1; 1-GFP (green) of plant cell cycle in the root apical meristem of plant lines that overexpress CesA2 (A2), CesA5 (A5) and CesA6 (A6) proteins as visualized using PI staining (red-fluorescent). Scale bars, 75 µm. FIG. 5E-5I illustrate altered expression of genes associated with cell growth by RNA sequencing. FIG. 5E illustrates numbers of differentially expressed genes (DEGs) identified by applying statistical tests (P<0.001) for the genes between D6 transgenic (A2, A5 and A6) and WT seedlings. Blue, green and yellow represent CesA2, CesA5 and CesA6 over-expressing seedlings, respectively; Two biological replicates for each sample, FIG. 5F graphically illustrates the numbers of up-regulated and down-regulated genes in each over-expression line as shown in FIG. 5E. FIG. 5G graphically illustrates Gene Ontology-Biological Process terms (GO-BP terms) of all DEGs in FIG. 5E for A2 transgenic plants lines (overexpressing CesA2). FIG. 5H graphically illustrates Gene Ontology-Biological Process terms (GO-BP terms) of all DEGs in FIG. 5E for A5 transgenic plants lines (overexpressing CesA5). FIG. 5I graphically illustrates Gene Ontology-Biological Process terms (GO-BP terms) of all DEGs in FIG. 5E for A6 transgenic plants lines (overexpressing CesA6). The enrichment analyses of GO-BP terms relative to expectations were performed using a weighted method in combination with Fisher's exact test.

FIG. 6A illustrates plant phenotypes at the flowering stage of plant genotypes for lines that overexpress CesA2 (A2), CesA5 (A5), and CesA6 (A6) compared to wild type. Scale bars, 15 mm. FIG. 6B graphically illustrates plant height (cm) of plant lines that overexpress CesA2 (A2), CesA5 (A5), and CesA6 (A6). FIG. 6C graphically illustrates dry weight (g) of 7-week-old mature plants of plant lines that overexpress CesA2 (A2), CesA5 (A5), and CesA6 (A6). Bars indicated means±SD (n=3 biological replicates), and at least 30 plants were measured for each replicate; **P<0.01 by Student's t-test. FIG. 6D shows transverse sections of 1st internode stems at the bolting stage of plant lines that overexpress CesA2 (A2), CesA5 (A5), and CesA6 (A6) compared to wild type using epilluorescence microscopy and calcofluor staining to visualize plant structures. Scale bars, 50 µm. FIG. 6E graphically illustrates absolute; crystalline cellulose contents per plant in 7-week-old inflorescence stems of mature plants of plant lines that overexpress CesA2 (A2), CesA5 (A5), and CesA6

(A6) compared to wild type plants. Bars indicated means±SD (n=3 biological replicates); **P<0.01 by Student's t-test.

Figure 7A:
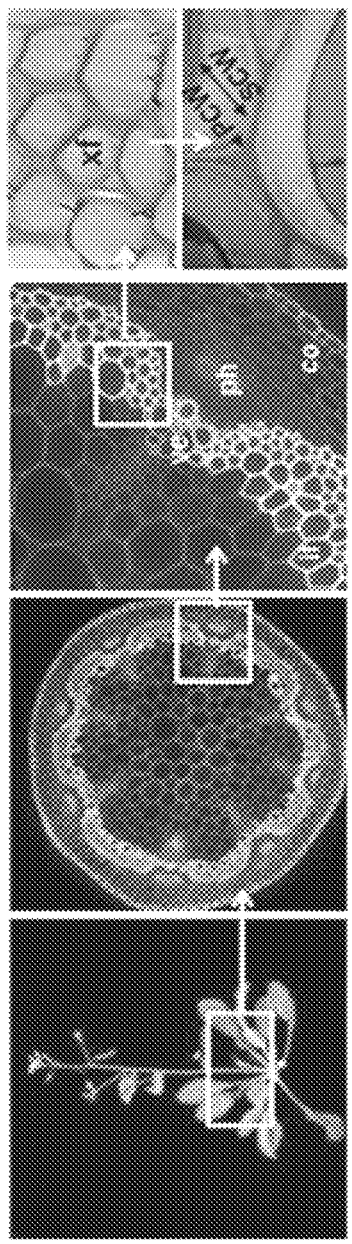
Figure 7B:
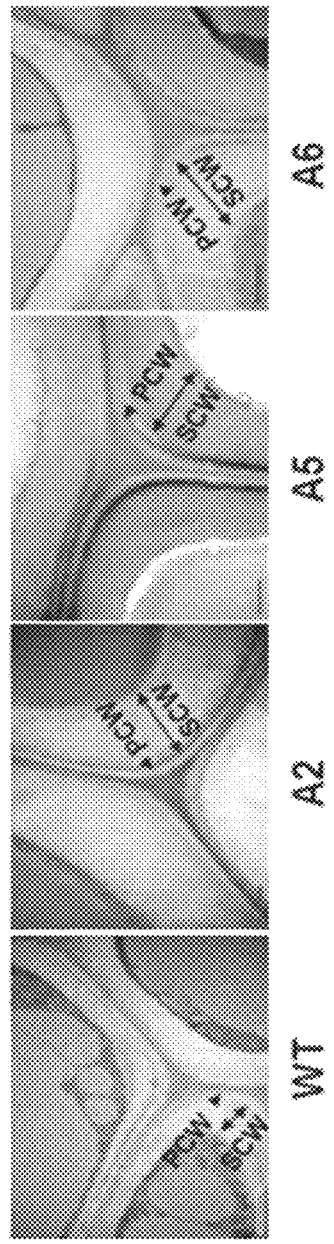
Figure 7C:
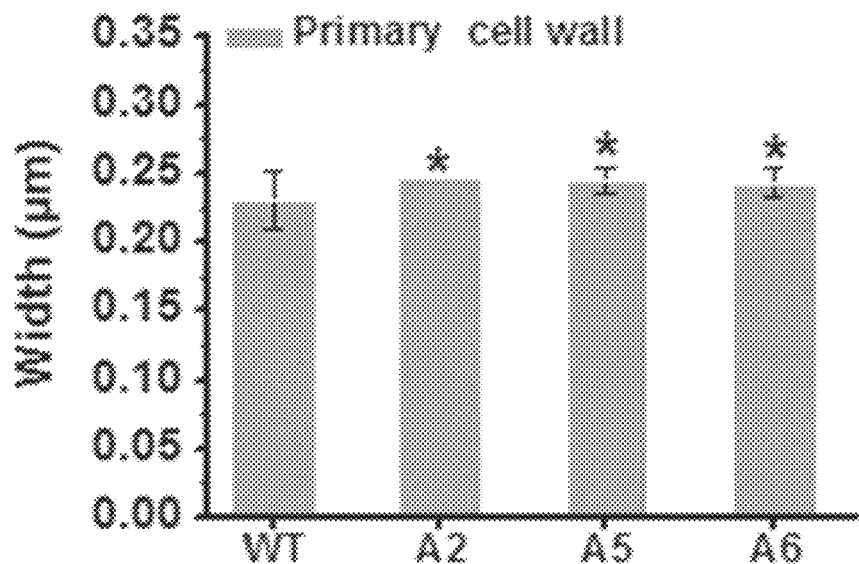
Figure 7D:
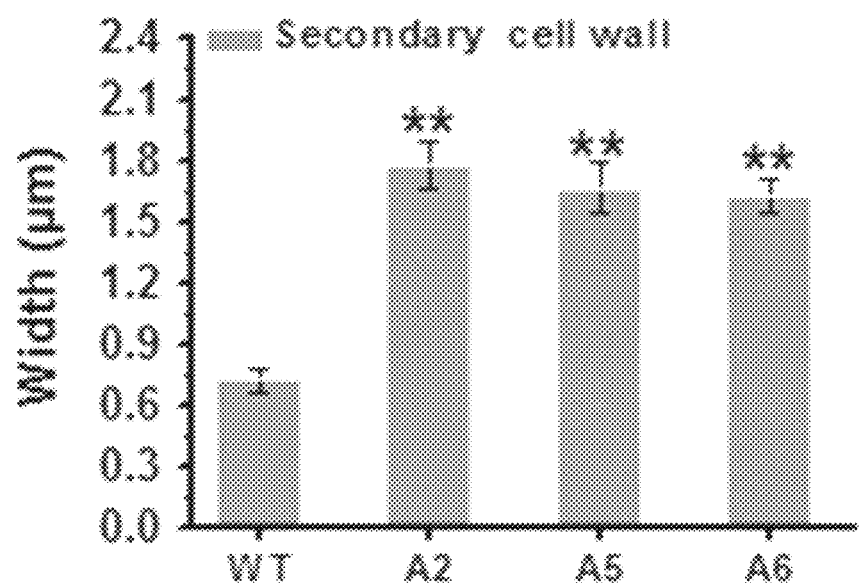
Figure 7E:
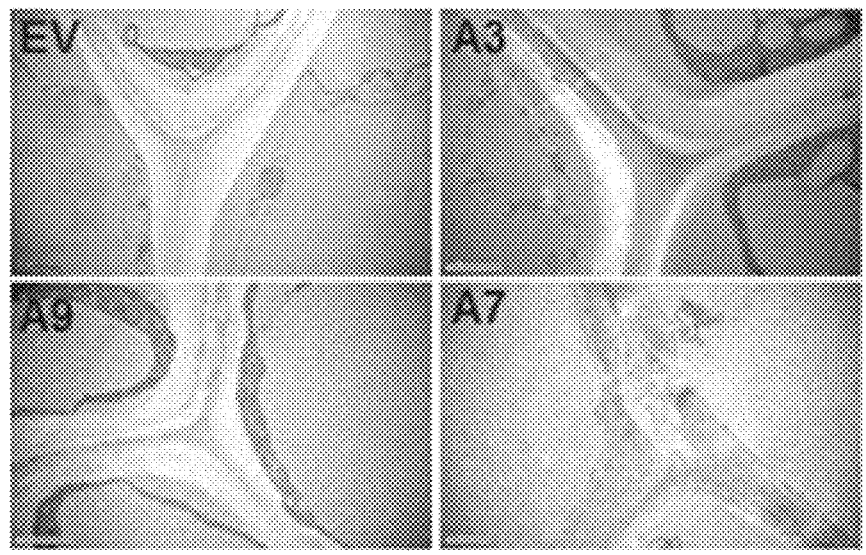
Figure 7F:
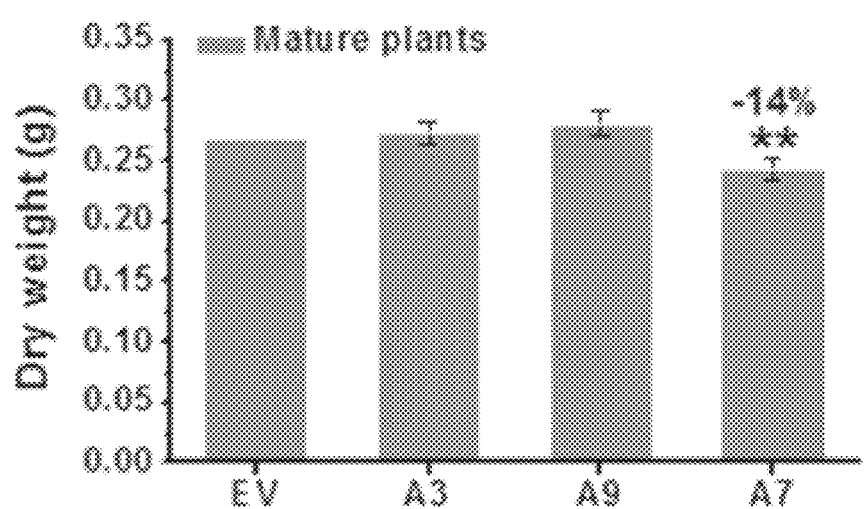

FIG. 7A-7F illustrate enhanced secondary cell wall deposition in plant lines overexpressing CesA2, CesA5 and CesA6. FIG. 7A shows sclerenchyma cell walls in the 1st internode stem of 7-week-old *Arabidopsis* plants using transmission electron microscopy (TEM). PCW, primary cell wall; SCW, secondary cell wall; co, cortex; ph, phloem; ye, vessel; xf, xylary fibre; if, interfascicular fibre. FIG. 7B shows cell walls in xylary fiber tissues of plants that over-express CesA2 (A2), CesA5 (A5), and CesA6 (A6). Scale bars, 1 µm. FIG. 7C graphically illustrates the width of the primary cell wall in plant lines overexpressing CesA2, CesA5 and CesA6. FIG. 7D graphically illustrates the width of the secondary cell walls of plant lines overexpressing CesA2, CesA5 and CesA6. Bars indicate means±SD (n=3 biological replicates); at least 60 cell walls were measured for each replicate; *P<0.05 and P<0.01 by Student's t-test. FIG. 7E shows TEM images of cell walls in xylary fibre tissues from transgenic plant lines overexpressing CesA3 (A3), CesA7 (A7), and CesA9 (A9). Scale bars, 1 µm. FIG. 7F graphically illustrates the dry weight of seven-week-old inflorescence stems of mature transgenic plant lines overexpressirtg CesA3 (A3), CesA7 (A7), and CesA9 (A9). Bars indicate means±SD (n=3 biological replicates), and at least 30 plants were measured for each replicate; Student's t-test as P<0.01 between empty vector (EV) and over-expression lines.

Figure 8A:
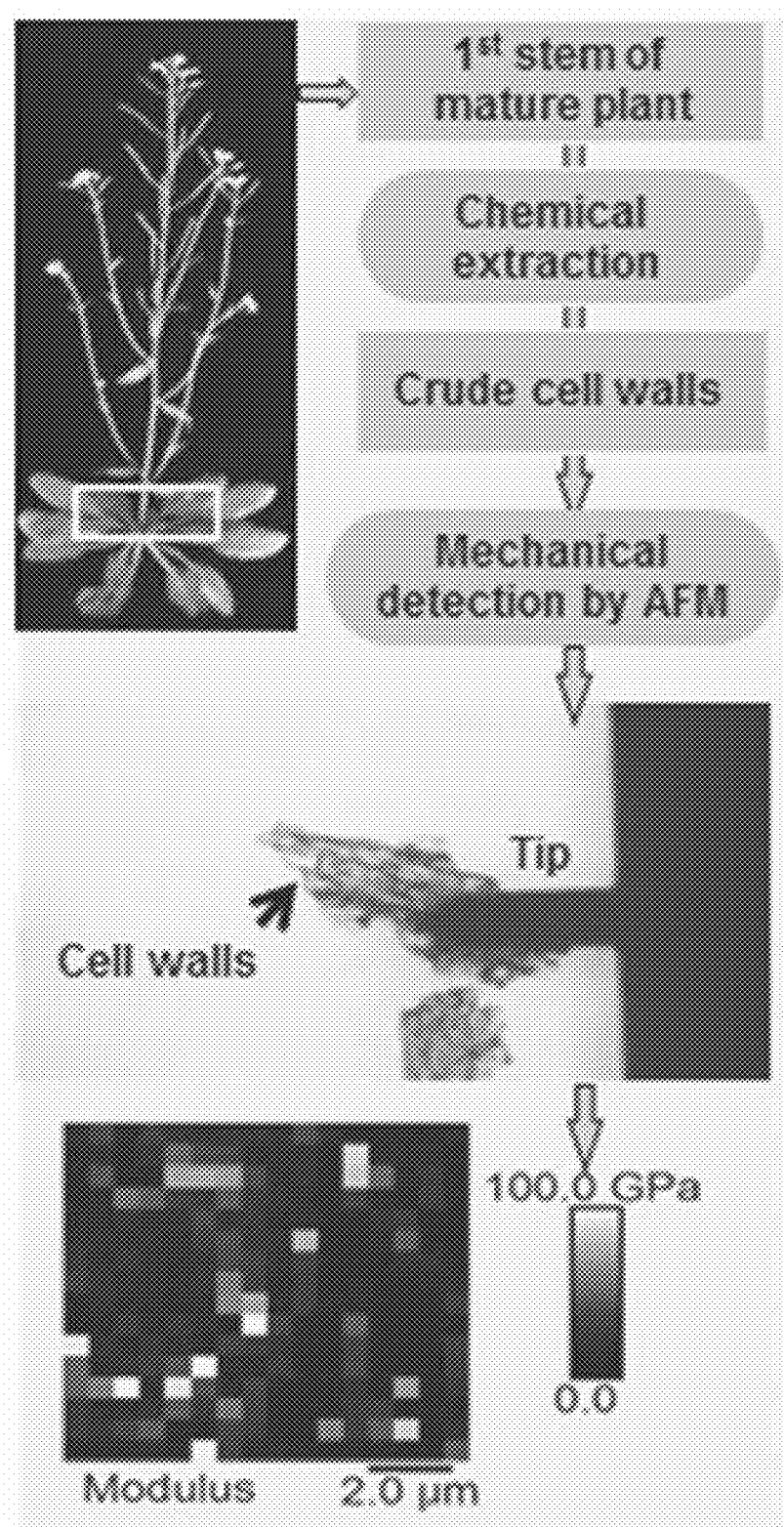
Figure 8B:
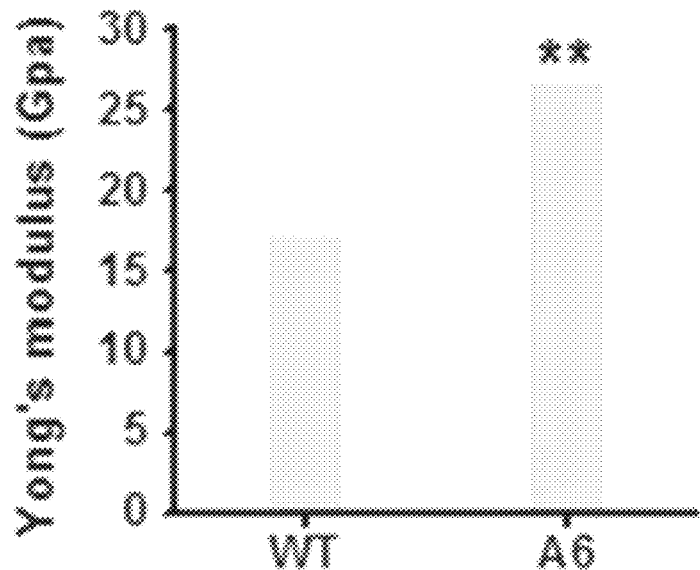
Figure 8C:
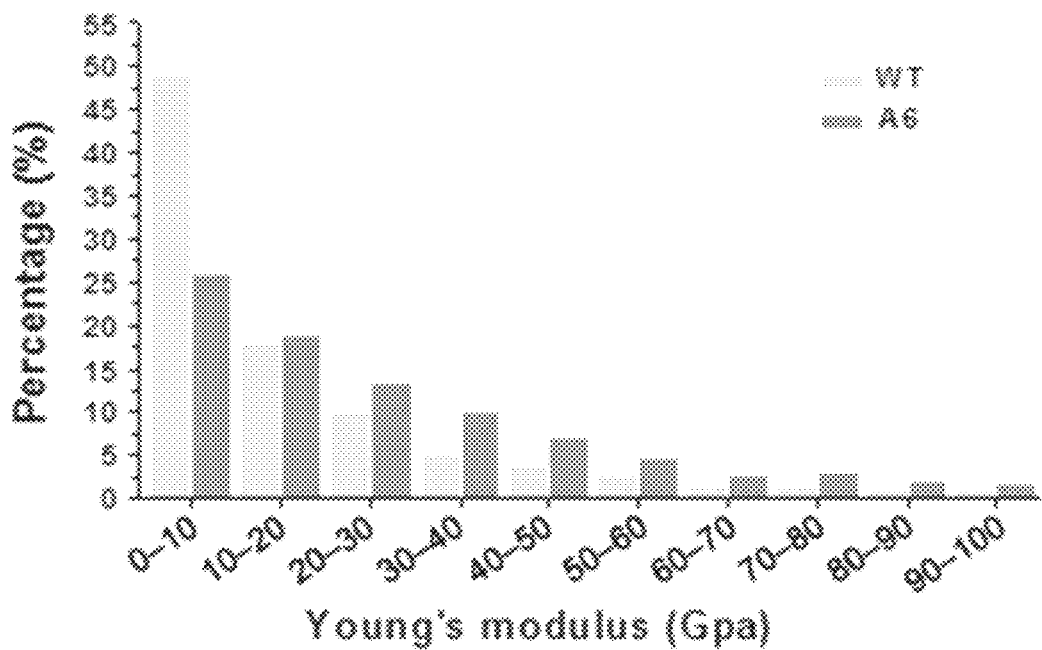

FIG. 8A-8C illustrate increased mechanical strength of reassembled crude cell walls in 1st internode stems of the plant lines overexpressing CesA6. FIG. 8A is a schematic flow diagram illustrating mechanical force measurements (Young's modulus) of reassembled crude cell walls in 1st internode stems of 7-week-old plants using atomic force microscopy (AFM), FIG. 8B graphically illustrates the mean values of Young's modulus of crude cell walls from transgenic plants that overexpress CesA6. FIG. 8C graphically illustrates the distribution of Young's modulus of crude cell walls from transgenic plants that overexpress CesA6. Bars indicated means of two biological replicates; 30 cell segments (n=30) were measured for each replicate; *P<0.05 and **P<0.01 by Wilcoxon test.

DETAILED DESCRIPTION

As described herein, increasing the expression levels of three primary cell wall cellulose synthase (CesA) genes (encoding CesA2, CesA5, and CesA6 enzymes), but not the CesA3, CesA9 or secondary cell wall CesA7 gene, can increase cellulose production within the cell walls of transgenic plant lines, as compared with wild-type plants that do not overexpress the CesA2, CesA5, and CesA6 enzymes.

Cellulose Synthases

Cellulose is composed of beta-1,4-linked glucan chains that interact with one another via hydrogen bonds to form paracrystalline microfibrils (Peng et al., 2002; Schneider et al., 2016; Somerville et al., 2004). As the most prominent and load-bearing component of many plant cell walls, cellulose plays a central role in plant mechanical strength and morphogenesis (Cosgrove, 2005; Liu et at, 2016). In most land plants, cellulose is synthesized by a large cellulose synthase (CesA) complex at the plasma membrane (Schneider et al 2016). In *Arabidopsis*, CesA1, CesA3 and one of four CesA6-like proteins (CesA6, CesA2, CesA5 and CesA9) are involved in primary wall cellulose synthesis, whereas CesA4, CesA7 and CesA8 are essential isoforms for secondary wall cellulose synthesis (Desprez et al., 2007; McFarlane et al., 2014; Persson et al., 2007; Taylor et al., 2003). Furthermore, CesA1 and CesA3 genes are essential for plant growth because mutation of each gene leads to lethality (Persson et al., 2007).

By comparison, mutations in any one of the CesA6-like genes (expressing CesA6, CesA2, CesA5 and CesA9 proteins) cause only mild growth phenotypes (Cann-Delgado et 2003; Scheible et al., 2001). However, cesa5 cesa6 double mutants are seedling lethal (Desprez et al., 2007), and cesa2 cesa6 cesa9 triple mutants are gamete lethal, probably due to CesA9 tissue-specific floral expression (Persson et al., 2007). CesA2 or CesA5 expression driven by a Cestio promoter onlypartially complements cesa6 mutant phenotypes (Desprez et al., 2007; Persson et al., 2007).

Because cellulose is important for plant biomass formation, increased production of this polymer in a plant is highly desirable, and many efforts have been undertaken to increase cellulose synthesis. However, even though CesA family genes were identified over two decades ago in some plants (Arioli et al., 1998; Pear et al, 1996), genetic manipulation of its members to enhance cellulose production has remained difficult. For instance, overexpression of CesA genes (mainly secondary wall CesAs) has not led to improved plant growth (Joshi et al., 2011; Li et al., 2017; Tan et al., 2015; Wang et al, 2016b).

However, as described herein, the inventors show that overexpression of any of the three CesA6-like genes CesA2, CesA5 or CesA6 can increase cellulose production in plants *Arabidopsis*. The overexpressing transgenic lines showed increased cell expansion and division, as well as enhanced secondary cell wall deposition. Hence, alterations in the expression of certain primary wall CesA genes (but not others) may enhance cellulose synthesis and biomass production in plants. An example of an *Arabidopsis thaliana* CesA2 protein is provided below as SEQ NO:1.

```
  1    MNTGGRLIAG  SHNRNEFVLI  NADESARIRS  VQELSGQTCQ
 41    ICGDEIELTV  SSELFVACNE  CAFPVCRPCY  EYERREGNQA
 81    CPQCKTRYKR  IKGSPRVDGD  DEEEEDIDDL  EYEFDHGMDP
121    EHAAEAALSS  RLNTGRGGLD  SAPPGSQIPL  LTYCDEDADM
161    YSDRHALIVP  PSTGYGNRVY  PAPFTDSSAP  PQARSMVPQK
201    DIAEYGYGSV  AWKDRMEVWK  RRQGEKLQVI  KHEGGNNGRG
241    SNDDDELDDP  DMPMMDEGRQ  PLSRKLPIRS  SRINPYRMLI
281    LCRLAILGLF  FHYRILHPVN  DAYGLWLTSV  ICEIWFAVSW
321    ILDQFPKWYP  IERETYLDRL  SLRYEKEGKP  SGLAPVDVFV
361    STVDLPKEPP  LITANTVLSI  LAVDYPVDKV  ACYVSDDGAA
401    MLTFEALSDT  AEFARKWVPF  CKKFNIEPRA  PEWYFSQKMD
441    YLKNKVHPAF  VRERRAMKRD  YEEFKVKINA  LVATAQKVPE
481    EGWTMQDGTP  WPGNNVRDHP  GMIQVFLGHS  GVRDTDGNEL
521    PRLVYVSREK  RPGFDHHKKA  GAMNSLIRVS  AVLSNAPYLL
561    NVDCDHYINN  SKAIRESMCF  MMDPQSGKKV  CYVQFPQRFD
601    GIDRHDRYSN  RNVVFFDINM  KGLDGTQGPI  YVGTGCVFRR
641    QALYGFDAPK  KKKPPGKTCN  CWPKWCCLCC  GLRKKSKTKA
681    KDKKTNTKET  SKQIHALENV  DEGVIVPVSN  VEKRSEATQL
```

-continued

```
 721  KLEKKFGQSP VFVASAVLQN GGVPRNASPA CLLREAIQVI
 761  SCGYEDKTEW GKEIGWIYGS VTEDILTGFK MHCHGWRSVY
 801  CMPKRAAFKG SAPINLSDRL HQVLRWALGS VEIFLSRHCP
 841  IWYGYGGGLK WLERFSYINS VVYPWTLSPL IVYCSLPAVC
 881  LLTGKFIVPE ISNYAGILFM LMFISIAVTG ILEMQWGGVG
 921  IDDWWRNEQF WVIGGASSHL FALFQGLLKV LAGVNTNFTV
1001  TSKAADDGAF SELYIFKWTT LLIPPTTLLI INIIGVIVGV
1041  SDAISNGYDS WGPLFGRLFF ALWVIVHLYP FLKGMLGKQD
1081  KMPTIIVVWS ILLASILTLL WVRVNPFVAK GGPVLEICGL
1121  NCGV
```

A nucleotide sequence encoding the *Arabidopsis thaliana* CesA2 protein with SEQ ID NO:1 is provided below as SEQ ID NO:2.

```
   1  ATGAATACTG GTGGTCGGCT CATTGGTGGC TCTCACAACA
  41  GAAACGAATT CGTTCTCATT AACGCCGATG AGAGTGCCAG
  81  AATACGATCA GTACAAGAAC TGAGTGGGCA AACATGTCAA
 121  ATCTGTGGAG ATGAAATCGA ATTAACGGTT AGCAGTGAGC
 161  TCTTTGTTGC TTGCAACGAA TGCGCATTCC CGGTTTGTAG
 201  ACCATGCTAT GAGTATGAAC GTAGAGAAGG AAATCAAGCT
 241  TGTCCTCAGT GCAAAACTCG ATACAAAAGG ATTAAAGGTA
 281  GTCCACGGGT TGATGGAGAT GATGAAGAAG AAGAAGACAT
 321  TGATGATCTT GAGTATGAGT TTGATCATGG GATGGACCCT
 361  GAACATGCCG CTGAAGCCGC ACTCTCTTCA CGCCTTAACA
 401  CCGGTCGTGG TGGATTGGAT TCAGCTCCAC CTGGCTCTCA
 441  GATTCCTCTT TTGACTTATT GTGATGAAGA TGCTGATATG
 481  TATTCTGATC GTCATGCTCT TATCGTGCCT CCTTCAACGG
 521  GATATGGGAA TCGCGTCTAT CCTGCACCGT TTACAGATTC
 561  TTCTGCACCT CCACAGGCGA GATCAATGGT TCCTCAGAAA
 601  GATATTGCGG AATATGGTTA TGGAAGTGTT GCTTGGAAGG
 641  ACCGTATGGA AGTTTGGAAG AGACGACAAG GCGAAAAGCT
 681  TCAAGTCATT AAGCATGAAG GAGGAAACAA TGGTCGAGGT
 721  TCCAATGATG ACGACGAACT AGATGATCCT GACATGCCTA
 761  TGATGGATGA AGGAAGACAA CCTCTCTCAA GAAAGCTACC
 801  TATTCGTTCA AGCAGAATAA ATCCTTACAG GATGTTAATT
 841  CTGTGTCGCC TCGCGATTCT TGGTCTTTTC TTTCATTATA
 881  GAATTCTCCA TCCAGTCAAT GATGCATATG GATTATGGTT
 921  AACGTCAGTT ATATGCGAGA TATGGTTTGC AGTGTCTTGG
 961  ATTCTTGATC AATTCCCCAA ATGGTATCCT ATAGAACGTG
1001  AAACATACCT CGATAGACTC TCTCAGGT ACGAGAAGGA
1041  AGGAAAACCG TCAGGATTAG CACCTGTTGA TGTTTTTGTT
1081  AGTACAGTGG ATCCGTTGAA AGAGCCACCC TTGATTACAG
1121  CAAACACAGT TCTTTCCATT CTAGCAGTTG ATTATCCTGT
1161  GGATAAGGTT GCGTGTTATG TATCAGACGA TGGTGCAGCT
1201  ATGCTTACAT TTGAAGCTCT CTCTGATAGA GCTGAGTTTG
1241  CTAGAAAATG GGTTCCTTTT TGTAAGAAGT TTAATATCGA
1281  GCCACGAGCT CCTGAGTGGT ATTTTTCTCA GAAGATGGAT
1321  TACCTGAAGA ACAAAGTTCA TCCTGGTTTT GTCAGGGAAC
1361  GTCGTGCTAT GAAGAGAGAT TATGAGGAGT TTAAAGTGAA
1401  GATAAATGCA CTGGTTGCTA CTGCACAGAA AGTGCCTGAG
1441  GAAGGTTGGA CTATGCAAGA TGGAACTCCT TGGCCTGGAA
1481  ACAACGTCCG TGACCATCCT GGAATGATTC AGGTGTTCTT
1521  GGGTCATAGT GGAGTTCGTG ATACGGATGG TAATGAGTTA
1561  CCACGTCTAG TGTATGTTTC TCGTGAGAAG CGGCCTGGAT
1601  TTGATCACCA CAAGAAAGCT GGAGCTATGA ATTCCTTGAT
1641  CCGAGTCTCT GCTGTTCTAT CAAACGCTCC TTACCTTCTT
1681  AATGTCGATT GTGATCACTA CATCAACAAC AGCAAAGCAA
1721  TTAGAGAATC TATGTGTTTC ATGATGGACC CGCAATCGGG
1761  AAAGAAAGTT TGTTATGTTC AGTTTCCGCA GAGATTTGAT
1801  GGGATTGATA GACATGATAG TACTCAAAC CGTAACGTTG
1841  TGTTCTTTGA TATTAACATG AAAGGTCTTG ATGGGATACA
1881  AGGACCGATA TATGTCGGGA CAGGTTGTGT GTTTAGAAGA
1921  CAGGCTCTTT ATGGTTTTGA TGCACCAAAG AAGAAGAAAC
1961  CACCAGGCAA AACCTGTAAC TGTTGGCCTA ATGGTGTTG
2001  TTTGTGTTGT GGGTTGAGAA AGAAGAGTAA AACGAAAGCC
2041  AAAGATAAGA AAACTAACAC TAAAGAGACT TCAAAGCAGA
2081  TTCATGCGCT AGAGAATGTC GACGAAGGTG TTATCGTCCC
2121  AGTGTCAAAT GTTGAGAAGA GATCTGAAGC AACACAATTG
2161  AAATTGGAGA AGAAGTTTGG ACAATCTCCG GTTTTCGTTG
2201  CCTCTGCTGT TCTACAGAAC GGTGGAGTTC CCCGTAACGC
2241  AAGCCCCGCA TGTTTGTTAA GAGAAGCCAT TCAAGTTATT
2281  AGCTGCGGGT ACGAAGATAA AACCGAATGG GGAAAAGAGA
2321  TCGGGTGGAT TTATGGATCG GTGACTGAAG ATATCCTGAC
2361  GGGTTTCAAG ATGCATTGCC ATGGATGGAG ATCTGTGTAC
2401  TGTATGCCTA AGCGTGCAGC TTTTAAAGGA TCTGCTCCTA
2441  TTAACTTGTC AGATCGTCTT CATCAAGTTC TACGTTGGGC
2481  TCTTGGCTCT GTAGAGATTT CTTGAGCAG ACATTGTCCG
2521  ATATGGTATG GTTATGGTGG TGGTTTAAAA TGGTTGGAGA
2561  GATTCTCTTA CATCAACTCT GTCGTCTATC CTTGGACTTC
2601  ACTTCCATTG ATCGTCTATT GTTCTCTCCC CGCGGTTTGT
2641  TTACTCACAG GAAAATTCAT CGTCCCTGAG ATAAGCAACT
2681  ACGCAGGTAT ACTCTTCATG CTCATGTTCA TATCCATAGC
```

```
2721  AGTAACTGGA ATCCTCGAAA TGCAATGGGG AGGTGTCGGA
2761  ATCGATGATT GGTGGAGAAA CGAGCAGTTT TGGGTAATCG
2801  GAGGGGCCTC CTCGCATCTA TTTGCTCTGT TTCAAGGTTT
2841  GCTCAAAGTT CTAGCCGGAG TTAACACGAA TTTCACAGTC
2881  ACTTCAAAAG CAGCAGACGA TGGAGCTTTC TCTGAGCTTT
2921  ACATCTTCAA GTGGACAACT TTGTTGATTC CTCCGACAAC
2961  ACTTCTGATC ATTAACATCA TTGGAGTTAT TGTCGGCGTT
3001  TCTGATGCCA TTAGCAATGG CTATGACTCA TGGGGACCTC
3041  TCTTTGGGAG ACTTTTCTTC GCTCTTTGGG TCATTGTTCA
3081  TTTATACCCA TTCCTCAAGG GAATGCTTGG GAAGCAAGAC
3121  AAAATGCCTA CGATTATTGT GGTCTGGTCT ATTCTTCTAG
3161  CTTCGATCTT GACACTCTTG TGGGTCAGAG TTAACCCGTT
3201  TGTGGCTAAA GGGGGACCAG TGTTGGAGAT CTGTGGTCTG
3241  AATTGTGGAA ACTAA
```

An example of an *Arabidopsis thaliana* CesA5 protein is provided below as SEQ ID NO:3.

```
  1  MNTGGRLIAG SHNRNEFVLI NADESARIRS VEELSGQTCQ
 41  ICGDEIELSV DGESFVACNE CAFPVCRPCY EYERREGNQS
 81  CPQCKTRYKR IKGSPRVEGD EEDDGIDDLD FEFDYSRSGL
121  ESETFSRRNS EFDLASAPPG SQIPLLTYGE EDVEISSDSH
161  ALIVSPSPGH IHRVHQPHFP DPAAHPRPMV PQKDLAVYGY
201  GSVAWKDRME EWKREQNEKY QVVKHDGDSS LGDGDDADIP
241  MMDEGRQPLS RKVPIKSSKI NPYRMLIVLR LVILGLFFHY
281  RILHPVNDAY ALWLISVICE IWFAVSWVLD QFPKWYPIER
321  ETYLDRLSLR YEKEGKPSEL AGVDVFVSTV DPMKEPPLIT
361  ANTVLSILAV DYPVDRVACY VSDDGAAMLT FEALSETAEF
401  ARKWVPFCKK YTIEPRAPEW YFCHKMDYLK NKVHPAFVRE
441  RRAMKRDYEE FKVKINALVA TAQKVPEEGW TMQDGTPWPG
481  NNVRDHPGMI QVFLGNNGVR DVENNELPRL VYVSREKRPG
521  FDHHKKAGAM NSLIRVSGVL SNAPYLLNVD CDHYINNSKA
561  LREAMCFMMD PQSGKKICYV QFPQRFDGID KSDRYSNRNV
601  VFFDINMKGL DGLQGPIYVG TGCVFRRQAL YGFDAPKKKK
641  TKRMTCNCWP KWCLFCCGLR KNRKSKTTDK KKKNREASKQ
681  IHALENIEEG TKGTNDAAKS PEAAQLKLEK KFGQSPVFVA
721  SAGMENGGLA RNASPASLLR EADQVISCGY EDKTEWGKEI
761  GWIYGSVTED ILTGFKMHSH GWRSVYCTPK IPAFKGSAPI
801  NLSDRLHQVL RWALGSVEIF LSRHCPIWYG YGGGLKWLER
841  LSYINSVVYP WTSIPLLVYC SLPAICLLTG KFIVPEISNY
881  ASILFMALFG SIAVTGILEM QWGKVGIDDW WRNEQFWVLG
921  GVSAHLFALF QGLLKVLAGV ETNFTVTSKA ADDGEFSELY
961  IFKWTSLLIP PTTLLIINVI GVIVGISDAI SNGYDSWGPL
1001 FGRLFFAFWV ILHLYPFLKG LLGKQDRMPT IILVWSILLA
1041 SILTLLWVRV NPFVAKGGPI LEICGLDCL
```

A nucleotide sequence encoding the *Arabidopsis thaliana* CesA5 protein with SEQ ID NO:3 is provided below as SEQ ID NO:4.

```
   1  ATGAATACTG GTGGTCGGCT CATCGCTGGT TCTCACAATA
  41  GGAATGAGTT CGTGTTGATT AATGCAGACG AGAGTGCCAG
  81  AATTAGATCA GTGGAAGAAC TAAGTGGACA AACATGTCAA
 121  ATCTGTGGAG ATGAGATTGA GCTAAGTGTT GATGGAGAGT
 161  CTTTTGTGGG ATGTAATGAA TGTGCTTTCC CTGTCTGTAG
 201  ACCTTGCTAT GAGTATGAGA GACGAGAAGG AAACCAATCT
 281  TGTCCTCAGT GCAAAACTCG TTACAAGCGC ATCAAAGGAA
 321  GTCCAAGGGT TGAAGGAGAT GAGGAGGATG ATGGAATTGA
 361  TGATCTTGAT TTTGAGTTTG ATTATAGTAG GAGTGGCCTT
 401  GAATCTGAAA CTTTCTCTCG CCGCAACTCG GAGTTTGATT
 441  TGGCCTCTGC TCCACCTGGC TCACAGATTC CTTTGTTAAC
 521  TTATGGAGAG GAGGACGTTG AAATTTCTTC TGATAGTCAT
 561  GCTCTCATTG TTTCTCCATC ACCTGGCCAT ATCCATAGGG
 601  TTCATCAACC TCATTTTCCT GACCCCGCTG CACATCCAAG
 641  ACCAATGGTA CCTCAGAAAG ACCTTGCGGT CTATGGATAT
 681  GGAAGTGTTG CGTGGAAGGA TCGTATGGAG GAGTGGAAGA
 721  GAAAGGAGAA CGAAAAATAT CAGGTGGTTA AACATGATGG
 761  AGATTCTAGT CTTGGAGACG GAGATGATGC TGATATTCCT
 801  ATGATGGATG AGGGAAGGCA GGCTTTGTCT AGGAAAGTAC
 841  CGATAAAGTC GAGCAAAATA AATCCGTAGA GGATGCTAAT
 881  TGTTCTGCGT CTTGTGATTC TCGGTCTCTT TTTCCATTAC
 921  CGTATTCTTC ACCCCGTCAA TGATGCTTAC GCCTTGTGGC
 961  TAATTTCTGT GATATGCGAA ATATGGTTTG CGGTTTCATG
1041  GGTTCTTGAT CAGTTCCCTA AATGGTATCC TATAGAAAGA
1081  GAGACATACT TGGACAGGCT CTCATTGAGG TACGAAAAAG
1121  AAGGGAAACC ATCTGAACTA GCTGGTGTTG ATGTTTTTGT
1161  GAGTACAGTG GATCCGATGA AAGAGGCTCC GCTTATTACA
1201  GCAAACACTG TTCTGTCTAT TCTTGGGGTT GATTATCCGG
1241  TAGACAGAGT TGCCTGTTAT GTTTCTGATG ATGGTGCTGG
1281  TATGCTTACT TTTGAAGCCC TTTCAGAAAC AGCAGAGTTT
1321  GCTAGGAAAT GGGTTCCTTT CTGTAAGAAA TACACTATCG
1361  AGGCACGAGG TCCCGAATGG TATTTTTGGC ACAAGATGGA
1401  TTATTTAAAG AATAAAGTTC ACCCTGCATT TGTTAGGGAA
1441  CGGCGAGCCA TGAAGAGAGA TTATGAAGAA TTGAAGGTTA
```

```
1481 AGATCAATGC TTTAGTTGCG AGTGCACAGA AAGTGGCTGA

1521 AGAAGGTTGG ACTATGCAAG AGGGTACTCC TTGGGCCGGT

1561 AATAACGTGC GAGATCACCC TGGCATGATC CAGGTATTCC

1601 TTGGAAATAA CGGTGTCCGC GATGTAGAAA CAACGAGTT

1641 GCCTCGGCTG GTTTATGTTT CTCGTGAGAA GAGACCCGGA

1681 TTTGACCATC ACAAGAAGGC TGGAGCCATG AACTCCCTGA

1721 TACGAGTCTC TGGAGTTCTA TCAAATGCTC CTTATCTTCT

1761 AAATGTCGAT TGTGATCACT ACATCAATAA TAGCAAAGCT

1801 CTTAGAGAAG CAATGTGTTT CATGATGGAT CCTCAGTCGG

1841 GAAAGAAAAT TTGTTATGTT CAATTCCCTC AAAGATTCGA

1881 TGGGATTGAT AAAAGTGACA GATACTCTAA TCGTAATGTT

1921 GTATTCTTCG ATATTAATAT GAAAGGTTTG GATGGATTAC

1961 AAGGGCCTAT ATACGTGGGA ACCGGGTGTG TTTTTAGGAG

2001 ACAAGCACTT TATGGATTTG ATGCGCCAAA AAAGAAGAAG

2041 ACTAAGCGTA TGACTTGCAA TTGCTGGCCT AAGTGGTGTT

2081 TGTTTTGTTG TGGTCTAAGA AAGAATCGTA AGTCAAAGAC

2121 AACGGATAAG AAAAAGAAGA ACAGGGAAGC CTCAAAGGAG

2161 ATACACGCGC TAGAAAATAT CGAAGAGGGC ACCAAAGGCA

2201 CTAATGATGC GGCGAAATCA CCAGAGGCGG CACAATTGAA

2241 GTTGGAGAAG AAGTTTGGAC AGTCTCCTGT TTTTGTTGCG

2281 TCTGCTGGTA TGGAGAATGG TGGGCTTGCT AGGAATGCGA

2321 GTCCAGCTTC TCTGCTTAGA GAAGCCATCC AAGTCATTAG

2361 TTGTGGATAC GAAGATAAAA CCGAATGGGG AAAAGAGATT

2401 GGGTGGATCT ACGGTTCTGT CACCGAGGAT ATCCTTACGG

2441 GTTTCAAGAT GCATTCTCAT GGCTGGAGAT CGGTTTACTG

2481 TACACCTAAG ATACCGGCCT TTAAAGGATC AGCACCTATC

2521 AATCTTTCTG ACCGTCTTCA TCAAGTTCTT CGGTGGGCGC

2561 TCGGGTCTGT TGAGATTTTC TTGAGCAGAC ATTGTCCTAT

2601 TTGGTATGGT TATGGAGGTG GTTTGAAATG GCTTGAGAGA

2641 TTGTCTTACA TCAACTCTGT GGTTTATCCA TGGACCTCTA

2681 TTCCACTCCT TGTTTACTGT CTCTCCCAG CTATCTGTCT

2721 TCTCACCGGA AAATTCATCG TCCCTGAGAT TAGCAACTAT

2761 GCAAGTATCC TCTTCATGGC ACTTTTCGGG TCGATTGCTG

2801 TAACGGGCAT TCTCGAGATG CAATGGGGTA AGTAGGGAT

2841 CGATGATTGG TGGAGAAACG AACAGTTTTG GGTGATTGGA

2881 GGTGTTTCAG CTCATCTCTT TGCTCTCTTC CAAGGTCTCC

2921 TAAAGGTTTT AGCCGGTGTT GAGACAAACT TCACAGTTAC

2961 ATCTAAAGCA GCAGATGATG GTGAATTCTC TGAGCTTTAC

3001 ATCTTCAAAT GGACATCACT CTTGATCCCT CCAACCACAC

3041 TACTCATCAT AAACGTAATC GGAGTCATTG TGGGAATATC

3081 TGATGCGATC AGTAAGGGAT ATGACTCGTG GGGTCCTCTT
```

```
3121 TTCGGAAGAT TGTTCTTTGC CTTTTGGGTC ATCCTCCATC

3161 TATATCCTTT CCTTAAAGGT CTGCTTGGGA AACAAGACAG

3201 AATGCCTACA ATCATTCTTG TCTGGTCGAT CCTTCTCGCC

3241 TCTATCCTTA CGCTTCTTTG GGTACGAGTC AATCCGTTTG

3281 TGGCGAAAGG CGGTCCTATC CTCGAGATAT GTGGCTTGGA

3321 CTGCCTTTGA
```

An example of an *Arabidopsis thaliana* CesA6 protein is provided below as SEQ ID NO:5.

```
   1 MNTGGRLIAG SHNRNEFVLI NADENARIRS VQELSGQTCQ
  41 ICRDEIELTV DGETFVACNE CAFPVGRPCY EYERREGNQA
  81 CPQCKTRFKR LKGSPRVEGD EEEDDIDLDD NEFEYGNNGI
 121 GFDQVSEGMS ISRRNSGFPQ SDLDSAPPGS QIPLLTYGDE
 161 DVEISSDRHA LIVPPSLGGH GNRVHPVSLS DPTVAAHPRP
 201 MVPQKDLAVY GYGSVAWKDR MEEWKRKQNE KLQVVRHEGD
 241 PDFEDGDDAD FPMMDEGRQP LSRKIPIKSS KINPYRMLIV
 281 LRLVILGLFF HYRILHPVKD AYALWLISVI CEIWFAVSWV
 321 LDQFPKWYPI ERETYLDRLS LRYEKEGKPS GLSPVDVFVS
 361 TVDPLKEPPL ITANTVLSIL AVDYPVDKVA CYVSDDGAAM
 401 LTFEALSETA EFARKWVPFC KKYCIEPRAP EWYFCHKMDY
 441 LKNKVHPAFV RERRAMKRDY EEFKVKINAL VATAQKVPED
 481 GWTMQDGTPW PGNSVPDHPG MIQVFLGSDG VRDVENNELP
 521 RLVYVSREKR PGFDHEKKAG ANNSLIRVSG VLSNAPYLLN
 561 VDCDHYINNS KALREAMCFM MDPQSGKKIC YVQFPQRFDG
 601 IDRHDRYSNR NVVFFDINMK GLDGLQGPIY VGTGCVFRRQ
 641 ALYGFDAPKK KKGPRKTCNC WPKWCLLCFG SRKNRKAKTV
 681 AADKKKKNRE ASKQIHALEN IEEGRVTKGS NVEQSTEAMQ
 721 MKLEKKFGQS PVFVASARME NGGMARNASP ACLLKEAIQV
 761 ISCGYEDKTE WGKEIGWIYG SVTEDILTGF KMHSHGWRSV
 801 YCTPKLAAFK GSAPINLSDR LHQVLRWALG SVEIFLSRHC
 841 PIWYGIGGGL KWLERLSYIN SVVYPWTSLP LIVYCSLPAI
 881 CLLTGKFIVP EISNYASILF MALFSSIAIT GILEMQWGKV
 921 GIDDWWRNEQ FWVIGGVSAH LFALFQGLLK VLAGVDTNFT
 961 VTSKAADDGE FSDLYLFKWT SLLIPPMTLL IINVIGVIVG
1001 VSDAISNGYD SWGPLFGRLF FALWVIIHLY PFLKGLLGKQ
1041 DRMPTIIVVW SILLASILTL LWVRVNPFVA KGGPILEICG
1081 LDCL
```

A nucleotide sequence encoding the *Arabidopis thaliana* CesA6 protein with SEQ ID NO:5 is provided below as SEQ ID NO:6.

```
   1  ATGAACACCG GTGGTCGGTT AATCGCCGGT TCTCACAACA
  41  GGAATGAGTT TGTCCTCATT AATGCCGATG AGAATGCCCG
  81  AATAAGATCA GTCCAAGAGC TGAGTGGACA GACATGTCAA
 121  ATCTGCAGAG ATGAGATCGA ATTGACTGTT GATGGAGAAC
 161  CGTTTGTGGC ATGTAACGAA TGTGCATTCC CTGTGTGTAG
 201  ACCTTGCTAT GAGTACGAAA GACGAGAAGG CAATCAAGCT
 241  TGTCCACAGT GGAAACCCG TTTCAAACGT CTTAAAGGAA
 281  GTCCAAGAGT TGAAGGTGAT GAAGAGGAAG ATGACATTGA
 321  TGATTAGAC AATGAGTTTG AGTATGGAAA TAATGGGATT
 361  GGATTTGATC AGGTTTCTGA AGGTATGTCA ATCTCTCGTC
 401  GCAACTCCGG TTTCCCACAA TCTGATTTGG ATTCAGCTCC
 441  ACCTGGCTCT CAGATTCCAT TGCTGACTTA CGGCGACGAG
 481  GACGTTGAGA TTTCTTCTGA TAGACATGCT CTTATTGTTC
 521  CTCCTTCACT TGGTGGTCAT GGCAATAGAG TTCATCCTGT
 561  TTCTCTTTCT GACCCGACCG TGGCTGCACA TCCAAGGCCT
 601  ATGGTACCTC AGAAAGATCT TGCGGTTTAT GGTTATGGAA
 641  GTGTCGCTTG GAAAGATCGG ATGGAGGAAT GGAAGAGAAA
 681  GCAGAATGAG AAACTTCAGG TTGTTAGGCA TGAAGGAGAT
 721  CCTGATTTTG AAGATGGTGA TGATGCTGAT TTTCCAATGA
 761  TGGATGAGGG AAGGCAGCCA TTGTCTAGGA AGATACCAAT
 801  GAAATCGAGC AAGATAAATC CTTACCGGAT GTTAATTGTG
 841  CTACGTCTTG TGATTCTTGG TCTCTTCTTT CACTACCGTA
 881  TTCTTCACCC CGTCAAAGAT GCATATGCTT TGTGGCTTAT
 921  TTCTGTTATA TGTGAGATAT GGTTTGCTGT TTCATGGGTT
 961  CTTGATCAGT TCCCTAAATG GTACCCTATC GAGCGAGAAA
1001  CGTACTTGGA CCGACTCTCA TTAAGATATG AGAAAGAAGG
1041  aAAACCGTCG GGACTATCCC CTGTGGATGT ATTTGTTAGT
1081  ACAGTGGATC CATTGAAAGA GCCTCCGCTT ATTACTGCAA
1121  ATACTGTCTT GTCTATTCTT GCTGTTGATT ATCCTGTCGA
1161  TAAGGTTGCT TGTTACGTAT CTGATGATGG TGCTGCTATG
1201  CTTACTTTCG AAGCTCTTTC TGAGACCGCT GAATTCGCAA
1241  GGAAATGGGT TCCTTTCTGC AAGAAATATT GTATTGAGCC
1281  TCGTGCTCCC GAATGGTATT TCTGCCATAA AATGGACTAC
1321  TTGAAGAATA AAGTTCATCC CGCATTTGTT AGGGAGCGGC
1361  GAGCCATGAA GAGAGATTAT GAAGAATTCA AAGTAAAGAT
1401  CAATGCTTTA GTAGCAACAG CACAGAAAGT GCCTGAGGAT
1441  GGTTGGACTA TGCAAGACGG TACACCTTGG CCCGGTAATA
1481  GTGTGCGAGA TCATCCTGGC ATGATTCAGG TCTTCCTTGG
1521  AAGTGACGGT GTTCGTGATG TCGAAAACAA CGAGTTGCCT
1561  CGATTAGTTT ACGTTTCTCG TGAGAAGAGA CCCGGATTTG
1601  ATCACCATAA GAAGGCTGGA GCTATGAATT CCCTGATACG
1641  AGTCTCTGGG GTTCTATCAA ATGCTCCTTA CCTTCTGAAT
1681  GTCGATTGTG ATCACTACAT CAACAATAGC AAAGCTCTTA
1721  GAGAAGCAAT GTGGTTCATG ATGGATCCTC AGTCAGGAAA
1761  GAAAATCTGT TATGTTCAGT TCCCTCAAAG GTTCGATGGG
1801  ATTGATAGGC ACGATCGATA CTCAAAGCGC AATGTTGTGT
1841  TCTTTGATAT CAATATGAAA GGTTTGGATG GGCTACAAGG
1881  GCCTATATAC GTCGGTACAG GTTGTGTTTT CAGGAGGCAA
1921  GCGCTTTACG GATTTGATGC ACCGAAGAAG AAGAAGGGCC
1961  CACGTAAGAC ATGCAATTGC TGGCCAAAAT GGTGTCTCCT
2001  ATGTTTTGGT TCAAGAAAGA ATCGTAAAGC AAAGACAGTG
2041  GCTGCGGATA AGAAGAAGAA GAATAGGGAA GCGTCAAAGC
2081  AGATCCACGC ATTAaAAAAT ATCGAAGAGG GCCGCGTCAC
2121  TAAAGGTTCT AACGTAGAAC AGTCAACCGA GGCAATGCAA
2161  ATGAAGTTGG AGAAGAAATT TGGGCAGTCT CCTGTATTTG
2201  TTGCATCTGC GCGTATGGAG AATGGTGGGA TGGCTAGAAA
2241  CGCAAGCCCG GCTTGTCTGC TTAAAGAAGC CATCCAAGTC
2281  ATTAGTTGCG GATATGAAGA TAAAACTGAA TGGGGAAAAG
2321  AGATTGGGTG GATCTATGGT TCTGTTACCG AAGATATTCT
2361  TACGGGTTTT AAGATGCATT CTCATGGTTG GAGATCTGTT
2401  TATTGTACAC CAAAGTTAGC GGCTTTCAAA GGATCAGCTC
2441  CAATCAATCT TTCGGATCGT CTCCATCAAG TTCTTCGATG
2481  GGCGCTTGGG TCGGTTGAGA TTTTCTTGAG TAGGCATTGT
2521  CCTATTTGGT ATGGTTATGG AGGTGGGTTG AAATGGCTTG
2561  AGCGGTTGTC CTACATTAAC TCTGTGGTTT ACCCGTGGAC
2601  CTCTCTACCG CTCATCGTTT ACTGTTCTCT CCCTGCCATC
2641  TGTCTTCTCA CTGGAAAATT CATCGTTCCC GAGATTAGCA
2681  ACTATGCGAG TATCCTCTTC ATGGCGCTCT TCTCGTCGAT
2721  TGCAATAACG GGTATTCTCG AGATGCAATG GGGCAAAGTT
2761  GGGATCGATG ATTGGTGGAG AAACGAACAG TTTTGGGTCA
2801  TTGGAGGTGT TTCTGCGCAT CTGTTTGCTC TCTTCCAAGG
2841  TCTCCTCAAG GTTCTTGCTG GTGTCGACAC TAACTTCACA
2881  GTCACATCAA AGCAGCTGA TGATGGAGAG TTCTCTGACC
2921  TTTACCTCTT CAAATGGACT TCACTTCTCA TCCCTCCAAT
2961  GACTCTACTC ATCATAAACG TCATTGGAGT CATAGTCGGA
3001  GTCTCTGATG CCATCAGCAA TGGATACGAC TCGTGGGGAC
3041  CGCTTTTCGG AAGACTGTTC TTTGCACTTT GGGTCATCAT
3081  TCATCTTTAC CCGTTCCTTA AAGGTTTGCT TGGGAAACAA
3121  GATAGAATGC CAACCATTAT TGTCGTCTGG TCCATCCTCC
```

-continued

```
3161   TGGCCTCGAT TCTTACACTT CTTTGGGTCC GGGTTAATCC
3201   GTTTGTGGCG AAAGGCGGTC CTATTCTCGA GATCTGTGGT
3241   TTAGACTGCT TGTGA
```

A *Gossypium hirsutum* (cotton) CesA2 protein sequence is provided below as SEQ ID NO:7.

```
  1   MDTGGRLIAG SHNRNEFVLI NADENARIKS VQELSGQTCQ
 41   ICGDEIEITV DGEPEVACNE CAFPVCRPCY EYERREGNQA
 81   CPQCKTRYKR IKGSPRVEGD EEEDGIDDLD NEFDYDASDP
121   QQVAEAMLNA RLNTGRGTHQ NASGMPASSE LDSSLPSSQI
161   PLLTYGEEDL EISADHHALI VPQFMGNGNR VHPMPCSDPS
201   VPLQPRPMVP KKDIAVYGYG SVAWKDRMEE WKKRQNDKLQ
241   VVKHEGGNDG GNFDGKELDD ADLPMMDEGR QPLSRKLPIP
281   SSKINPYRMI IILRLAILGL FFHYRLLHPV RDAYGLWLTS
321   VICEIWFAVS WILDQFPKWC PIERETYLDR LSLRYEKEGK
361   PSELASVDIF VSTVDPMKEP PLITANTVLS ILAVDYPVDK
401   VACYVSDDGA AMLTFEALSE TAEFARKWVP FCKKFNIEPR
441   APEWYFSQKI DYLRNKVHPA FVRERRAMKR EYEEFKVQIN
481   GLVATAQKVP EDGWTMQDGT PWPGNNVRDH PGMIQVFLGD
521   NGVRDVEGNE LPSLVYVSRE KRPGFEHHKK AGAMNALIRV
561   SAVLSNAPYL LNVDCDHYIN NSKALREAMC FMMDPTSGKK
601   VCYVQFPQRF DGIDRHDRYS NRNVVFFDIN MKGLDGLQGP
641   IYVGTGCVFR RQALYGFDAP VTKKPPGKTC NCLPKWCCFL
681   CCCSRKNKKQ KQKKEKTKKS KQREASKQIH ALENIEGAIS
721   ESNSQSSVTS QMKLEKKFGQ SPVFVASTLP EDGGVPQNAS
761   PASLLREAIQ VISCGYEDKT EWGKEVGWIY GSVTEDILTG
801   FKMHCHGWRS VYCIPKRPAF KGSAPINLSD RLHQVLRWAL
841   GSVEIFLSRH CPIWYGYGGG LKWLERFSYI NSVVYPWTSI
881   PLLVYCTLPA ICLLTGKFIV PEISNYASLV FMGLFISIAA
921   TGILEMQWGG VGIDDWWRNE QFWVIGGVSS HLFALFQGLL
961   KVLAGVSTSF TVTSKAADDG EFSELYLFKW TSLLIPPTTL
1001  LIINIVGVVV GISDAINNGY DSWGPFLGRL FFAFWVIIHL
1041  YPFLKGLLGK QDRMPTIILV WSILLASILT LMWVRINPFV
1081  SKDGPVLEIC GLNCDD
```

The *Gossypium hirsutum* (cotton) CesA2 protein sequence with SEQ ID NO:7 has substantial sequence identity (more than 83%) to the *Arabidopsis thaliana* CesA2 protein with SEQ ID NO:1, as illustrated below.

```
83.7% identity in 1099 residues overlap; Score: 4885.0; Gap
frequency: 2.0%
Seq1     1 MNTGGRLIAGSHNRNEFVLINADESARIRSVQELSGQTCQICGDEIELTVSSELFVACNE
Seq7     1 MDTGGRLIAGSHNRNEFVLINADENARIKSVQELSGQTCQICGDEIEITVDGEPFVACNE
           * ********************* *** ****************** ** * ******

Seq1    61 CAFPVCRPCYEYERREGNQACPQCKTRYKRIKGSPRVGDDEEEEDIDDLEYEFDH-GMD
Seq7    61 CAFPVCRPCYEYERREGNQACPQCKTRYKRIKGSPRVEGD-EEEDGIDDLDNEFDYDASD
           ************************************ ** **  **** *** *  *

Seq1   120 PEHAAEAALSSRLNTGRGG------------LDSAPPGSQIPLLTYCDEDADMYSDRHAL
Seq1   120 PQQVAEAMLNARLNTGRGTHQNASGMPASSELDSSLPSSQIPLLTYGEEDLEISADHHAL
           *   *** * ** ******            *** * **** **** *    * ***

Seq1   168 IVPPSTGYGNRVYPAPFTDSSAPPQARSMVPQKDIAEYGYGSVAWKDRMEVWKRRQGEKL
Seq7   180 IVPQFMGNGNRVHPMPCSDPSVPLQPRPMVPKKDIAVYGYGSVAWKDRMEEWKKRQNDKL
           ***   * * *** * *  ** * *  *** **** ************ ** **  **

Seq1   228 QVIKHEGGNNGRGSNDDDELDDPDMPMMDEGRQPLSRKLPIRSSRINPYRMLILCRLAIL
Seq7   240 QVVKHEGGNDG-GNFDGKELDDADLPMMDEGRQPLSRKLPIPSSKINPYRMIIILRLAIL
           ** ****** *  *  * ****  ****************  ** ******  * ****

Seq1   288 GLFFHYRILHPVNDAYGLWLTSVICEIWFAVSWILDQFPKWYPIERETYLDRLSLRYEKE
Seq7   299 GLFFHYRLLHPVRDAYGLWLTSVICEIWFAVSWILDQFPKWCPIERETYLDRLSLRYEKE
           ******* **** **************************** *******************

Seq1   348 GKPSGLADVDVFVSTVDPLKEPPLITANTVLSILAVDYPVDKVACYVSDDGAAMLTFEAL
Seq7   359 GKPSELASVDIFVSTVDPMKEPPLITANTVLSILAVDYPVDKVACYVSDDGAAMLTFEAL
           ****  ** ** ****** ***************************************

Seq1   408 SDTAEFARKWVPFCKKFNIEPRAPEWYESQKMDYLKNKVHPAFVRERRAMKRDYEEFKVK
Seq7   419 SETAEFARKWVPFCKKFNIEPRAPEWYFSQKIDYLRNKVHPAFVRERRAMKREYEEFKVQ
           * ************************** ***  *** *********** ********  *

Seq1   468 INALVATAQKVPEEGWTMQDGTPWPGNNVRDHPGMIQVFLGHSGVRDTDGNELPRLVYVS
Seq7   479 INGLVATAQKVPEDGWTMQDGTPWPGNNVRDHPGMIQVFLGDNGVRDVEGNELPSLVYVS
           ** ********** *************************  ****  **** *****

Seq1   528 REKRPGFDHHKKAGAMNSLIRVSAVLSNAPYLLNVDCDHYINNSKAIRESMCFMMDPQSG
Seq7   539 REKRPGFEHHKKAGAMNALIRVSAVLSNAPYLLNVDCDHYINNSKALREAMCFMMDPTSG
           ******* ********* ***************************  **  ********  **
```

```
-continued
Seq1  588  KKVSYVQFPQRFDGIDRHDRYSNRNVVFFDINMKGLDGIQGPIYVGTCVFRRQALYGFD
Seq7  599  KKVCYVQFPQRFDGIDRHDRYSNRNVVFFDINMKGLDGLQGPIYVGTCVFRRQALYGFD
           *** ****************************** *** ********************

Seq1  648  APKKKKPPGKTCNCWPKWCC-LCCGLRKKSKTKAKDKKTNT---KETSKQIHALENVDEG
Seq7  659  APVTKKPPGKTCNCLPKWCCFLCCCSRKNKKQKQKKEKTKKSKQREASKQIHALENI-EG
           ** ********** ***** *** ** ** * ** **         ********* **

Seq1  704  VIVPVSNVEKRSEATQLKLEKKFGQSPVFVASAVLQNGGVPRNASPACLLREAIQVISCG
Seq7  718  AISESNS--QSSVTSQMKLEKKFGQSPVFVASTLPEDGGVPQNASPASLLREATQVISCG
            *          *    ***************     **** **** ******* ****

Seq1  764  YEDKTEWGKEIGWIYGSVTEDILTGFKMHCHGWRSVYCMPKRAAFKGSAPINLSDRLHQV
Seq7  776  YEDKTEWGKEVGWIYGSVTEDILTGFKMHCHGWRSVYCIPKRPAFKGSAPINLSDRLHQV
           ********** **************************  *** *****************

Seq1  824  LRWALGSVEIFLSRHCPIWYGYGGGLKWLERFSYINSVVYPWTSLPLIVYSSLPAVCLLT
Seq7  836  LRWALGSVEIFLSRHCPIWYGYGGGLKWLERFSYINSVVYPWTSIPLLVYCTLPAICLLT
           ******************************************* ** **  *** ****

Seq1  884  GKFIVPEISNYAGILFMLMFISIAVTGILEMQWGGVGIDDWWRNEQFWVIGGASSHLFAL
Seq7  896  GKFIVPEISNYASLVFMGLFISIAATGILEMQWGGVGIDDWWRNEQFWVIGGVSSHLFAL
           ************  ** ****** *************************** *******

Seq1  944  FQGLLKVLAGVNTNFTVTSKAADDGAFSELYIFKWTTLLIPPTTLLIINIIGVIVGVSDA
Seq7  956  FQGLLKVLAGVSTSFTVTSKAADDGEFSELYLFKWTSLLIPPTTLLIINIVGVVVGISDA
           *********** * *********** ***** **** ************ ** ** ***

Seq1  1004 ISNGYDSWGPLFGRLFFALWVIVHLYPFLKGMLGKQDKMPTIIVVWSILLASILTTLWVR
Seq7  1016 INNGYDSWGPLFGRLFFAFWVIIHLYPFLKGLLGKQDRMPTTILVWSILLASILTLMWVR
           * **************** *** ******** ***** *** * ********** ***

Seq1  1064 VNPFVAKGGPVLEICGLNC
Seq7  1016 INPFVSKDGPVLEICGLNC
           **** * ***********
```

Another *Gossypium hirsutum* (cotton) CesA2 protein sequence is provided below as SEQ ID NO:8.

```
  1  MDTGGRLIAG SHNRNEFVLI NADENARIKS VQELSGQTCQ
 41  ICGDEIEITV DGEPFVACNE CAFPVCRPCY EYERREGNQV
 81  CPQCKTRYKR IKGSPRVEGD EEEDDIDDLD NEFDYDALDP
121  QQVAEAMLNA RINTGRGTHQ NAYGMPASSE LDSSLPSSQI
161  PLLTYGEEDS EISADHHALI VPQFMGNGNR VHPMPCSDPS
201  VPLQPRPMVP KKDIAVYGYG SVAWKDRMEE WKKRQNDKLQ
241  VVKHEGGNDG GNFDGKELDD ADLPMMDEGR QPLSRKLPIP
281  SSKINPYRMI IILRIAILGL FFHYRLLHPV RDAYGLWLTS
321  VICEIWFAVS WILDQFPKWC HTERETYLDR LSLRYEKEGK
361  PSELASVDIF VSTVDPMKEP PLITANTVLS ILAVDYPVDK
401  VACYVSDDGA AMLTFEALSE TAEFARKWVP FCKKFNIEPR
441  APEWYFSQKI DYLRNKVHPA FVRERRAMKR EYEEFKVQIN
481  GLVATAQKVP EDGWTMQDGT PWPGNNVRDH PGMIQVFLGD
521  NGVRDVEGNE LPSLVYVSRE KRPGFEHHKK AGAMNALIRV

-continued
561  SAVLSNAPYL LNVDCDHYIN NSKALREAMC FMMDPTSGKK
601  VCYVQFPQRF DGIDRHDRYS NRNVVFFDIN MKGLDGIQGP
641  IYVGTGCVFR QALYGFDAP  VTKYPPGKTC NCLPKWCCFL
681  CCCSRKNKKQ KQKKEKTKKS KQREASKQIH ALENIEGAIS
721  ESNSQSSVTS EMKLEKKFGQ SPVFVASTLL EDGGVPQNAS
761  PASLLREAIQ VISCGYEDKT EWGKEVGWMY GAVTEDILTG
801  FKMHCHGWRS VYCIPKRPAF KGSAPINLSD RLHQVLRWAL
841  GSVEIFLSRH CPIWYGYGGG LKWLERFSYI NSVVYPWTSI
881  PLLVYCTLPA ICLLTGKFIV PEISNYASLV FMGLFISIAA
921  TGILEMQWGG VGIDDWWRNE QFWVIGGVSS HLFALFQGLL
961  KVLAGVSTSF TVTSKAADDG EFSELYLFKW TSLLIPPTTL
1001 LIINIVGVVV GISDAINNGY DSWGPLFGRL FFAFWVIIHL
1041 YPFLKGLLGK QDRMPTIILV WSILLASILT LMWVRINPFV
1081 SKDGPLLEIC GLNCDD
```

The *Gossypium hirsutum* (cotton) CesA2 protein sequence with SEQ ID NO:8 has substantial sequence identity (more than 83%) to the *Arabidopsis thaliana* CesA2 protein with SEQ ID NO:1, as illustrated below.

```
83.3% identity in 1099 residues overlap; Score. 48%9,0; Gap frequency: 2.0%
Seq1  1  MNTGGRLIAGSHNRNEFVLINADESARIRSVQELSGQTCQICGDEIELTVSSELFVACNE
Seq8  1  MDTGGRLIAGSHNREEFVLINADENARIKSVQELSGQTCQICGDEIEITVDGEPFVACNE
         * ************ ******** *** ****************** **   * *****
```

-continued

```
Seq1    61 CAFPVCRPCYEYERREGNQACPQCKTRYKRIKGSPRVDGDDEEEEDIDDLEYEFDH-GMD
Seq8    61 CAFPVCRPCYEYERREGNQVCPQCKTRYKRIKGSPRVEGD-EEEDDIDDLDNEFDYDALD
           *******************  ************** ****   *** *****  ***  *

Seq1   120 PEHAAEAALSSRLNTGRGG------------LDSAPPGSQIPLLTYCDEDADMYSDRHAL
Seq8   120 PQQVAEAMLNARINTGRGTHQNAYGMPASSELDSSLPSSQIPLLTYGEEDSEISADHHAL
           *  *** *   *****              ***  * ********  **     * ***

Seq1   168 IVPPSTGYGNRVYPAPFTDSSAPPQARSMVPQKDIAEYGYGSVAWKDRMEVWKRRQGEKL
Seq8   180 IVPQFMGNGNRVHPMPCSDPSVPLQPRPMVPKKDIAVYGYGSVAWKDRMEEWKKRQNDKL
           ***    * ****  *  *   * *  ****  *** *************  **  **

Seq1   228 QVIKHEGGNNGRGSNDDDELDDPDMPMMDEGRQPLSRKLPIRSSRINPYRMLILCRLAIL
Seq8   240 QVVKHEGGNDG-GNFDGKELDDADLPMMDEGRQPLSRKLPIPSSKINPYRMIIILRLAIL
           ** ****** *    *  **** * ****************** ******* * *****

Seq1   238 GLFFHYRILHPVNDAYGLWLTSVICEIWFAVSWILDQFPKWYPIERETYLDRISLRYEKE
Seq8   299 GLFFHYRLLHPVRDAYGLWLTSVICEIWFAVSWILDQFPKWCHIERETYLDRLSLRYEKE
           ******* **** ***************************  ********* *******

Seq1   348 GKPSGLAPVDVFVSTVDPLKEPPLITANTVLSILAVDYPVDKVACYVSDDGALMLTFEAL
Seq8   339 GKPSELASVDIFVSTVDPMKEPPLITANTVLSILAVDYPVDKVACYVSDDGAAMLTFEAL
           ****  * **************************************** *********

Seq1   408 SDTAEFARKWVPFCKKFNIEPRAPEWYFSQKMDYLKNKVHPAFVRERRAMKRDYEEFKVK
Seq8   419 SETAEFARKWVPFCKKFNIEPRAPEWYESQKIDYLRNKVHPAFVRERRAMKREYEEFKVQ
           * *************************  *** **************** ******

Seq1   468 INALVATAQKVPEEGWTMQDGTPWPGNNVRDHPGMIQVFLGHSGVRDTDGNELPRLVYVS
Seq8   479 INGLVATAQKVPEDGWTMQDGTPWPGNNVRDHPGMIQVFLGDNGVRDVEGNELPSLVYVS
           ** **********  *************************   ****  ****  *****

Seq1   528 REKRPGFDHHKKAGAMNSLIRVSAVLSNAPYLLNVDCDHYINNSKAIRESMCFMMDPQSG
Seq8   539 REKRPGFEHHKKAGAMNALIRVSAVLSNAPYLLNVDCDHYINNSKALREAMCFMMDPTSG
           ******* ********* ****************************  ** ******* **

Seq1   538 KKVCYVQFPQRFDGIDRHDRYSNRNVVFFDINMKGLDGIQGPIYVGTGCVFRRQALYGFD
Seq8   599 KKVCYVQFPQRFDGIDRHDRYSNRNVVFFDINMKGLDGIQGPIYVGTGCVFRRQALYGFD
           ************************************************************

Seq1   648 APKKKKPPGKTCNCWPKWCC-LCCGLRKKSKTKAKDKKTNT---KETSKQIHALENVDEG
Seq8   659 APVTKKPPGKTCNCLPKWCCFLCCCSRKNKKQKQKKEKTKKSKQREASKQIHALENI-EG
           ** ********** ****** ***  ** ** *  *  **       ********* **

Seq1   704 VIVPVSNVEKRSEATQLKLEKKEGQSPVFVASAVLQNGGVPRNASPACLLREAIQVISCG
Seq8   718 AISESNS--QSSVTSEMKLEKKEGQSPVFVASTLLEDGGVPQNASPASLLREAIQVISCG
            *        *        ************  *   ****  ***** ************

Seq1   764 YEDKTEWGKEIGWIYGSVTEDILTGFKMHCHGWRSVYCMPKRAAFKGSAPINLSDRLHQV
Seq8   776 YEDKTEWGKEVGWMYGAVTEDILTGFKMHCHGWRSVYCIPKRPAFKGSAPINLSDRLHQV
           **********  ** ** ******************** *** *****************

Seq1   824 LRWALGSVEIFLSRHCPIWYGYGGGLKWLERFSYINSVVYPWTSLPLIVYCSLTAVCLLT
Seq6   836 LRWALGSVEIFLSRHCPIWYGYGGGLKWLERFSYINSVVYPWTSIPLLVYCTLPAICLLT
           ****************************************** ** *** *  * ****

Seq1   884 GKFIVPEISNYAGILFMLMFISIAVTGILEMQWGGVGIDDWWRNEQFWVIGGASSHLFAL
Seq8   896 GKFIVPEISNYASLVFMGLFISIAATGILEMQWGGVGIDDWWRNEQFWVIGGVSSHLFAL
           ************   **  ***** *************************** ******

Seq1   944 FQGLLKVLAGVNTNFTVTSKAADDGANSELYIFKWTTLLIPPTTLLIINIIGVIVGVSDA
Seq8   956 FQGLLKVLAGVSTSFTVTSKAADDGEFSELYLFKWTSLLIPPTTLLIINIVGVVVGISDA
           *********** *  **********  **** **** *************  ** * ***

Seq1  1004 ISNGYDSWGPLFGRLFFALWVIVHLYPFLKGMLGKQDKMPTIIVVWSILLASILTLLWVR
Seq8  1016 INNGYDSWGPLFGRLFFAFWVIIHLYPFLKGLLGKQDRMPTIILVWSILLASILTLMWVR
           * **************** *** ******** ***** **** ************* ***

Seq1  1064 VNPFVAKGGPVLEICGLNC
Seq8  1076 INPFVSKDGPLLEICGLNC
            **** * ** ********
```

An example of *Gossypium hirsutum* (cotton) CesA5 protein is provided below as SEQ ID NO:9.

```
  1   MDTKGRLVAG SHNRNEFVLI NADEVARVTS VKELSGQICQ

41   ICGDEIEISV DGEPFVACNE CAFPVCRACY EYERREGNQA

81   CPQCKTRYKR IKGCPRVEGD EEEDGADDLE NEFDIASHDR

121   RDPHHIAAAM LSGRYNINHG SQPHVSGIST PAELDAASVA

161   AGIPLLTYGQ EDVGISPDKH ALIVPPFMSR GKRVHPMPMP
```

```
201 DPSMTLPPRP MDPKKDLAVY GYGTVAWKER MEDWKKKQNE
241 KLQVVKHEGN NGDEFEDSDL PMMDEGRQPL SRKLPIPSSK
281 INPYRLIILL RLAVLGLFFH YRILHPVNDA YVLWLISVIC
321 EIWFAVSWIL DQFPKWYPIE RETYLDRLSL RYEKEGKPSE
361 LASVDVFVST VDPMKEPPLI TANTVLSILS VDYPVDKVAC
401 YVSDDGAAML TFEALSETSE FARKWVPFCK KFSIEPRAPE
441 WYFAQKVDYL RDKVDPTFVR ERRAMKREYE EFKVRINSLV
481 AMAQKVPEEG WTMQDGTPWP GNNVRDHPGM IQVFLGHDGV
521 RDIEGNELPR LIYVSREKRP GFDHHKKAGA MNSLVRVSAV
561 ISNAPFLLNV DCDHYINNSK ALREAMCFMM DPISGKKICY
601 VQFPQRFDGI DRHDRYSNRN VVFFDINMKG LDGIQGPIYV
641 GTGCVFRRQA LYGYDAPVKK KFPRRTCNCL PKWCCCCCCC

681 RSKRKNKKSK SIDKKKKEVP KHKHALENIE EGIEGIDNEK
721 SAIMPQIKFE KKFGQSPVFI ASTLMEDGGI PKGATTASLL
761 KEAIHVISCG YEDKTDWGKE VGWIYGSVTE DILTGFKMHC
801 HGWRSVYCIP KRPAFKGSAP INLSDRLHQV LRWALGSVEI
841 FLSRHCPIWY GYGCGLKSLE RFSYIASVVY PLTSVPLLVY
881 CTLPAICLLT GKFIVPEISN YASLLFMSLF IVIAVTSILE
921 MQWGGVGIHD WWRNEQFWVI GGVSSHLFAL FQGLLKVLAG
961 VNTNFTVTSK GGDDGEFSEL YLFKWTSLLI PPMTLLIINI
1001 IGVIVGISDA ISNGYDSWGP LFGRLFFAFW VIVHLYPFLK
1041 GLMGKQDRLP TIIVVWSILL ASIFSLLWAR VNPFISKGGI
1081 VLEVCGLNCD
```

The *Gossypium hirsutism* (cotton) CesA5 protein sequence with SEQ ID NO:9 has substantial sequence identity (more than 79%) to the *Arabidopsis thaliana* CesA5 protein with SEQ ID NO:3, as illustrated below.

```
79.6% identity in 1093 residues overlap; Score: 4559,0; Gap frequency: 2,7%
Seq3    1 MNTGGRLIAGSHNRNEFVLINADESARIRSVEELSGQTCQICGDEIELSVDGESFVACNE
Seq9    1 MDTKGRLVAGSHNRNEFVLINADEVARVTSVKELSGQICQICGDEIEISVDGEPFVACNE
          * * *** ************* **  ** ***** ********* ***** ******

Seq3   61 CAFPVCRPCYEYERREGNQSCPQCKTRYKRIKGSPRVEGDEEDDGIDDLDFEFD------
Seq9   61 CAFPVCRACYEYERREGNQACPQCKTRYKRIKGCPRVEGDEEEDGADDLENEFDIASHDR
          ******* *********** ************ ********* ** *** ***

Seq3  115 --------------YSRSGLESETFSRRNSEFDLASAPPGSQIPLLTYGEEDVEISSDSH
Seq9  121 RDPHHIAAAMLSGRYNINHGSQPHVSGISTPAELDAASVAAGIPLLTYGQEDVGISPDKH
                        *         *    *  *     ******* *** ** * *

Seq3  161 ALIVSPSPGHIHRVHQPHFPDPAAH--PRPMVPQKDLAVYGYGSVAWKDRMEEWKRKQNE
Seq9  161 ALIVPPFMSRGKRVHPMPMPDPSMTLPPRPMDKKDLAVYGYGTVAWKERMEDWKKKQNE
          ****  *     ***   ***     **** * ********  **** *** ** ****

Seq3  219 KYQVVKHDGDSSLGDGDDADIPMMDEGRQPLSRKVPIKSSKINPYRMLIVLRLVILGLFF
Seq9  241 KLQVVKHEGNNG-DEFEDSDLPMMDEGRQPLSRKLPIPSSKINPYRLIILLRLAVLGLFF
          * ***** *   *   * ** ************ ** ********  *   ***  *****

Seq3  279 HYRILHPVNDAYALWLISVICEIWFAVSWVLDQFPKWYPIERETYLDRLSLRYEKEGKPS
Seq9  300 HYRILHPVNDAYVLWLISVICEIWFAVSWILDQFPKWYPIERETYLDRLSLRYEKEGKPS
          ************ *************** *******************************

Seq3  339 ELAGVDVFVSTVDPMKEPPLITANTVLSILAVDYPVDRVACYVSDDGAAMLTFEALSETA
Seq9  360 ELASVDVFVSTVDPMKEPPLITANTVLSILSVDYPVDKVACYVSDDGAAMLTFEALSETS
          *** ************************** ****** *********************

Seq3  399 EFARKWVPFCKKYTIEPRAPEWYFCHKMDYLKNKVHPAFVRERRAMKRDYEEFKVNINAL
Se39  420 EFARKWVPFCKKFSIEPRAPEWYFAQKVDYLRDKVDPTFVRERRAMKREYEEFKVRINSL
          ************  **********  * *** **    *********  ****** *

Seq3  459 VATAQKVPEEGWTMQDGTPWPGNNVRDHPGMIQVFLGNNGVRDVENNELPRLVYVSREKR
Seq9  480 VAMAQKVPEEGWTMQDGTPWPGNNVRDHPGMIQVFLGHDGVRDIEGNELPRLIYVSREKR
          ** ********************************* **** *  ***** ********

Seq3  519 PGFDHHKKAGAMNSLIRVSGVLSNAPYLLNVDCDHYINNSKALREAMCFMMDPQSGKKIC
Seq9  540 PGFDHHKKAGAMNSLVRVSAVISNAPFLLNVDCDHYINNSKALREAMCFMMDPISGKKIC
          *************** *** *  ***  ************************ ******

Seq3  579 YVQFPQRFDGIDKSDRYSNRNVVFFDINMKGLDGIQGPIYVGTGCVERRQALYGFDAPKK
Seq9  600 YVQFPQRFDGIDRHDRYSNRNVVFFDINMKGLDGIQGPIYVGTGCVFRRQALYGYDAPVK
          ************  ******************************* ****** *** *

Seq3  639 KKTKRMTCNCWPKWCLFCC---GLRKNRKSKTTDKKKKNREASKQIHALENIEEGTKGTN
Seq9  660 KKPPRRTCNCLPKWCCCCCCCRSKRKNKKSKSIDKKKK--EVPKHKHALENIEEGIEGI-
          **    * **** ****   **  *** *****   * *    ********* * *
```

```
-continued
Seq3   696 DAAKSPEAAQLKLEKKEGQSPVFVASAGMENGGLARNASPASLLREAIQVISCGYEDKTE
Seq9   717 DNEKSALMPQIKFEKKFGQSPVFIASTLMEDGGIPKGATTASLLKEAIHVISCGYEDKTD
            *  **       *  * **********  **    ** **       *  **** ***  **********

Seq3   756 WGKEIGWIYGSVTEDILTGFKMHSHGWRSVYCTPKIPAFKGSAPINLSDRLHQVLRWALG
Seq9   777 WGKEVGWIYGSVTEDILTGFKMHCHGWRSVYCIPKRPAFKGSAPINLSDRLHQVLRWALG
            ****  ****************  ********  **  **  **************************

Seq3   816 SVEIFLSRHCPIWYGYGGGLKWLERLSYINSVVYPWTSIPLLVYCSLPAICLLTGKFIVP
Seq9   837 SVEIFLSRHCPIWYGYGCGLKSLERFSYIASVVYPLTSVPLLVYCTLPAICLLTGKFIVP
            *****************  ***  ***  ***  *****  **  ******  **************

Seq3   876 EISNYASILFMALFGSIAVTGILEMQWGKVGIDDWWRNEQFWVIGGVSAHLFALFQGLLK
Seq9   897 EISNYASLLFMSLFIVIAVTSILEMQWGGVGIHDWWRNEQFWVIGGVSSHLFALFQGILK
            *******  ***  **  ****  *******  ***  ***************  **********

Seq3   936 VLAGVETNTTVTSKAADDGEFSELYIFKWTSLLIPPTTLLIINVIGVIVGISDAISNGYD
Seq9   957 VLAGVNTNFTVTSKGGDDGEFSELYLFKWTSLLIPPMTLLIINIIGVIVGISDAISNGYD
            *****  ********  *********  **********  ******  *****************

Seq3   996 SWGPLFGRLFFAFWVILHLYPPLKGLLGKQDRMPTIILVWSILLASILTLLWVRVNPFVA
Seq9  1017 SWGPLFGRLFFAFWVIVHLYPPLKGLMGKQDRLPTIIVVWSILLASIFSLLWARVNPFIS
            ****************  ********** ********  *****  ****  ***********  ***  *****

Seq3  1056 KGGPILEICGLDC
Seq9  1077 KGGIVLEVCGLNC
            ***  **  *** *
```

An example of a *Gossypium hirsutum* (cotton) CesA6 protein lionaolog is provided below as SEQ NO:10.

```
  1 MDTGGRLIAG SHNRNEFVLI NADENARIKS VKELSGQTCQ
 41 ICGDEIEITV DGEPFVACNE CAFPVCRPCY EYERREGNQA
 81 CPQCKTRYKR IKGSPRVEGD EEEDDIDDLD NEFDYDALDP
121 QQVAEAMLGG HLNTGRGFHP NGSGLPAHSE IDSFPPSSQI
161 PLLTYGEEHS EISADHHALI VPPFMGHGNR VHPMPYTDPA
201 VPLQPRPMVP KKDIAVYGYG SVAWKDRMEE WKKWQNEKLQ
241 VVKHKGGNDG GNGEELDDAD LPMNDEGRQP LSRKLPIPSS
281 KINPYRMIII IRLAILGLFF HYRLLHPVRD AYGLWLTSVI
321 CEIWFAVSWI LDQFPKWYPI ERETYLDRLS LRYEKEGKLS
361 ELAGIDVFVS TVDPMKEPPL ITANTVLSIL AVDYPVDKVA
401 CYVSDDGAAM LTFEALSETS EFARKWVPFC KKFNIEPRAP
441 EWYFSQKIDY LKNKVHPAFV RERRAMKREY EEFKVRINGL
481 VSAAQKVPED GWTMQDGTPW PGNCVRDHPG MIQVFLGHSG
521 VRDVEGNELP HLVYVSREKR PGFEHHKKAG AMNALIRVSS
561 VLSNAPYLLN VDCDHYINNS KALREAMCFM MDPTSGKKVC
601 YVQFPQRFDG IDRHDRYSNR NVVFFDINMK GLDGIQGPIY
641 VGTGCVFRRQ ALYGFDAPIT KKPPGKTCNC LPKWCCCLCC
681 CSRKNKKTKQ KKDKTKKSKQ REASKQIHAL ENIEEGISES
721 NTLKSSEASQ IKLEKKFGQS PVFVASTLLE DGGIPQNASP
761 ASLLSEAIQV ISCGYEDKTE WGKEVGWIYG SVTEDILTGF
801 KMHCHGWRSV YCIPKRPAFK GSAPINLSDR LHQVLRWALG
841 SVEIFLSRHC PIWYGYGGGL KNLERFSYIN SVVYPWTSIP
881 LLVYCTLPAI CLLTGKFIVP EISNYASLIF MALFISIAAT
921 GILEMQWGGV GIDDWWRNEQ FWVIGGVSSH LFALFQGLLK
961 VLAGVSTSFT VTSKAADDGE FSELYLFKWT SLLIPPTTLL
1001 VINIIGVVVG ISDAINNGYD SWGPLFGRLF FAFWVIIHLY
1041 PFLKGLLGKQ DRMPTIILVW SILLASILTL MWVRINPFVS
1081 KDGPVLEVCG LNCDD
```

The *Gossypium hirsutum* (cotton) CesA6 protein sequence with SEQ ID NO:10 has substantial sequence identity (more than 83) to the *Arabidopsis thaliana* CesA5 protein with SEQ ID NO:5, as illustrated below.

```
83;3% identity in 1096 residues overlap; Score: 4859.0; Gap frequency: 1.5%
Seq5   1 MNTGGRLIAGSHNRNEFVLINADENARIRSVQELSGQTCQICRDEIELTVDGEPFVACNE
Seq10  1 MDTGGRLIAGSHNRNEFVLINADENARIKSVKELSGQTCQICGDEIEITVDGEPFVACNE
          * *************************  **  *********  ******  ****  *************

Seq5   61 CAFPVCRPCYEYERREGNQACPQCKTRFKRLKGSPRVEGDEEEDDIDDLDNEFEYGN---
Seq10  61 CAFPVCRPCYEYERREGNQACPQCKTRYKRIKGSPRVEGDEEEDDIDDLDNEFDYDALDP
          ***************************  ***  ************************  *

Seq5  118 ----NGIGFDQVSEGMSISRRNSGFP-QSDLDSAPPGSQIPLLTYGDEDVEISSDRHALI
Seq10 121 QQVAEAMLGGHLNTGRGFHPNGSGLPAHSEIDSFPPSSQIPLLTYGEEHSEISADHHALI
               *        **  *  **  **   *********** **  ***  ****
```

-continued

```
Seq5   173 VPPSLGGHGNRVHPVSLSDPTVAAHPRPMVPQKDLAVYGYGSVAWKDRMEEWKRIQNEKL
Seq10  181 VPPFMG-HGNRVHPMPYTDPAVPLQPRPMVPKKDIAVYGYGSVAWKDRMEEWKKWQNENL
           ***  *  ******   **  *  ****** ** ****************** *****

Seq5   233 QVVRHEGDPDFEDG---DDADFPMMDEGRQPLSRKIPIKSSKINPYRMLIVLRLVILGLF
Seq10  240 QVVKHKGGNDGGNEELDDADLPMMDEGRQPLSRKLPIPSSNINPYRMIIIIRLAILGLF
           *** * *  *    *    **** *************  ** *** ****  ** *****

Seq5   290 FHYRILHPVKDAYALWLISVICEIWFAVSWVLDQFPKWYPIERETYLDRLSLRYEKEGKP
Seq10  300 FHYRLLHPVRDAYGLWLTSVICEIWFAVSWILDQFPKWYPIERETYLDRLSLRYEKEGKL
           **** **** *** *** ***********  **************************

Seq6   350 SGLSPVDVFVSTVDPLKEPPLITANTVLSILAVDYPVDKVACYVSDDGAAMLTFEALSET
Seq10  360 SELASIDVFVSTVDPMKEPPLITANTVLSILAVDYPVDKVACYVSDDGAAMLTFEALSET
           *  *  ************ *****************************************

Seq5   410 AEFARKWVPFCKKYCIEPRAPEWYFCHKMDYLKNKVHPAFVRERRAMKRDYEEFKVKINA
Seq10  420 SEFARKWVPFCKKFNIEPRAPEWYFSQKIDYLKNKVHPAFVRERRAMKREYEEFKVRING
            ************  ********* *  ********************* ******* *

Seq5   470 LVATAQKVPEDGWTMQDGTPWPGNSVRDHPGMIQVFLGSDGVRDVENNELPRLVYVSREK
Seq10  480 LVSAAQKVPEDGWTMQDGTPWPGNCVRDHPGMIQVFLGHSGVRDVEGNELPHLVYVSREK
           ** ********************* ************* ****** **** ********

Seq5   530 RPGFDHHKKAGAMNSLIRVSGVLSNAPYLLNVDCDHYINNSKALREAMCFMMDPQSGKKI
Seq10  540 RPGFEHHKKAGAMNALIRVSSVLSNAPYLLNVDCDHYINNSKALREAMCFMMDPTSGKKV
           **** ********* ***** ******************************** ****

Seq5   590 CYVQFPQRFDGIDRHDRYSNRNVVFFDINMKGLDGLQGPIYVGTGCVFRRQALYGFDAPK
Seq10  600 CYVQFPQRFDGIDRHDRYSNRNVVFFDINMNGLDGIQGPIYVGIGCVFRRQALYGFDAPI
           ****************************** **** ****** ***************

Seq5   650 KKKGPRKTCNCWPKWCL-LCFGSRKNRKAKTVA-ADKKKKNREASKQIHALENIEEGRVT
Seq10  660 TKKPPGKTCNCLPKWCCCLCCCSRKNKKTKQKKDTKKKSKQREASKQIHALENIEEG--I
            ** * ***** ****   *  **** *  * *  ***  *****************

Seq5   708 KGSNVEQSTEAMQMKLEKKFGQSPVFVASARMENGGMARNASPACLLKEAIQVISCGYED
Seq10  718 SESNTLKSSEASQIKLEKKFGQSPVFVASTLLEDGGIPQNASPASLLSEASQVISCGYED
             **  * **    ***************   *  **  ****** ** *  ********

Seq5   768 KTEWGKEIGWIYGSVTEDILTGFKMHSHGWRSVYCTPKLAAFKGSAPINLSDRLHQVLRW
Seq10  778 KTEWGKEVGWIYGSVTEDILTGFKMHCHGWRSVYCIPKRPAFKGSAPINLSDRLHQVLRW
           ******* ****************** ******* **  ********************

Seq5   828 ALGSVEIFLSRHCPIWYGYGGGLKWLERLSYINSVVYPWTSLPLIVYCSLPAICLLTGKF
Seq10  838 ALGSVEIFLSRHCPIWYGYGGGLKWLERFSYINSVVYPWTSIPLLVYCTLPAICLLIGKF
           **************************** *********** ** ****  ******* ****

Seq5   888 IVPEISNYASILFMALFSSIAITGILEMQWGKVGIDDWWRNEQFWVIGGVSAHLFALFQG
Seq10  898 IVPEISNYASLIFMALFISIAATGILEMQWGGVGIDDWWRNEQFWVIGGVSSHLFALFQG
           ********** ***** *** *********** ***************** ********

Seq5   948 LLKVLAGVDTNFTVISKAADDGEFSDLYLFKWTSLLIPPMTLLIINVIGVIVGVSDAISN
Seq10  958 LLKVLAGVSTSFTVTSKAADDGEFSELYLFKWTSLLIPPTTLLVINIIGVVVGISDAINN
           ******** * *** ********** ************* *** ** *** ** **** *

Seq5   1008 GYDSWGPLFGRLFFALWVIIHLYPFLKGLLGKQDRMPTIIVVWSILLASILTLLWVRVNP
Seq10  1018 GYDSWGPLFGRLFFAFWVIIHLYPFLKGLLGKQDRMPTIILVWSILLASILTLMWVRINP
            *************** ****************************** *****  **** **

Seq5   1068 FVAKGGPILEICGLDC
Seq10  1078 FVSKDGPVLEVCGLNC
            **  * ** ** *** *
```

An example of an *Populus tomentosa* (poplar) CesA2 homolog protein is provided below as SEQ ID NO:11 (having at least 84% sequence identity to SEQ NO:1)

```
  1  MNTGGRLIAG SHNRNEFVLI NADENARIKS VQELSGQVCH
 41  ICGDEIEITV DGELFVACNE CAFPVCRPCY EYERREGNQA
 81  CPQCKTRYKR LKGSPRVEGD EEEDDIDDLE HEFDYGNFDG
121  LSPEQVAEAM LASRMNTGRA SHSNISGIPT HGELDSSPLN
161  SKIPLLTYGE EDTEISSDRH ALIVPPSHGN RFHPISFPDP
201  SIPLAQPRPM VPKKDIAVYG YGSVAWKDRM EDWKKRQNDK
241  LQVVKHEGGN DNGNFEGDEL DDPDLPMMDE GRQPLSRKLP
281  IPSSKINPYR MIIIIRLVVV GLFFHYRILH PVNDAYGIWL
321  TSVICEIWFA VSWILDQFPK WYPIERETYL DRLSLRYEKE
361  GKPSELASVD VFVSTVDPMK EPPLITANTV LSILAVDYPV
401  DKVACYVSDD GAAMLTFEAL SETSEFARKW VPFCKKFNIE
441  PRAPEWYFSQ KMDYLKNKVH PAFVRERRAM KREYEEFKVK
```

```
481  INGLVATAQK VPEDGWTMQD GTPWPGNNVR DHPGMIQVFL
521  GQSGVRDVEG NELPRLVYVS REKRPGFEHH KKAGAMNALM
561  RVTAVLSNAP YLLNVDCDHY INNSRALREA MCFLMDPTSG
601  KKVCYVQFPQ RFDGIDRHDR YSNRNVVFFD INMKGLDGLQ
641  GPIYVGTGCV FRRQALYGYD APVKKRPPGK TCNCWPKWCC
681  LCCGSRKNKK LKQKKEKKKS KNREASKQIH ALENIEEGIE
721  ESTSEKSSET SQMKLEKKFG QSPVFVASTL LENGGVPRDA
761  SPASLLREAI QVISCGYEDK TEWGKEVGWI YGSVTEDILT
801  GFKMHCHGWR SVYCIPKRPA FKGSAPINLS DRLEQVLRWA
841  LGSVEIFFSR HCPIWYGYGG GLKWLERFSY INSVVYPWTS
881  IPLLVYCTLP AICLLTGKFI VPEISNYASI VFMALFISIA
921  ATGILEMQWG GVGIDDWWRN EQFWVIGGAS AHLFALFQGL
961  LKVLAGVSTN FTVTSKAADD GEFSELYLFK WTSLLIPPTT
1001 LIIMNIVGVV VGVSDAINNG YDSWGPLFGR LFFALWVIIH
1041 LYPFLKGLLG KQDRMPTIIL VWSILLASIL TLLWVRINPF
1081 VSKGGPVLEL CGLNCD
```

An example of a *Populus trichocarpa* (poplar) CesA5 protein is provided below as SEQ ID NO:12 (having at least 83% sequence identity to SEQ ID NO:3).

```
  1  MNTGGRLIAG SHNRNEFVLI NADENARIKS VQELSGQVCH
 41  ICGDEIEITV DGEPFVACNE CAFPVCRPCY EYERREGNQA
 81  CPQCKTRYKR LKGSPRVEGD EEEDDIDDLE REFDYGNFDG
121  LSPEQVAEAM LSSRMNTGRA SHSNISGIPT HGELDSSPLN
161  SKIPLLTYGE EDTEISSDRH ALIVPPSHGN RFHPISFPDP
201  SIPLAQPRPM VPKKDIAVYG YGSVAWKDRM EDWKKRQNDK
241  LQVVKHEGGH DNGNFEGDEL DDPDLPMMDE GRQPLSRKLP
281  IPSSKINPYR MIIILRLVVV GLFFHYRILH PVNDAYGLWL
321  TSVICEIWFA VSWILDQFPK WYPIERETYL DRLSLRYEKE
361  GKFSELASVD VFVSTVDPMK EPPLITANTV LSILAVDYPV
401  DKVACYVSDD GAAMLTFEAL SETSEFARKW VPFCKKFNIE
441  PRAPEWYFSQ KMDYLKNKVH PAFVRERRAM KREYEEFKVK
481  INGLVATAQK VPEDGWTMQD GTPWPGNNVR DHPGMIQVFL
521  GQSGVRDVEG NELPRLVYVS REKRPGFEHH KKAGAMNALM
561  RVTAVLSNAP YLLNVDCDHY INNSRALREA MCFLMDPTSG
601  KKVCYVQFPQ RFDGIDRHDR YSNRNVVFEF INMKGLDGLQ
641  GPIYVGTGCV FRRQALYGYD APVKKRPPGK TCNCWPNWCC
681  LFCGSRKNKK SKQKKEKKKS KNREASKQIH ALENIEEGIE
721  ESTSEKSSET SQMKLEKKFG QSPVFVASTL LENGGVPRDA
761  SPASLLREAI QVISCGYEDK TEWGKEVGWI YGSVTEDILT
801  GFKMHCHGWR SVYCIPKRPA FKGSAPINLS DRLHQVLRWA
841  LGSVEIFFSR HCPIWYGYGG GLKWLERFSY INSVVYPWTS
881  IPLLVYCTLP AICLLTGKFI VPEISNYASI VFMALFISIA
921  ATGILEMQWG GVGIDDWWRN EQFWVIGGAS AHLFALFQGL
961  LKVLAGVSTN FTVTSKAADD GEFSELYLFK WTSLLIPPTT
1001 LIIMNIVGVV VGVSDAINNG YDSWGPLFGR LFFALWVIIH
1041 LYPFLKGLLG KQDRMPTIIL VWSILLASIL TLLWVRINPF
1081 VSKGGPVLEL CGLNCD
```

An example of a *Populus trichocarpa* CesA6 homolog protein sequence is provided below as SEQ ID NO:13 (having at least 71%, sequence identity to SEQ ID NO:5).

```
  1  MEVSAGLVAG SHNRNELVVI RRDGEFAPRS LERVSRQICH
 41  ICGDDVGLTV DGELFVACNE CAFPICRTCY EYERKEGNQV
 81  CPQCKTRFKR LKGCARVHGD DEEDGTDDLE NEFNFDGRNS
121  NRHDMQHHGG PESMLYDPD LPHDLHHPLP RVPLLTNGQM
161  VDDIPPEQHA LVPSYMAPVG GDGKRIHPLP FSDSSLPAQP
201  RSLDPSKDLA AYGYGSIAWK ERMESWKQKQ DKLQIMKREN
241  GDYDDDDPDL PLMDEARQPL SRKMPIPSSQ INPYRMIIII
281  RLVVLGFFFH YRVTHPVNDA FALWLISVIC EIWFAVSWIL
321  DQFPKWLPID RETYLDRLSL RYEKEGQPSQ LSPVDIYVST
361  VDPLKEPPLV TANTVLSILA VDYPVDKISC YVSDDGAAML
401  TFEALSETSE FAKKWVPFCK KFSIEPRAPE FYFAQKIDYL
441  KDKVDASFVK ERRAMKREYE EFKVRVNALV AKAHKVPEDG
481  WTMQDGTPWP GNNVRDHPGM IQVFLGQSGG HDTDGNELPR
521  LVYVSREKRP GFNHHKKAGA MNALVRVSAV LSNARYLLNL
561  DCDHYINNSK ALRESMCFMM DPLLGKRVCY VQFPQRFDGI
601  DRNDRYANRN TVFFDINMKG LDGIQGPIYV GTGCVFRRHA
641  LYGYDAPKTK KPPTRTCNCL PKWCCGCFCS GRKKKKKTNK
681  PKSELKKRNS RTFAPVGTLE GIEEGIEGIE TENVAVTSEK
721  KLENKFGQSS VFVASTLLED GGTLKSASPA SLLKEAIHVI
761  SCGYEDKTEW GKEVGWIYGS VTEDILTGFK MHCHGWRSIY
801  CIPARPAFKG SAPINLSDRL HQVLRWALGS VEIFLSRHCP
841  LWYGYGGGLK WLERLSYINA TVYPLTSIPL LAYCTLPAVC
881  LLTGKFITPE LSNAASLWFL SLFICIFATS ILEMRWSGVG
921  IDEWWRNEQF WVIGGVSAHL FAVFQGLLKV LAGVDTNFTV
961  TSKGGDDDEF SELYAFKWTT LLIPPTTLLI INLVGVVAGV
1001 SNAINNGYES WGPLFGKLFF AFWVIVHLYP FLKGLLGRQN
1041 RTPTIIIVWS ILLASIFSLL WVRIDPFLAK SNGPLLEECG
1081 LDCN
```

An example of a *Eucalyptus grandis* (eucalyptus) CesA2 homolog protein is provided below as SEQ ID NO:14 (having at least 83% sequence identity to SEQ ID NO: 1).

```
  1 MNTGGRLIAG SHNRNEFVLI NADESSRIKS VKELSGQICQ

41 ICGDEVEIAD GELFVACNEC AFPVCRPCYE YERREGNQAC

81 PQCKTRYKRL KGSPRVEGDE EEDDIDDLDN EFDYDPSDPQ

121 HVAEKTFSSR LNYGRGAHRN ASGMPTDVES SPLSSQIPLL

161 TYGQEDAEIS PDQHALIVPP ATGHAYRVHP MPYPDSSNPL

201 HPRPMAPEKD ITLYGYGSVA WKDKMEKWRK KQNEKLQVVK

241 HEGAGDGGDF GSDELDDPDL PMMDEGRQPL SRKLPIPSSK

281 INPYRLLIIL RLVILGLFLH YRILHPVNDA YGLWLTSVIC

321 EIWFAVSWIL DQFPKWYPIE RETYLDRLSL RYEREGKPSE

361 LAPVDVFVST VDPMKEPPLI TANTVLSILA VDYPVDKVAC

401 YVSDDGAAML TFEALSETSE FAKKWVPFCK RFNIEPRAPE

441 WYFSQKMDYL KNKVHPEFVR ERRAIKREYE EFKVRINALV

481 AMAQKVPEEG WTMQDGTPWP GNNVRDHPGM IQVFLGHSGV

521 CDDDGNELPR LVYVSREKRP GFEHHKKAGA MNALIRVSAV

561 ISNAPYLLNV DCDHYINNSK ALREAMCFMM DPTSGKKVCY

601 VQFPQRFDGI DRHDRYSNRN VVFFDINMKG LDGLQGPIYV

641 GTGCVFRRQA LYGHDAPSKK KPPSKTCNCW PKWCCLCCGG

681 RKNKKGKTKK ERSKKTKNRE TSKQIHALEN IEEGVSEVSN

721 EKSSEMTQIK LEKKFGQSPV FVASTTLEDG GVPPDASPAS

761 LLKEAIQVIS CGYEDKTEWG KEVGWIYGSV TEDILTGFKM

801 HCHGWRSVYC IPKRPAFFGS APINISDRIH QVLRWALGSV

841 EIFLSRHCPI WYGYGGGLKW LERFSYINSV VYPWTSIPLI

881 VYCSLPAICL LTGQFIVPEI SNYASLVFMA LFISIAATGI

921 LEMQWGGVGI DDWWRNEQFW VIGGVSSHLF ALVQGLLKVL

961 GGVNTNFTVT SKAADDGAFS ELYIFKWTSL LIPPMTLLIM

1001 NIVGVVVGIS DAINNGYDSW GPLFGRLFFA FWVIVHLYPF

1041 LKGLLGKQDR MPTIVVWSI LLASILTLLW VRINPFVSRD

1081 GPVLEVCGLN CD
```

An example of a *Eucalyptus grandis* (eucalyptus) CesA5 protein is provided below as SEQ NO:15 (having at least 70% sequence identity to SEQ NO:3).

```
  1 MEVSSGLVAG SHNRNELVVI RRENELGQKP LQKLSGQICQ

41 ICGDDVGLTV DGELFVACNE CAFPICRTCY EYERREGSQI

81 CPQCKTRFKR LRGCARVDGD EEEDGVDDLE NEFNEDGRHR

121 QEMDRQGYGA EAMLHGHMSY GRGSDLDLPH VHPLPQVPLL

161 ANGQMVDDVP PEHHALVPAY MGAGGGGGGG GKRIHPLPFT

201 DSGLPVQPRS MDPSKDLAAY GYGSVAWKER MESWKQKQEK

241 LQTMKNEKGG KEWDDDGDNP DLPLMDEARQ PLSRRLPISS

281 SQINPYRMII VIRLVVLGFF FHYRVVHPVN DAYALWLISV

321 ICEIWFGLSW ILDQFPKWLP IDRETYLDRL SLRYEKEGQP

361 SQLAPVDIFV STVDPLKEPP LVTANTVLSI LAVDYPVDKV
```

```
401 SCYVSDDGAA MLTFEALSET SEFARKWAPF CKKFNIEPRA

441 PEFYFAQKID YLKDKVEASF VKERRAMKRE YEEFKVRINA

481 LVAKAQKVPE EGWTMQDGTP WPGNNVRDHP GMIQVFLGQS

521 GGHDSDGNEL PRLVYVSREK RPGYNHHKKA GAMNALVRVS

561 AVLTNAPYLL NLDCDHYFNN SKAIREAMCF MVDPLIGKRV

601 CYVQFPQRFD GIDRHDRYAN RNTVFFDINM KGLDGIQGPI

641 YVGTGCVFRR LALYGYDAPK AKKPPTRTCN CLPKWCCCGC

681 CCSGKKKKKK TTKPKTELKK RFFKKKDAGT PPPLEGIEEG

721 IEVIESENPT PQHKLEKKFG QSSVFVASTL LEDGGTLKGT

761 SPASLLKEAI HVISCGYEDK TEWGKEVGWI YGSVTEDILT

801 GFKMHCHGWR SIYCIPARPA FKGSAPINLS DRLHQVLRWA

841 LGSIEIFLSR HCPLWYGYGG GLKWLERLSY INATVYPWTS

881 IPLLAYCTLP AVCLLTGKFI TPELSNVASL WFLSLFICIF

921 ATSILEMRWS GVGIEEWWRN EQFWVIGGVS AHLFAVFQGL

961 LKVLAGVDTN FTVTSKGGDD KEFSELYAFK WTTLLIPPTT

1001 LLIINLIGVV AGVSNAINNG HESWGPLFGK LFFAFWVIVH

1041 LYPFLKGLLG RQNRTPTIII VWSILLASTF SLLWVRIDPF

1081 LAKSDGPLLE ECGLDCN
```

An example of a *Eucalyptus grandis* (eucalyptus) CesA6 homolog protein sequence is provided below as SEQ ID NO:16 (having at least 78% sequence identity to SEQ ID NO:5).

```
  1 MDTGRLVTGS HNRNEIILIN ADEVGRVTCV KHLSGKICQI

41 CADEIEITGD GEPFVACNEC AFPVCRHCYE YERSEGTQAC

81 PHCKTRYKRI KGSPRVEGDE EEENTDDLER EFDIGESGRG

121 NLHCMAEGMP STHLNFGPNL QTHASGFTTP SELDASSVVP

161 EIPLLTYGQE NVGISFNKHA LIIPPLMGQG RRIHPMPNSD

201 SSVPLPPRTL DPNKDSAVYG YGTVAWKERM EEWKKKQNER

241 IQVVKHDRGS DGQEPDDADL PTMDEGRQPL SRKLPIPSSK

281 ISPYRLIIIL RLVILGLFFH YRILHPVNDA YGLNLTSVIC

321 EIWFAMSWIL DQFPKWYPIK RETYLDRLSL RYEKEERPSK

361 LADIDIFVST VDPMKEPPLI TANTVLSILA VDYPVDKVAC

401 YVSDDGAAML TFEALSETSE FAMKWVPFCK RFNIEPRAPE

441 WYFSQKVDYL KDKVNPEFVR ERRDMKREYE EFKVRINGLV

481 AMAQKVPEEG WTMQDGTPWP GNNVRDHPGM IQVFLGQNGD

521 RDVEGNELPR LVYVSREKRP GFDHHKKAGA MNALVRVSAV

561 ITNAPYLLNV DCDHYINNSK ALREAMCFMM DPISGKKICY

601 VQFPQRFDGI DRHDRYSNRN VVFFDINMKG LDGIQGPIYV

641 GTGCVFRRQA LYGYDAPIKK KPPGKTCNCW PKWCCLCCGS

681 RKRGRKMKSN EQKKTLRNRE ASKQIHALEN IEEGIEGIDN

721 EKSSLMSRVK FEKKFGQSPV FIATTLMEEG GVPKGATTAS
```

```
 761  LLKEAIHVIS  CGYEDKTEWG  KEVGWIYGSV  TEDILTGFKM

801  HCHGWRSVYC  IPKRPAFKGS  APINLSDRLH  QVLRWALGSV

841  EILLSRHCPI  WYGYGCGLKW  LERFSYINSV  VYPLTSIPLI

881  AYCTLPAVCL  LTGKFIVPEI  SNYASLIFMA  LFISIAATGI

921  LEMQWGGVGI  HDWWRNEQFW  VIGGVSCHLF  ALFQGLLKVL

961  AGVNTNFTVT  SKAGDDGEFS  ELYLFKWTSL  LIPPLTLLIL

1001  NIIGVIVGVS  DAINNGYETW  GPLFGKLLFA  LWVIVHLYPF

1041  LKGFMGKQDR  LPTIIIVWAI  LLASILTLLW  VRINPFISKD

1081  GIVLEVCGLD  CN
```

Transformation of Plant Cells

Plant cells can be modified to include expression cassettes or transgenes that can express any of the CesA proteins described herein. Such an expression cassette or transgene can include a promoter operably linked to a nucleic acid segment that encodes any of the CesA proteins described herein.

Promoters provide for expression of nRNA from the CesA nucleic acids. A CesA nucleic acid is operably linked to the promoter, for example, when it is located downstream from the promoter.

In some cases, the promoter can be a CesA native promoter. However, the promoter can in some cases be heterologous to the CesA nucleic acid segment. In other words, such a heterologous promoter may not be naturally linked to such a CesA nucleic acid segment. Instead, some expression cassettes and expression vectors have been recombinantly engineered to include a CesA nucleic acid segment operably linked to a heterologous promoter. Hence, the promoter can be heterologous to the nucleic acid segment that encodes the CesA protein. The nucleic acid segment that encodes the CesA protein can also be heterologous to the promoter.

A variety of promoters can be included in the expression cassettes and/or expression vectors. In some cases, the endogenous CesA promoter can be employed. Promoter regions are typically found in the flanking DNA upstream from the coding sequence in both prokaryotic and eukaryotic cells. A promoter sequence provides for regulation of transcription of the downstream gene sequence and typically includes from about 50 to about 2,000 nucleotide base pairs. Promoter sequences can also contain regulatory sequences such as enhancer sequences that can influence the level of gene expression. Some isolated promoter sequences can provide for gene expression of heterologous DNAs, that is a DNA different from the native or homologous DNA.

Promoters can be strong or weak, or inducible. A strong promoter provides for a high level of gene expression, whereas a weak promoter provides for a very low level of gene expression. An inducible promoter is a promoter that can turn on and off gene expression in response to an exogenously added agent, or in response to an environmental stimulus, or in response to a developmental stimulus. For example, a bacterial promoter such as the $P_{tac}$ promoter can be induced to vary levels of gene expression depending on the level of isothiopropylgalactoside added to the transformed cells. Promoters can also provide for tissue specific or developmental regulation. Hence, in some cases, the promoter within such expression cassettes/vectors can be functional during plant development or growth. A strong promoter for heterologous DNAs can also be used and, in some cases, such a strong promoter can be advantageous because it provides for a sufficient level of gene expression for easy detection and selection of transformed cells and provides for a high level of gene expression when desired.

Expression cassettes/vectors can include, but are not limited to, a plant promoter such as the CaMV 35S promoter (Odell et al., *Nature*. 313:810-812 (1985)), or others such as CaMV 19S (Lawton et al., *Plant Molecular Biology*. 9:315-324 (1987)), nos (Ebert et al, *Proc. Natl. Acad. Sci. USA*. 84:5745-5749 (1987)), Adh1 (Walker et al., *Proc. Natl. Acad. Sci. USA*. 84:6624-6628 (1987)), sucrose synthase (Yang et al., *Proc. Natl. Acad. Sci. USA*. 87:4144-4148 (1990)), α-tubulin, ubiquitin, actin (Wang et al., *Mol. Cell. Biol.* 12:3399 (1992)), cab (Sullivan et al., *Mol. Gen. Genet.* 215:431 (1989)), PEPCase (Hudspeth et al., *Plant Molecular Biology*. 12:579-589 (1989)) or those associated with the R gene complex (Chandler et al., *The Plant Cell*. 1:1175-1183 (1989)). Further suitable promoters include the poplar xylem-specific secondary cell wall specific cellulose synthase 8 promoter, cauliflower mosaic virus promoter, the Z10 promoter from a gene encoding a 10 kD zein protein, a Z27 promoter from a gene encoding a 27 kD zein protein, inducible promoters, such as the light inducible promoter derived from the pea rbcS gene (Coruzzi et al., *EMBO J.* 3:1671 (1971)) and the actin promoter from rice (McElroy et al., *The Plant Cell*. 2:163-171 (1990)). Seed specific promoters, such as the phaseolin promoter from beans, may also be used (Sengupta-Gopalan, *Proc. Natl. Acad. Sci. USA*. 83:3320-3324 (1985). Other promoters useful in the practice of the invention are available to those of skill in the art.

Alternatively, novel tissue specific promoter sequences may be employed in the practice of the present invention. cDNA clones from particular tissues can be isolated and those clones that are expressed specifically in that tissue are identified, for example, using Northern blotting, Preferably, the gene isolated is not present in a high copy number but is relatively abundant in specific tissues. The promoter and control elements of corresponding genomic clones can then be localized using techniques available to those of skill in the art.

A CesA nucleic acid can be combined with the promoter by available methods to yield an expression cassette or transgene, for example, as described in Sambrook et al. (MOLECULAR CLONING: A LABORATORY MANUAL. Second Edition (Cold Spring Harbor, NY: Cold Spring Harbor Press (1989); MOLECULAR CLONING: A LABORATORY MANUAL. Third Edition (Cold Spring Harbor, NY: Cold Spring Harbor Press (2000)). Briefly, a plasmid containing a promoter such as the 35S CaMV promoter can be constructed as described in Jefferson (*Plant Molecular Biology Reporter* 5:387-405 (1987)) or obtained from Clontech Lab in Palo Alto, California (e.g., pBI121 or pBI221). Typically, these plasmids are constructed to have multiple cloning sites having specificity for different restriction enzymes downstream from the promoter. The CesA nucleic acids can be subcloned downstream from the promoter using restriction enzymes and positioned to ensure that the DNA is inserted in proper orientation with respect to the promoter so that the DNA can be expressed as sense or antisense RNA. Once the CesA nucleic acid is operably linked to a promoter, the expression cassette so formed can be subcloned into a plasmid or other vector (e.g., an expression vector).

In some embodiments, a cDNA clone encoding a CesA protein is synthesized, isolated, and/or obtained from a selected cell. In other embodiments, cDNA clones from other species (that encode a CesA protein) are isolated from selected plant tissues. For example, the nucleic acid encoding a CesA protein can be any nucleic acid with a coding region that hybridizes to SEQ ID NO:2, 4 or 6 and that has CesA activity. In another example, the CesA nucleic acid can encode a CesA protein with an amino acid sequence that has at least 90%, or at least 95%, or at least 96%, or at least 97%, at least 98%, or at least 99% sequence identity to SEQ ID NO:1, 3, 5, 7, 9, 10, 11, 12, 13, 14, 15, or 16. Using restriction endonucleases, the entire coding sequence for the CesA nucleic acid is subcloned downstream of the promoter in a 5' to 3' sense orientation.

In some cases, the endogenous CesA gene can be deleted and plant cells with such a deleted endogenous CesA gene can be can be transformed to include a CesA transgene, for example, by transformation of the plant cells with a CesA expression cassette or expression vector.

The frequency of occurrence of cells taking up exogenous (foreign) DNA can sometimes vary. However, certain cells from virtually any dicot or monocot species can be stably transformed, and these cells can be regenerated into transgenic plants, through the application of the techniques disclosed herein and those available to one of skill in the art. The plant cells, plants, and seeds can therefore be monocotyledons or dicotyledons.

The cell(s) that undergo transformation may be in a suspension cell culture or may be in an intact plant part, slidh as an immature embryo, or in a specialized plant tissue, such as callus, such as Type I or Type II callus.

Transformation of the cells of the plant tissue source can be conducted by any method available to those of skill in the art. Examples are: Transformation by direct DNA transfer into plant cells by electroporation (U.S. Pat. Nos. 5,384,253 and 5,472,869, Dekeyser et al., The Plant Cell. 2:591 602 (1990)); direct DNA transfer to plant cells by PEG precipitation (Hayashimoto et al., Plant Physiol. 93:857 863 (1990)); direct DNA transfer to plant cells by microprojectile bombardment (McCabe et al., Bio/Technology. 6:923 926 (1988); Gordon Kamm et al., The Plant Cell. 2:603 618 (1990); U.S. Pat. Nos. 5,489,520; 5,538,877; and 5,538,880) and DNA transfer to plant cells via infection with *Agrobacterium*. Methods such as microprojectile bombardment or electroporation can be carried out with "naked" DNA where the expression cassette may be simply carried on any *E. coli* derived plasmid cloning vector. In the case of viral vectors, it is desirable that the system retain replication functions, but lack functions for disease induction.

One method for dicot or monocot transformation, for example, involves infection of plant cells with *Agrobacterium tumefaciens* using the leaf disk protocol (Hoesch et al., Science 227:1229 1231 (1985). For example, fiber-producing plants (e.g., dicots) such as cotton, flax, hemp, jute, sisal, poplar, and eucalyptus can be transformed via use of *Agrobacterium tumefaciens*. *Arabidopsis* is a dicot that is useful for experimental purposes.

Monocots such as *Zea mays* can be transformed via microprojectile bombardment of embryogenic callus tissue or immature embryos, or by electroporation following partial enzymatic degradation of the cell wall with a pectinase containing enzyme (U.S. Pat. Nos. 5,384,253; and 5,472, 869). For example, embryogenic cell lines derived from immature *Zea mays* embryos can be transformed by accelerated particle treatment as described by Gordon Kamm et al. (The Plant Cell. 2:603 618 (1990)) or U.S. Pat. Nos. 5,489,520; 5,538,877 and 5,538,880, cited above. Excised immature embryos can also be used as the target for transformation prior to tissue culture induction, selection and regeneration as described in U.S. application Ser. No. 08/112,245 and PCT publication WO 95/06128. Furthermore, methods for transformation of monocotyledonous plants utilizing *Agrobacterium tumcfaciens* have been described by Hiei et al. (European Patent 0 604 662, 1994) and Saito et al. (European Patent 0 672 752, 1995).

Methods such as microprojectile bombardment or electroporation are carried out with "naked" DNA where the expression cassette may be simply carried on any convenient plasmid cloning vector. In some cases, it may convenient to use a *E. coli* derived plasmid or cloning vector. In the case of viral vectors, it is desirable that the system retain replication functions, but lack functions for disease induction.

The choice of plant tissue source for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. The tissue source is selected and transformed so that it retains the ability to regenerate whole, fertile plants following transformation, i.e., contains totipotent cells. Selection of tissue sources for transformation of monocots is described in detail in U.S. application Ser. No. 08/112,245 and PCT publication WO 95/06128.

The transformation is carried out under conditions directed to the plant tissue of choice. The plant cells or tissue are exposed to the DNA or RNA carrying the targeting vector and/or other nucleic acids for an effective period of time. This may range from a less than one second pulse of electricity for electroporation to a 2-3 day co-cultivation in the presence of plasmid bearing *Agrobacterium* cells. Buffers and media used will also vary with the plant tissue source and transformation protocol. Many transformation protocols employ a feeder layer of suspended culture cells (tobacco or Black Mexican Sweet corn, for example) on the surface of solid media plates, separated by a sterile filter paper disk from the plant cells or tissues being transformed.

Where one wishes to introduce DNA by means of electroporation, itis contemplated that the method of Krzyzek et al., (U.S. Pat. No. 5,384,253) may be advantageous. In this method, certain cell wall degrading enzymes, such as pectin degrading enzymes, are employed to render the target recipient cells more susceptible to transformation by electroporation than untreated cells. Alternatively, recipient cells can be made more susceptible to transformation, by mechanical wounding.

To effect transformation by electroporation, one may employ either friable tissues such as a suspension cell cultures, or embryogenic callus, or alternatively, one may transform immature embryos or other organized tissues directly. The cell walls of the preselected cells or organs can be partially degraded by exposing them to pectin degrading enzymes (pectinases or pectolyases) or mechanically wounding them in a controlled manner. Such cells would then be receptive to DNA uptake by electroporation, which may be carried out at this stage, and transformed cells then identified by a suitable selection or screening protocol dependent on the nature of the newly incorporated DNA.

A further advantageous method for delivering transforming DNA segments to plant cells is microprojectile bombardment. In this method, microparticles may be coated with DNA and delivered into cells by a propelling force. Exemplary particles include those comprised of tungsten, gold, platinum, and the like.

It is contemplated that in some instances DNA precipitation onto metal particles would not be necessary for DNA delivery to a recipient cell using microprojectile bombardment. In an illustrative embodiment, non-embryogenic cells were bombarded with intact cells of the bacteria *E. coli* or

*Agrobacterium tumefaciens* containing plasmids with either the β-glucoronidase or bar gene engineered for expression in maize. Bacteria were inactivated by ethanol dehydration prior to bombardment. A low level of transient expression of the β-glucoronidase gene was observed 24-48 hours following DNA delivery. In addition, stable transformants containing the bar gene were recovered following bombardment with either *E. coli* or *Agrobacterium tumefaciens* cells. It is contemplated that particles may contain DNA rather than be coated with DNA. Hence it is proposed that particles may increase the level of DNA delivery but are not, in and of themselves, necessary to introduce DNA into plant cells.

An advantage of microprojectile bombardment, in addition to being an effective means of reproducibly stably transforming monocots, is that the isolation of protoplasts (Christou et al., PNAS. 84:3962 3966 (1987)), the formation of partially degraded cells, or the susceptibility to *Agrobacterium* infection is not required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with maize cells cultured in suspension (Gordon Kamm et al., The Plant Cell. 2:603 618 (1990)). The screen disperses the particles so that they are not delivered to the recipient cells in large aggregates. It is believed that a screen intervening between the projectile apparatus and the cells to be bombarded reduces the size of projectile aggregate and may contribute to a higher frequency of transformation, by reducing damage inflicted on the recipient cells by an aggregated projectile.

For bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. The techniques set forth here can provide up to 1000 or more foci of cells transiently expressing a marker gene. The number of cells in a focus which express the exogenous gene product 48 hours post bombardment often range from about 1 to 10 and average about 1 to 3.

In bombardment transformation, one may optimize the prebombardment culturing conditions and the bombardment parameters to yield the maximum numbers of stable transformants. Both the physical and biological parameters for bombardment can influence transformation frequency. Physical factors are those that involve manipulating the DNAlmicroprojectile precipitate or those that affect the path and velocity of either the macroprojectiles or microprojectiles. Biological factors include all steps involved in manipulation of cells before and immediately after bombardment, the osmotic adjustment of target cells to help alleviate the trauma associated with bombardment, and the nature of the transforming DNA, such as linearized DNA or intact super-coilecl plasmid DNA.

One may wish to adjust various bombardment parameters in small scale studies to fully optimize the conditions and/or to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. Execution of such routine adjustments will be known to those of skill in the art.

Examples of plants and/or plant cells that can be modified as described herein include fiber-producing, alfalfa (e.g., forage legume alfalfa), algae, apple, avocado, balsam, barley, broccoli, Brussels sprouts, cabbage, canola, cassava, cauliflower, cocoa, tole vegetables, collards, corn, cotton, cottonwood, crucifers, earthmoss, eucalyptus, grain legumes, grasses (e.g., forage grasses), hemp, jatropa, kale, kohlrabi, maize, miscanthus, moss, mustards, nut, nut sedge, oats, oil firewood trees, poplar, sorghum, sunflower, switchgrass, tobacco, tomato, turnips, and wheat. In some embodiments, the plant is a Brassicaceae or other Solanaceae species. In some embodiments, the plant or cell can be a fiber-producing plant, plant seed, or plant cell such as a cotton, hemp, poplar, or eucalyptus plant, seed, or cell. In some cases, the plant, seed, or plant cell can be a cotton species. In some cases, the plant, seed, or plant cell can be a tree species. In some embodiments, the plant, plant seed, and plant cell is not a species of *Arabidopsis*, for example, in some embodiments, the plant, plant seed, or plant cell is not an *Arobidopsis thaliona* plant, plant seed, or plant cell.

An exemplary embodiment of methods for identifying transformed cells involves exposing the bombarded cultures to a selective agent, such as a metabolic inhibitor, an antibiotic, herbicide or the like. Cells which have been transformed and have stably into grated a marker gene conferring resistance to the selective agent used, will grow and divide in culture. Sensitive cells will not be amenable to further culturing.

To use the bar-bialaphos or the EPSPS-glyphosate selective system, bombarded tissue is cultured for about 0-28 days on nonselective medium and subsequently transferred to medium containing from about 1-3 mg/l hialaphos or about 1-3 mM glyphosate, as appropriate. While ranges of about 1-3 mg/l hialaphos or about 1-3 mM glyphosate can be employed, it is proposed that ranges of at least about 0.1-50 mg/l hialaphos or at least about 0.1-50 mM glyphosate will find utility in the practice of the invention. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

An example of a screenable marker trait is the red pigment produced under the control of the R-locus in maize. This pigment may be detected by culturing, cells on a solid support containing nutrient media capable of supporting growth at this stage and selecting cells from colonies (visible aggregates of cells) that are pigmented. These cells may be cultured further, either in suspension or on solid media. The R-locus is useful for selection of transformants from bombarded immature embryos. In a similar fashion, the introduction of the C1 and B genes will result in pigmented cells and/or tissues.

The enzyme luciferase is also useful as a screenable marker in the context of the present invention. In the presence of the substrate luciferin, cells expressing luciferase emit light which can be detected on photographic or X-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time.

It is further contemplated that combinations of screenable and selectable markers may be useful for identification of transformed cells. For example, selection with a growth inhibiting compound, such as bialaphos or glyphosate at concentrations that provide 100% inhibition followed by screening of growing tissue for expression of a screenable marker gene such as luciferase would allow one to recover transformants from cell or tissue types that are not amenable to selection alone.

Regeneration and Seed Production

Cells that survive the exposure to the selective agent, or cells that have been scored positive in a screening assay, are cultured in media that supports regeneration of plants, One example of a growth regulator that can be used for such purposes is dicamba or 2,4-D. However, other growth regulators may be employed, including NAA, NAA+2,4-D or perhaps even picloram. Media improvement in these and like ways can facilitate the growth of cells at specific developmental stages. Tissue can be maintained on a basic media with growth regulators until sufficient tissue is available to begin plant regeneration efforts, or following repeated rounds of manual selection, until the morphology of the tissue is suitable for regeneration, at least two weeks, then transferred to media conducive to maturation of embryoids. Cultures are typically transferred every two weeks on this medium. Shoot development signals the time to transfer to medium lacking growth regulators.

The transformed cells, identified by selection or screening and cultured in an appropriate medium that supports regeneration, can then be allowed to mature into plants. Developing plantlets are transferred to soilless plant growth mix, and hardened, e.g., in an environmentally controlled chamber at about 85% relative humidity, about 600 ppm $CO_2$, and at about 25-250 microeinsteins/sec·m$^2$ of light. Plants can be matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petty dishes and Plant Con™. Regenerating plants can be gown at about 19° C. to 28° C. After the regenerating plants have reached the stage of shoot and root development, they may be transferred to a greenhouse for further growth and testing.

Mature plants are then obtained from cell lines that are known to have the mutations. In some embodiments, the regenerated plants are self-pollinated. In addition, pollen obtained from the regenerated plants can be crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

Regenerated plants can be repeatedly crossed to inbred plants to introgress the transgene into the genome of the inbred plants. This process is referred to as backcross conversion. When a sufficient number of crosses to the recurrent inbred parent have been completed to produce a product of the backcross conversion process that is substantially isogenic with the recurrent inbred parent except for the presence of the introduced expression cassette encoding a CesA, the plant can be self-pollinated at least once to produce a homozygous backcross converted inbred containing the transgene or expression cassette. Progeny of these plants are true breeding.

Alternatively, seed from transformed plant lines regenerated from transformed tissue cultures can be grown in the field and self-pollinated to generate true breeding plants.

Seed from the fertile transgenic plants can then be evaluated for the presence of the desired CesA genomic modification, e.g., the desired CesA expression cassette, and/or the expression of the desired CesA protein. Transgenic plant and/or seed tissue can be analyzed using standard methods such as SDS polyacrylamide gel electrophoresis, liquid chromatography (e.g., HPLC) or other means of detecting a mutation.

Once a transgenic plant with a mutant sequence and having improved growth and pathogen resistance is identified, seeds from such plants can be used to develop true breeding plants. The true breeding plants are used to develop a line of plants with improved growth and pathogen resistance relative to wild type, and acceptable insect resistance while still maintaining other desirable functional agronomic traits. Adding the mutation to other plants can be accomplished by hack-crossing with this trait and with plants that do not exhibit this trait and studying the pattern of itilieritiance in segregating generations. Those plants expressing the target trait (e.g., CesA overexpression, good growth) in a dominant fashion are preferably selected. Back-crossing is carried out by crossing the original fertile transgenic plants with a plant from an inbred line exhibiting desirable functional agronomic characteristics while not necessarily expressing the trait of increased herbicide and pathogen resistance and good plant growth. The resulting progeny are then crossed back to the parent that expresses the increased herbicide and pathogen resistance and good plant growth. The progeny from this cross will also segregate so that some of the progeny carry the trait and some do not. This back-crossing is repeated until an inbred line with the desirable functional agronomic traits, and with expression of the trait involving an increase in herbicide and pathogen resistance and good plant growth. Such herbicide and pathogen resistance as well as good plant growth can be expressed in a dominant fashion.

The new transgenic plants can also be evaluated for a battery of functional agronomic characteristics such as growth, lodging, kernel hardness, yield, resistance to disease and insect pests, drought resistance, and/or herbicide resistance.

Plants that may be improved by these methods include but are not limited to agricultural plants of all types, fiber-producing plants (cotton, flax, hemp, jute, sisal, poplar, and/or eucalyptus), forage plants (alfalfa, clover and fescue), grains (maize, wheat, barley, oats, rice, sorghum, millet and rye), grasses (switchgrass, prairie grass, wheat grass, sudangrass, sorghum, straw-producing plants), softwood, hardwood and other woody plants (e.g., those used for paper production such as poplar species, pine species, and eucalyptus). In some embodiments, the plant, cell or seed is of a fiber-producing plant species such as a cotton, flax, hemp, jute, sisal, poplar, and/or eucalyptus plant, cell or seed. In some embodiments, the plant type is a eucalyptus plant type. Examples of plants useful for pulp and paper production include most pine species such as loblolly pine, Jack pine, Southern pine, Radiata pine, spruce, Douglas fir and others. Hardwoods that can be modified as described herein include aspen, poplar, eucalyptus, and others. Trees such as poplar, aspen, willow, and the like can also be modified as described herein.

Determination of Stably Transformed Plant Tissues

To confirm the presence of CesA expression cassette in the regenerating plants, or seeds or progeny derived from the regenerated plant, a variety of assays may be performed. Such assays include, for example, molecular biological assays available to those of skill in the art, such as Southern and Northern blotting and PCR; biochemical assays, such as detecting the presence of a protein product, e.g., by immunological means (ELISAs and Western blots) or by enzymatic function; plant part assays, such as leaf, seed or root assays; and also, by analyzing the phenotype of the whole regenerated plant.

Whereas DNA analysis techniques may be conducted using DNA isolated from any part of a plant, RNA may only be expressed in particular cells or tissue types and so RNA for analysis can be obtained from those tissues. PCR techniques may also be used for detection and quantification of RNA produced from introduced CesA transgene or expression cassette. For example, PCR also be used to reverse transcribe RNA into DNA, using enzymes such as reverse transcriptase, and then this DNA can be amplified through PCR techniques.

Further information about the nature of the RNA product may be obtained by Northern blotting. This technique will demonstrate the presence of an RNA species and give information about the integrity of that RNA. The presence or absence of an RNA species (e.g., CesA RNA) can also be determined using dot or slot blot Northern hybridizations. These techniques are modifications of Northern blotting and also demonstrate the presence or absence of an RNA species.

While Southern blotting and PCR may used to detect the presence of a CesA expression cassette, they do not provide information as to whether the preselected DNA segment is being expressed. Expression may be evaluated by specifically identifying the protein products of the introduced CesA expression cassette or the introduced mutations, by detecting expression of CesA proteins, or evaluating the phenotypic changes brought about by such mutation.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange, liquid chromatography or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products, or the rbsence thereof, that have been separated by electrophoretic techniques. Additional techniques may be employed to absolutely confirm the identity of a mutation such as evaluation by screening for reduced transcription (or no transcription) of CesA mRNAs, by screening for the CesA mRNA or CesA protein expression. Amino acid sequencing following purification can also be employed. The Examples of this application also provide assay procedures for detecting and quantifying infection and plant growth. Other procedures may be additionally used.

The expression of a gene product can also be determined by evaluating the phenotypic results of its expression. These assays also may take many forms including but not limited to analyzing changes growth or growth characteristics (e.g., taller plants), detection of stronger fibers, observation of greater mechanical strength, or other physiological properties of the plant. Expression of selected DNA segments encoding different amino acids or having different sequences and may be detected by amino acid analysis or sequencing.

Definitions

Sequences of proteins and nucleic acids of the same function can vary from one organism to another (or from one species to another). Sequences described herein can also vary while retaining the same function. For example, in some cases the sequences described herein can have at least one, or at least two, or at least three, or at least five, or at least ten, or more amino acid or nucleotide differences relative to the sequence provided herein or relative to a wild type sequence. Such sequence variation can be expressed as a variation (or percent) sequence identity. As used herein "sequence identity" refers to amino acids or nucleotides that are the same at analogous positions between two amino acid or nucleic acid sequences. The sequence identity can be expressed as a percentage. The positions of identical amino acids or nucleotides within a protein or nucleic acid can also vary but alignment of two sequences can illuminate which positions are analogous. Hence, variant proteins timid nucleic acids can have at least 30%, at least 40%, at least 50%, 60%, at least 70%, or at least 75%, or at least 80%, or at least 85%, or at least 90%, or at least 95%, or at least 96%, or at least 97%, or at least 98%, or at least 99%, or at least 99.5% sequence identity to any of the sequences described herein, for example, by SEQ ID NO.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

A promoter operable in a specified species or type of organism means that the promoter can facilitate expression of a coding region that is linked thereto.

The following Examples describe some experimental work performed during development of the invention.

Example 1

Materials and Methods

This Example describes some of the materials and methods used in the development of the invention.

Complete *Arabidopsis* AtCesA (AtCesA6, AtCesA2, AtCesA 5, AtCesA3, AtCesA9 and AtCesA7) coding regions (cDNAs) were cloned and driven by double 35S promoter in the binary vector pD1301s plasmid (Table 1).

TABLE 1

Primers for over-expression vector construction.

| Genes | Primer name | Primer sequence (5'-3') | Restriction Enzyme cutting site | TM (° C.) | Length (bp) |
|---|---|---|---|---|---|
| AtCesA3 | A3-F SEQ ID NO: 17 | GCTCTAGAATGGAATCC GAAGGAGAAACC | XbaI | 60 | 3329 |
| | A3-R SEQ ID NO: 18 | AACTGCAGCACCAAGA CAGAAGAACGAACAG | PstI | | |
| AtCesA6 | A6-F SEQ ID NO: 19 | AAAGAGCTCATGAACA CCGGTGGTCGG | SacI | 58 | 3255 |
| | A6-R SEQ ID NO: 20 | AAATCTAGATCACAAG CAGTCTAAACCACAG | XbaI | | |
| AtCesA2 | A2-F SEQ ID NO: 21 | GCTCTAGAATGAATAC TGGTGGTCGGCTCAT | XbaI | 58 | 3255 |
| | A2-R SEQ ID NO: 22 | AACTGCAGTTAGTTTC CACAATTCAGACCACAGA | PstI | | |
| AtCesA5 | A5-F SEQ ID NO: 23 | GCTCTAGAATGAATA CTGGTGGTCGGCTCATC | XbaI | 58 | 3210 |
| | A5-R SEQ ID NO: 24 | AACTGCAGTCAAAGGC AGTCCAAGCCACATAT | PstI | | |
| AtCesA9 | A9-F SEQ ID NO: 25 | GCTCTAGAATGAACA CTGGAGGGAGACTC | XbaI | 56 | 3268 |
| | A9-R SEQ ID NO: 26 | AACTGCAGCTCACTTT AAACAGTCAAGACCAC | PstI | | |
| AtCesA7 | A7-F SEQ ID NO: 27 | GGGGTACCATGGAAG CTAGCGCCGGTC | KpnI | 60 | 3081 |
| | A7-R SEQ ID NO: 28 | ACGCGTCGACTCAGC AGTTGATGCCACACTTG | SalI | | |

The lines transformed with an empty vector (EV) were used as control, Transgenic plants were generated by introducing the constructs into an *Agrobacterium tumfaciens* strain GV3101, and transformation was carried out by floral dipping method.
(Zhang et al., 2006). T1 transgenic seedlings were selected on half (½) MS medium containing 50 mg/L hygromycin, and further confirmed by RT-PCR or Q-PCR. More than three hygromycin-resistant lines (independent transformation events) for each construct were selected to and propagated to homozygous states. Phenotypic characterization was performed on T5 homozygous transgenic lines.

*Arabidopsis* seeds were surface sterilized using 75% ethanol for 4 min, 10% sodium hypochlorite with 0.01% Triton X-100 for 3 min and washed in sterile water several times, then imbibed at 4° C. in the dark in sterile water containing 0.1% agar for three days and germinated on plates containing half MS media (1% sucrose; pH 5.8) in 1% agar. Plates were incubated in a near-vertical position at 22° C. under light-grown conditions (16-hours light/5-hours dark) for photo-morphogenesis or dark-grown conditions (24-hours dark) for skotomorphogenesis (development of seeds in the dark). The seedlings were transplanted to the soil after the second real leaf is clearly visible.

RNA Extraction and Q-PCR Measurement

Seedlings were germinated and grown on ½ MS medium for indicated number of days under light- or dark-grown conditions, and seedlings (hypocotyls, roots) were harvested in liquid nitrogen. Total RNA was isolated from the collected tissues using Trizol reagent (invitrogen, Carlsbad, CA). First-strand cDNA was obtained using OligodT and M-MLV reverse transcriptase (Promega, Madison, WI, USA). Q-PCR amplification was carried out on a Bio-Rad MyCycler thermal cycler with SYBER Premix ExTaq (TakaRa, Tokyo, Japan) according to the manufacturer's instruction, and AtGAPDH was used as the internal control. The PCR thermal cycle conditions were as follows: one cycle of 95° C. for 2 minutes, followed by 45 cycles of 95° C. for 15 seconds, 58° C. for 15 seconds and 72° C. for 25 seconds. The expression value of GAPDH was defined as 100, and the expression level of CesA genes was thus normalized to the expression level of GAPDH. All of the primers used in these assays are listed in Table 2. Three biological replications were performed.

TABLE 2

Q-PCR primers

| Genes | Primer name | Primer sequence (5'-3') | TM (° C.) | Length (bp) DNA | cDNA |
|---|---|---|---|---|---|
| AtCesA1 | QA1-F SEQ ID NO: 29 | AAGTGCTGCTATGTC CAGTTCCC | 58 | 401 | 295 |
| | QA1-R SEQ ID NO: 30 | TGTTGATGCCTCTCC TCTTTTCG | | | |
| AtCesA3 | QA3-F SEQ ID NO: 31 | CCCTATCACCTCCAT TCCTCTTCT | 58 | 334 | 179 |
| | QA3-R SEQ ID NO: 32 | CGTCTATGCCTACGC CACTCC | | | |
| AtCesA6 | QA6-F SEQ ID NO: 33 | ACAGCACAGAAAGT GCCTGAG | 58 | 448 | 251 |
| | QA6-R SEQ ID NO: 34 | GGAGCATTTGATAGA ACCCCA | | | |
| AtCesA2 | QA2-F SEQ ID NO: 35 | TCGTCCCTGAGATAA GCAACTAC | 58 | 231 | 147 |
| | QA2-R SEQ ID NO: 36 | CCCCTCCGATTACCC AAAA | | | |
| AtCesA5 | QA5-F SEQ ID NO: 37 | GATGCAATGGGGTA AAGTAGGG | 58 | 233 | 233 |
| | QA5-R SEQ ID NO: 38 | TGATGAGTAGTGTGG TTGGAGGG | | | |
| AtCesA9 | QA9-F SEQ ID NO: 39 | GGAGGGAGACTCATT GCTGG | 58 | 675 | 255 |
| | QA9-R SEQ ID NO: 40 | TGTATCGGGTTCCGCA CTG | | | |
| AtCesA4 | QA4-F SEQ ID NO: 41 | ATTCTGGGTGATTTGG CGG | 58 | 190 | 190 |
| | QA4-R SEQ ID NO: 42 | AATAATGAGAGTTGT CGGAGGG | | | |
| AtCesA7 | QA7-F SEQ ID NO: 43 | TTCTTGCCTACTGTA TCCTTCC | 58 | 231 | 152 |
| | QA7-R SEQ ID NO: 44 | GCTAACTCCGCTCCA TCTCA | | | |
| AtCesA8 | QA8-F SEQ ID NO: 45 | CATCCCAACGCTATC AAACCTA | 58 | 152 | 152 |
| | QA8-R SEQ ID NO: 46 | CTGAGACACCTCCAA TAACCCA | | | |
| AtGAPDH | QGAPDH-F SEQ ID NO: 47 | GCAACATACGACGA AATCAAGAA | 58 | 398 | 217 |
| | QGAPDH-R SEQ ID NO: 48 | CGACACGAGAACTG TAACCCC | | | |

Total Protein Extraction and Western Blot Analysis

D9 seedlings were ground to a fine powder in liquid nitrogen, and 1.0 g powder was extracted using Plant Total Protein Lysis Buffer (Sangon Biotech, Shanghai, China; PL011) (1 mL Solution A, 10 μL Solution B, 10 μL Solution C) with protease inhibitors (1.0 mM Phenylmethanesulfonyl fluoride, 1.0 μM pepstatin A and 1.0 μM leupeptin). The extracts were transferred to 2-mL tubes under ultrasonic treatment on the ice for 20 min. The suspension liquid was incubated for 30 min at 4° C. under continuous stirring in the presence of 50 μL, 1% digitonin or 100 μL 20% Triton X-100. The homogenate was centrifuged at 12000 g for 30 min at 4° C. The protein concentration in the supernatant was determined using bicinchoninic acid Protein Assay Kit (Qcbio S&T). The AtCesA2, AtCesA5 and AtCesA6 protein levels were detected by Western blot analysis as described by Li et al. (2017). Purification of primary antibodies was performed using Protein A-Agarose and detected by Western blot analysis in WT. Antibody dilutions were performed as 1:250, 1:125 and 1:30 for AtCesA6, AtCesA2 and AtCesA5 antibodies, respectively.

Velocity and Density Measurements of GFP-CesA3 at the Plasma Membrane

To investigate the CesA dynamics in seedlings, the *Arabidopsis* transgenic overexpression lines were crossed with CesA marker proAtCesA3:GFP-AtCesA3 (Desprez et al., 2007). F1 seeds were surface sterilized and sown on ½ MS (plus 1% sucrose) plates where the seeds were stratified at 4° C. for 2 days. Afterwards, the plates were transferred to a growth chamber (22° C., light/dark 16 hours/8 hours), exposed to light about 3 hours and then covered with the aluminum foil. Etiolated hypocotyls were used for imaging after being vertically grown for 3 days. Images were obtained from epidermal cells within 2 mm below the apical hook. The enhanced etiolated hypocotyl phenotype of the overexpression lines was confirmed to assure that gene silencing of the overexpression constructs was not occurring.

The CesA velocity measurement and analysis were performed as described Ivakov et al. (2017). The density of CesAs was measured with the plugin TrackMate (see website at fiji.sc/TrackMate) in Fiji (see website at fiji.sc/Fiji). The time lapses were used for analysis and a median filter was applied. The particle diameter and the maximum/minimum signal intensity were used to avoid the interference of the noise and Golgi-localized CesAs. Significant differences were performed by Student's t-test. There were 578-1257 CesA3 particles detected with n≥4 cells from four different seedlings for each genotype.

Observation of Cellulose Macrofibrils by Atomic Force Microscopy (AFM)

The purified cellulose sample fractionations of D9 hypocotyls were performed as described by Li et al. (2017), with some minor modifications that hypocotyls were milled into fine powder under liquid nitrogen and then add 8% NaClO2 (10 mL). The precipitated residue was treated with 4 M KOH for 1 hour, washed with distilled water six times and resuspended in water for AFM scanning. The cellulose samples were suspended in ultra-high-purity water and placed on mica using a pipette. The mica was glued onto a metal disc (15 mm diameter) after removal of extra water under nitrogen and then placed on the piezo scanner of AFM (MultiMode VIII; Bruker, Santa Barbara, CA). AFM imaging was carried out in ScanAsyst-Air mode using Bruker-ScanAsyst-Air probes (tip radius, 2 nm and silicon nitride cantilever; spring constant, 0.4 N/m) with a slow scan rate of 1 Hz. All AFM images were 3rd-flattened and analyzed quantitatively using NanoScope Analysis software (Bruker). Three biological replications were performed each experiment, and 10 dots of each AFM image were randomly selected to measure the width (nm) 9 length (nm) by NanoScope Analysis software (Bruker). The average particle length/width of each image was calculated from the selected ten particles (n=10).

Hypocotyl, Root and Cell Length Measurements

To observe hypocotyl and root growth, Arabiclopsis seedlings were scanned using an HP Scanjet 8300 scanner at 600 dpi, the hypocotyl length of vertically grown seedlings was measured from hypocotyl base to the apical hook and the root length was measured (root tip to hypocotyl base) using ImageJ 1.32j (see website at rsb.info.nih.gov/ij/). Two-tailed t-tests were performed with Microsoft Excel software. For images of epidermal cell patterns, D9 hypocotyls were mounted and images of epidermal cells were viewed using differential interference contrast (80i; Nikon, Japan).

At least three biological replicates were performed each experiment, and more than 30 seedlings were measured each genotype. Cell lengths in recorded images were quantified using ImageJ, and epidermal cells of hypocotyl were visualized under confocal laser scanning microscopy (p58; Leica, Leica Microsystems, Nussloch, Germany) using 4-day-old dark-grown (D4) hypocotyls incubated in the dark for 10 min in a fresh solution of 115 mM (10 mg/mL) propidium iodide (PI; Naseer et al., 2012). PI was excited at 488 nm, and fluorescence was detected at 600-700 nm.

Cell Division Observation

Root meristem size was highlighted as the distance between the quiescent centre (QC) and the transition zone (TZ, indicating the position of the first elongating cortical cell), and the number of cortical cells was counted in a file extending from QC to TZ (Beemster and Baskin, 1998). To count the number of cortical cells, L9 root tips were mounted, and images viewed by differential interference contrast (80i; Nikon, Japan). At least three biological replications were performed each experiment, and more than 30 seedlings were measured each genotype. To visualize cell cycle progression in living cells, G2/M-specific marker proAtCYCB1; 1:AtCYCB1; 1-GFP (Ubeda-Tomas et al 2009) was crossed with different homozygous AtCesA6-like transgenic lines. Measurements of F1 hybrid seedlings were performed using confocal images of light-grown roots stained with P1. GFP was excited at 473 nm, and fluorescence was detected at 485-545 nm.

Observation of Cell Wall Structures by Transmission Electron Microscopy (TEM)

TEM was used to observe cell wall structures in the xylary fibre (xf) cells of the 1st inflorescence stems of 7-week-old plants. The samples were post-fixed in 2% (w/v) osmium tetroxide ($OsO_4$) for 1 hour after extensively washing in the PBS buffer and embedded with Super Kit (Sigma-Aldrich, St. Louis, MO, USA). Sample sections were cut with an Ultracut E ultramicrotome (Leica) and picked up on formvar-coated copper grids. After post-staining with uranyl acetate and lead citrate, the specimens were viewed under a Hitachi H7500 transmission electron microscope. The width of three relatively fixed points on each cell wall was measured using ImageJ. More than 60 cell walls for each t genotype were measured. Significance differences were performed by Student's t-test. Three biological replications were performed.

Crude Cell Wall Extraction and Mechanical Force Measurement by AFM

The basal (1 cm) florescence stems from 7-week-old plants were ground under liquid nitrogen and then incubated at 70° C. in 96% (v/v) ethanol for 30 min. The pellet was successively washed with absolute ethanol, twice with 2:3 (v/v) chloroform:methanol, then once each with 65% (v/v), 80% (v/v) and absolute ethanol, and the remaining pellet was freeze-dried as crude cell wall material. The crude cell wall material was suspended in ultra-high-purity water, placed on new mica using a pipette and dried in air overnight. The mica was glued onto a metal disc (15 mm diameter) and placed on the piezo scanner of an AFM (MultiMode VIII; Bruker), A hard tip (RTESP; Milker) with radius of 8 nm, and spring constant of 40 N/m was used in the mechanical properties measurement. The precise spring constant was corrected by Sader method, and the deflection sensitivity was average determined by measuring a set of force-distance curves on the mica. The scan size was 10 μm×10 μm, and 16×16 FD curves were collected for every measurement, and 10 different cell segments were randomly selected for mechanical measurements each sample. The Young's modulus was calculated using Hertz model of the NanoScope analysis software, and Wilcoxon test was used to test significance of average Young's modulus (He et al., 2015). Two biological replications were performed each experiment.

Plant Height and Dry Weight Measurement

The homozygous lines were transplanted into soil as individual plant per basin; the plants were grown in a glasshouse at 22° C. under light-grown condition for 7 weeks in a fully randomized experimental design. The plant height was measured from the basal stem to the peaks of the mature Arabidopsis plants. Harvested 7-week-old inflorescence stems per plant, then dried under suitable temperature (55° C.) for 3-5 days and finally weighed by analytical balance. Three biological replications were performed each experiment, and more than 30 plants were measured each genotype. Significance analysis was performed by Student's t-test.

Plant Cell Wall Composition Fractionation and Determination

Plant cell wall fractionations and determination were performed as described by Jin et al. (2016), with some minor modifications for crystalline cellulose extraction. For crystalline cellulose extraction, one hundred D9 or L9 seedlings or the dry biomass powder of 7-week-old inflorescence steins (40 mesh) samples (0.1-1.0 g) were suspended in 5.0 mL acetic acid\nitric acid\water (8:1:2, v/v/v) and heated for 1 h in a boiling water bath with stirring every 10 min. After centrifugation, the pellet was washed several times with 5.0 mL water and the remaining pellet was defined as crystalline cellulose sample. Total lignin was determined as described previously (Sun et al., 2017). At least three biological replications were performed.

Determining Monosaccharide Composition of Total Wall Polysaccharides by GC-MS

Both the seedlings and the dry biomass powder (40 mesh) samples (0.1-1.0 g) were washed twice with 5.0 ml, buffer and twice with 5.0 mL distilled water. The remaining pellet was stirred with 5.0 mL chloroform-methanol (1:1, v/v) for 1 h at 40° C. and washed twice with 5.0 mL methanol, followed by 5.0 mL acetone. The pellet was washed once with 5.0 mL distilled water. The remaining pellet was added with 5.0 mL aliquot of DMSO-water (9:1, v/v), vortexed for 3 min and then rocked gently on a shaker overnight. After centrifugation, the pellet was washed twice with 5.0 mL DMSO-water and then with 5.0 mL distilled water three times. The remaining pellet was defined as total wall polysaccharides and confirmed by determining monosaccharide composition with GC-MS as described previously (Xu et al., 2012). Three biological replications were performed.

RNA Sequencing and Analysis

Total RNA was isolated from the 6-day-old dark-grown (D6) seedlings (four samples, two biological replications) using Trizol reagent (Invitrogen). The RNA was checked for purity before performing RNA sequencing using NanoDrop 2000 (NanoDrop, Thermo-Fisher, USA). RNA samples with RNA integrity numbers greater than eight (>8) were selected for library preparation, and RNA concentration was detected on Qubit 2.0 (Invitrogen). The optimized total RNA of 0.1-4 µg was used for this protocol. For cDNA library construction, total RNA was processed using a TruSeq™ RNA Sample Preparation Kit (Illumina, Tokyo, Japan) according to the manufacturer's instructions. All samples were sequenced using an Illumina HiSeq 2000 sequencer (Anders et al., 2015).

Raw reads were described previously (Mortazavi et al., 2008). DEGs were applying the statistical tests for the group between transgenetic lines with wide type and performed by the DESeq R package (1.12.0). Then, P values were adjusted using the Benjamini and Hochberg method. A corrected P value of 0.001 and log 2 (fold change) of 1 was set as the thresholds for significant differential expression (Anders and Huber, 2010).

Gene ontology (GO) terms of differential expressed genes were derived from agriGO. GO subontology 'biological process' (GO-BP) was used for the gene-set enrichment analysis. TopGO from Bioconductor in R (see website at www.r-project.org/) was used to identify enriched GO terms (Du et al., 2010). This was performed for all DEGs. The enrichment analysis of GO-BP terms relative to its expectation was performed using a weighted method in combination with Fisher's exact test.

Microscopy Observation

Seven-week-old *Arabidopsis* 1st inflorescence stems were embedded with the 4% agar and then cut into sections of 100 µm thick by microtome (VT1000S; Leica). Stem sections were stained in calcofluor for 3 min and then rinsed, mounted in water, and observed and photographed under epilluorescence microscopy (Olympus BX-61, Retiga-4000DC digital camera).

Example 2

Overexpression of Three CesA6-Like Genes Enhances Seedling Growth

Figures 1, 1A:
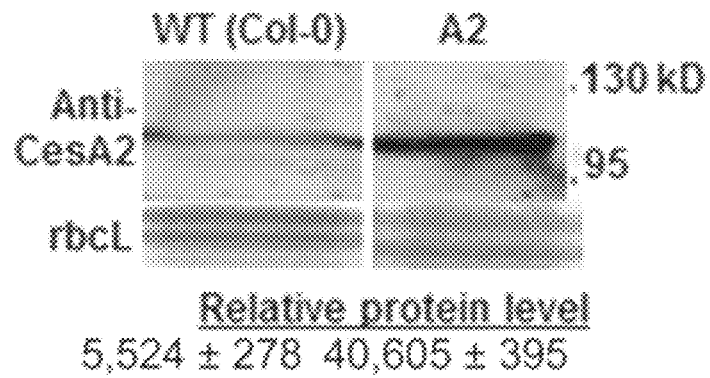
Figures 1, 1A, 2:
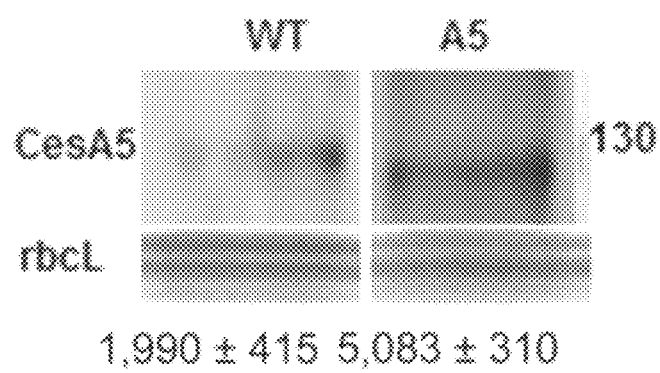
Figures 1, 1A, 2, 3:
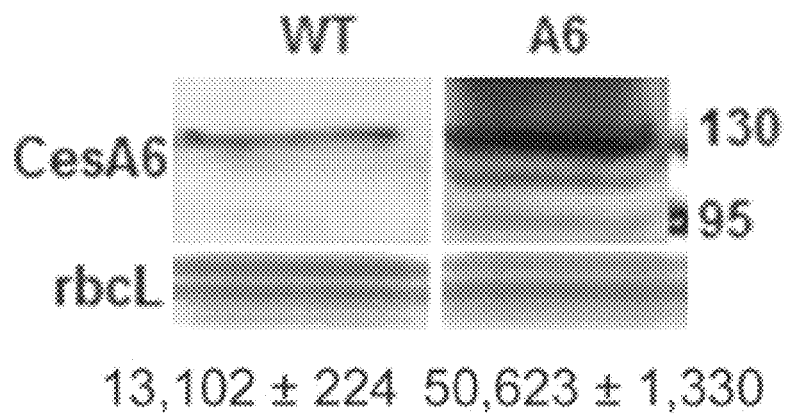

Either dark-grown (D) or light-grown (L) seedlings were studied to ascertain how different aspects of plant development correlated with changes in cellulose synthesis. The growth and transcript levels were investigated of the CesA genes associated with primary and secondary wall cellulose synthesis using real-time PCR (Q-PCR) analysis in *Arabidopsis* wild-type (WT; Col-0) seedlings (FIG. 1A-1G). Growth was consistently enhanced at both 9-day-old dark-grown (D9) hypocotyls and 9-day-old light-grown (L9) roots (FIG. 1E). These tissues were chosen to measure primary cell wall deposition relating to cell length and cell numbers, due to their relatively large tissue size and high primary wall CesA expression levels.

To ascertain whether overexpression of certain CesA proteins may improve plant growth and cellulose synthesis, CesA overexpressing lines driven by 35S promoter were generated in *Arabidopsis* wild type background, Growth of the homozygous transgenic progeny was monitored. At least three genetically independent homozygous transgenic lines were selected for analysis of each gene, and the lines were verified by Western blot analysis of protein levels (FIG. 1).

Figure 1B:
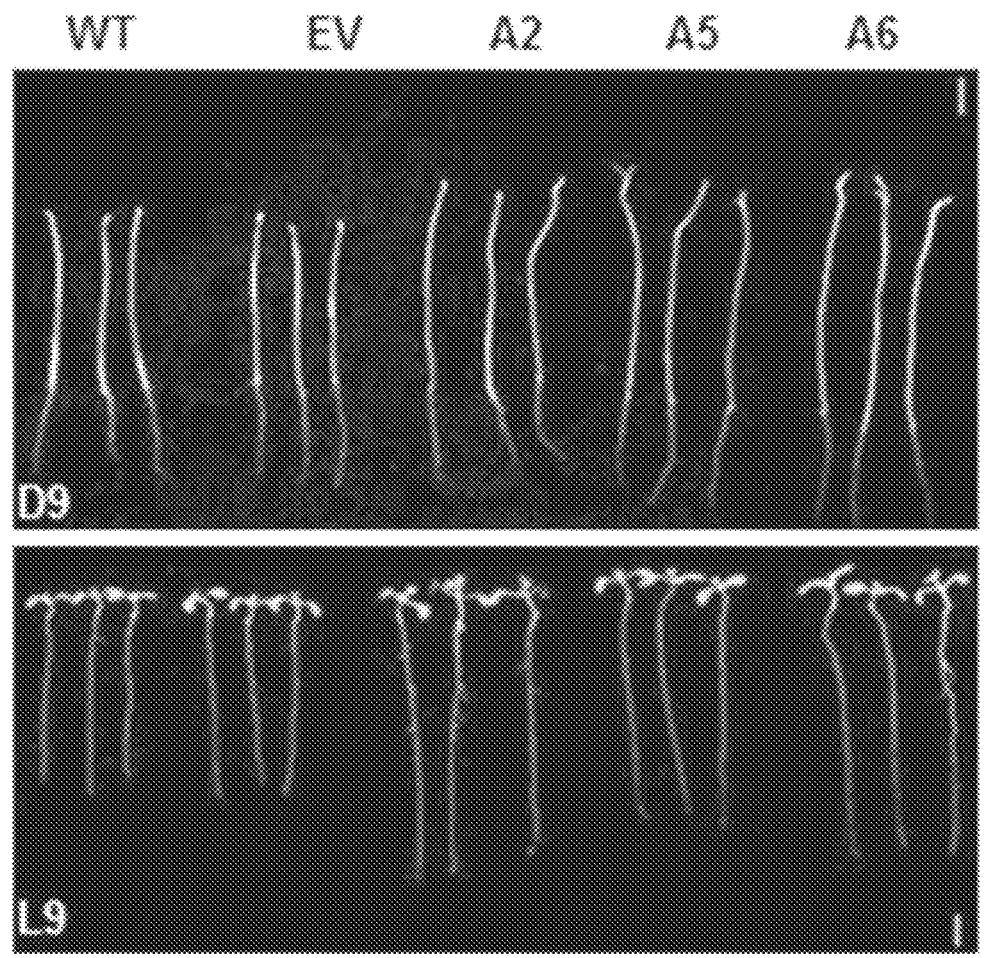
Figure 1C:
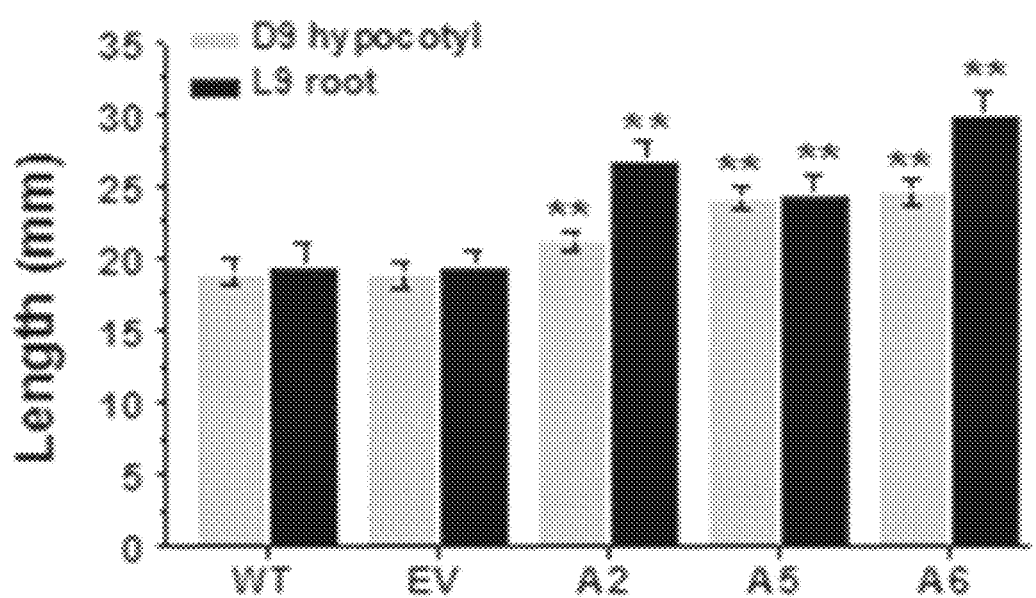
Figures 1, 1D:
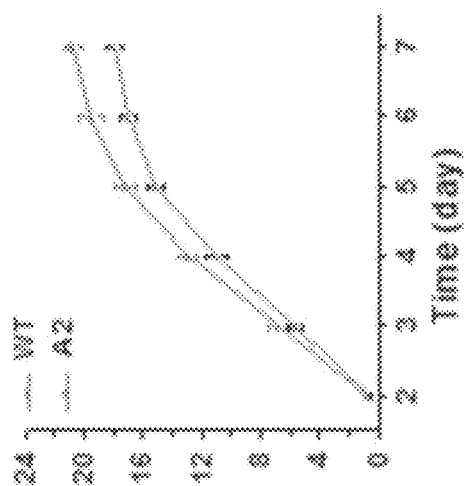
Figures 1, 1D, 2:
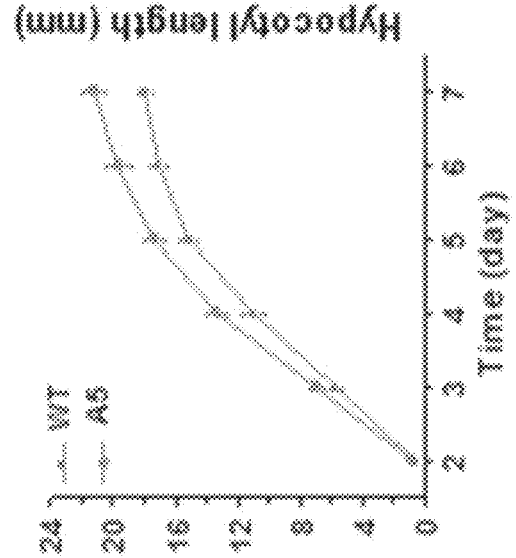
Figures 1, 1D, 2, 3:
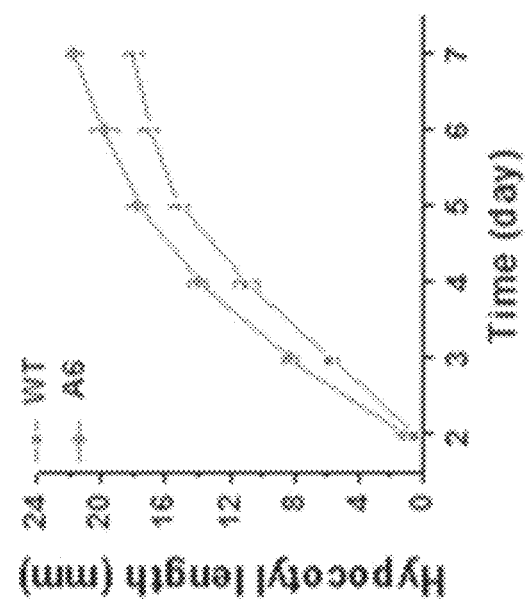
Figure 1E:
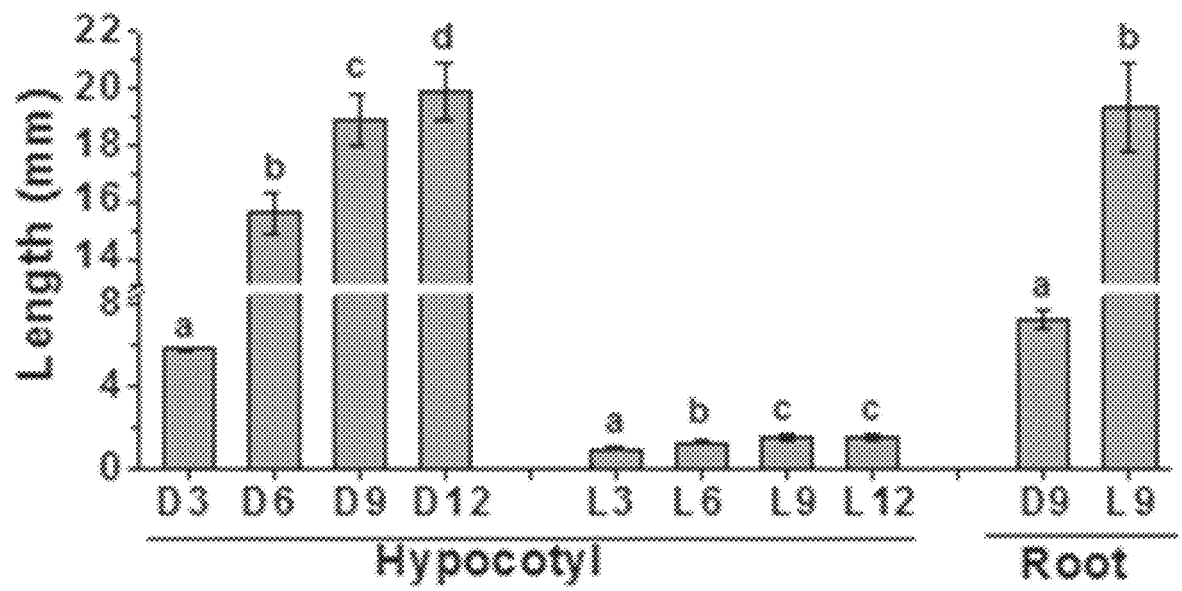
Figure 1F:
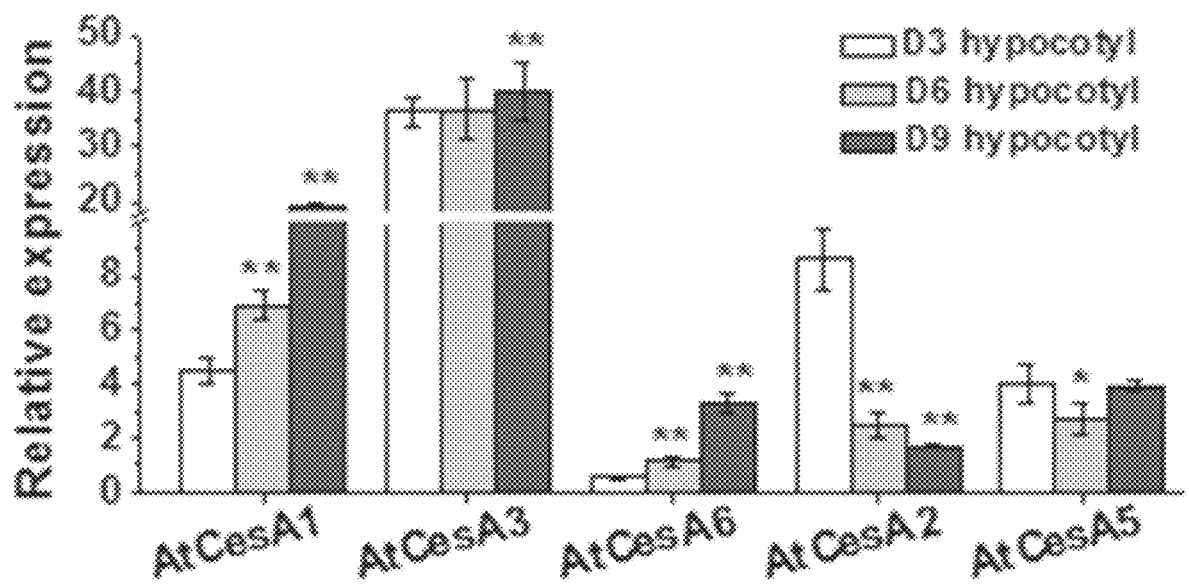
Figure 1G:
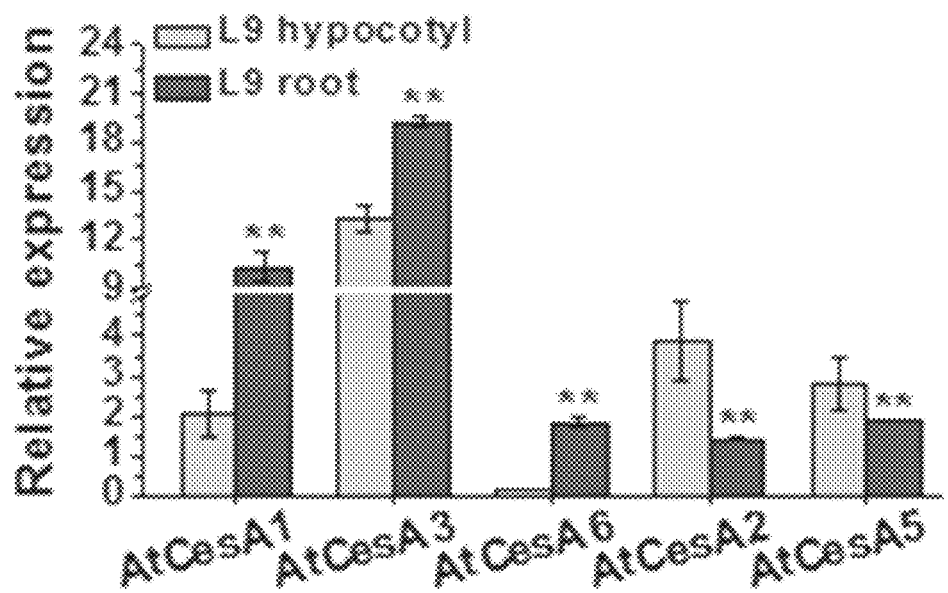

Compared with wild type and empty vector (EV) plants, plants of transgenic lines that overexpressed CesA2 (A2), CesA5 (A5) and CesA6 (A6), but not CesA3 (A3), CesA9 (A9) and CesA7 (A7), showed longer hypocotyl or root length (FIGS. 1B-1D). These data indicate that overexpression of certain CesA6-like genes can enhance seedling growth.

Example 3

CesA6-Like Gene Overexpression Increases Other Primary Wall CesA Expression

To investigate how the enhanced seedling growth was supported in the CesA overexpression lines (CesA2, CesA5 and CesA6), the expression levels of major CesA genes were evaluated in young transgenic seedlings by Q-PCR.

Figure 2A:
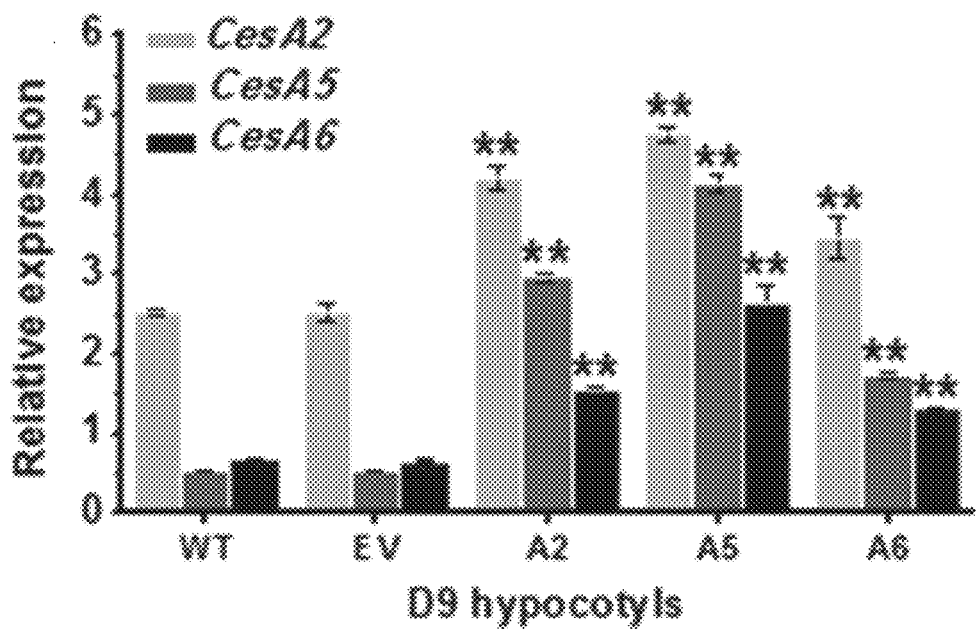
FIG. 2A-2F graphically illustrates the relative expression levels of CesA genes in D9 hypocotyls or roots of three CesA6-like genes overexpressing lines as detected by Q-PCR analyses.
Figure 2B:
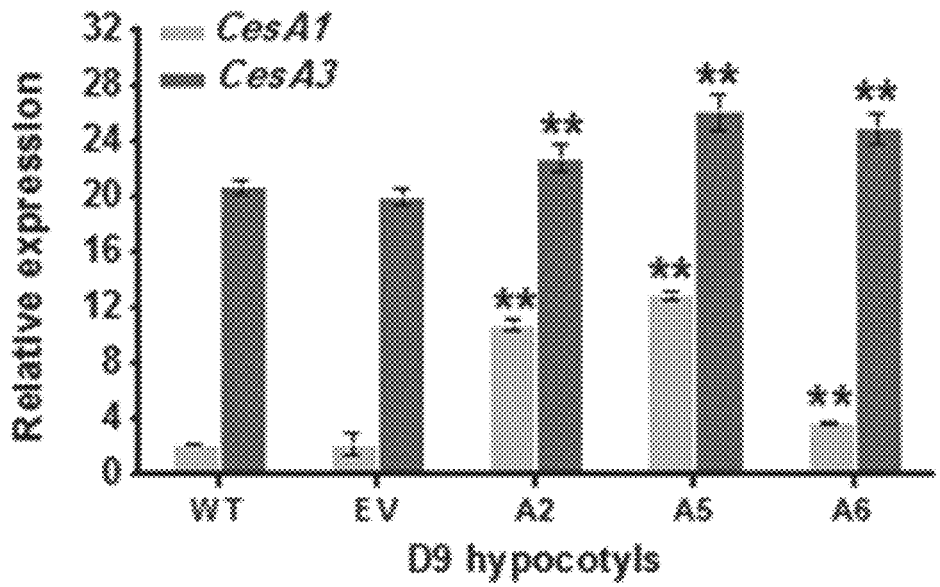
Figure 2C:
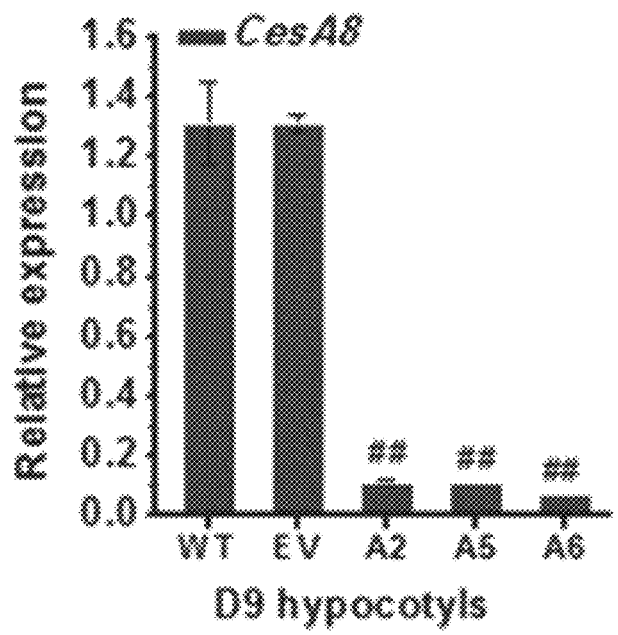
Figure 2D:
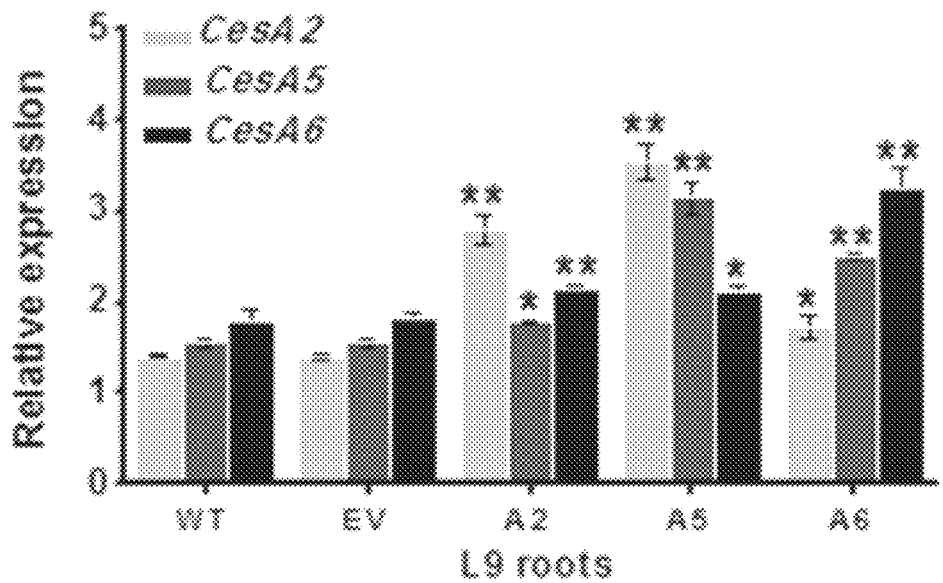
Figure 2E:
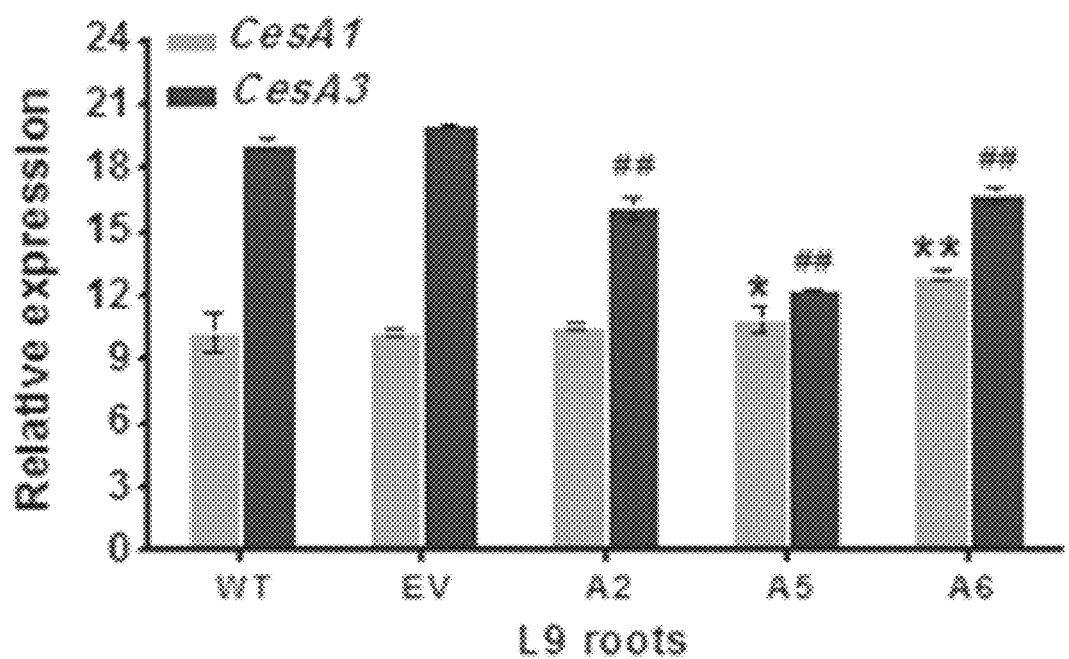
Figure 2F:
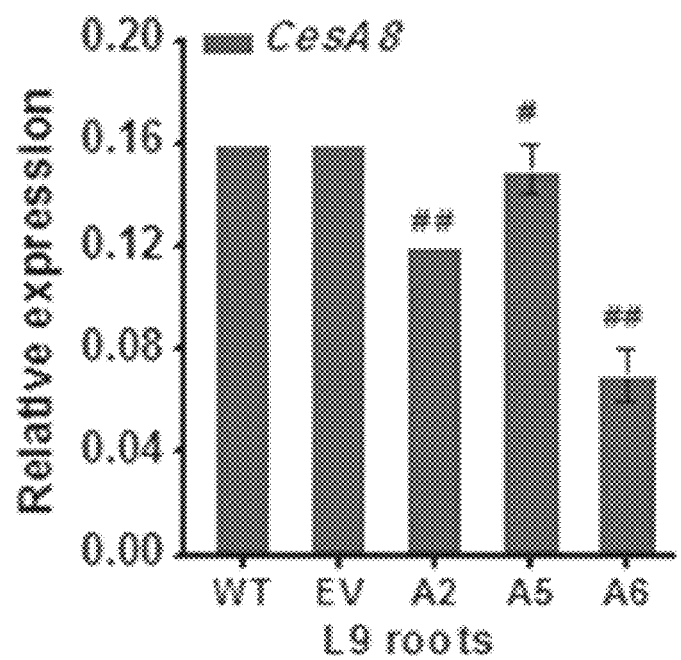

As shown in FIG. 2A-2F overexpression of one of the CesA2, CesA5 and CesA6 genes can enhance the expression of other CesA genes both in D9 hypocotyls (FIG. 2A) and in L9 roots (FIG. 2D). Notably, as shown in FIG. 2B, two major primary CesA genes (CesA1 and CesA3) also exhibited significantly increased expression levels, especially in D9 hypocotyls. While expressions of nearly all primary wall CesA genes were increased in the transgenic lines, the CesA3 expression was reduced in seedling roots of the lines (FIG. 2B, 2E). However, one of the major secondary wall CesA genes, the CesA8 gene, showed markedly decreased expression levels in both D9 hypocotyls and L9 roots (FIG. 2C, 2F). These data indicate that overexpression of any of the three CesA6-like genes could increase the expression of other primary wall CesA genes, with the exception of CesA9, which is mainly expressed in pollen tissues.

Example 4

Figure 3A:
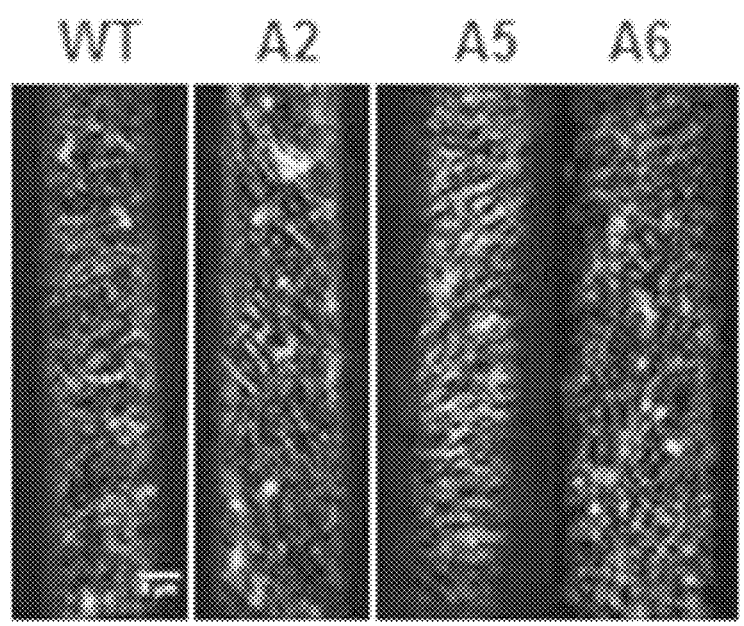
FIG. 3A-3D illustrates increased dynamic movements of primary wall GFP-CesA3 at plasma membrane in the CesA6-like overexpressing transgenic seedlings.
Figure 3B:
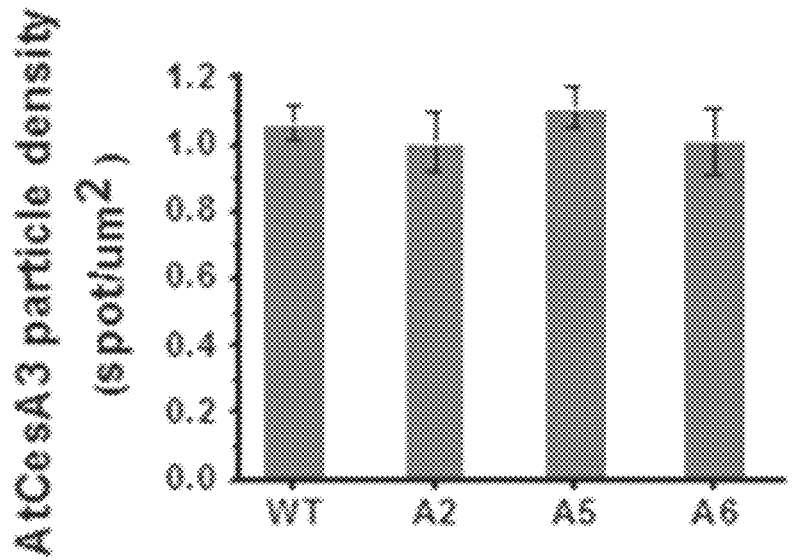
Figure 3C:
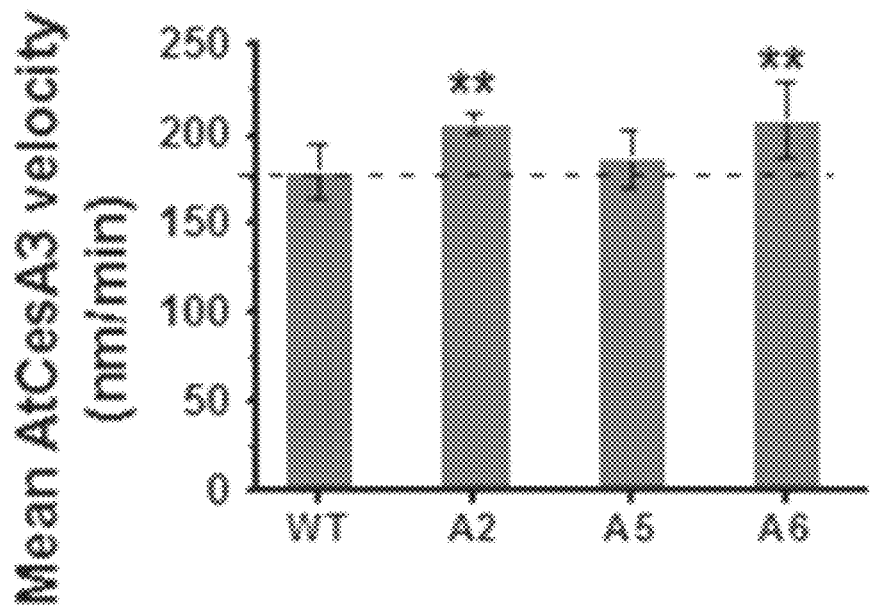
Figure 3D:
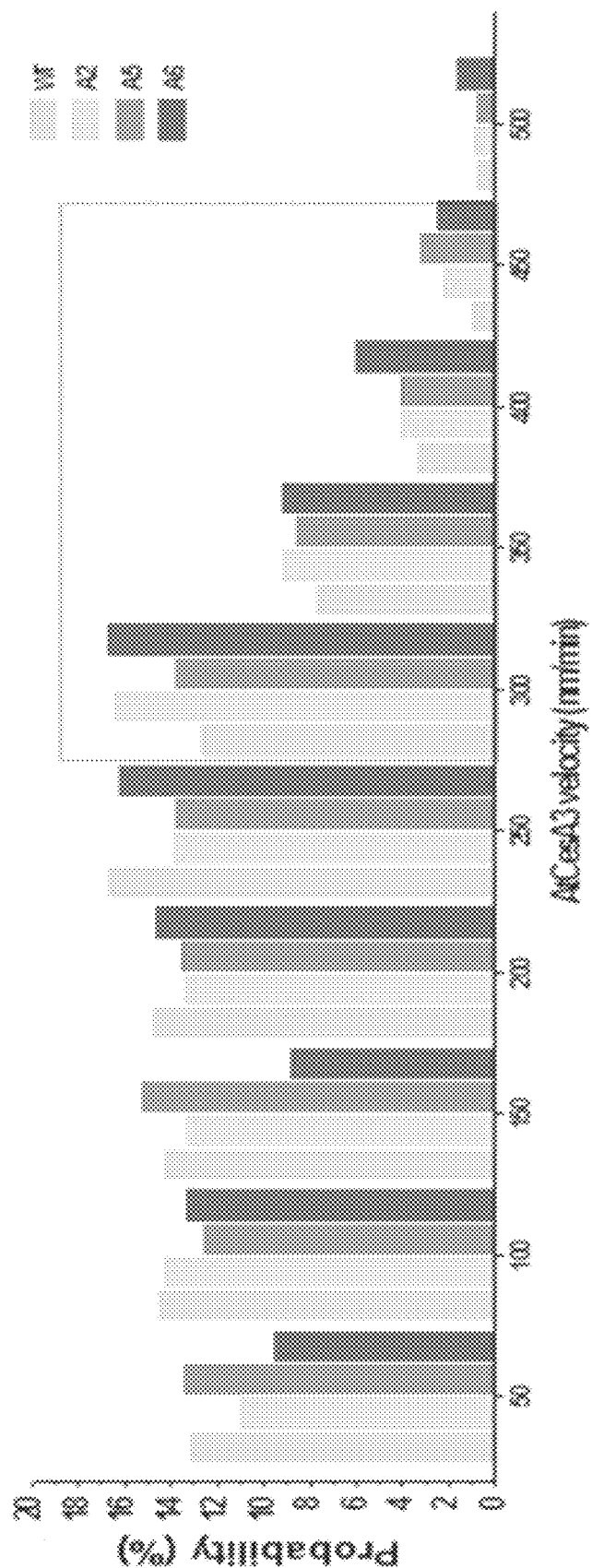

CesA6-Like Gene Overexpression Increases Dynamic Movement of Primary Wall CesAs in the Plasma Membrane To assess the behavior of increased primary wall CesA genes or the cellulose synthase complexes (CSCs), three overexpressing lines (A2, A5 and A6) were crossed the with the proAtCesA3:GFP-AtCes A3 marker line, in which primary wall CSC behavior may be assessed (Desprez et al., 2007). FIG. 3A illustrates that GFP-CesA3 is visible; and can be used to show dynamic movements of CesA3 in epidermal cells of D3 hypocotyls. As shown in FIG. 3B, compared to wild type, no major differences in GFP-CesA3 particle density were observed at the plasma membrane between the overexpressing lines and control in D3 hypocotyls. However, the GFPCesA3 particles in the plasma membrane moved significantly faster in the overexpressing lines, especially in A6 and A2 lines (FIG. 3C). Notably, the three overexpressing lines (A2, A5 and A6) showed a larger proportion of GFP-CesA3 particles moving with speeds higher than 300 nm/min (FIG. 3D). Thus, overexpression of the three CesA6-like genes may cause an increase in CSC motility at the plasma membrane.

Example 5

Cellulose Synthesis is Enhanced in *Arabidopsis* Transgenic Seedlings

To assess whether the transgenic lines produced more cellulose than wild type (WT), crystalline cellulose levels were measured in seedlings.

Figure 4A:
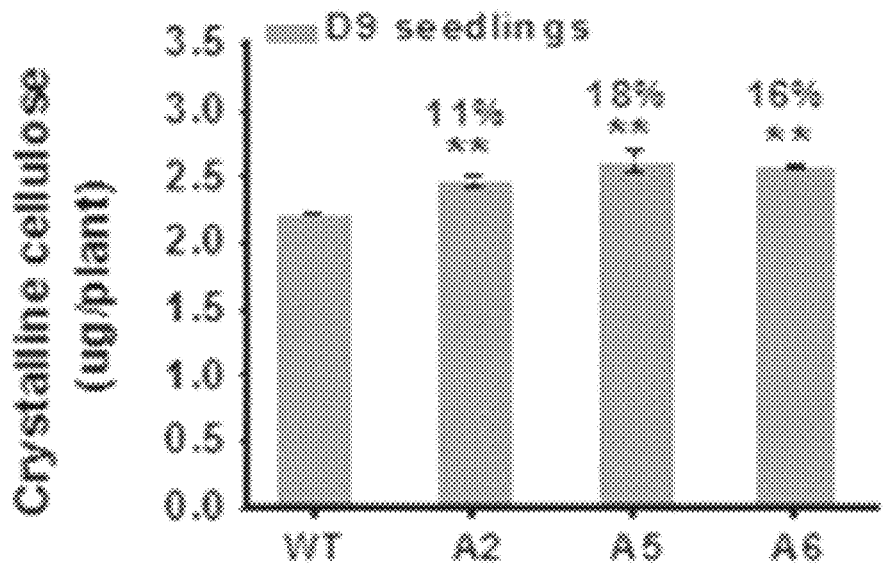
FIG. 4A-4G illustrates enhanced cellulose synthesis in three CesA6-like overexpressing seedlings.
Figure 4B:
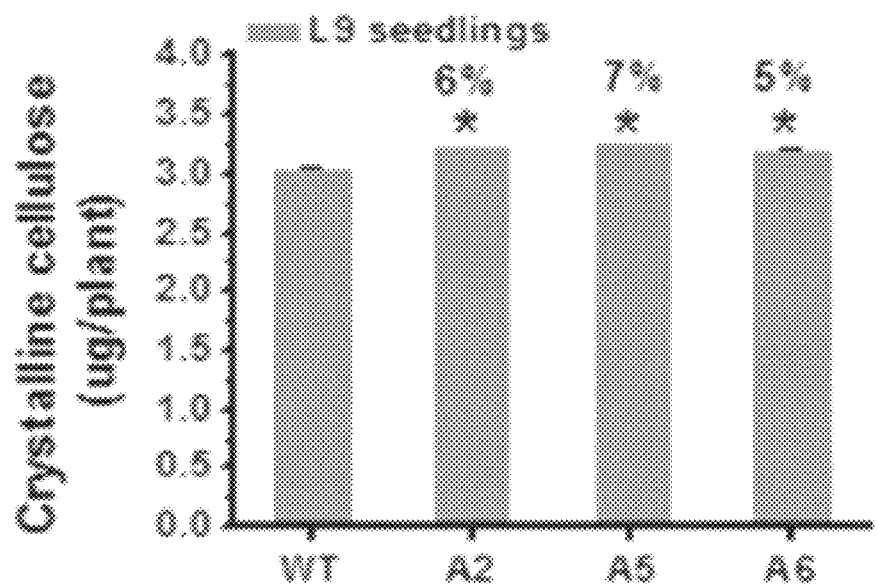
Figure 4C:
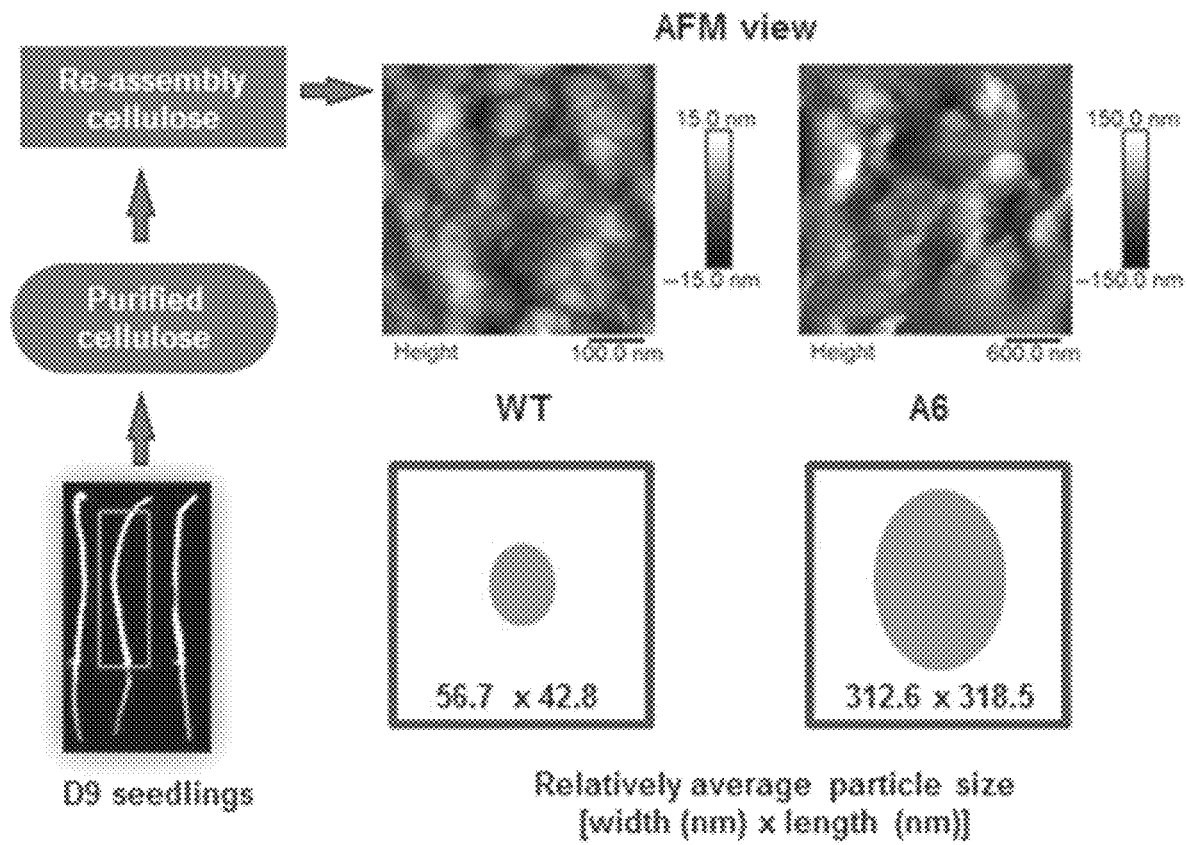
Figures 4D, 4E:
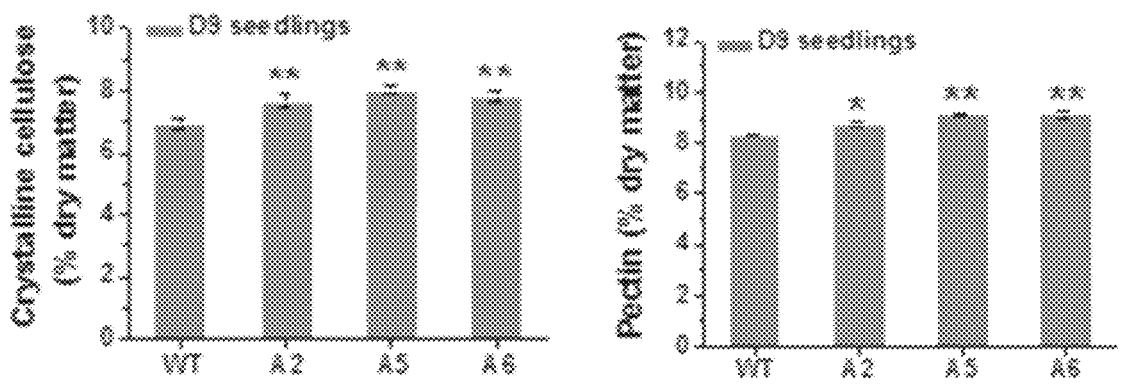
Figure 4F:
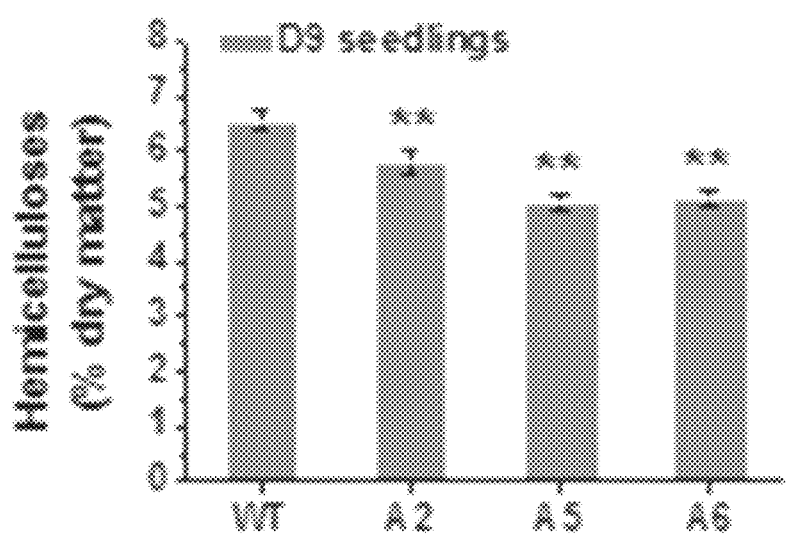
Figure 4G:
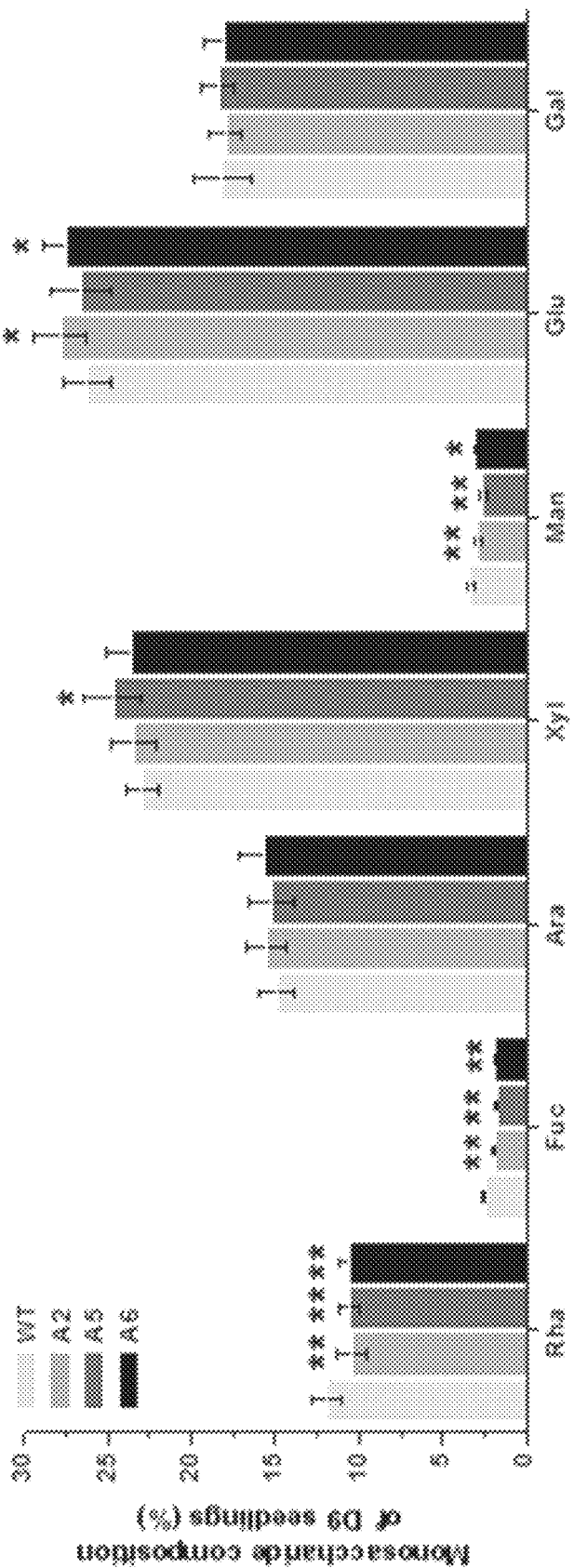

As shown in FIG. 4A-4B, compared to wild type, overexpression of one of the CesA2, CesA5 and CesA6 genes in plant lines A2, A5 and A6 shows that significantly increased levels of crystalline cellulose were present per plant in D9 and L9 seedlings. The increase in crystalline cellulose ranged from 5% to 11%. In terms of cell wall compositions, D9 seedlings of the three overexpressing lines had higher crystalline cellulose and pectin levels and relatively lower hemicelluloses levels per dry weight than those of WT (FIGS. 4D-4F). Based on the monosaccharide composition analysis of total wall polysaccharides, all three transgenic lines showed significantly lower proportions of rhamnose, fucose and mannose, with variations of other monosaccharides, compared to WT (FIG. 4G).

The properties of the cellulose were examined by observing the reassembly of macrofibrils in vitro under atomic force microscopy (AFM) from D9 hypocotyls. As shown in FIG. 4C, the CesA6 overexpressing plant lines exhibited larger, egg-shaped macrolibrils as compared to the WT material (exhibiting a five-fold increase in size), suggesting that overexpression of CesA6 genes can affect microfibril organization (FIG. 4C).

In summary, overexpression of CesA2, CesA5 and CesA6 proteins can enhance cellulose biosynthesis and influence the size of cellulose microfibril aggregates in vitro, perhaps caused by the increased movement of primary wall CesA proteins.

Example 6

Enhanced Cell Elongation and Division in Transgenic Seedlings

To assess what aspects of seedling growth were enhanced by the overexpression of CesA2, CesA5 and CesA6 proteins, cell elongation and division were evaluated.

Figure 5A:
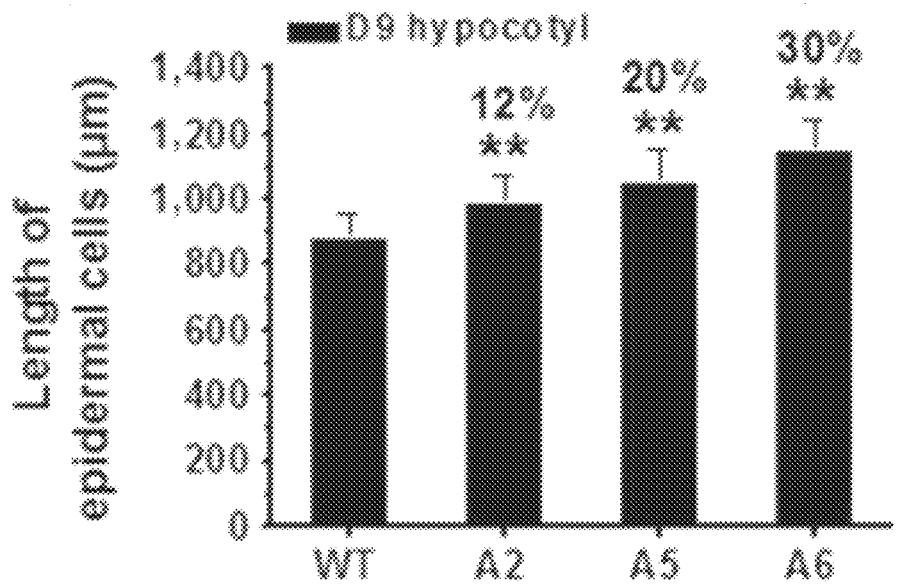
FIG. 5A-5I illustrate enhanced cell elongation and division in seedlings of plant lines that overexpress CesA2 (A2), CesA5 (A5) and CesA6 (A6) proteins.
Figure 5B:
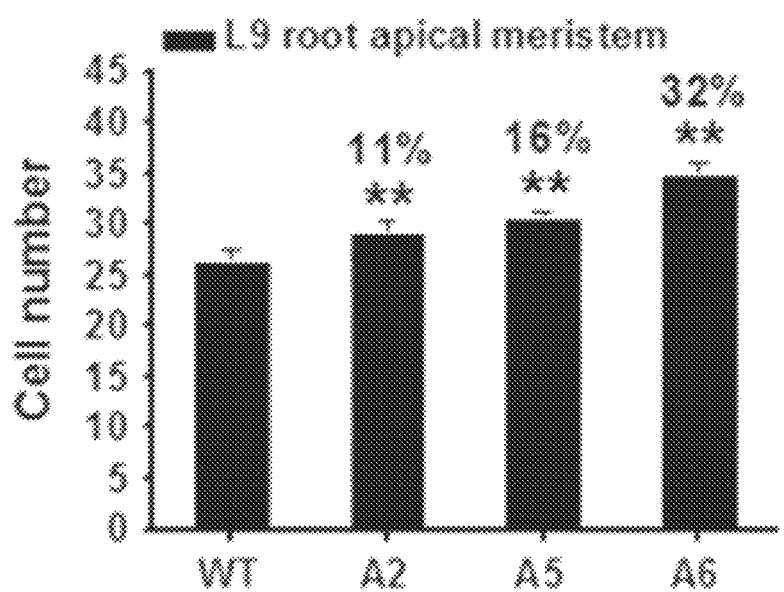
Figure 5C:
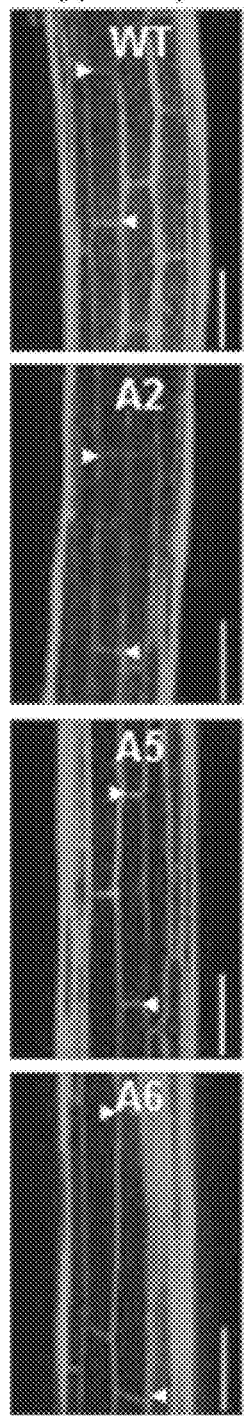

First, the size of basal epidermal cells of D9 hypocotyls were measured. These cells were significantly longer in plant lines that overexpressed CesA2, CesA5 and CesA6 proteins as compared to WT (FIGS. 5A & 5C). Because the number of epidermal cells in a single vertical cal file (parallel to the direction of growth) is genetically fixed to approximately 20 cells in *Arabidopsis* hypocotyls (Gendreau et al., 1997), the inventors presumed that the increased hypocotyl lengths would mainly be due to enhanced cell elongation in the transgenic plants.

Figure 5D:
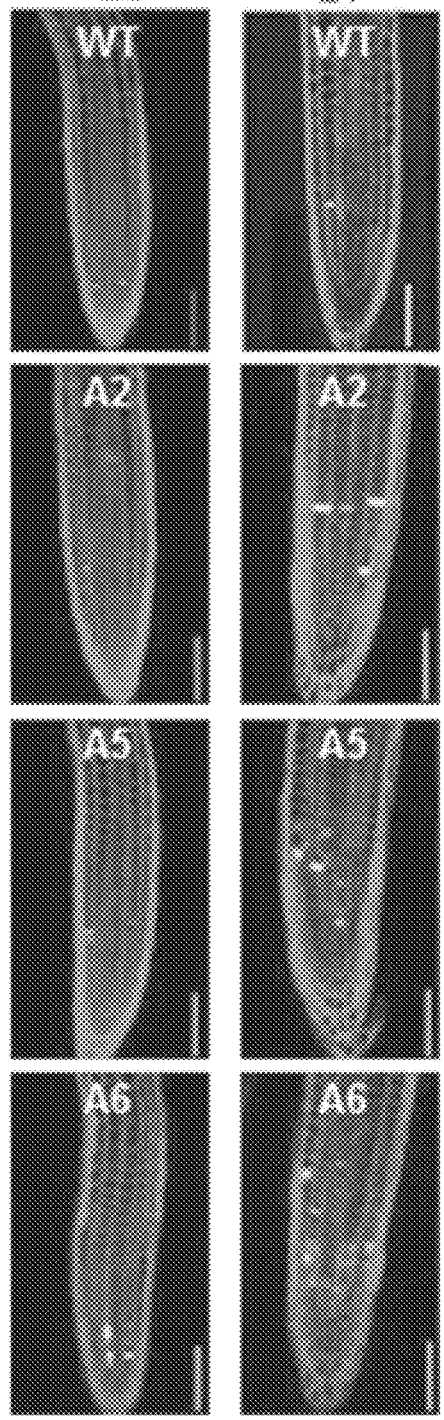
Figure 5E:
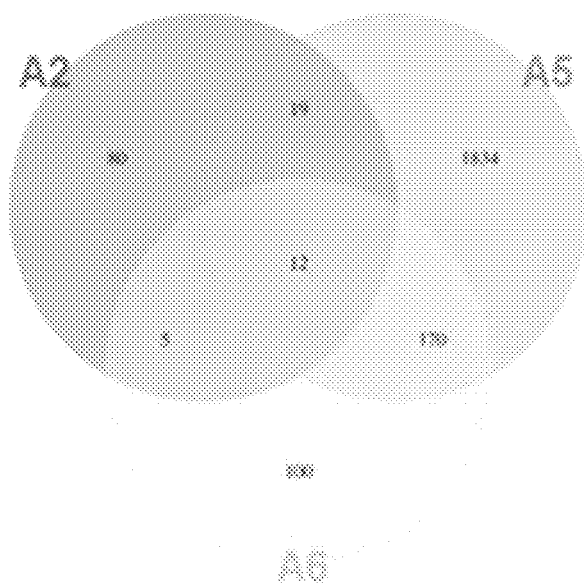
Figure 5F:
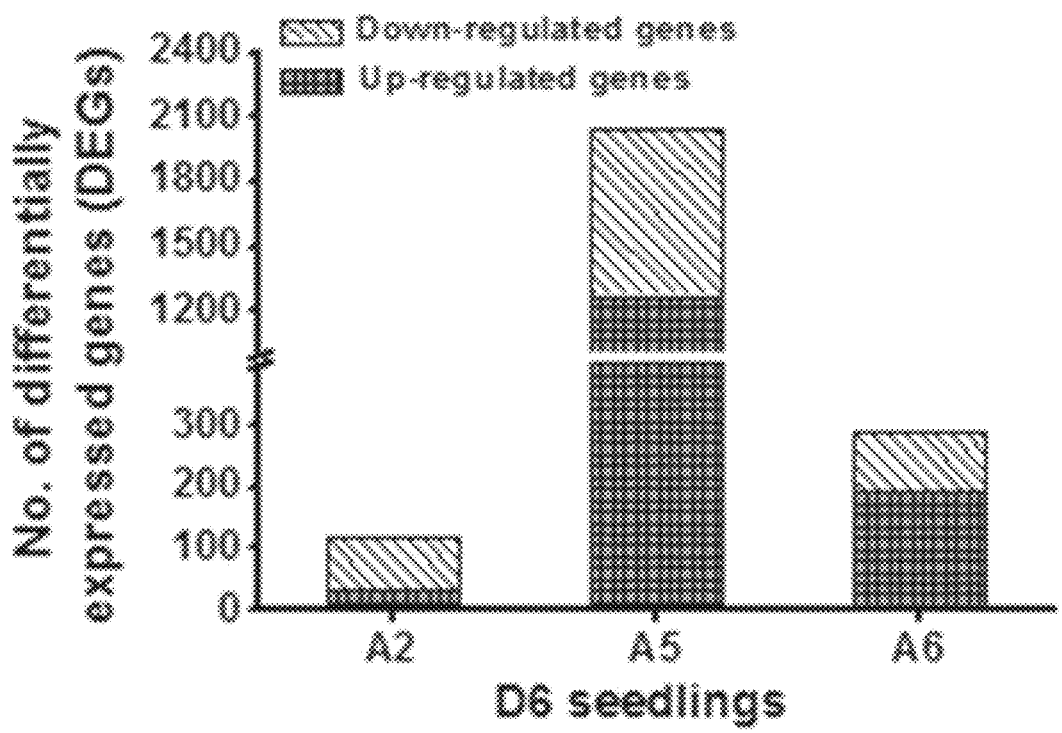
Figure 5G:
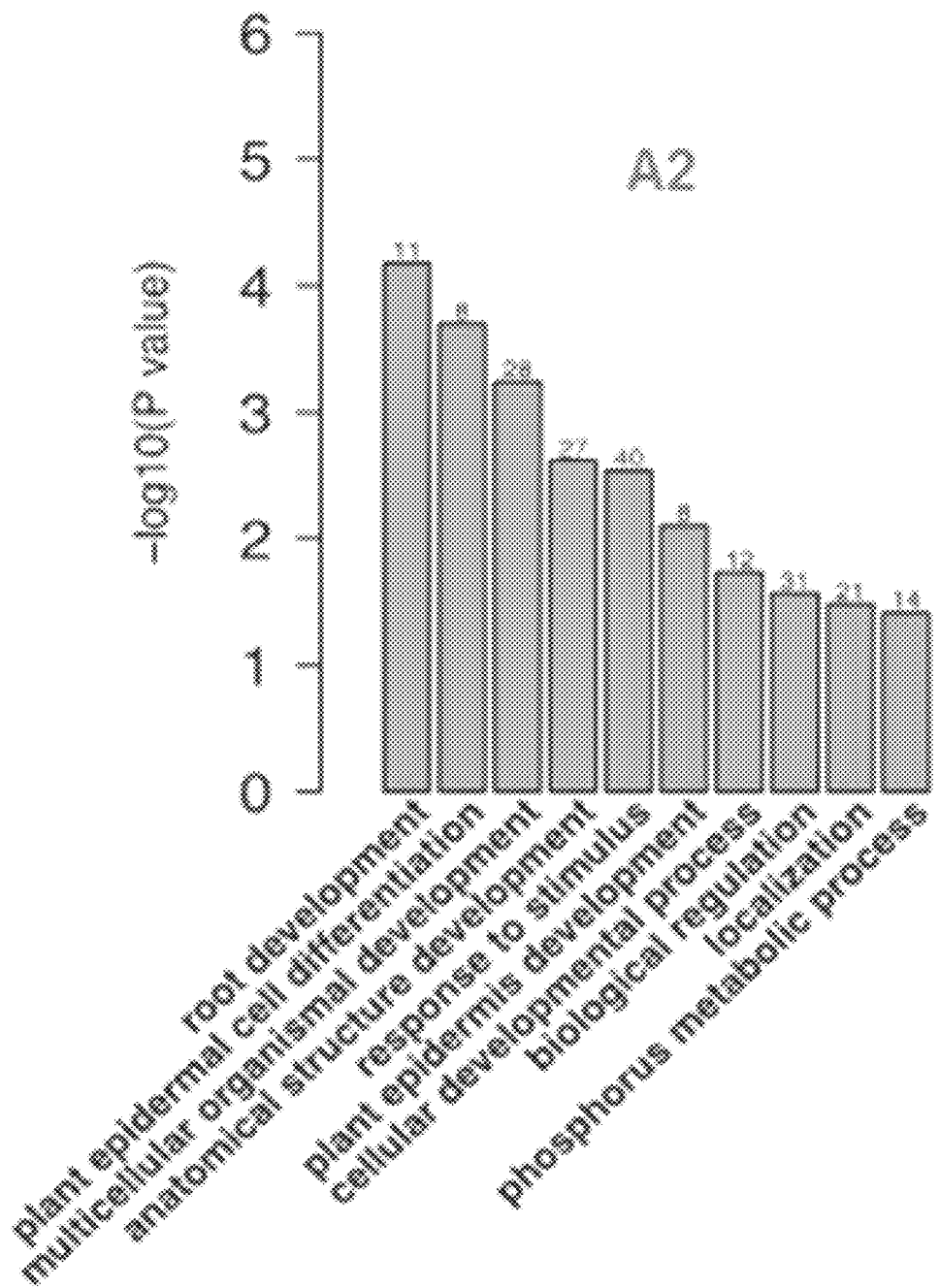
Figure 5H:
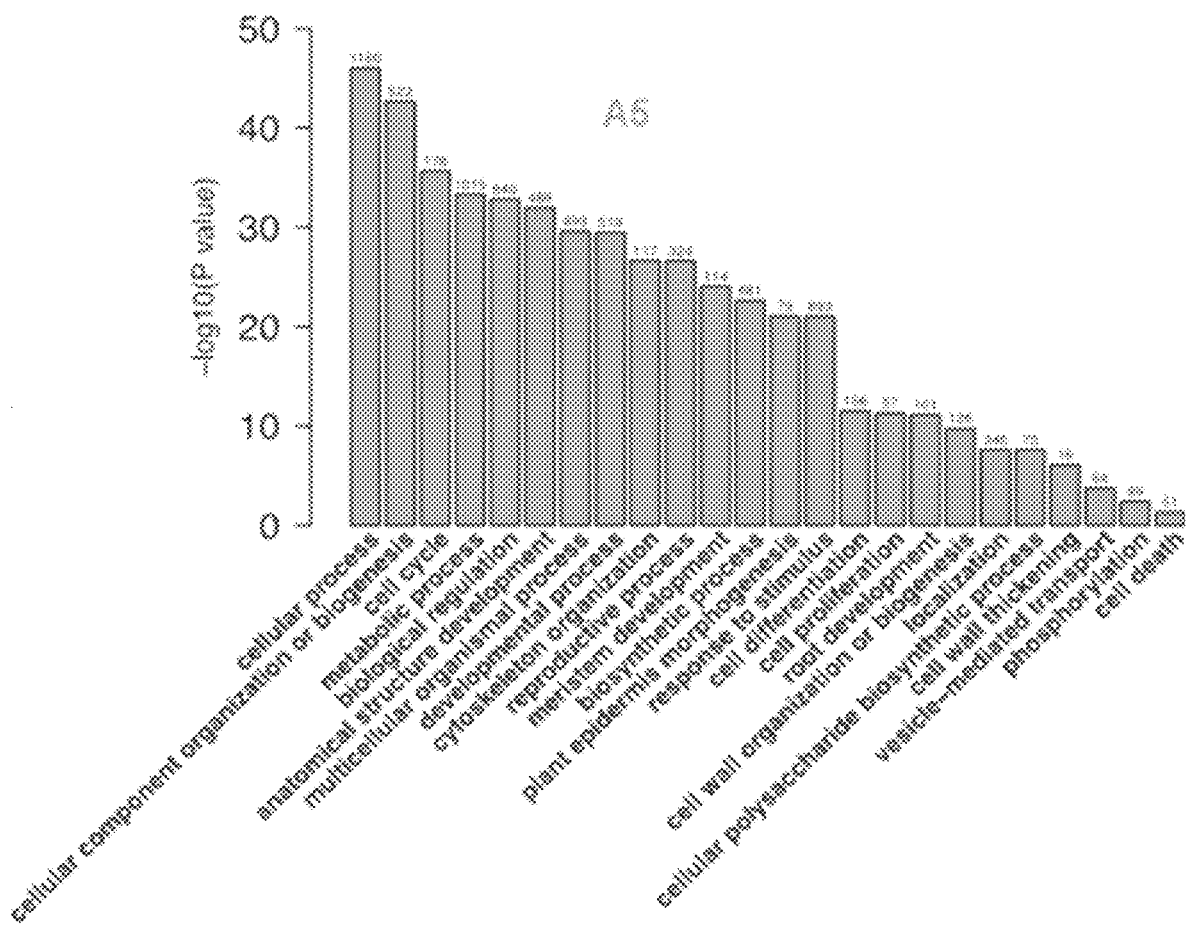
Figure 5I:
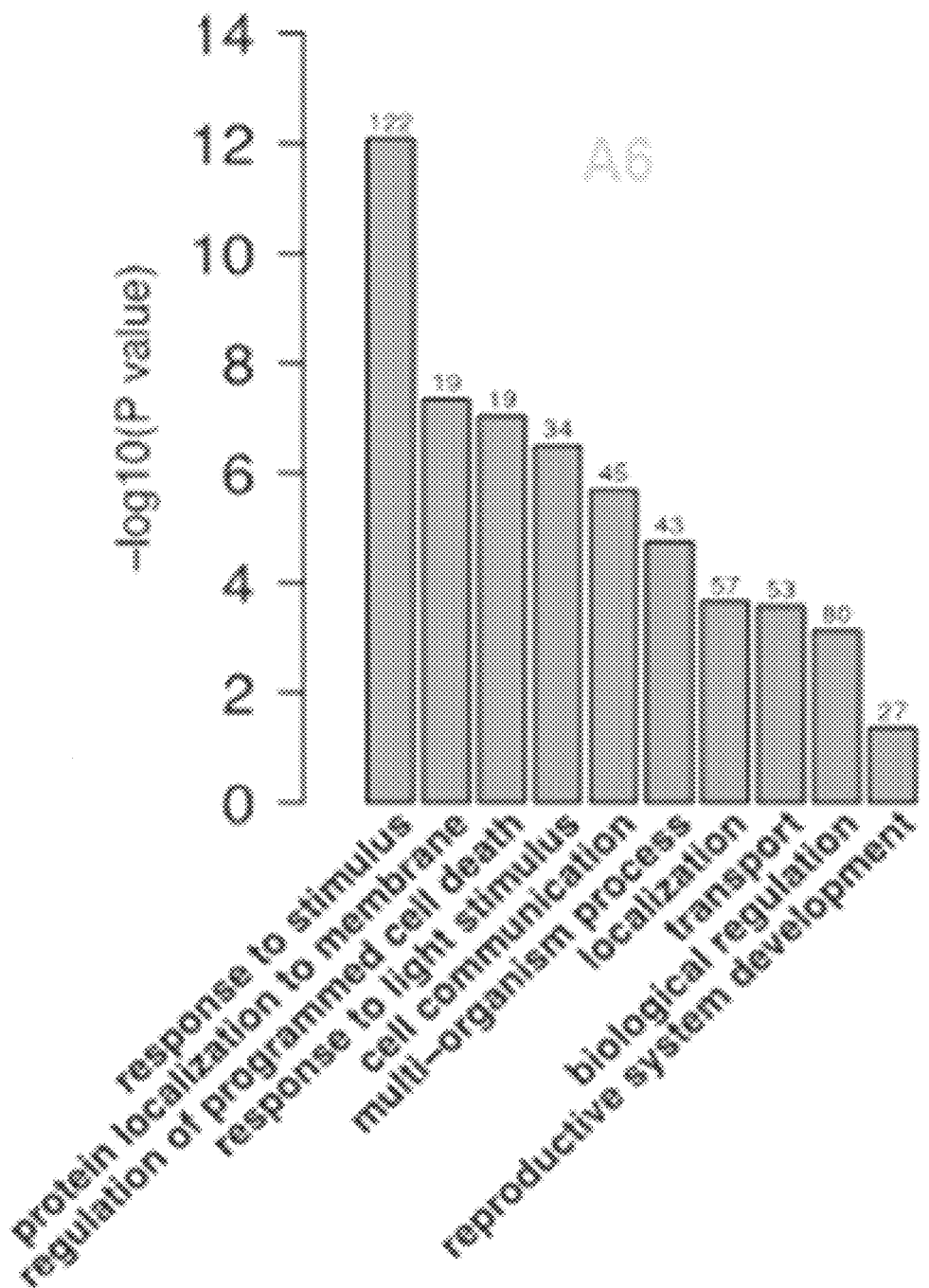

The cortical cell numbers of root apical meristems from the quiescent centres (QC) to the transition zone (TZ) in L9 seedlings were estimated to assess the causes for the increased root growth. The transgenic lines contained more cells in this region as compared to WT, indicating an enhanced cell division in these lines (FIG. 5B). To test this, plant lines overexpressing CesA2, CesA5 and CesA6 proteins were crossed with the proAtCYCB1; 1:AtCYCB1; 1-GFP marker line, a classic G2 (interphase) to M (mitotic phase) specific marker of the cell division cycle (Ferreira et al., 1994; Uheda-Tomas et al., 2009). Analyses of the progeny of these crosses revealed that the transgenic lines had more cells undergoing division than WT in L4 root tips, are detected by the increased green fluorescent foci visible in the roots (FIG. 5D). Thus, overexpression of CesA2, CesA5 and CesA6 proteins can enhance both cell elongation and division in *Arabidopsis* seedlings.

To investigate how overexpression of CesA2, CesA5 and CesA6 proteins influenced general gene expression, RNA sequencing experiments were performed of 6-day-old dark-grow (D6) WT, A2, A5 and A6 transgenic seedlings. Many genes included under Gene Ontology and Biological Process terms (GO and BP terms) associated with cell growth and cellulose synthesis showed clear differences in their expression in the transgenic lines, compared to wild type (FIG. 5E-5I). These changes indicate that the increase in the primary wall CesA genes can affect plant growth in other ways than simply making more cellulose.

Example 7

Increased Biomass Yields in Three CesA6-Like Transgenic Mature Plants

Figure 6A:
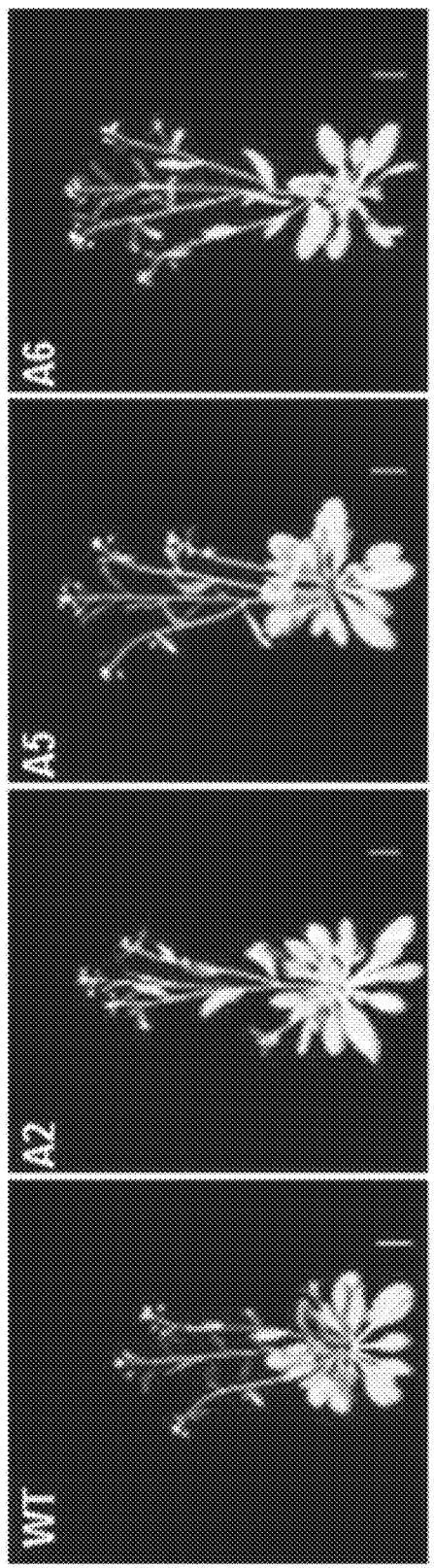
FIG. 6A-6E illustrate increased cellulose synthesis and biomass production in plant lines that overexpress CesA2 (A2), CesA5 (A5), and CesA6 (A6).
Figure 6B:
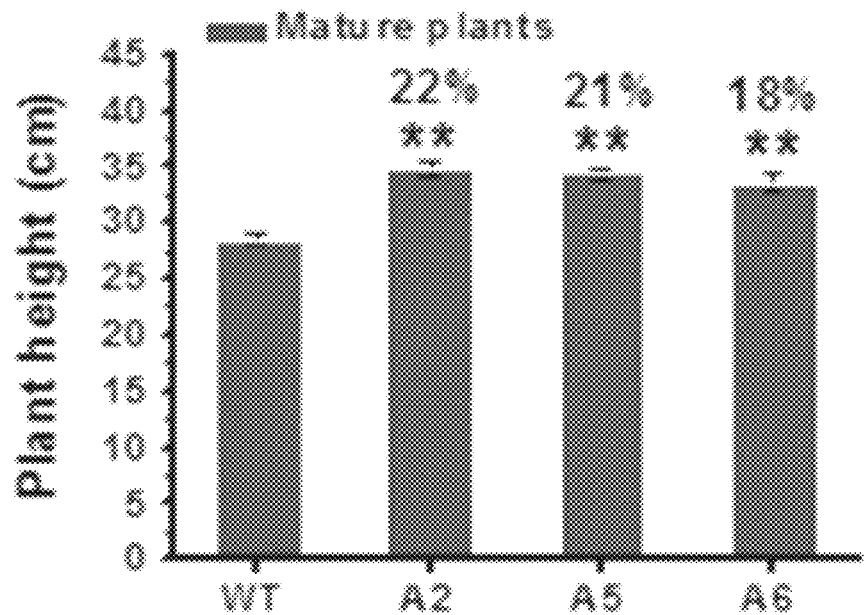
Figure 6C:
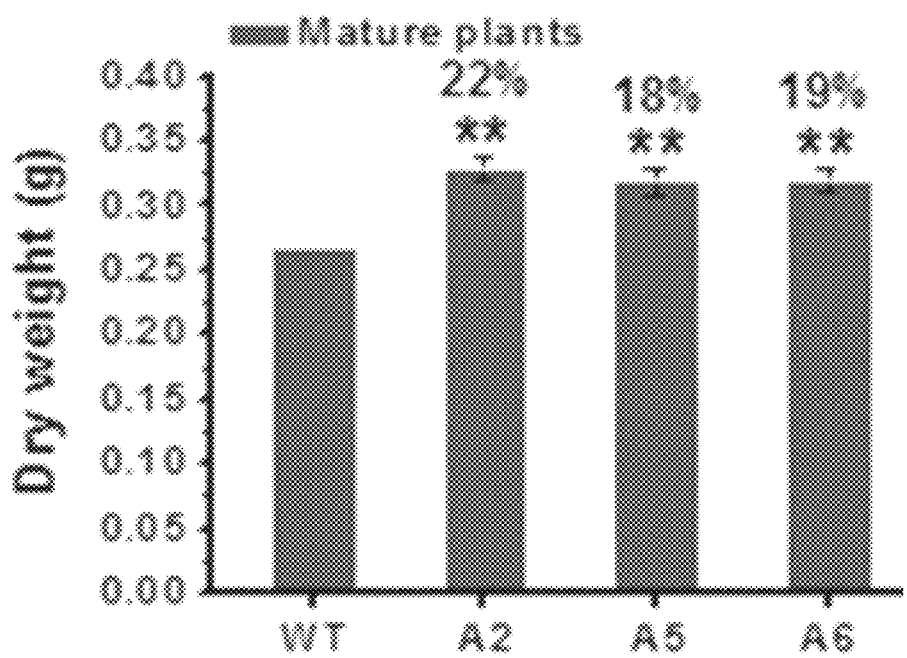

When the CesA2, CesA5 and CesA6 transgenic plants were grown on soil, it was noted that these plants were taller. These CesA2, CesA5 and CesA6 transgenic plants also had more dry weight compared to wild type plants after 7 weeks of growth (FIG. 6A-6C).

Figure 6D:
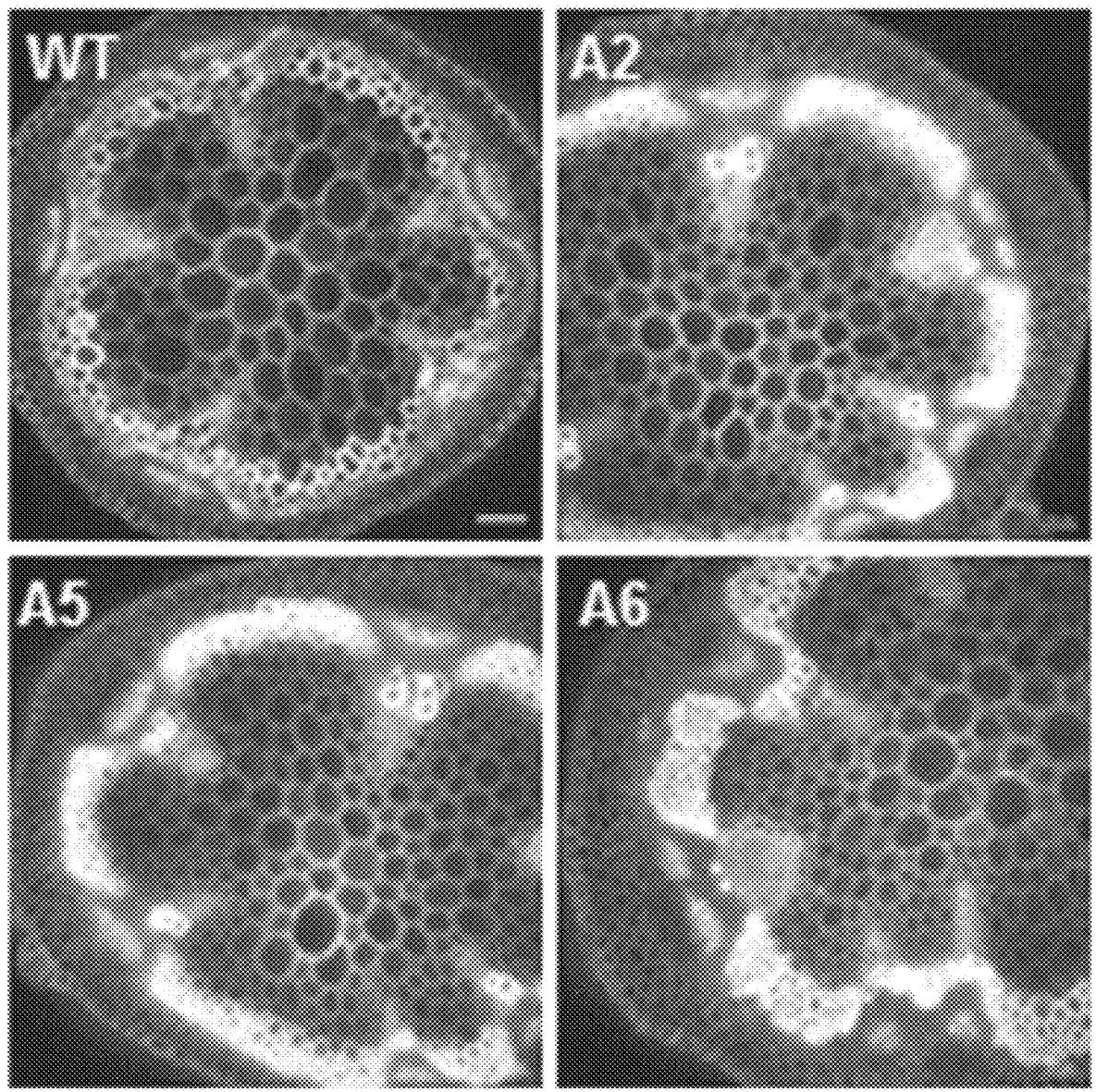

Microscopic observations were made of transverse sections of 1st internode stem that were stained with calcofluor, which stains glucans including cellulose (Haigler et al., 1980). FIG. 6D shows that stronger calcofluor fluorescence was present in plant lines overexpressing CesA2, CesA5 and CesA6 compared to wild type.

Figure 6E:
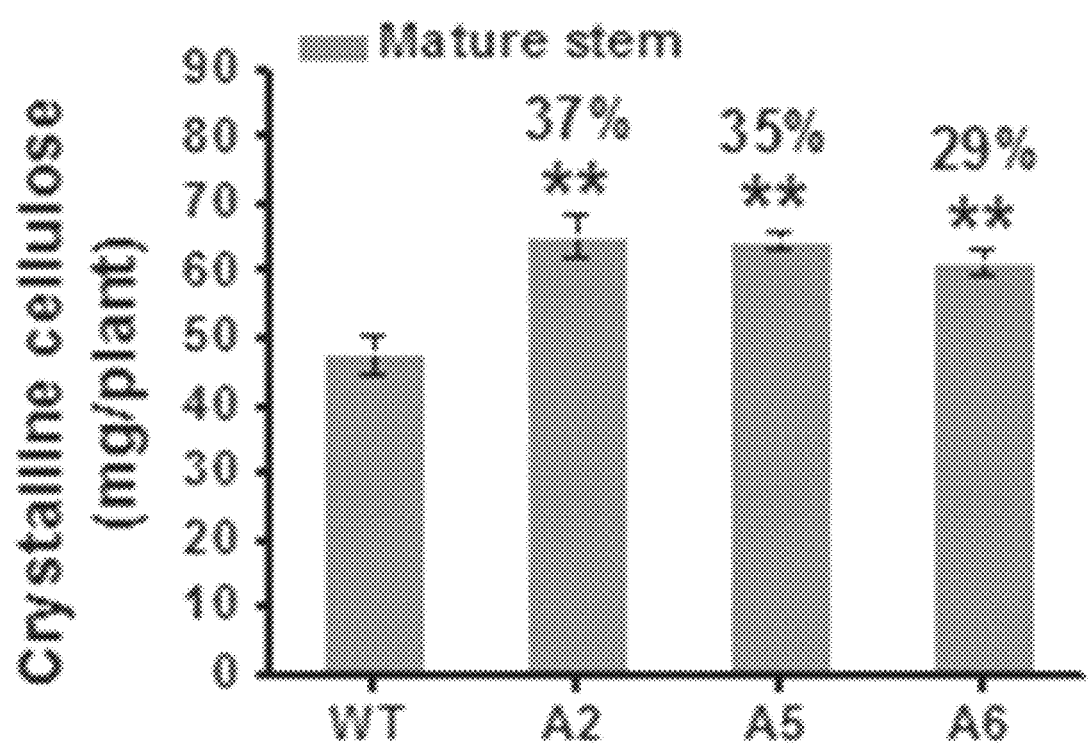

The cell wall composition of the 7-week-old inflorescence stems of mature plants were then analyzed. As shown in FIG. 6E, plant lines that overexpressed the CesA2, CesA5 and CesA6 genes contained more crystalline cellulose per plant (ranging from 29% to 37% increase) than wild type plants. These transgenic plants that overexpress CesA2, CesA5 and/or CesA6 also exhibited significantly higher crystalline cellulose and lignin levels with relatively lower hemicelluloses content per dry weight compared to wild type. However, no significant difference was found in the relative pectin levels among all enic lines and wild type plants.

Based on monosaccharide composition analysis of total wall polysaccharides, all mature transgenic plants showed a significant increase in xylose and a decrease in other monosaccharides, as compared to wild type. These data indicate that the enhanced biomass yields are mainly due to an increase in cellulose and lignin levels in the three plant lines that overexpress CesA2, CesA5 and/or CesA6 genes.

Example 8

Increased Secondary Wall Thickness in Transgenic Mature Plants

Because plant secondary cell walls represent the major biomass production site (Fan et al., 2017; Li et al., 2017), transmission electron microscopy (TEM) was used to observe the xylary fibre (xt) sclerenchyma cells in the 1st internode stem of 7-week-old Arahidopsis plants. As illustrated in FIG. 7A-7B, TEM revealed that plant lines that overexpress CesA2, CesA5 and/or CesA6 genes had much thicker cell walls in xylary fibre tissues, which are largely comprised of secondary walls. Quantification of the cell wall width showed that plant lines that overexpress CesA2, CesA5 anchor CesA6 genes have thicker primary walls than those of wild type plants (see FIG. 7C), consistent with their increased cellulose levels and large macrofibrils in reassembly assays of seedlings (see FIG. 4).

Notably, plant lines that overexpress CesA2, CesA5 and/or CesA6 genes also had remarkably increased secondary cell wall widths (more than two-fold) compared with wild type plants (FIG. 7D).

Hence, overexpression of CesA2, CesA5 and/or CesA6 genes can increase both primary and secondary wall deposition.

The impact of CesA3 and CesA9 overexpression on secondary cell wall formation was also examined in CesA3 and CesA9 transgenic plants (A3 and A9). Unlike CesA2 and CesA5, overexpression of CesA3 or CesA9 did not increase secondary cell wall widths (FIG. 7E-7F), consistent with its inability to enhance young seedling growth (FIG. 1B) and plant growth (FIG. 7F).

Surprisingly, despite the similar phenotypes observed in the young seedlings in comparison with wild type (FIG. 1B), the CesA7 overexpressing plants (A7) exhibited incomplete xylary fibre (xf) cell walls (FIG. 7E), indicating that simply overproducing secondary CesA genes is unlikely to increase secondary wall deposition. The incomplete walls observed for CesA7 overexpressing plants (A7) may be due to defects in cell wall integrity or may indicate cosuppression of other secondary wall genes (FIG. 7F).

Example 8

Increased Wall Mechanical Strength in Transgenic Mature Plants

As cell walls provide plants with mechanical strength (Fan et al., 2017). To evaluate the mechanical strength of transgenic plant, crude cell walls were extracted from the 1st internode stem of 7-week-old plants. The wall forces of these cell walls were evaluated by measuring the Young's modulus of the cell walls using AFM technology (FIG. 8A).

As shown in FIG. 8B, compared to wild type, plant lines that trans enically overexpress CesA2, CesA5 and/or CesA6 genes exhibited significantly enhanced mean mechanical strength with a higher proportion of Young's modulus values in the range from 10 to 100 GPa (FIG. 8C). Therefore, the CesA6 overexpression plants had relatively higher mechanical strength in the basal stems of plants, likely due to the enhanced secondary wall synthesis.

REFERENCES

Anders, S. and Huber, W. (2010) Differential expression analysis for sequence count data, *Genome Biol.* 11, R106.

Anders, S., Pyl, P. T. and Huber, W. (2015) HTSeq-a Python framework to work with high-throughput sequencing data. *Bioinformatics,* 31, 166-169.

Arioli, T., Peng, L., Betzner, A. S., Burn, J., Wittke, W., Herth, W., Camilleri, C. et al. (1998) Molecular analysis of cellulose biosynthesis in *Arabidopsis. Science,* 279, 717-720.

Beemster, G. T. and Baskin, T. I. (1998) Analysis of cell division and elongation underlying the developmental acceleration of root growth in *Arabidopsis thaliana. Plant Physiol.* 116, 1515-4526.

Bischoff, V., Desprez, T., Mouille, G., Verabettes, S., Gotinean, M. and Hoffte, H. (2011) Phytochrome regulation of cellulose synthesis in *Arabidopsis. Curr. Biol.* 21, 1822-1827.

Bringmann, M., Li, E., Sampathkumar, A., Kocabek, T., Hauser, M. T. Persson, S. (2012) POM-POM2/CELLULOSE SYNTHASE INTERACTING-1 is essential for the functional association of cellulose synthase and microtubules in *Arabidopsis. Plant Cell,* 24, 163-177.

Burton, R. A. and Fincher, G. B. (2014) Plant cell wall engineering applications in biofuel production and improved human health. *Curr. Opin. Plant Biol.* 26, 79-84.

Cano-Delgado, A., Penfield, S., Smith, C., Catley, M. Bevan, M. (2003) Reduced cellulose synthesis invokes lignification and defense responses in *Arabidpsis thaliana. Plant J.* 34, 351-362.

Carroll, A. and Somerville, C. (2009) Cellulosic biofuels. *Annu. Rev. Plant Biol.* 60, 165-182.

Carroll, A., Mansoori, N., Li, S., Lei, L., Verahettes, S., Visser, R. G. F., Somerville, C. et al. (2012) Complexes with mixed primary and secondary cellulose synthases are functional in *Arabidopsis* plants. *Plant Physiol.* 160, 726-737. Chen, S., Ehrhardt, D. W. and Somerville, C. R. (2010) Mutations of cellulose synthase (CESAI) phosphorylation sites modulate anisotropic cell expansion and bidirectional mobility of cellulose synthase. *Proc. Natl Acad. Sci. USA,* 107, 17188-17193.

Chen, S., Jia, H., Zhao, H., Liu, D., Liu, Y., Liu, B., Bauer, S. et al. (2016) Anisotropic cell expansion is affected through the bidirectional mobility of cellulose synthase complexes and phosphorylation at two critical residues on CESA3. *Plant Physiol.* 171, 242-250.

Cosgrove, D. J. (2005) Growth of plant cell wall. *Nat. Rev. Mol. Cell Biol.* 6, 850-861.

Desprez, T., Jaranice, M., Crowell, E. F., Jouy, H., Poehylova, Z., Parcy, F., Hoffte, H. et al. (2007) Organization of cellulose synthase complexes involved in primary cell wall synthesis in *Arabidopsis thaliana. Proc. Natl Acad. Sci. USA,* 104, 15572-15577.

Dolan, L., Janmaar, K., Willemsen, V., Linstead, P., Poethig, S., Roberts, K. and Scheres, B. (1993) Cellular organisation of the *Arabidopsis thaliana* root. *Development*, 110, 71-84.

Du, Z., Thou, X., Ling, Y., Zhang, Z. and Sn, Z. (2010) agriGO: a GO analysis toolkit for the agricultural community. *Nucleic Acids Res.* 38, 64-70.

Fagard, M., Desnos, T., Desprez, T., Goubet, F., Refregier, G., Mouille, G., McCann, M. et al. (2000) PROCUSTE1 encodes a cellulose synthase required for normal cell elongation specifically in roots and dark-grown hypocotyls of *Arabidopsis*. *Plant Cell*, 12, 2409-2424.

Fan, C., Li, Y., Hu, Z., Hu, H., Wang, G., Li, A., Wang, Y. et al. (2017) Ectopic expressions of a novel OsExtenstin-like gene consistently enhance plant lodging resistance by regulating cell elongation and ca wall thickening in rice. *Plant Biotechnol. J.*, https://doi.org/10.1111/pbi.12766.

Farrokhi, N., Burton, R. A., Brownfield, L., Hrmova, M., Wilson, S. M., Bacic, A. and Fincher, G. B. (2006) Plant cell wall biosynthesis: genetic, biochemical and functional genomics approaches to the identification of key genes. *Plant Biotechnol. J.* 4, 145-167.

Ferreira, P. C., Hemerly, A. S., Engler, J. D., van Montagu. M., Engler, G. and Inze, (1994) Developmental expression of the *Arabidopsis* cyclin gene cycl At. *Plant Cell*, 6, 1763-1774.

Fujita, M., Himmelspach, R., Ward, J., Whittington, A., Hasenbein, N., Liu. C., Truong, T. T. et al. (2013) The anisotropyl D604N mutation in the *Arabidopsis* cellulose synthase1 catalytic domain reduces cell wall crystallinity and the velocity of cellulose synthase complexes. *Plant Physiol.* 162, 74-85.

Gendreau, E., Trans, J., Desnos, T., Grandjean, O., Caboche, M. and Hofte, H. (1997) Cellular basis of hypocotyl growth in *Arabidopsis thaliana*. *Plant Physiol.* 114, 295-305.

Griffiths, J. S., Tsai, A. Y. L., Xuc, H., Voinicine, C., Sola, K., Seifert, G. J., Mansfield, S. D. et al. (2014) SALT-OVERLY SENSITIVE5 mediates *Arabidopsis* seed coat mucilage adherence and organization through pectins. *Plant Physiol.* 165, 991-1004.

Gu, F. W., Bringmann, M., Combs, J. R. Yang, J., Bergmann, D. C. and Nielsen, (2016) *Arabidopsis* CSLD5 functions in cell plate formation in a cell cycle-dependent manner. *Plane Cell*, 28, 1722-1737.

Gutierrez, R., Lindeboom, J. J., Paredez, A. R., Emons, A. M. C. and Ehrhardt, D. W. (2009) *Arabidopsis* cortical microtubules position cellulose synthase delivery to the plasma membrane and interact with cellulose synthase trafficking compartments. *Nat. Cell Biol.* 11, 797-806.

Haigler, C. H., Brown, R. M. Jr and Benziman, M. (1980) Calaoflror white ST alters the in vivo assembly of cellulose microfibrils. *Science.* 210, 903-906. Harholt, J., Suttangkakul. A. and Scheller, H. V. (2010) Biosynthesis of Pectin. *Plant Pkvsiol.* 153, 384-395.

He, C., Ma, J. and Wang, L. (2015) A hemicellulose-bound form of silicon with potential to improve the mechanical properties and regeneration of the cell wall of rice. *New Phytol.* 206, 1051-1062.

Hematy, K., Sado, P. E., Van Tuinen, A., Rochange, S., Desnos, T., Balzergue, S., Pelletier. S. et al. (2007) A receptor-like kinase mediates the response of *Arabidopsis* cells to the inhibition of cellulose synthesis. *Curr Biol.* 17, 922-931.

Hunter, C. T., Kirienko, D. H., Sylvester, A. W., Peter, G. F., McCarty, D. R. and Koch, K. E. (2012) Cellulose synthase-like D1 is integral to normal cell division, expansion, and leaf development in maize. *Plant Physiol.* 158, 708-724.

Ivakov. A., Flis, A., Apelt, F., Finfgeld, M., Scherer, U., Stitt, M., Kragier, F. et al. (2017) Cellulose synthesis and cell expansion are regulated by different mechanisms in growing *Arabidopsis* hypocotyls. *Plant Cell*, 29, 1305-1315.

Jin, W. X., Chen. L., Hu, M., Sun, D., Li, A., Li, Y., Hu, Z. et al. (2016) Tween-80 is effective for enhancing steam-exploded biomass enzymatic saccharification and ethanol production by specifically lessening cellulase absorption with lignin in common reed. *Appl. Energ.* 175, 82-90.

Joshi, C. P., Thamannagowda, S., Fujino, T., Gou, J. Q., Avci, U., Haigler, C. H., McDonnell, L. M., et al. (2011) Perturbation of wood cellulose synthesis causes pleiotropic effects in transgenic Aapen. *Mol. Plant*, 4, 331-345.

Keegstra, K. (2010) Plant cell walls. *Plant Physiol.* 154, 483-486.

Landrein, B. and Hamant, O. (2013) How mechanical stress controls microtubule behavior and morphogenesis in plants: history, experiments and revisited theories. *Plant J.* 75, 324-338.

Le Gall, H., Philippe, F., Domon, J. M., Gillet, F., Pelloux, J. and Rayon. C. (2015) Cell wall metabolism in response to abiotic stress. *Plants*, 4, 12-166.

Li, F., Xie, G., Huang, J., Zhang, R., Li, Y., Zhang, M., Wang, Y. et al. (2017) OsCESA9 conserved-site mutation leads to largely enhanced plant lodging resistance and biomass enzymatic saccharification by reducing cellulose DP and crystallinity in rice. *Plant Biotechnol. J.*, 15, 1093-1104.

Liu, Z., Schneider, R., Kesten, C., Zhang, Y., Somssich, M., Fernie, A. R. and Persson, S. (2016) Cellulose-microtubule uncoupling proteins prevent lateral displacement of microtubules during cellulose synthesis in *Arabidopsis*. *Dev. Cell*, 38, 305-315.

Malinovsky, F. G., Fangel. J. U. and Willats, W. G. T. (2014) The role of the cell wall in plant immunity. *Front. Plant Sci.* 5, 178.

McFarlane, H. E., Doring, A. and Persson, S. (2014) The cell biology of cellulose synthesis. *Annu. Rev. Plant Biol.* 65, 69-94.

Mende, V., Griffiths, J. S., Persson, S., Stork, J., Downie A. B., Voiniciuc, C., Haughn, G. W. et al. (2011) Subfunctionalization of cellulose synthases in seed coat epidermal cells mediates secondary radial wall synthesis and mucilage attachment. *Plant Physiol.* 157, 441-453.

Miart, F., Desprez, T., Biot, F., Morin, H., Belcram, K., Hofte, H., Gonneau. M. et al. (2014) Spatio-tetnporal analysis of cellulose synthesis during cell plate formation in *Arabidopsis*. *Plant J.* 77, 71-84.

Mortazavi, A., Williams, B. A., Mccue, K., Schaeffer. L. and Wold, B. (2008) Mapping and quantifying mammalian transcriptones by RNA-Seq. *Nat. Methods.* 5, 621-628.

Naseer, S., Lee, Y., Lapierre, C., Franke, R., Nawrath, C. and Geldner, N. (2012) Casparian strip diffusion barrier in *Arabidopsis* is made of a lignin polymer without suberin. *Proc. Natl Acad. Sci. USA*, 109, 10101-10106.

Paredez, A. R., Somerville, C. R. and Ehrhardt, D. W. (2006) Visualization of cellulose synthase demonstrates functional association with microtubules. *Science*, 312, 1491-1495.

Pear, J. R., Kawagoe, Y., Schreckengost, W. E., Delmer, D. P. and Stalker, D. M. (1996) Higher plants contain homologs of the bacterial celA genes encoding the catalytic subunit of cellulose synthase. *Proc. Natl Acad. Sci. USA.* 93, 12637-12642.

Peng, L., Kawagoe, Y., Hogan, P. and Delmer, D. (2002) Sitosterol-beta-glucoside as primer for cellulose synthesis in plants. *Science,* 295, 147-150.

Persson, S., Paredez, A., Carroll. A., Palsdottir. H., Doblin, M., Poindexter, P., Khitrov, N. et al. (2007) Genetic evidence for three unique components in primary cell-wall cellulose synthase complexes in *Arabidopsis. Proc. Nati Acad. Sci. USA,* 104, 15566-15571.

Sanchez-Rodriguez, C., Ketelaar, K., Schneider, R., Villalobos, J. A., Somerville, C. R., Persson. S. and Wallace, I. S. (2017) BRASSINOSTEROID INSENSITIVE2 negatively regulates cellulose synthesis in *Arabidopsis* by phosphorylating cellulose synthase 1. *Proc. Natl Acad. Sci. USA,* 114, 3533-3538.

Scheible, W. R., Eshed, R., Richmond, T., Delmer, D. and Somerville, C. (2001) Modifications of cellulose synthase confer resistance to isoxaben and thiazolichnone herbicides in *Arabidopsis* Ixrl mutants. *Proc. Natl Acad. Sci. USA,* 98, 10079-10084.

Scheller, H. V. and Ulvskov, P. (201.0) Hemicelluloses. *Annu. Rev. Plant Biol.* 61, 263-289.

Schneider. R., Hanak, T., Persson. S. and Voigt, C. A. (2016) Cellulose and callose synthesis and organization in focus, what's new? *Curr. Opin. Plant Biol.* 34, 9-16. Schuetz, M., Smith, R. and Ellis, B. (2013) Xylem tissue specification, patterning, and differentiation mechanisms. *J. Exp. Bot.* 64, 11-31.

Somerville. C. (2006) Cellulose synthesis in higher plants. *Annu. Rev. Cell Dev. Biol.* 22, 53-78.

Somerville, C., Bauer, S., Brininstool. G., Facette, M., Hamann, T., Milne, J., Osborne, E. et al. (2004) Toward a systems approach to understanding plant-cell walls. *Science,* 306, 2206-2211.

Sullivan, S., Ralet, M. C., Berger, A., Diatloff, E., Bischoff, V., Gonneau, M., Marion-Poll, A. et al. (2011) CESA5 is required for the synthesis of cellulose with a role in structuring the adherent mucilage of *Arabidopsis* seeds. *Pleat Physiol.* 156, 1725-1739.

Sun, D., Alam, A., Tu, Y., Zhou, S., Wang, Y., Xia, T., Huang, J. et al. (20 17) Steam-exploded biomass saccharification is predominately ected ba lignocellulose porosity and largely enhanced by Tween-80 in *Miscanthus. Bioresour. Technol.* 239, 74-81.

Szymanski., D. B. and Cosgrove, D. J. (2009) Dynamic coordination of cytoskeletal and cell wall systems during plant cell morphogenesis. *Curr. Biol.* 19, 800-811.

Tan, H., Shirley, N. J., R. R., Henderson, M., Dhugga, K. S., Mayo, G. M., Fincher, G. B. et al. (2015) Powerful regulatory systems and post-transcriptional gene silencing resist increases in cellulose content in cell walls of barley. *BMC Plant Biol.* 15, 62.

Taylor, N. G., Howells, R. M., Huttly, A. K., Vickers, K. and Turner, S. R. (2003) Interactions among three distinct CesA proteins essential for cellulose synthesis. *Proc. Natl Acad. Sci. USA,* 100, 1450-4455.

Ubeda-Tomas, S., Federici, F., Casimiro, I., Beemster, G. T., Bhalerao, R., Swarup, R., Doerner, P. et al, (2009) Gibberellin signaling in the endodermis controls *Arabidopsis* root meristem size. *Curr. Biol.* 19, 1194-1199.

Wang, T., McFarlane, H. E. and Persson, S. (2016a) The impact of abiotic factors on cellulose synthesis. *J. Exp. Bot.* 67, 543-552.

Wang. Y., Fan. C., Hu, H., Li, Y., Sun. D. and Peng, L. (2016b) Genetic modification of plant cell walls to enhance biomass yield and hiofuel production in bioenergy crops. *Biotechnol. Adv.* 34, 997-1017.

Xu, N., Zhang, W., Ken, S. F., Liu, F., Zhao, C. Q., Liao, H. F., Xu, Z. L. et al. (2012) Hemicelluloses negatively affect lignocellulose crystallinity for MO biomass digestibility under NaOH and H2SO4 pretreatments in *Miscanthus. Biotechnol. Biofuels.* 5, 58.

Yoshikawa, T., Eiguchi, M., Hibara, K., Ito, J. and Nagato, Y. (2013) Rice slender leaf 1 gene encodes cellulose synthase-like D4 and is specifically expressed in M-phase cells to regulate cell proliferation. *J. Exp. Bot.* 64, 2049-2061.

Zhang, X., Henriques, R., Lin, S., Niu, Q. and Chua. N. H. (2006) *Agrobacterium*-mediated transformation of *Arabidopsis thaliana* using the floral dip method, *Nat. Protec.* 1, 641-646.

Zhang, L., Bai, M., Wu, J., Zhu, J., Wang, H., Zhang, Z., Wang, W. et al (2009) Antagonistic HLH/bHLH transcription factors mediate brassinosteroid regulation of cell elongation and plant development in rice and *Arabidopsis, Plant Cell,* 21, 3767.

All patents and publications referenced or mentioned herein are indicative of the levels of skill of those skilled in the art to which the invention pertains, and each such referenced patent or publication is hereby specifically incorporated by reference to the same extent as if it had been orporated by reference in its entirety individually or set forth herein in its entirety. Applicants reserve the right to physically incorporate into this specification any and all materials and information from any such cited patents or publications.

The following statements are intended to describe and summarize various embodiments of the invention according to the foregoing description in the specification.

Statements:

1. A transgenic plant, plant seed, or plant cell comprising an expression cassette comprising a promoter operably linked to a nucleic acid segment encoding a CesA protein with at least 70% sequence identity to any of SEQ ID NO:1, 3 5, 7, 8, 9, 10, 11, 12, 13, 14, 15, or 16.
2. The transgenic plant, plant seed, or plant cell of statement 1, wherein the nucleic acid segment can selectively hybridize to a DNA with a SEQ ID NO:2, 4, or 6 sequence.
3. The transgenic plant, plant seed, or plant cell of statement 1 or 2, wherein the nucleic acid segment can selectively hybridize to a DNA with a SEQ ID NO:2, 4, or 6 sequence under stringent hybridization conditions.
4. The transgenic plant, plant seed, or plant cell of statement 1, 2, or 3, wherein the nucleic acid segment can selectively hybridize to a DNA with a SEQ NO:2, 4, or 6 sequence under stringent hybridization conditions comprising a wash in 0.1×SSC, 0.1% SDS at 65° C.
5. The transgenic plant, plant seed, or plant cell of statement 1-3 or 4, wherein the CesA protein is not a CesA3, CesA9, or CesA7 protein.
6. The transgenic plant, plant seed, or plant cell of statement 1-4 or 5, wherein the CesA protein is a CesA2, CesA5, or CesA6 protein.
7. The transgenic plant, plant seed, or plant cell of statement 1-5 or 6, wherein the CesA protein enhances seedling growth.
8. The transgenic plant, plant seed, or plant cell of statement 1-6 or 7, wherein the transgenic plant is at 9. The transgenic plant, plant seed, or plant cell of statement 1-7 or 8, wherein the transgenic plant or the transgenic plant cell has increased CesA1 and CesA3 expression compared to CesA1 and CesA3 expression a control plant without the expression cassette (e.g., a wild type or parental plant without the expression cassette).
10. The transgenic plant, plant seed, or plant cell of statement 1-8 or 9, wherein the transgenic plant or the transgenic plant cell has at least 2-fold, at least 3-fold, at least 4-fold, at least 5-fold greater CesA1 expression compared to CesA1 expression a control plant without the expression cassette (e.g., a wild type or parental plant without the expression cassette),
11. The transgenic plant, plant seed, or plant cell of statement 1-9 or 10, wherein the transgenic plant or the transgenic plant cell has at least about 1%, or about 2%, or about 3%, or about 4%, or about 5%, or about 6%, or about 7%, or about 8%, or about 9%, or about 10%, or about 11%, or about 12%, or about 13%, or about 14%, or about 15% greater CesA3 expression compared to CesA3 expression a control plant without the expression cassette (e.g., a wild type or parental plant without the expression cassette).
12. The transgenic plant, plant seed, or plant cell of statement 1-10 or 11, wherein the transgenic plant has CesA3 particles that move faster than CesA3 panicle in a control plant without the expression cassette (e.g., a wild type or parental plant without the expression cassette).
13. The transgenic plant, plant seed, or plant cell of statement 1-11 or 12, wherein the transgenic plant has CesA3 particles that move at speeds at least 50 nm/min, or at least 100 mm/min, or at least 150 nm/min, or at least 200 nm/min, or at least 250 nm/min, or at least 275 nm/min, or at least 300 nm/min faster than CesA3 particle in a control plant without the expression cassette (e.g., a wild type or parental plant without the expression cassette).
14. The transgenic plant, plant seed, or plant cell of statement 1-12 or 13, wherein the transgenic plant has increased cellulose synthesis than cellulose synthesis in a control plant without the expression cassette (e.g., a wild type or parental plant without the expression cassette).
15. The transgenic plant, plant seed, or plant cell of statement 1-13 or 14, wherein the transgenic plant has at least 2%, or at least 3%, or at least 4%, or at least 5%, or at least 6%, or at least 7%, or at least 8%, or at least 9%, or at least 10%, or at least 11% more cellulose compared to cellulose content in a control plant without the expression cassette (e.g., a wild type or parental plant without the expression cassette).
16. The transgenic plant, plant seed, or plant cell of statement 1-14 or 15, wherein the transgenic plant has hypocotyl basal epidermal cells that are at least 5%, or at least 8%, or at least 9%, or at least 10%, or at least 11%, or at least 12%, or at least 13%, or at least 15%, or at least 17%, or at least 18%, or at least 20%, or at least 21%, or at least 22%, or at least 23%, or at least 25%, or at least 27%, or at least 28%, or at least 30%, or at least 31%, or at least 32%, or at least 33%, or at least 35%, or at least 37%, or at least 40% longer than hypocotyl basal epidermal cells in a control plant without the expression cassette (e.g., a wild type or parental plant without the expression cassette).
17. The transgenic plant, plant seed, or plant cell of statement 1-15 or 16, wherein the transgenic plant has at least 5%, or at least 8%, or at least 9%, or at least 10%, or at least 11%, or at least 12%, or at least 13%, or at least 15%, or at least 17%, or at least 18%, or at least 20%, or at least 21%, or at least 22%, or at least 23%, or at least 25%, or at least 27%, or at least 28%, or at least 30%, or at least 31%, or at least 32%, or at least 33%, or at least 35%, or at least 37%, or at least 40% more or longer root tip (apical meristem) cells than in a control plant without the expression cassette (e.g., a wild type or parental plant without the expression cassette).
18. The transgenic plant, plant seed, or plant cell of statement 1-16 or 17, wherein the transgenic plant has at least 5%, or at least 10%, or at least 12%, or at least 15%, or at least 20%, or at least 22%, or at least 23%, or at least 25%, or at least 27%, or at least 28%, or at least 29%, or at least 30%, or at least 31%, or at least 32%, or at least 254% or at least 27%, or at least 28%, or at least 30%, or at least 31%, or at least 32%, or at least 33%, or at least 34%, or at least 35%, or at least 36%, or at least 37%, or at least 38%, or at least 39%, or at least 40% more crystalline cellulose than in a control plant without the expression cassette (e.g., a wild type or parental plant without the expression cassette).
19. The transgenic plant, plant seed, or plant cell of statement 1-17 or 18, wherein the transgenic plant has at least 1.5-fold, at least 1.7-fold, at least 2-fold, at least 2.2-fold, least 2.5-fold, least 2.7-fold, at least 3-fold wider secondary cell wall than in a control plant without the expression cassette (e.g., a wild type or parental plant without the expression cassette).
20. The transgenic plant, plant seed, or plant cell of statement 1-18 or 19, wherein the plant is a monocot or a dicot.
21. The transgenic plant, plant seed, or plant cell of statement 1-19 or 20, wherein the plant, plant seed, or plant cell is an agricultural plant.
22. The transgenic plant, plant seed, or plant cell of statement 1-20 or 21, wherein the plant, plant seed, or plant cell is a fiber-producing plant (cotton, flax, hemp, jute, sisal, poplar, eucalyptus), forage plant (alfalfa, clover and fescue), grain (maize, wheat, barley, oats, rice, sorghum, millet and rye), grass (switchgrass, prairie grass, wheat grass, sudangrass, sorghum, straw-producing plants), softwood, or hardwood (e.g., those used for paper production such as poplar species, pine species, and eucalyptus) plant, plant seed, or plant cell.
23. The transgenic plant, plant seed, or plant cell of statement 1-21 or 22, wherein the plant, plant seed, or plant cell is a cotton, flax, hemp, jute, sisal, poplar, or eucalyptus plant, plant seed, or plant cell.
24. An expression cassette comprising a promoter operably linked to a nucleic acid segment encoding a CesA protein with at least 70% sequence identity to any of SEQ ID NO:1, 3, 5, 7, 8, 9, 10, 11, 12, 13, 14, 15, or 16.
25. The expression cassette of statement 24, wherein the nucleic acid segment can selectively hybridize to a DNA with a SEQ ID NO:2, 4, or 6 sequence.

26. The expression cassette of statement 24 or 25, wherein the nucleic acid segment can selectively hybridize to a DNA with a SEQ ID NO:2, 4, or 6 sequence under stringent hybridization conditions.
27. The expression cassette of statement 24, 25, or 26, wherein the nucleic acid segment can selectively hybridize to a DNA with a SEQ ID NO:2, 4, or 6 sequence under stringent hybridization conditions comprising a wash in 0.1×SSC, 0.1% SDS at 65° C.
28. The expression cassette of statement 24-26 or 27, wherein the CesA protein is not a CesA3, CesA9, or CesA7 protein.
29. The expression cassette of statement 24-27 or 28, wherein the CesA protein is a CesA2, CesA5, or CesA6 protein.
30. A method comprising transforming a plant cell with the expression cassette of statement 24-28 or 29 to generate a transgenic pant cell and generating a transgenic plant therefrom.
31. The method of statement 30, which does not comprise transforming a plant cell with the expression cassette that comprises a promoter operably linked to a nucleic acid segment encoding a CesA3, CesA9, or CesA7 protein.
32. The method of statement 30 or 31, wherein the plant cell and the plant are each a monocot or a dicot.
33. The method of statement 30, 31 or 32, wherein the plant and the plant cell are each an agricultural plant.
34. The method of statement 30-32, or 33, wherein the plant and the plant cell are each a fiber-producing plant (cotton, flax, hemp, jute, sisal, poplar, or eucalyptus), forage plant (alfalfa, clover and fescue), grain (maize, wheat, barley, oats, rice, sorghum, millet and rye), grass (switchgrass, prairie grass, wheat grass, sudangrass, sorghum, straw-producing plants), softwood, or hardwood (e.g., those used for paper production such as poplar species, pine species, and eucalyptus) plant, plant seed, or plant cell.
35. The method of statement 30-33 or 34, wherein the plant and the plant cell are each a cotton, flax, hemp, jute, sisal, poplar, or eucalyptus plant, plant seed, or plant cell.
36. The method of statement 30-34 or 35, wherein the transgenic plant is at least about 1%, or about 2%, or about 3%, or about 4%, or about 5%, or about 6%, or about 7 or about 8%, or about 9%, or about 10% taller than a control plant without the expression cassette (e.g., a wild type or parental plant without the expression cassette).
37. The method of statement 30-35 or 36, wherein the transgenic plant or the transgenic plant cell has increased CesA1 and CesA3 expression compared to CesA1 and CesA3 expression a control plant without the expression cassette (e.g., a wild type or parental plant without the expression cassette).
38. The method of statement 30-36 or 37, wherein the transgenic plant or the transgenic plant cell has at least 2-fold, at least 3-fold, at least 4-fold, at least 5-fold greater CesA1 expression compared to CesA1 expression a control plant without the expression cassette (e.g., a wild type or parental plant without the expression cassette).
39. The method of statement 30-37 or 38, wherein the transgenic plant or the transgenic plant cell has at least about 1%, or about 2%, or about 3%, or about 4%, or about 5%, or about 6%, or about 7%, or about 8%, or about 9%, or about 10%, or about 12%, or about 13%, or about 14%, or about 15% greater CesA3 expression compared to CesA3 expression a control plant without the expression cassette (e.g., a wild type or parental plant without the expression cassette).
40. The method of statement 30-38 or wherein the transgenic plant has CesA3 particles that move faster than CesA3 particle in a control plant without the expression cassette (e.g., a wild type or parental plant without the expression cassette).
41. The method of statement 30-39 or 40, wherein the transgenic plant has CesA3 particles that move at speeds at least 50 nm/min, or at least 100 nm/min, or at least 150 nm/min, or at least 200 nm/min, or at least 250 nm/min, or at least 275 nm/min, or at least 300 nm/min faster than CesA3 particle in a control plant without the expression cassette (e.g., a wild type or parental plant without the expression cassette).
42. The method of statement 30-40 or 41, wherein the transgenic plant has increased cellulose synthesis than cellulose synthesis in a control plant without the expression cassette (e.g., a wild type or parental plant without the expression cassette).
43. The method of statement 30-41 or 42, wherein the transgenic plant has at least 2%, or at least 3%, or at least 4%, or at least 5%, or at least 6%, or at least 7%, or at least 8%, or at least 9%, or at least 10%, or at least 11% increased cellulose synthesis than cellulose synthesis in a control plant without the expression cassette (e.g., a wild type or parental plant without the expression cassette).
44. The method of statement 30-42 or 43, wherein the transgenic plant has hypocotyl nasal epidermal cells that are at least 5%, or at least 8%, or at least 9%, or at least 10%, or at least 11%, or at least 12%, or at least 13%, or at least 15%, or at least 17%, or at least 18%, or at least 20%, or at least 21% or at least 22%, or at least 23%, or at least 25%, or at least 27%, or at least 28%, or at least 30%, or at least 31%, or at least 32%, or at least 33%, or at least 35%, or at least 37%, or at least 40% longer than hypocotyl basal epidermal cells in a control plant without the expression cassette (e.g., a wild type or parental plant without the expression cassette).
45. The method of statement 30-43 or 44, wherein the transgenic plant has at east 5%, or at least 8%, or at least 9%, or at least 10%, or at least 11%, or at least 12%, or at least 13%, or at least 15%, or at least 17%, or at least 18%, or at least 20%, or at least 21%, or at least 22%, or at least 23%, or at least 25%, or at least 27%, or at least 28%, or at least 30%, or at least 31%, or at least 32%, or at least 33%, or at least 35%, or at least 37%, or at least 40% more root tip (apical meristem) cells than in a control plant without the expression cassette (e.g., a wild type or parental plant without the expression cassette).
46. The method of statement 30-44 or 45, wherein the transgenic plant has at least 5%, or at least 10%, or at least 12%, or at least 15%, or at least 20%, or at least 22%, or at least 23%, or at least 25%, or at least 27%, or at least 28%, or at least 29%, or at least 30%, or at least 31%, or at least 32%, or at least 25%, or at least 27%, or at least 28%, or at least 30%, or at least 31%, or at least 32%, or at least 33%, or at least 34%, or at least 35%, or at least 36%, or at least 37%, or at least 38%, or at least 39%, or at least 40% more crystalline cellulose than in a control plant without the expression cassette (e.g., a wild type or parental plant without the expression cassette).

47. The method of statement 30-45 or 46, wherein the transgenic plant has at least 1.5-fold, at least 1.7-fold, at least 2-fold, at least 2.2-fold, least 2.5-fold, least 2.7-fold, at least 3-fold wider secondary cell wall than in a control plant without the expression cassette (e.g., wild type or parental plant without the expression cassette).

48. The method of statement 30-46 or 47, wherein primary wall CesA complex (cellulose synthase complex, CSC) movement is accelerated in the transgenic plant relative to primary wall CesA complex (cellulose synthase complex, CSC) movement in a control plant without the expression cassette (e.g., a wild type or parental plant without the expression cassette).

49. The method of statement 30-47 or 48, wherein average primary wall CesA complex (cellulose synthase complex, CSC) movement is accelerated in the transgenic plant by at least 2%, or at least 3%, or at least 4%, or at least 5%, or at least 6%, or at least 7%, or at least 8%, or at least 9%, or at least 10%, or at least 11%, or at least 12%, or at least 13%, or at least 14%, or at least 15% relative to average primary wall CesA complex (cellulose synthase complex, CSC) movement in a control plant without the expression cassette (e.g., a wild type or parental plant without the expression cassette).

50. The method of statement 30-48 or 49, wherein the transgenic plant has an increased mean fiber length in the transgenic plant hypocotyl, root, stem, cotton boll, or a combination thereof, relative to mean fiber length of hypocotyls, roots, stems, or cotton bolls, respectively, in a control plant without the expression cassette (e.g., a wild type or parental plant without the expression cassette).

51. The method of statement 30-49 or 50, wherein the transgenic plant has a mean fiber length in the transgenic plant hypocotyl fibers, root fibers, stem fibers, or cotton (boll) fibers, that is at least 2%, or at least 3%, or at least 4%, or at least 5%, or at least 6%, or at least 7%, or at least 8%, or at least 9%, or at least 10%, or at least 11%, or at least 12%, or at least 13%, or at least 14%, or at least 15%, or at least 16%, or at least 17%, or at least 18%, or at least 19%, or at least 20%, or at least 21%, or at least 22%, or at least 23%, or at least 24%, or at least 25% longer than mean fiber length of fibers in hypocotyls, roots, stems, or cotton (boll), respectively, in a control plant without the expression cassette (e.g., a wild type or parental plant without the expression cassette).

52. The method of statement 30-50 or 51, further comprising harvesting biomass or fiber from the transgenic plant.

53. The method of statement 30-51 or 52, further comprising harvesting cotton from the transgenic plant.

The specific products, consortia, methods and compositions described herein are representative of preferred embodiments and are exemplary and not intended as limitations on the scope of the invention. Other objects, aspects, and embodiments will occur to those skilled in the art upon consideration of this specification and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential.

The specific plants, seeds, cells, expression cassettes, products, methods and compositions illustratively described herein suitably may be practiced in differing orders of steps, and the methods and processes are not necessarily restricted to the orders of steps indicated herein or in the claims. As used herein and in the appended claims, the singular forms "a," "an," and "the" include plural reference unless the context clearly dictates otherwise. Thus, for example, a reference to "a plant," "a microbe," "a compound," "a nucleic acid" or "a promoter" includes a plurality of such microbes, compounds, nucleic acids or promoters (for example, a solution of plants, microbes, compounds or nucleic acids, or a series of promoters), and so forth.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of and there is no intent in the use of such terms and expressions to exclude any equivalent of the features shown and described or portions thereof, but it is recognized that various modifications are possible within the scope of the invention as claimed. Thus, it will understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

What is claimed:

1. A transgenic plant, plant seed, or plant cell comprising an expression cassette comprising a promoter operably linked to a nucleic acid segment encoding a CesA protein with at least 95% sequence identity to any of SEQ ID NO: 3, 5, 7, 8, 9, 10, 11, 12, 13, 14, 15, or 16, wherein the plant has a longer mean fiber length of fibers in hypocotyls, roots, stems, or cotton bolls than control plants.

2. The transgenic plant, plant seed, or plant cell of claim 1, which is a cotton, flax, hemp, jute, sisal, poplar, or eucalyptus plant, plant seed, or plant cell.

3. The transgenic plant, plant seed or plant cell of claim 1, wherein CesA movement in plasma membranes is accelerated by at least 5% in the transgenic plant relative to CesA movement in plasma membranes in a control plant without the expression cassette.

4. The transgenic plant, plant seed or plant cell of claim 1, wherein the transgenic plant has at least 5% more crystalline cellulose than in a control plant without the expression cassette.

5. The transgenic plant, plant seed or plant cell of claim 1, wherein the transgenic plant has a mean fiber length in the transgenic plant hypocotyl fibers, root fibers, stem fibers, cotton (boll) fibers, or a combination thereof, that is at least 10% longer than mean fiber length of fibers in hypocotyls, roots, stems, or cotton bolls, respectively, in a control plant without the expression cassette.

6. A method comprising cultivating a seed or plant comprising an expression cassette comprising a promoter operably linked to a nucleic acid segment encoding a CesA protein with at least 95% sequence identity to any of SEQ ID NO: 3, 5, 7, 8, 9, 10, 11, 12, 13, 14, 15, or 16 and harvesting biomass or fiber from the plant or from a plant grown from the seed.

7. The method of claim 6, wherein the seed or the plant is a cotton, flax, hemp, jute, sisal, poplar, or eucalyptus plant seed, or a cotton, flax, hemp, jute, sisal, poplar, or eucalyptus seed or plant.

8. The method of claim 7, comprising harvesting cotton from the cotton plant.

9. The method of claim 6, wherein the seed or plant does not comprise an expression cassette that comprises a promoter operably linked to a nucleic acid segment encoding a CesA3, CesA9, or CesA7 protein.

10. The method of claim 6, wherein the plant or plant grown from the seed has at least 5% more crystalline cellulose than in a control plant without the expression cassette.

11. The method of claim 6, wherein the plant or plant grown from the seed has a mean fiber length in the transgenic plant hypocotyl fibers, root fibers, stem fibers, cotton (boll) fibers, or a combination thereof, that is at least 10% longer than mean fiber length of fibers in hypocotyls, roots, stems, or cotton bolls, respectively, in a control plant without the expression cassette.

12. The method of claim 7, wherein the cotton plant has cotton fibers with a mean length that is at least 10% longer than mean fiber length of cotton fibers of cotton plants that do not have the expression cassette.

13. The method of claim 6, wherein CesA movement in plasma membranes of the plant or in plasma membranes of a plant grown from the seed is accelerated by at least 5% relative to CesA movement in plasma membranes in a control plant without the expression cassette.

* * * * *